(12) United States Patent
Bartels et al.

(10) Patent No.: US 12,365,687 B2
(45) Date of Patent: Jul. 22, 2025

(54) BENZODIAZEPINE DERIVATIVES AS GABA A GAMMA 1 PAM

(71) Applicant: Hoffmann-La Roche Inc., Little Falls, NJ (US)

(72) Inventors: Bjoern Bartels, Schopfheim (DE); Giuseppe Cecere, Basel (CH); Guido Galley, Rheinfelden (DE); Luca Gobbi, Buus (CH); Maria-Clemencia Hernandez, Delémont (CH); Andreas Koblet, Bottmingen (CH); Andrés Miguel Olivares Morales, Binningen (CH); Angélique Patiny-Adam, Kembs (FR); Valerie Runtz-Schmitt, Rixheim (FR)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 17/935,961

(22) Filed: Sep. 28, 2022

(65) Prior Publication Data

US 2023/0136326 A1    May 4, 2023

(30) Foreign Application Priority Data

Sep. 29, 2021   (EP) .................................. 21199653

(51) Int. Cl.
*C07D 487/04* (2006.01)
*C07D 519/00* (2006.01)

(52) U.S. Cl.
CPC ......... *C07D 487/04* (2013.01); *C07D 519/00* (2013.01); *C07B 2200/05* (2013.01)

(58) Field of Classification Search
CPC ............................ C07D 487/04; C07D 519/00
See application file for complete search history.

(56) References Cited

U.S. PATENT DOCUMENTS

| | | | |
|---|---|---|---|
| 3,681,343 A | 8/1972 | Hester, Jr. | |
| 3,734,922 A | 5/1973 | Hester, Jr. | |
| 3,927,016 A * | 12/1975 | Hester, Jr. | C07D 487/04 540/562 |
| 3,987,052 A | 10/1976 | Hester, Jr. | |
| 4,201,712 A | 5/1980 | Weber et al. | |
| 4,621,083 A | 11/1986 | Casals-Stenzel et al. | |
| 5,185,442 A | 2/1993 | Weber et al. | |
| 5,532,233 A | 7/1996 | Weber et al. | |
| 11,739,095 B2 | 8/2023 | Cecere et al. | |
| 2012/0295892 A1 | 11/2012 | Cook et al. | |
| 2023/0109111 A1 | 4/2023 | Cecere et al. | |
| 2023/0141603 A1 | 5/2023 | Cecere et al. | |
| 2023/0142171 A1 | 5/2023 | Bartels et al. | |
| 2024/0002393 A1 | 1/2024 | Cecere et al. | |

FOREIGN PATENT DOCUMENTS

| | | |
|---|---|---|
| DE | 2533924 A1 | 2/1977 |
| DE | 3724031 A1 | 1/1988 |
| EP | 0176927 A2 | 4/1986 |
| WO | 2003/082832 A2 | 10/2003 |
| WO | 2015/200766 A2 | 12/2015 |
| WO | 2018/035246 A1 | 2/2018 |
| WO | 2020/198275 A1 | 1/2022 |

OTHER PUBLICATIONS

WebMD. (Jun. 1, 2022). Fragile X syndrome: Symptoms, causes, diagnosis, and treatment. WebMD. https://www.webmd.com/children/what-is-fragile-x-syndrome (Year: 2022).*
Fiakpui et al., "Synthesis and anticonvulsant activities of 5-(2-Chlorophenyl)-7H-pyrido [4, 3-f][1, 2, 4] triazolo [4, 3-a] [1, 4] diazepines" Journal of heterocyclic chemistry (March-Apr. 1999), 36(2):377-380.
Forkuo, G., et al., "Alleviation of Multiple Asthmatic Pathologic Features with Orally Available and Subtype Selective Gaba A Receptor Modulators" Mol Pharm 14(6):2088-2098 (Jun. 5, 2017).
"International Search Report—PCT/EP2022/076738" (w/Written Opinion),:pp. 1-10 (Dec. 5, 2022).
Kolbah, D., et al., "Stereoselective in-vitro aromatic-ring oxygenations of chiral 1,4-benzodiazepin-2-ones" HEL V CHIM ACTA 60(1):265-283 (Jan. 26, 1977).
Kooistra, T., et al., "Triazolobenzodiazepines: a new class of stimulators of tissue-type plasminogen activator synthesis in human endothelial cells" Biochem Pharmacol 46(1):61-67 (Jul. 6, 1993).
Lee, S., et al., "Axial chirality and affinity at the GABA(A) receptor of pyrimido[1,2-a][1,4]benzodiazepines and related compounds" Bioorg Med Chem 16(21):9519-9523 (Nov. 1, 2008).

(Continued)

*Primary Examiner* — John S Kenyon
*Assistant Examiner* — John D McAnany
(74) *Attorney, Agent, or Firm* — Dechert LLP

(57) ABSTRACT

The invention provides novel heterocyclic compounds having the general formula (I), and pharmaceutically acceptable salts thereof, wherein the variables are as described herein.

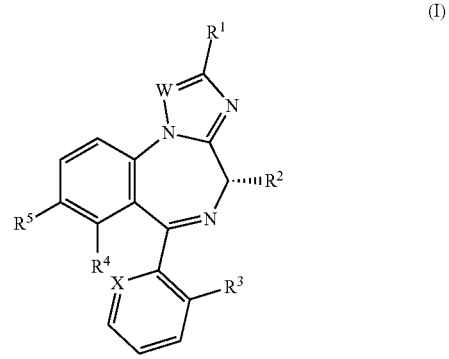

(I)

Further provided are pharmaceutical compositions including the compounds, processes of manufacturing the compounds and methods of using the compounds as medicaments, in particular methods of using the compounds for the treatment or prevention of acute neurological disorders, chronic neurological disorders and/or cognitive disorders.

2 Claims, No Drawings

(56) References Cited

OTHER PUBLICATIONS

Svetlov, S., et al., "The specific binding of the platelet-activating factor (PAF) receptor antagonist WEB 2086 and the benzodiazepine flunitrazepam to rat hepatocytes" Life Sci 58(5):PL81-PL86 (Dec. 1, 1995).

Waters, L. et al., "The use of a quantitative structure-activity relationship (QSAR) model to predict GABA-A receptor binding of newly emerging benzodiazepines" Sci Justice 58(5):219-225 (May 1, 2018).

Watjen, F., et al., "Novel benzodiazepine receptor partial agonists: oxadiazolylimidazobenzodiazepines" J Med Chem 32(10):2282-2291 (Jan. 1, 1989).

\* cited by examiner

BENZODIAZEPINE DERIVATIVES AS GABA A GAMMA 1 PAM

CROSS REFERENCE TO RELATED APPLICATIONS

This Application claims priority to European Application No. 21199653.3 filed on Sep. 29, 2021, the disclosure of which is incorporated herein by reference.

FIELD OF THE INVENTION

The present invention relates to organic compounds useful for therapy or prophylaxis in a mammal, and in particular to new benzodiazepine derivatives that exhibit activity as GABAA γ1 receptor positive allosteric modulators (PAMs) and are thus useful for the treatment or prophylaxis of GABAA γ1 receptor related diseases or conditions.

BACKGROUND OF THE INVENTION

Receptors for the major inhibitory neurotransmitter, gamma-aminobutyric acid (GABA), are divided into two main classes: (1) $GABA_A$ receptors, which are members of the ligand-gated ion channel superfamily and (2) $GABA_B$ receptors, which are members of the G-protein linked receptor family. The $GABA_A$ receptor complex which is a membrane-bound heteropentameric protein polymer is composed principally of α, β and γ subunits. $GABA_A$ receptors are ligand-gated chloride channels and the principal mediators of inhibitory neurotransmission in the human brain.

There are 19 genes encoding for $GABA_A$ receptor subunits that assemble as pentamers with the most common stoichiometry being two α, two β and one γ subunit. $GABA_A$ subunit combinations give rise to functional, circuit, and behavioral specificity. $GABA_A$ receptors containing the γ1 subunit ($GABA_A$ γ1) are of particular interest due to their enriched expression in the limbic system and unique physiological and pharmacological properties. The $GABA_A$ γ1 subunit-containing receptors, while less abundant (around 5-10% of total expression of $GABA_A$ receptors in the brain) than γ2 subunit-containing receptors exhibit an enriched brain mRNA and protein distribution in key brain areas such as extended amygdala (central, medial, and bed nucleus of the stria terminalis), lateral septum, hypothalamus, and pallidum/nigra. These structures form the interconnected core of a subcortical limbic circuit regulating motivated social and affective behaviors. In abnormal or disease conditions, hyper-recruitment of this circuit promotes anxiety, arousal, aggression, fear and defense while inhibiting foraging and social interactions.

Hyperactivity in limbic cortical regions (known to form a coordinated functional network with extended amygdala/hypothalamus regions) which are key areas for processing of social and emotionally relevant stimuli, is the common hallmark of a variety of psychiatric, neurological, neurodevelopmental, neurodegenerative, mood, motivational and metabolic disorders. In such a disease state, and given the characteristic anatomical distribution of the y1 subunit-containing $GABA_A$ receptors, a $GABA_A$ γ1 positive allosteric modulator (PAM) may be an effective treatment as a symptomatic or disease-modifying agent.

Multiple lines of evidence suggest that an imbalance between excitatory/inhibitory (E/I) neurotransmission arising from dysfunction of GABAergic signaling system, the main inhibitory neurotransmitter system in the brain, to be at the core of the pathogenesis a variety of CNS disorders.

Given the distribution and function of $GABA_A$ γ1 subunit-containing receptors in the CNS, they are very attractive targets for restoring levels of inhibition within key brain circuits and consequently the E/I balance in these conditions.

A CNS disorders of particular interest in the context of the present invention is autism spectrum disorder (ASD), including its core symptoms and associated comorbidities, such as anxiety and irritability, social anxiety disorder (social phobia) and generalized anxiety disorder. ASD is a complex, heterogeneous neurodevelopmental disorder characterized by impairments in two core domains: impairments in social interaction and communication, and presence of repetitive or restricted behaviors, interests, or activities (American Psychiatric Association 2013).

No approved pharmacological treatment exists for core symptoms of social deficits and restricted/repetitive behaviour of ASD, while only inadequate therapeutic options are available for most of ASD's affective and physiological co-morbidities. As a result, this disorder continues to be an area of high unmet medical need. Current approved treatments for associated symptoms of ASD are limited to the antipsychotics (Risperidone and Aripiprazole) indicated for the treatment of irritability associated with ASD symptoms. Emerging evidence suggests that the GABAergic system, the main inhibitory neurotransmitter system in the brain, plays a key role in the pathophysiology of ASD.

Both genetic and imaging studies using positron emission tomography study (PET) and magnetic resonance spectroscopy (MRS) suggest alterations in GABAergic signaling in ASD. The gene encoding $GABA_A$ γ1, GABRG1, is located on chromosome 4 (mouse Chr.5) in a cluster with genes encoding α2, α4 and β1 $GABA_A$ receptor subunits. Rare CNVs, including inversion of chromosome 4p12 disrupting GABRG1 have been observed in autistic siblings (Horike et al., 2006), as well as GABRG1 loss in one case of ADHD. Mutations in 4p12 gene cluster have been linked to increased risk of anxiety, substance abuse and eating disorders—providing a link between GABRG1/4p12 and affective dysfunction. MRS studies found altered GABA levels in ASD and in particular some recent studies showed reduced GABA and altered somatosensory function in children with ASD and. In line with these observations, a reduced number of inhibitory interneurons were found from postmortem tissues of ASD and TS patients. Furthermore, reduced GABA synthesizing enzymes, glutamic acid decarboxylase (GAD) 65 and 67 were found in parietal and cerebellar cortices of patients with autism. Strong evidence in humans points to specific dysfunction in ASD of the limbic cortical regions known to form a coordinated functional network with $GABA_A$ γ1 subunit-containing extended amygdala/hypothalamus regions. These areas: Cortical/lateral amygdala, Insula, PFC, and Cingulate are recognized key for processing of social and emotionally relevant stimuli. While subcortical subnuclei that form specific partnerships with these areas, coordinating behavioural outcomes, are often difficult to study due to spatial resolution limitations, many lines of evidence point to hyper-recruitment of these cortical- to sub cortical connections in ASD. Moreover, recent high resolution studies provide a clear link between extended amygdala activity/functional connectivity and emotional state. Targeting such highly specified limbic subcortical regions, which exhibit substantial molecular and cellular diversity compared to the neocortex, will create a precision entry point for safe and specific therapeutic modulation of ASD-affected socio-affective circuits, while avoiding broad modulation of global brain state. Enhancement of GABA$_A$ receptor activity by non-selective BZDs have been shown to ameliorate behavioral deficits in mouse models of ASD, however very narrow therapeutic margins were observed due to sedation mediated by the GABA$_A$ α1γ2 subtype. These findings support the notion that rebalancing of GABAergic transmission via GABA$_A$ γ1 receptors can improve symptoms in ASD without the side effects of non-selective benzodiazepines.

SUMMARY OF THE INVENTION

Compounds of the present invention are selective GABA$_A$ γ1 receptor positive allosteric modulators (PAMs) that selectively enhance the function of γ1-containing GABA$_A$ receptors by increasing GABAergic currents (influx of chloride) at a given concentration (e.g. EC$_{20}$) of gamma amino butyric acid (GABA). The compounds of the present invention have high PAM efficacy and binding selectivity for the γ1-containing subtypes (α5γ1, α2γ1, α1γ1) relative to the γ2-containing subtypes (e.g. α1γ2, α2γ2, α3γ2 and α5γ2). As such, compounds of the present invention are strongly differentiated from classical benzodiazepine drugs such as Alprazolam, Triazolam, Estazolam, and Midazolam, which are selective for the γ2-containing GABA$_A$ subtypes and possess low affinity for the γ1-containing subtypes. Compatible with the γ1-subtypes brain distribution, selective GABA$_A$ γ1 PAMs will restore GABAergic signaling in key brain regions (e.g. extended amygdala: central, medial, and bed nucleus of the stria terminalis, lateral septum, hypothalamus, and pallidum/nigra) without the side-effects of non-selective GABA$_A$ modulators (e.g. benzodiazepines).

In view of the above, the selective GABA$_A$ γ1 PAMs described herein and their pharmaceutically acceptable salts and esters are useful, alone or in combination with other drugs, as disease-modifying or as symptomatic agents for the treatment or prevention of acute neurological disorders, chronic neurological disorders and/or cognitive disorders, including autism spectrum disorders (ASD), Angelman syndrome, age-related cognitive decline, Rett syndrome, Prader-Willi syndrome, amyotrophic lateral sclerosis (ALS), fragile-X disorder, negative and/or cognitive symptoms associated with schizophrenia, tardive dyskinesia, anxiety, social anxiety disorder (social phobia), panic disorder, agoraphobia, generalized anxiety disorder, disruptive, impulse-control and conduct disorders, Tourette's syndrome (TS), obsessive-compulsive disorder (OCD), acute stress disorder, post-traumatic stress disorder (PTSD), attention deficit hyperactivity disorder (ADHD), sleep disorders, Parkinson's disease (PD), Huntington's chorea, Alzheimer's disease (AD), mild cognitive impairment (MCI), dementia, behavioral and psychological symptoms (BPS) in neurodegenerative conditions, multi-infarct dementia, agitation, psychosis, substance-induced psychotic disorder, aggression, eating disorders, depression, chronic apathy, anhedonia, chronic fatigue, seasonal affective disorder, postpartum depression, drowsiness, sexual dysfunction, bipolar disorders, epilepsy and pain.

In a first aspect, the present invention provides a compound of formula (I)

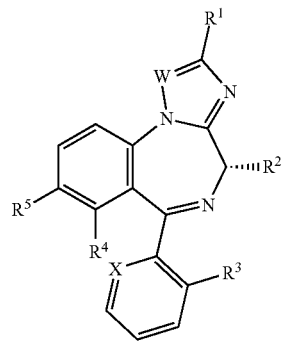

or a pharmaceutically acceptable salt thereof, wherein the variables are as defined herein.

In one aspect, the present invention provides a process of manufacturing the compounds of formula (I) described herein, wherein said process is as described in any one of Schemes 1 to 9 herein.

In a further aspect, the present invention provides a compound of formula (I) as described herein, when manufactured according to the processes described herein.

In a further aspect, the present invention provides a compound of formula (I) as described herein, or a pharmaceutically acceptable salt thereof, for use as therapeutically active substance.

In a further aspect, the present invention provides a pharmaceutical composition comprising a compound of formula (I) as described herein, or a pharmaceutically acceptable salt thereof, and a therapeutically inert carrier.

In a further aspect, the present invention provides a compound of formula (I) as described herein, or a pharmaceutically acceptable salt thereof, for use in a method for treating or preventing acute neurological disorders, chronic neurological disorders and/or cognitive disorders in a subject.

DETAILED DESCRIPTION OF THE INVENTION

Definitions

Features, integers, characteristics, compounds, chemical moieties or groups described in conjunction with a particular aspect, embodiment or example of the invention are to be understood to be applicable to any other aspect, embodiment or example described herein, unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The term "alkyl" refers to a mono- or multivalent, e.g., a mono- or bivalent, linear or branched saturated hydrocarbon group of 1 to 6 carbon atoms ("C$_1$-C$_6$-alkyl"), e.g., 1, 2, 3, 4, 5, or 6 carbon atoms. In some embodiments, the alkyl group contains 1 to 3 carbon atoms, e.g., 1, 2 or 3 carbon atoms. Some non-limiting examples of alkyl include methyl, ethyl, propyl, 2-propyl (isopropyl), n-butyl, iso-butyl, sec-butyl, tert-butyl, and 2,2-dimethylpropyl. Particularly preferred, yet non-limiting examples of alkyl include methyl and ethyl.

The term "alkoxy" refers to an alkyl group, as previously defined, attached to the parent molecular moiety via an oxygen atom. Unless otherwise specified, the alkoxy group contains 1 to 6 carbon atoms ("$C_1$-$C_6$-alkoxy"). In some preferred embodiments, the alkoxy group contains 1 to 4 carbon atoms. In still other embodiments, the alkoxy group contains 1 to 3 carbon atoms. Some non-limiting examples of alkoxy groups include methoxy, ethoxy, n-propoxy, iso-propoxy, n-butoxy, isobutoxy and tert-butoxy. A particularly preferred, yet non-limiting example of alkoxy is ethoxy.

The term "halogen" or "halo" refers to fluoro (F), chloro (Cl), bromo (Br), or iodo (I). Preferably, the term "halogen" or "halo" refers to fluoro (F), chloro (Cl) or bromo (Br). Particularly preferred, yet non-limiting examples of "halogen" or "halo" are fluoro (F) and chloro (Cl).

The term "cycloalkyl" as used herein refers to a saturated or partly unsaturated monocyclic or bicyclic hydrocarbon group of 3 to 10 ring carbon atoms ("$C_3$-$C_{10}$-cycloalkyl"). In some preferred embodiments, the cycloalkyl group is a saturated monocyclic hydrocarbon group of 3 to 8 ring carbon atoms. "Bicyclic cycloalkyl" refers to cycloalkyl moieties consisting of two saturated carbocycles having two carbon atoms in common, i.e., the bridge separating the two rings is either a single bond or a chain of one or two ring atoms, and to spirocyclic moieties, i.e., the two rings are connected via one common ring atom. Preferably, the cycloalkyl group is a saturated monocyclic hydrocarbon group of 3 to 6 ring carbon atoms, e.g., of 3, 4, 5 or 6 carbon atoms. Some non-limiting examples of cycloalkyl include cyclopropyl, cyclobutyl, cyclopentyl, cyclohexyl, cycloheptyl, and spiro[2.3]hexan-5-yl.

The term "heterocyclyl" or "heterocycloalkyl" refers to a saturated or partly unsaturated mono- or bicyclic, preferably monocyclic ring system of 3 to 14 ring atoms, preferably 3 to 10 ring atoms, more preferably 3 to 8 ring atoms wherein 1, 2, or 3 of said ring atoms are heteroatoms selected from N, O and S, the remaining ring atoms being carbon. Preferably, 1 to 2 of said ring atoms are selected from N and O, the remaining ring atoms being carbon. "Bicyclic heterocyclyl" refers to heterocyclic moieties consisting of two cycles having two ring atoms in common, i.e., the bridge separating the two rings is either a single bond or a chain of one or two ring atoms, and to spirocyclic moieties, i.e., the two rings are connected via one common ring atom. Some non-limiting examples of heterocyclyl groups include azetidin-3-yl; azetidin-2-yl; oxetan-3-yl; oxetan-2-yl; oxazolidinyl; piperidyl; piperazinyl; pyrrolidinyl; 2-oxopyrrolidin-1-yl; 2-oxopyrrolidin-3-yl; 5-oxopyrrolidin-2-yl; 5-oxopyrrolidin-3-yl; 2-oxo-1-piperidyl; 2-oxo-3-piperidyl; 2-oxo-4-piperidyl; 6-oxo-2-piperidyl; 6-oxo-3-piperidyl; 1-piperidinyl; 2-piperidinyl; 3-piperidinyl; 4-piperidinyl; morpholino (e.g., morpholin-2-yl or morpholin-3-yl); thiomorpholino; pyrrolidinyl (e.g., pyrrolidin-3-yl); 1-oxa-6-azaspiro[3.3]heptane; 2-oxa-6-azaspiro[3.3]heptane; 5-oxa-2-azaspiro[3.4]octane; 6-oxa-2-azaspiro[3.4]octane; 5-oxa-2-azaspiro[3.5]nonane; 6-oxa-2-azaspiro[3.5]nonane; 7-oxa-2-azaspiro[3.5]nonane; 3-oxa-6-azabicyclo[3.1.1]heptane; 3-thia-6-azabicyclo[3.1.1]heptane; 3-azabicyclo[3.1.0]hexan-6-yl; 2,5-diazabicyclo[2.2.1]heptan-2-yl; 2-azaspiro[3.3]heptan-2-yl; 2,6-diazaspiro[3.3]heptan-2-yl; and 2,3,3a,4,6,6a-hexahydro-1H-pyrrolo[3,4-c]pyrrol-5-yl. Preferred, yet non-limiting examples of heterocyclyl include azetidin-3-yl; azetidin-2-yl; oxetan-3-yl; oxetan-2-yl; oxazolidinyl; thiomorpholino; 1-oxa-6-azaspiro[3.3]heptane; 2-oxa-6-azaspiro[3.3]heptane; 5-oxa-2-azaspiro[3.4]octane; 6-oxa-2-azaspiro[3.4]octane; 5-oxa-2-azaspiro[3.5]nonane; 6-oxa-2-azaspiro[3.5]nonane; 7-oxa-2-azaspiro[3.5]nonane; 3-oxa-6-azabicyclo[3.1.1]heptane; and 3-thia-6-azabicyclo[3.1.1]heptane.

The term "hydroxy" refers to an —OH group.

The term "carbonyl" refers to a C=O group.

The term "oxo" refers to an oxygen atom that is bound to the parent moiety via a double bond (=O).

The term "cyano" refers to a —CN (nitrile) group.

The term "sulfamoyl" refers to a group —$SO_2$—$NH_2$.

The term "haloalkyl" refers to an alkyl group, wherein at least one of the hydrogen atoms of the alkyl group has been replaced by a halogen atom, preferably fluoro. Preferably, "haloalkyl" refers to an alkyl group wherein 1, 2 or 3 hydrogen atoms of the alkyl group have been replaced by a halogen atom, most preferably fluoro. Non-limiting examples of haloalkyl are fluoromethyl, difluoromethyl, trifluoromethyl, trifluoroethyl, 2-fluoroethyl, and 2,2-difluoroethyl. A particularly preferred, yet non-limiting example of haloalkyl is difluoromethyl or trifluoromethyl.

The term "cyanoalkyl" refers to an alkyl group, wherein at least one of the hydrogen atoms of the alkyl group has been replaced by a cyano group. Preferably, "cyanoalkyl" refers to an alkyl group wherein 1, 2 or 3 hydrogen atoms of the alkyl group have been replaced by a cyano group. A non-limiting example of cyanoalkyl is cyanomethy.

The term "deuterioalkyl" refers to an alkyl group, wherein at least one of the hydrogen atoms of the alkyl group has been replaced by a deuterium ($^2$H) atom. Preferably, "deuterioalkyl" refers to an alkyl group wherein 1, 2 or 3 hydrogen atoms of the alkyl group have been replaced by a deuterium atom. A particularly preferred, yet non-limiting example of deuterioalkyl is trideuteriomethyl.

The term "alkoxyalkyl" refers to an alkyl group, wherein at least one of the hydrogen atoms of the alkyl group has been replaced by an alkoxy group. Preferably, "alkoxyalkyl" refers to an alkyl group wherein 1, 2 or 3 hydrogen atoms of the alkyl group have been replaced by an alkoxy group. Most preferably, "alkoxyalkyl" refers to an alkyl group wherein 1 hydrogen atom of the alkyl group has been replaced by an alkoxy group. A preferred, yet non-limiting example of alkoxyalkyl is 2-methoxyethyl.

The term "haloalkoxy" refers to an alkoxy group, wherein at least one of the hydrogen atoms of the alkoxy group has been replaced by a halogen atom, preferably fluoro. Preferably, "haloalkoxy" refers to an alkoxy group wherein 1, 2 or 3 hydrogen atoms of the alkoxy group have been replaced by a halogen atom, most preferably fluoro. Particularly preferred, yet non-limiting examples of haloalkoxy are fluoromethoxy ($FCH_2O$—), difluoromethoxy ($F_2CHO$—), and trifluoromethoxy ($F_3CO$—).

The term "deuterioalkoxy" refers to an alkoxy group, wherein at least one of the hydrogen atoms of the alkoxy group has been replaced by a deuterium ($^2$H) atom. Preferably, "deuterioalkoxy" refers to an alkoxy group wherein 1, 2 or 3 hydrogen atoms of the alkoxy group have been replaced by a deuterium atom. A particularly preferred, yet non-limiting example of deuterioalkoxy is trideuteriomethoxy ($FCH_2O$—).

The term "hydroxyalkyl" refers to an alkyl group, wherein at least one of the hydrogen atoms of the alkyl group has been replaced by a hydroxy group. Preferably, "hydroxyalkyl" refers to an alkyl group wherein 1, 2 or 3 hydrogen atoms, most preferably 1 hydrogen atom of the alkyl group have been replaced by a hydroxy group. Preferred, yet non-limiting examples of hydroxyalkyl are hydroxymethyl, hydroxyethyl (e.g. 2-hydroxyethyl), and hydroxypropyl (e.g., 2-hydroxypropyl).

The term "pharmaceutically acceptable salt" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as formic acid, acetic acid, trifluoroacetic acid, propionic acid, glycolic acid, pyruvic acid, oxalic acid, maleic acid, malonic acid, succinic acid, fumaric acid, tartaric acid, lactic acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are hydrochlorides, fumarates, formates, lactates (in particular derived from L-(+)-lactic acid), tartrates (in particular derived from L-(+)-tartaric acid) and trifluoroacetates.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention, the asymmetric carbon atom can be of the "R" or "S" configuration.

The term "treatment" as used herein includes: (1) inhibiting the state, disorder or condition (e.g. arresting, reducing or delaying the development of the disease, or a relapse thereof in case of maintenance treatment, of at least one clinical or subclinical symptom thereof); and/or (2) relieving the condition (i.e., causing regression of the state, disorder or condition or at least one of its clinical or subclinical symptoms). The benefit to a patient to be treated is either statistically significant or at least perceptible to the patient or to the physician. However, it will be appreciated that when a medicament is administered to a patient to treat a disease, the outcome may not always be effective treatment.

The term "prophylaxis" or "prevention" as used herein includes: preventing or delaying the appearance of clinical symptoms of the state, disorder or condition developing in a subject and especially a human that may be afflicted with or predisposed to the state, disorder or condition but does not yet experience or display clinical or subclinical symptoms of the state, disorder or condition.

The term "subject" as used herein includes both humans and non-humans and includes but is not limited to humans, non-human primates, canines, felines, murines, bovines, equines, and porcines. In a particularly preferred embodiment, the term "subject" refers to humans.

The abbreviation uM means microMolar and is equivalent to the symbol μM.

The abbreviation uL means microliter and is equivalent to the symbol μL.

The abbreviation ug means microgram and is equivalent to the symbol μg.

Compounds of the Invention

In a first aspect, the present invention provides a compound of formula (I)

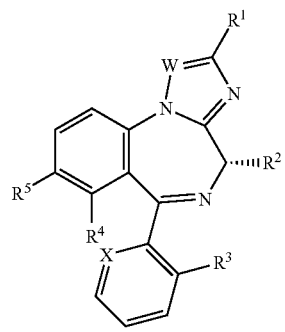

or a pharmaceutically acceptable salt thereof, wherein:

W is C—$R^6$ or N;

X is C—$R^7$ or N;

$R^1$ is selected from hydrogen, $C_1$-$C_6$-alkyl, hydroxy-$C_1$-$C_6$-alkyl, halo-$C_1$-$C_6$-alkyl, $C_1$-$C_6$-alkoxy, $C_1$-$C_6$-alkoxy-$C_1$-$C_6$-alkyl, cyano, $NR^8R^9C(O)$—, sulfamoyl, $C_1$-$C_6$-alkyl-NH—C(O)—NH—, $C_3$-$C_{10}$-cycloalkyl-NH—C(O)—NH—, $C_1$-$C_6$-alkyl-$SO_2$—, $C_1$-$C_6$-alkyl-NH—$SO_2$—, $C_1$-$C_6$-alkyl-C(O)—NH—$C_1$-$C_6$-alkyl-, and a group

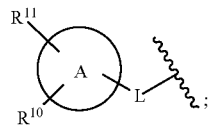

$R^2$ is selected from hydrogen and $C_1$-$C_6$-alkyl;

$R^3$ is selected from fluoro and chloro;

$R^4$ is selected from chloro and bromo;

$R^5$ is selected from halogen, $C_1$-$C_6$-alkyl, and halo-$C_1$-$C_6$-alkyl;

$R^6$ is selected from hydrogen, $C_1$-$C_6$-alkyl, and hydroxy-$C_1$-$C_6$-alkyl; or $R^6$ and $R^1$, taken together with the carbon atoms to which they are attached, form a $C_3$-$C_{10}$-cycloalkyl;

$R^7$ is selected from hydrogen, fluoro and chloro;

$R^8$ is selected from hydrogen, $C_1$-$C_6$-alkyl, deuterio-$C_1$-$C_6$-alkyl, halo-$C_1$-$C_6$-alkyl, hydroxy-$C_1$-$C_6$-alkyl, cyano-$C_1$-$C_6$-alkyl, $C_1$-$C_6$-alkoxy-$C_1$-$C_6$-alkyl, and $(C_1$-$C_6$-alkyl$)_2N$—;

$R^9$ is selected from hydrogen, $C_1$-$C_6$-alkyl, and deuterio-$C_1$-$C_6$-alkyl;

$R^{10}$ is selected from hydrogen, hydroxy, oxo, cyano, halogen, $C_1$-$C_6$-alkyl, halo-$C_1$-$C_6$-alkyl, $C_1$-$C_6$-alkoxy, deuterio-$C_1$-$C_6$-alkoxy, and halo-$C_1$-$C_6$-alkoxy;

$R^{11}$ is selected from hydrogen and oxo;

A is selected from 3-14-membered heterocycloalkyl and $C_3$-$C_{10}$-cycloalkyl; and L is selected from a covalent bond, carbonyl, O, C(O)NH, NHC(O), and NHC(O)NH.

In one embodiment, the present invention provides a compound of formula (I) as described herein, or a pharmaceutically acceptable salt thereof, wherein W is C—$R^6$.

In a preferred embodiment, the present invention provides a compound of formula (I) as described herein, or a pharmaceutically acceptable salt thereof, wherein W is N.

In one embodiment, the present invention provides a compound of formula (I) as described herein, or a pharmaceutically acceptable salt thereof, wherein X is C—$R^7$.

In one embodiment, the present invention provides a compound of formula (I) as described herein, or a pharmaceutically acceptable salt thereof, wherein X is N.

In a preferred embodiment, the present invention provides a compound of formula (I) as described herein, or a pharmaceutically acceptable salt thereof, wherein
$R^1$ is selected from $NR^8R^9C(O)$— and a group

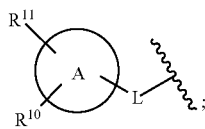

$R^8$ is selected from hydroxy-$C_1$-$C_6$-alkyl and ($C_1$-$C_6$-alkyl)$_2$N—;
$R^9$ is hydrogen;
$R^{10}$ is selected from hydrogen, oxo, and $C_1$-$C_6$-alkoxy;
$R^{11}$ is selected from hydrogen and oxo;
A is a 3-14-membered heterocycloalkyl; and
L is carbonyl.

In a particularly preferred embodiment, the present invention provides a compound of formula (I) as described herein, or a pharmaceutically acceptable salt thereof, wherein
$R^1$ is selected from $NR^8R^9C(O)$— and a group

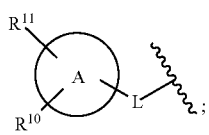

$R^8$ is selected from 2-hydroxyethyl, 2-hydroxypropyl, and ($CH_3$)$_2$N—;
$R^9$ is hydrogen;
$R^{10}$ is selected from hydrogen, oxo, and ethoxy;
$R^{11}$ is selected from hydrogen and oxo;
A is selected from azetidine and thiomorpholine; and
L is carbonyl.

In a preferred embodiment, the present invention provides a compound of formula (I) as described herein, or a pharmaceutically acceptable salt thereof, wherein
$R^1$ is $NR^8R^9C(O)$—;
$R^8$ is hydroxy-$C_1$-$C_6$-alkyl; and
$R^9$ is hydrogen.

In a particularly preferred embodiment, the present invention provides a compound of formula (I) as described herein, or a pharmaceutically acceptable salt thereof, wherein
$R^1$ is $NR^8R^9C(O)$—;
$R^8$ is 2-hydroxyethyl; and
$R^9$ is hydrogen.

In a preferred embodiment, the present invention provides a compound of formula (I) as described herein, wherein $R^2$ is $C_1$-$C_6$-alkyl.

In a particularly preferred embodiment, the present invention provides a compound of formula (I) as described herein, wherein $R^2$ is methyl.

In a preferred embodiment, the present invention provides a compound of formula (I) as described herein, or a pharmaceutically acceptable salt thereof, wherein $R^3$ is fluoro.

In a preferred embodiment, the present invention provides a compound of formula (I) as described herein, or a pharmaceutically acceptable salt thereof, wherein $R^4$ is chloro.

In one embodiment, the present invention provides a compound of formula (I) as described herein, or a pharmaceutically acceptable salt thereof, wherein $R^5$ is selected from halogen and halo-$C_1$-$C_6$-alkyl.

In a preferred embodiment, the present invention provides a compound of formula (I) as described herein, or a pharmaceutically acceptable salt thereof, wherein $R^5$ is halo-$C_1$-$C_6$-alkyl.

In a particularly preferred embodiment, the present invention provides a compound of formula (I) as described herein, or a pharmaceutically acceptable salt thereof, wherein $R^5$ is $CF_3$.

In one embodiment, the present invention provides a compound of formula (I) as described herein, or a pharmaceutically acceptable salt thereof, wherein $R^7$ is selected from hydrogen and fluoro.

In a preferred embodiment, the present invention provides a compound of formula (I) as described herein, or a pharmaceutically acceptable salt thereof, wherein $R^7$ is fluoro.

In one embodiment, the present invention provides a compound of formula (I) as described herein, or a pharmaceutically acceptable salt thereof, wherein:
W is C—$R^6$ or N;
X is C—$R^7$ or N;
$R^1$ is selected from hydrogen, $C_1$-$C_6$-alkyl, hydroxy-$C_1$-$C_6$-alkyl, halo-$C_1$-$C_6$-alkyl, $C_1$-$C_6$-alkoxy, $C_1$-$C_6$-alkoxy-$C_1$-$C_6$-alkyl, cyano, $NR^8R^9C(O)$—, sulfamoyl, $C_1$-$C_6$-alkyl-NH—C(O)—NH—, $C_3$-$C_{10}$-cycloalkyl-NH—C(O)—NH—, $C_1$-$C_6$-alkyl-SO$_2$—, $C_1$-$C_6$-alkyl-NH—SO$_2$—, $C_1$-$C_6$-alkyl-C(O)—NH—$C_1$-$C_6$-alkyl-, and a group

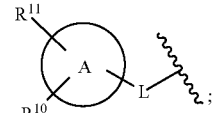

$R^2$ is selected from hydrogen and $C_1$-$C_6$-alkyl;
$R^3$ is fluoro;
$R^4$ is chloro;
$R^5$ is selected from halogen and halo-$C_1$-$C_6$-alkyl;
$R^6$ is selected from hydrogen, $C_1$-$C_6$-alkyl, and hydroxy-$C_1$-$C_6$-alkyl; or
$R^6$ and $R^1$, taken together with the carbon atoms to which they are attached, form a $C_3$-$C_{10}$-cycloalkyl;
$R^7$ is selected from hydrogen and fluoro;
$R^8$ is selected from hydrogen, $C_1$-$C_6$-alkyl, deuterio-$C_1$-$C_6$-alkyl, halo-$C_1$-$C_6$-alkyl, hydroxy-$C_1$-$C_6$-alkyl, cyano-$C_1$-$C_6$-alkyl, $C_1$-$C_6$-alkoxy-$C_1$-$C_6$-alkyl, and ($C_1$-$C_6$-alkyl)$_2$N—;
$R^9$ is selected from hydrogen, $C_1$-$C_6$-alkyl, and deuterio-$C_1$-$C_6$-alkyl;
$R^{10}$ is selected from hydrogen, hydroxy, oxo, cyano, halogen, $C_1$-$C_6$-alkyl, halo-$C_1$-$C_6$-alkyl, $C_1$-$C_6$-alkoxy, deuterio-$C_1$-$C_6$-alkoxy, and halo-$C_1$-$C_6$-alkoxy;

$R^{11}$ is selected from hydrogen and oxo;
A is selected from 3-14-membered heterocycloalkyl and $C_3$-$C_{10}$-cycloalkyl; and
L is selected from a covalent bond, carbonyl, O, C(O)NH, NHC(O), and NHC(O)NH.

In a preferred embodiment, the present invention provides a compound of formula (I) as described herein, or a pharmaceutically acceptable salt thereof, wherein:
W is N;
X is C—$R^7$ or N;
$R^1$ is selected from $NR^8R^9C(O)$— and a group

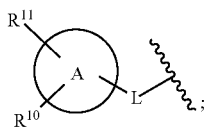

$R^2$ is $C_1$-$C_6$-alkyl;
$R^3$ is fluoro;
$R^4$ is chloro;
$R^5$ is halo-$C_1$-$C_6$-alkyl;
$R^7$ is fluoro;
$R^8$ is selected from hydroxy-$C_1$-$C_6$-alkyl and ($C_1$-$C_6$-alkyl)$_2$N—;
$R^9$ is hydrogen;
$R^{10}$ is selected from hydrogen, oxo, and $C_1$-$C_6$-alkoxy;
$R^{11}$ is selected from hydrogen and oxo;
A is a 3-14-membered heterocycloalkyl; and
L is carbonyl.

In a particularly preferred embodiment, the present invention provides a compound of formula (I) as described herein, or a pharmaceutically acceptable salt thereof, wherein:
W is N;
X is C—$R^7$ or N;
$R^1$ is selected from $NR^8R^9C(O)$— and a group

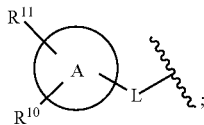

$R^2$ is methyl;
$R^3$ is fluoro;
$R^4$ is chloro;
$R^5$ is $CF_3$;
$R^7$ is fluoro;
$R^8$ is selected from 2-hydroxyethyl, 2-hydroxypropyl, and $(CH_3)_2N$—;
$R^9$ is hydrogen;
$R^{10}$ is selected from hydrogen, oxo, and ethoxy;
$R^{11}$ is selected from hydrogen and oxo;
A is selected from azetidine and thiomorpholine; and
L is carbonyl.

In a preferred embodiment, the present invention provides a compound of formula (I) as described herein, or a pharmaceutically acceptable salt thereof, wherein:
W is N;
X is C—$R^7$;
$R^1$ is $NR^8R^9C(O)$—;
$R^2$ is $C_1$-$C_6$-alkyl;
$R^3$ is fluoro;
$R^4$ is chloro;
$R^5$ is halo-$C_1$-$C_6$-alkyl;
$R^7$ is fluoro;
$R^8$ is hydroxy-$C_1$-$C_6$-alkyl; and
$R^9$ is hydrogen.

In a particularly preferred embodiment, the present invention provides a compound of formula (I) as described herein, or a pharmaceutically acceptable salt thereof, wherein:
W is N;
X is C—$R^7$;
$R^1$ is $NR^8R^9C(O)$—;
$R^2$ is methyl;
$R^3$ is fluoro;
$R^4$ is chloro;
$R^5$ is $CF_3$;
$R^7$ is fluoro;
$R^8$ is 2-hydroxyethyl; and
$R^9$ is hydrogen.

In one embodiment, the present invention provides a compound of formula (I) as described herein, or a pharmaceutically acceptable salt thereof, wherein said compound of formula (I) is selected from:
(7,8-dichloro-6-(2-fluorophenyl)-4H-benzo[f]imidazo[1,2-a][1,4]diazepin-2-yl)(3-methoxyazetidin-1-yl)methanone;
(7,8-dichloro-6-(2,6-difluorophenyl)-4H-benzo[f]imidazo[1,2-a][1,4]diazepin-2-yl)(3-methoxyazetidin-1-yl)methanone;
8-bromo-7-chloro-2-(difluoromethyl)-6-(2,6-difluorophenyl)-4H-benzo[f]imidazo[1,2-a][1,4]diazepine;
(8-bromo-7-chloro-6-(2,6-difluorophenyl)-4H-benzo[f]imidazo[1,2-a][1,4]diazepin-2-yl)methanol;
7,8-dichloro-6-(2,6-difluorophenyl)-2-(methoxymethyl)-4H-benzo[f]imidazo[1,2-a][1,4]diazepine;
7,8-dichloro-6-(2,6-difluorophenyl)-N-methyl-4H-[1,2,4]triazolo[1,5-a][1,4]benzodiazepine-2-carboxamide;
7,8-dichloro-6-(2,6-difluorophenyl)-N-(trideuteriomethyl)-4H-[1,2,4]triazolo[1,5-a][1,4]benzodiazepine-2-carboxamide;
azetidin-1-yl-[7,8-dichloro-6-(2,6-difluorophenyl)-4H-[1,2,4]triazolo[1,5-a][1,4]benzodiazepin-2-yl]methanone;
7,8-dichloro-6-(2,6-difluorophenyl)-N,N-dimethyl-4H-[1,2,4]triazolo[1,5-a][1,4]benzodiazepine-2-carboxamide;
7,8-dichloro-6-(2,6-difluorophenyl)-N-(oxetan-3-yl)-4H-[1,2,4]triazolo[1,5-a][1,4]benzodiazepine-2-carboxamide;
[7,8-dichloro-6-(2,6-difluorophenyl)-4H-[1,2,4]triazolo[1,5-a][1,4]benzodiazepin-2-yl]-(3-methoxyazetidin-1-yl)methanone;
7,8-dichloro-6-(3-fluoro-2-pyridyl)-N-methyl-4H-imidazo[1,2-a][1,4]benzodiazepine-2-carboxamide;
[(4S)-7,8-dichloro-6-(2,6-difluorophenyl)-4-methyl-4H-[1,2,4]triazolo[1,5-a][1,4]benzodiazepin-2-yl]methanol;
azetidin-1-yl-[(4S)-7,8-dichloro-6-(2,6-difluorophenyl)-4-methyl-4H-[1,2,4]triazolo[1,5-a][1,4]benzodiazepin-2-yl]methanone;
(4S)-7,8-dichloro-6-(2,6-difluorophenyl)-4-methyl-4H-[1,2,4]triazolo[1,5-a][1,4]benzodiazepine;
[(4S)-7,8-dichloro-6-(2,6-difluorophenyl)-4-methyl-4H-[1,2,4]triazolo[1,5-a][1,4]benzodiazepin-2-yl]-(3-methoxyazetidin-1-yl)methanone;
[(4S)-7,8-dichloro-6-(2,6-difluorophenyl)-4-methyl-4H-[1,2,4]triazolo[1,5-a][1,4]benzodiazepin-2-yl]-[3-(trideuteriomethoxy)azetidin-1-yl]methanone;
(4S)-7,8-dichloro-2-(difluoromethyl)-6-(2,6-difluorophenyl)-4-methyl-4H-[1,2,4]triazolo[1,5-a][1,4]benzodiazepine;

(4S)-7,8-dichloro-6-(2,6-difluorophenyl)-4-methyl-N,N-bis(trideuteriomethyl)-4H-[1,2,4]triazolo[1,5-a][1,4]benzodiazepine-2-carboxamide;

(4S)-7,8-dichloro-6-(2,6-difluorophenyl)-4-methyl-N-(trideuteriomethyl)-4H-[1,2,4]triazolo[1,5-a][1,4]benzodiazepine-2-carboxamide;

(4S)-7,8-dichloro-6-(2,6-difluorophenyl)-2,4-dimethyl-4H-[1,2,4]triazolo[1,5-a][1,4]benzodiazepine;

(4S)-7-chloro-6-(2,6-difluorophenyl)-4-methyl-8-(trifluoromethyl)-4#H!-[1,2,4]triazolo[1,5-a][1,4]benzodiazepine;

[(4S)-7-chloro-6-(2,6-difluorophenyl)-4-methyl-8-(trifluoromethyl)-4H-[1,2,4]triazolo[1,5-a][1,4]benzodiazepin-2-yl]-(3-methoxyazetidin-1-yl)methanone;

[7,8-dichloro-6-(2,6-difluorophenyl)-4H-[1,2,4]triazolo[1,5-a][1,4]benzodiazepin-2-yl]-(3-hydroxyazetidin-1-yl)methanone;

[(4S)-7,8-dichloro-6-(2,6-difluorophenyl)-4-methyl-4H-[1,2,4]triazolo[1,5-a][1,4]benzodiazepin-2-yl]-(3-hydroxyazetidin-1-yl)methanone;

azetidin-1-yl-[(4S)-7-chloro-6-(2,6-difluorophenyl)-4-methyl-8-(trifluoromethyl)-4H-[1,2,4]triazolo[1,5-a][1,4]benzodiazepin-2-yl]methanone;

(4S)-7,8-dichloro-6-(2,6-difluorophenyl)-2-(methoxymethyl)-4-methyl-4H-[1,2,4]triazolo[1,5-a][1,4]benzodiazepine;

(4S)-7,8-dichloro-6-(2,6-difluorophenyl)-N-(2-methoxyethyl)-4-methyl-4H-[1,2,4]triazolo[1,5-a][1,4]benzodiazepine-2-carboxamide;

(4S)-7-chloro-6-(2,6-difluorophenyl)-2,4-dimethyl-8-(trifluoromethyl)-4H-[1,2,4]triazolo[1,5-a][1,4]benzodiazepine;

(4S)-7,8-dichloro-6-(2,6-difluorophenyl)-N-(2-fluoroethyl)-4-methyl-4H-[1,2,4]triazolo[1,5-a][1,4]benzodiazepine-2-carboxamide;

[(4S)-7,8-dichloro-6-(2,6-difluorophenyl)-4-methyl-4H-[1,2,4]triazolo[1,5-a][1,4]benzodiazepin-2-yl]-[3-(difluoromethoxy)azetidin-1-yl]methanone;

7,8-dichloro-6-(2,6-difluorophenyl)-2-methyl-4H-[1,2,4]triazolo[1,5-a][1,4]benzodiazepine;

7,8-dichloro-2-(difluoromethyl)-6-(2,6-difluorophenyl)-4H-[1,2,4]triazolo[1,5-a][1,4]benzodiazepine;

(4S)-7-chloro-6-(2,6-difluorophenyl)-4-methyl-N-(trideuteriomethyl)-8-(trifluoromethyl)-4H-[1,2,4]triazolo[1,5-a][1,4]benzodiazepine-2-carboxamide;

(4S)-7,8-dichloro-6-(2,6-difluorophenyl)-4-methyl-4H-[1,2,4]triazolo[1,5-a][1,4]benzodiazepine-2-carboxamide;

[(4S)-7,8-dichloro-6-(2,6-difluorophenyl)-4-methyl-4H-[1,2,4]triazolo[1,5-a][1,4]benzodiazepin-2-yl]-(1,1-dioxo-1,4-thiazinan-4-yl)methanone;

[7-chloro-6-(2,6-difluorophenyl)-8-(trifluoromethyl)-4H-[1,2,4]triazolo[1,5-a][1,4]benzodiazepin-2-yl]-(3-methoxyazetidin-1-yl)methanone;

[(4S)-7,8-dichloro-6-(3-fluoro-2-pyridyl)-4-methyl-4H-[1,2,4]triazolo[1,5-a][1,4]benzodiazepin-2-yl]-(3-methoxyazetidin-1-yl)methanone;

[(4S)-7,8-dichloro-6-(3-fluoro-2-pyridyl)-4-methyl-4H-[1,2,4]triazolo[1,5-a][1,4]benzodiazepin-2-yl]-[3-(trideuteriomethoxy)azetidin-1-yl]methanone;

[(4S)-7,8-dichloro-6-(2,6-difluorophenyl)-4-methyl-4H-[1,2,4]triazolo[1,5-a][1,4]benzodiazepin-2-yl]-(3-fluoroazetidin-1-yl)methanone;

1-[(4S)-7,8-dichloro-6-(2,6-difluorophenyl)-4-methyl-4H-[1,2,4]triazolo[1,5-a][1,4]benzodiazepine-2-carbonyl]azetidine-3-carbonitrile;

azetidin-1-yl-[(4S)-7,8-dichloro-6-(3-fluoro-2-pyridyl)-4-methyl-4H-[1,2,4]triazolo[1,5-a][1,4]benzodiazepin-2-yl]methanone;

[(4S)-7,8-dichloro-6-(2,6-difluorophenyl)-4-methyl-4H-[1,2,4]triazolo[1,5-a][1,4]benzodiazepin-2-yl]-[(3S)-3-hydroxypyrrolidin-1-yl]methanone;

[(4S)-7,8-dichloro-6-(3-fluoro-2-pyridyl)-4-methyl-4H-[1,2,4]triazolo[1,5-a][1,4]benzodiazepin-2-yl]-(3-hydroxyazetidin-1-yl)methanone;

[(4S)-7,8-dichloro-6-(2,6-difluorophenyl)-4-methyl-4H-[1,2,4]triazolo[1,5-a][1,4]benzodiazepin-2-yl]-[(3S)-3-methoxypyrrolidin-1-yl]methanone;

[(4S)-7,8-dichloro-6-(2,6-difluorophenyl)-4-methyl-4H-[1,2,4]triazolo[1,5-a][1,4]benzodiazepin-2-yl]-[(3R)-3-methoxypyrrolidin-1-yl]methanone;

[(4S)-7,8-dichloro-6-(2,6-difluorophenyl)-4-methyl-4H-[1,2,4]triazolo[1,5-a][1,4]benzodiazepin-2-yl]-[(3R)-3-hydroxypyrrolidin-1-yl]methanone;

azetidin-1-yl-[(4S)-8-bromo-7-chloro-6-(3-fluoro-2-pyridyl)-4-methyl-4H-[1,2,4]triazolo[1,5-a][1,4]benzodiazepin-2-yl]methanone;

(4S)-7,8-dichloro-2-cyclopropyl-6-(2,6-difluorophenyl)-4-methyl-4H-[1,2,4]triazolo[1,5-a][1,4]benzodiazepine;

1-[(4S)-7,8-dichloro-6-(2,6-difluorophenyl)-4-methyl-4H-[1,2,4]triazolo[1,5-a][1,4]benzodiazepin-2-yl]pyrrolidin-2-one;

[3-(difluoromethoxy)azetidin-1-yl]-[(4S)-7-chloro-6-(2,6-difluorophenyl)-4-methyl-8-(trifluoromethyl)-4H-[1,2,4]triazolo[1,5-a][1,4]benzodiazepin-2-yl]methanone;

4-[(4S)-7,8-dichloro-6-(2,6-difluorophenyl)-4-methyl-4H-[1,2,4]triazolo[1,5-a][1,4]benzodiazepin-2-yl]-1,4-thiazinane 1,1-dioxide;

(4S)-7,8-dichloro-6-(2,6-difluorophenyl)-4-methyl-4H-[1,2,4]triazolo[1,5-a][1,4]benzodiazepine-2-carbonitrile;

(4S)-7,8-dichloro-6-(2,6-difluorophenyl)-N-(2-hydroxyethyl)-4-methyl-4H-[1,2,4]triazolo[1,5-a][1,4]benzodiazepine-2-carboxamide;

(4S)-7,8-dichloro-6-(2,6-difluorophenyl)-4-methyl-N-(oxetan-3-yl)-4H-[1,2,4]triazolo[1,5-a][1,4]benzodiazepine-2-carboxamide;

(4S)-7,8-dichloro-N-(cyanomethyl)-6-(2,6-difluorophenyl)-4-methyl-4H-[1,2,4]triazolo[1,5-a][1,4]benzodiazepine-2-carboxamide;

3-fluoro-N-[(4S)-7,8-dichloro-6-(2,6-difluorophenyl)-4-methyl-4H-[1,2,4]triazolo[1,5-a][1,4]benzodiazepin-2-yl]azetidine-1-carboxamide;

(3-hydroxyazetidin-1-yl)-[(4S)-7-chloro-6-(2,6-difluorophenyl)-4-methyl-8-(trifluoromethyl)-4H-[1,2,4]triazolo[1,5-a][1,4]benzodiazepin-2-yl]methanone;

(4S)-7,8-dichloro-N-(2,2-difluoroethyl)-6-(2,6-difluorophenyl)-4-methyl-4H-[1,2,4]triazolo[1,5-a][1,4]benzodiazepine-2-carboxamide;

3-methoxy-N-[(4S)-7,8-dichloro-6-(2,6-difluorophenyl)-4-methyl-4H-[1,2,4]triazolo[1,5-a][1,4]benzodiazepin-2-yl]azetidine-1-carboxamide;

(4S)-7,8-dichloro-N-(1-cyanocyclopropyl)-6-(2,6-difluorophenyl)-4-methyl-4H-[1,2,4]triazolo[1,5-a][1,4]benzodiazepine-2-carboxamide;

[7,8-dichloro-6-(3-fluoro-2-pyridyl)-4H-[1,2,4]triazolo[1,5-a][1,4]benzodiazepin-2-yl]-(3-methoxyazetidin-1-yl)methanone;

(4S)-7,8-dichloro-6-(2,6-difluorophenyl)-4-methyl-N-[(2S)-2-hydroxypropyl]-4H-[1,2,4]triazolo[1,5-a][1,4]benzodiazepine-2-carboxamide;

(4S)-7,8-dichloro-6-(2,6-difluorophenyl)-N-ethyl-4-methyl-4H-[1,2,4]triazolo[1,5-a][1,4]benzodiazepine-2-carboxamide;

(4S)-7,8-dichloro-6-(2,6-difluorophenyl)-4-methyl-N-[(2R)-2-hydroxypropyl]-4H-[1,2,4]triazolo[1,5-a][1,4]benzodiazepine-2-carboxamide;

1-[(4S)-7,8-dichloro-6-(2,6-difluorophenyl)-4-methyl-4H-[1,2,4]triazolo[1,5-a][1,4]benzodiazepin-2-yl]azetidin-3-ol;

N-[[(4S)-7,8-dichloro-6-(2,6-difluorophenyl)-4-methyl-4H-[1,2,4]triazolo[1,5-a][1,4]benzodiazepin-2-yl]methyl]acetamide;

(3-hydroxyazetidin-1-yl)-[(4S)-7,8-dichloro-6-(2,6-difluorophenyl)-4-methyl-4H-imidazo[1,2-a][1,4]benzodiazepin-2-yl]methanone;

(4S)-7,8-dichloro-6-(2,6-difluorophenyl)-4-methyl-4H-[1,2,4]triazolo[1,5-a][1,4]benzodiazepine-2-sulfonamide;

azetidin-1-yl-[(4S)-7,8-dichloro-6-(2,6-difluorophenyl)-4-methyl-4H-imidazo[1,2-a][1,4]benzodiazepin-2-yl]methanone;

1-[(4S)-7,8-dichloro-6-(2,6-difluorophenyl)-4-methyl-4H-imidazo[1,2-a][1,4]benzodiazepine-2-carbonyl]azetidine-3-carbonitrile;

[3-(fluoromethyl)azetidin-1-yl]-[(4S)-7,8-dichloro-6-(2,6-difluorophenyl)-4-methyl-4H-[1,2,4]triazolo[1,5-a][1,4]benzodiazepin-2-yl]methanone;

(4S)-7,8-dichloro-6-(2,6-difluorophenyl)-N,4-dimethyl-4H-[1,2,4]triazolo[1,5-a][1,4]benzodiazepine-2-sulfonamide;

(4S)-7,8-dichloro-6-(2,6-difluorophenyl)-4-methyl-4H-imidazo[1,2-a][1,4]benzodiazepine-2-carbonitrile;

[3-(difluoromethyl)azetidin-1-yl]-[(4S)-7,8-dichloro-6-(2,6-difluorophenyl)-4-methyl-4H-[1,2,4]triazolo[1,5-a][1,4]benzodiazepin-2-yl]methanone;

[(4S)-7,8-dichloro-6-(2,6-difluorophenyl)-4-methyl-4H-[1,2,4]triazolo[1,5-a][1,4]benzodiazepin-2-yl]-[rac-(3R)-3-fluoropyrrolidin-1-yl]methanone;

1-[(4S)-7,8-dichloro-6-(2,6-difluorophenyl)-4-methyl-4H-[1,2,4]triazolo[1,5-a][1,4]benzodiazepin-2-yl]azetidine-3-carbonitrile;

[(4S)-7,8-dichloro-6-(3-fluoro-2-pyridyl)-4-methyl-4H-[1,2,4]triazolo[1,5-a][1,4]benzodiazepin-2-yl]-[(3R)-3-fluoropyrrolidin-1-yl]methanone;

[(4S)-7,8-dichloro-6-(3-fluoro-2-pyridyl)-4-methyl-4H-[1,2,4]triazolo[1,5-a][1,4]benzodiazepin-2-yl]-[(3S)-3-fluoropyrrolidin-1-yl]methanone;

[(4S)-7,8-dichloro-6-(2,6-difluorophenyl)-4-methyl-4H-[1,2,4]triazolo[1,5-a][1,4]benzodiazepin-2-yl]-[(3S)-3-fluoropyrrolidin-1-yl]methanone;

(4S)-7,8-dichloro-6-(2,6-difluorophenyl)-4-methyl-2-(oxetan-3-yl)-4H-[1,2,4]triazolo[1,5-a][1,4]benzodiazepine;

(4S)-7,8-dichloro-6-(2,6-difluorophenyl)-4-methyl-2-methylsulfonyl-4H-[1,2,4]triazolo[1,5-a][1,4]benzodiazepine;

(4S)-7-chloro-6-(3-fluoro-2-pyridyl)-2,4-dimethyl-8-(trifluoromethyl)-4H-[1,2,4]triazolo[1,5-a][1,4]benzodiazepine;

(4S)-7,8-dichloro-6-(3-fluoro-2-pyridyl)-2,4-dimethyl-4H-[1,2,4]triazolo[1,5-a][1,4]benzodiazepine;

azetidin-1-yl-[(4S)-7-chloro-6-(3-fluoro-2-pyridyl)-4-methyl-8-(trifluoromethyl)-4H-[1,2,4]triazolo[1,5-a][1,4]benzodiazepin-2-yl]methanone;

(3-ethoxyazetidin-1-yl)-[(4S)-7,8-dichloro-6-(3-fluoro-2-pyridyl)-4-methyl-4H-[1,2,4]triazolo[1,5-a][1,4]benzodiazepin-2-yl]methanone;

[(4S)-7,8-dichloro-6-(3-fluoro-2-pyridyl)-4-methyl-4H-[1,2,4]triazolo[1,5-a][1,4]benzodiazepin-2-yl]-(3-methylazetidin-1-yl)methanone;

(4S)-7,8-dichloro-N-cyclopropyl-6-(3-fluoro-2-pyridyl)-4-methyl-4H-[1,2,4]triazolo[1,5-a][1,4]benzodiazepine-2-carboxamide;

[(4S)-7,8-dichloro-6-(3-fluoro-2-pyridyl)-4-methyl-4H-[1,2,4]triazolo[1,5-a][1,4]benzodiazepin-2-yl]-[(3S)-3-methoxypyrrolidin-1-yl]methanone;

[(4S)-7,8-dichloro-6-(3-fluoro-2-pyridyl)-4-methyl-4H-[1,2,4]triazolo[1,5-a][1,4]benzodiazepin-2-yl]-[3-(difluoromethoxy)azetidin-1-yl]methanone;

(4S)-7,8-dichloro-6-(2,6-difluorophenyl)-2-methoxy-4-methyl-4H-[1,2,4]triazolo[1,5-a][1,4]benzodiazepine;

(4S)-7,8-dichloro-6-(2,6-difluorophenyl)-4-methyl-2-(oxetan-3-yloxy)-4H-[1,2,4]triazolo[1,5-a][1,4]benzodiazepine;

[(4S)-7,8-dichloro-6-(2,6-difluorophenyl)-4-methyl-4H-[1,2,4]triazolo[1,5-a][1,4]benzodiazepin-2-yl]-(2-oxa-6-azaspiro[3.3]heptan-6-yl)methanone;

[(4S)-7,8-dichloro-6-(2,6-difluorophenyl)-4-methyl-4H-[1,2,4]triazolo[1,5-a][1,4]benzodiazepin-2-yl]-(1-oxa-6-azaspiro[3.3]heptan-6-yl)methanone;

7-oxa-2-azaspiro[3.5]nonan-2-yl-[(4S)-7,8-dichloro-6-(3-fluoro-2-pyridyl)-4-methyl-4H-[1,2,4]triazolo[1,5-a][1,4]benzodiazepin-2-yl]methanone;

[(4S)-7,8-dichloro-6-(2,6-difluorophenyl)-4-methyl-4H-[1,2,4]triazolo[1,5-a][1,4]benzodiazepin-2-yl]-(5-oxa-2-azaspiro[3.5]nonan-2-yl)methanone;

[(4S)-7,8-dichloro-6-(3-fluoro-2-pyridyl)-4-methyl-4H-[1,2,4]triazolo[1,5-a][1,4]benzodiazepin-2-yl]-(5-oxa-2-azaspiro[3.4]octan-2-yl)methanone;

[(4S)-7,8-dichloro-6-(3-fluoro-2-pyridyl)-4-methyl-4H-[1,2,4]triazolo[1,5-a][1,4]benzodiazepin-2-yl]-(1-oxa-6-azaspiro[3.3]heptan-6-yl)methanone;

[(4S)-7,8-dichloro-6-(2,6-difluorophenyl)-4-methyl-4H-[1,2,4]triazolo[1,5-a][1,4]benzodiazepin-2-yl]-(7-oxa-2-azaspiro[3.5]nonan-2-yl)methanone;

[(4S)-7,8-dichloro-6-(3-fluoro-2-pyridyl)-4-methyl-4H-[1,2,4]triazolo[1,5-a][1,4]benzodiazepin-2-yl]-(6-oxa-2-azaspiro[3.4]octan-2-yl)methanone;

[(4S)-7,8-dichloro-6-(3-fluoro-2-pyridyl)-4-methyl-4H-[1,2,4]triazolo[1,5-a][1,4]benzodiazepin-2-yl]-(5-oxa-2-azaspiro[3.5]nonan-2-yl)methanone;

[(4S)-7,8-dichloro-6-(3-fluoro-2-pyridyl)-4-methyl-4H-[1,2,4]triazolo[1,5-a][1,4]benzodiazepin-2-yl]-(2-oxa-6-azaspiro[3.3]heptan-6-yl)methanone;

[(4S)-7-chloro-6-(3-fluoro-2-pyridyl)-4-methyl-8-(trifluoromethyl)-4H-[1,2,4]triazolo[1,5-a][1,4]benzodiazepin-2-yl]-(3-methoxyazetidin-1-yl)methanone;

[(4S)-7-chloro-6-(3-fluoro-2-pyridyl)-4-methyl-8-(trifluoromethyl)-4H-[1,2,4]triazolo[1,5-a][1,4]benzodiazepin-2-yl]-[3-(trideuteriomethoxy)azetidin-1-yl]methanone;

(4S)-7-chloro-6-(2,6-difluorophenyl)-N-[(2R)-2-hydroxypropyl]-4-methyl-8-(trifluoromethyl)-4H-[1,2,4]triazolo[1,5-a][1,4]benzodiazepine-2-carboxamide;

(4S)-7-chloro-6-(2,6-difluorophenyl)-N-(2-fluoroethyl)-4-methyl-8-(trifluoromethyl)-4H-[1,2,4]triazolo[1,5-a][1,4]benzodiazepine-2-carboxamide;

(4S)-7-chloro-6-(2,6-difluorophenyl)-N-(2-hydroxyethyl)-4-methyl-8-(trifluoromethyl)-4H-[1,2,4]triazolo[1,5-a][1,4]benzodiazepine-2-carboxamide;

[(4S)-7,8-dichloro-6-(2,6-difluorophenyl)-4-methyl-4H-[1,2,4]triazolo[1,5-a][1,4]benzodiazepin-2-yl]-(5-oxa-2-azaspiro[3.4]octan-2-yl)methanone;

(4S)-7-chloro-6-(2,6-difluorophenyl)-N-[(2S)-2-hydroxypropyl]-4-methyl-8-(trifluoromethyl)-4H-[1,2,4]triazolo[1,5-a][1,4]benzodiazepine-2-carboxamide;

(4S)-7-chloro-N-(cyanomethyl)-6-(2,6-difluorophenyl)-4-methyl-8-(trifluoromethyl)-4H-[1,2,4]triazolo[1,5-a][1,4]benzodiazepine-2-carboxamide;

(4S)-7,8-dichloro-6-(2,6-difluorophenyl)-1,4-dimethyl-4H-imidazo[1,2-a][1,4]benzodiazepine;

[(4S)-7-chloro-6-(3-fluoro-2-pyridyl)-4-methyl-8-(trifluoromethyl)-4H-[1,2,4]triazolo[1,5-a][1,4]benzodiazepin-2-yl]-(2-oxa-6-azaspiro[3.3]heptan-6-yl)methanone;

[(4S)-7-chloro-6-(3-fluoro-2-pyridyl)-4-methyl-8-(trifluoromethyl)-4H-[1,2,4]triazolo[1,5-a][1,4]benzodiazepin-2-yl]-(5-oxa-2-azaspiro[3.4]octan-2-yl)methanone;

[(4S)-7-chloro-6-(2,6-difluorophenyl)-4-methyl-8-(trifluoromethyl)-4H-[1,2,4]triazolo[1,5-a][1,4]benzodiazepin-2-yl]-(1,1-dioxo-1,4-thiazinan-4-yl)methanone;

(4S)-7-chloro-6-(2,6-difluorophenyl)-1,4-dimethyl-8-(trifluoromethyl)-4H-imidazo[1,2-a][1,4]benzodiazepine;

(4S)-8-bromo-7-chloro-6-(2,6-difluorophenyl)-1,4-dimethyl-4H-imidazo[1,2-a][1,4]benzodiazepine;

(4S)-7-chloro-6-(2,6-difluorophenyl)-N'',N'',4-trimethyl-8-(trifluoromethyl)-4H-[1,2,4]triazolo[1,5-a][1,4]benzodiazepine-2-carbohydrazide;

(4S)-7-chloro-6-(2,6-difluorophenyl)-4-methyl-N-pyrrolidin-1-yl-8-(trifluoromethyl)-4H-[1,2,4]triazolo[1,5-a][1,4]benzodiazepine-2-carboxamide;

1-oxa-6-azaspiro[3.3]heptan-6-yl-[rac-(4S)-7-chloro-6-(3-fluoro-2-pyridyl)-4-methyl-8-(trifluoromethyl)-4H-[1,2,4]triazolo[1,5-a][1,4]benzodiazepin-2-yl]methanone;

6-oxa-2-azaspiro[3.4]octan-2-yl-[rac-(4S)-7-chloro-6-(3-fluoro-2-pyridyl)-4-methyl-8-(trifluoromethyl)-4H-[1,2,4]triazolo[1,5-a][1,4]benzodiazepin-2-yl]methanone;

3-[(4S)-7-chloro-6-(2,6-difluorophenyl)-4-methyl-8-(trifluoromethyl)-4H-[1,2,4]triazolo[1,5-a][1,4]benzodiazepin-2-yl]oxazolidin-2-one;

[(4S)-7-chloro-6-(2,6-difluorophenyl)-4-methyl-8-(trifluoromethyl)-4H-[1,2,4]triazolo[1,5-a][1,4]benzodiazepin-2-yl]-[3-(difluoromethyl)azetidin-1-yl]methanone;

[(4S)-7-chloro-6-(3-fluoro-2-pyridyl)-4-methyl-8-(trifluoromethyl)-4H-[1,2,4]triazolo[1,5-a][1,4]benzodiazepin-2-yl]-[(3S)-3-fluoropyrrolidin-1-yl]methanone;

[(4S)-7-chloro-6-(3-fluoro-2-pyridyl)-4-methyl-8-(trifluoromethyl)-4H-[1,2,4]triazolo[1,5-a][1,4]benzodiazepin-2-yl]-(1,1-dioxo-1,4-thiazinan-4-yl)methanone;

1-[(4S)-7-chloro-6-(2,6-difluorophenyl)-4-methyl-8-(trifluoromethyl)-4H-[1,2,4]triazolo[1,5-a][1,4]benzodiazepin-2-yl]-3-(oxetan-3-yl)urea;

1-[(4S)-7-chloro-6-(2,6-difluorophenyl)-4-methyl-8-(trifluoromethyl)-4H-[1,2,4]triazolo[1,5-a][1,4]benzodiazepin-2-yl]-3-cyclopropyl-urea;

N-[(4S)-7-chloro-6-(2,6-difluorophenyl)-4-methyl-8-(trifluoromethyl)-4H-[1,2,4]triazolo[1,5-a][1,4]benzodiazepin-2-yl]-3-methoxy-azetidine-1-carboxamide;

N-[(4S)-7-chloro-6-(2,6-difluorophenyl)-4-methyl-8-(trifluoromethyl)-4H-[1,2,4]triazolo[1,5-a][1,4]benzodiazepin-2-yl]-3-fluoro-azetidine-1-carboxamide;

1-[(4S)-7-chloro-6-(2,6-difluorophenyl)-4-methyl-8-(trifluoromethyl)-4H-[1,2,4]triazolo[1,5-a][1,4]benzodiazepin-2-yl]-3-methyl-urea;

N-[(4S)-7-chloro-6-(2,6-difluorophenyl)-4-methyl-8-(trifluoromethyl)-4H-[1,2,4]triazolo[1,5-a][1,4]benzodiazepin-2-yl]-3-oxa-6-azabicyclo[3.1.1]heptane-6-carboxamide;

N-[(4S)-7-chloro-6-(2,6-difluorophenyl)-4-methyl-8-(trifluoromethyl)-4H-[1,2,4]triazolo[1,5-a][1,4]benzodiazepin-2-yl]-1,1-dioxo-1,4-thiazinane-4-carboxamide;

[(4S)-7-chloro-6-(2,6-difluorophenyl)-4-methyl-8-(trifluoromethyl)-4H-imidazo[1,2-a][1,4]benzodiazepin-1-yl]methanol;

(10S)-6-chloro-8-(2,6-difluorophenyl)-10-methyl-5-(trifluoromethyl)-1,9,12-triazatetracyclo[9.6.0.02,7.013,17]heptadeca-2,4,6,8,11,13(17)-hexaene;

N-[(4S)-7-chloro-6-(2,6-difluorophenyl)-4-methyl-8-(trifluoromethyl)-4H-[1,2,4]triazolo[1,5-a][1,4]benzodiazepin-2-yl]-3,3-dioxo-3?6-thia-6-azabicyclo[3.1.1]heptane-6-carboxamide;

[(4S)-7-chloro-6-(3-fluoro-2-pyridyl)-4-methyl-8-(trifluoromethyl)-4H-[1,2,4]triazolo[1,5-a][1,4]benzodiazepin-2-yl]-(3-methylazetidin-1-yl)methanone;

(4S)-7-chloro-6-(3-fluoro-2-pyridyl)-1,4-dimethyl-8-(trifluoromethyl)-4H-imidazo[1,2-a][1,4]benzodiazepine;

[(4S)-7-chloro-6-(3-fluoro-2-pyridyl)-4-methyl-8-(trifluoromethyl)-4H-[1,2,4]triazolo[1,5-a][1,4]benzodiazepin-2-yl]-(3-ethoxyazetidin-1-yl)methanone;

(4S)-7-chloro-6-(3-fluoro-2-pyridyl)-N-(2-hydroxyethyl)-4-methyl-8-(trifluoromethyl)-4H-[1,2,4]triazolo[1,5-a][1,4]benzodiazepine-2-carboxamide;

(4S)-7-chloro-6-(3-fluoro-2-pyridyl)-2,4-dimethyl-8-(trifluoromethyl)-4H-imidazo[1,2-a][1,4]benzodiazepine;

[(4S)-7-chloro-6-(3-fluoro-2-pyridyl)-4-methyl-8-(trifluoromethyl)-4H-[1,2,4]triazolo[1,5-a][1,4]benzodiazepin-2-yl]-[3-(difluoromethoxy)azetidin-1-yl]methanone;

(4S)-7-chloro-6-(3-fluoro-2-pyridyl)-N-(2-hydroxyethyl)-4-methyl-8-(trifluoromethyl)-4H-imidazo[1,2-a][1,4]benzodiazepine-2-carboxamide;

[(4S)-7-chloro-6-(3-fluoro-2-pyridyl)-4-methyl-8-(trifluoromethyl)-4H-[1,2,4]triazolo[1,5-a][1,4]benzodiazepin-2-yl]-[3-(difluoromethyl)azetidin-1-yl]methanone;

1-[(4S)-7-chloro-6-(3-fluoro-2-pyridyl)-4-methyl-8-(trifluoromethyl)-4H-[1,2,4]triazolo[1,5-a][1,4]benzodiazepin-2-yl]-3-cyclopropyl-urea;

2-[(4S)-7-chloro-6-(3-fluoro-2-pyridyl)-4-methyl-8-(trifluoromethyl)-4H-[1,2,4]triazolo[1,5-a][1,4]benzodiazepin-2-yl]-5-methyl-1,3,4-oxadiazole;

[(4S)-7-chloro-6-(3-fluoro-2-pyridyl)-4-methyl-8-(trifluoromethyl)-4H-imidazo[1,2-a][1,4]benzodiazepin-2-yl]-(3-methoxyazetidin-1-yl)methanone;

1-[(4S)-7-chloro-6-(3-fluoro-2-pyridyl)-4-methyl-8-(trifluoromethyl)-4H-[1,2,4]triazolo[1,5-a][1,4]benzodiazepin-2-yl]-3-(oxetan-3-yl)urea;

3-[(4S)-7-chloro-6-(3-fluoro-2-pyridyl)-4-methyl-8-(trifluoromethyl)-4H-[1,2,4]triazolo[1,5-a][1,4]benzodiazepin-2-yl]oxazolidin-2-one;

(4S)-7-chloro-6-(2,6-difluorophenyl)-2,4-dimethyl-8-(trifluoromethyl)-4H-imidazo[1,2-a][1,4]benzodiazepine;

[(4S)-7-chloro-6-(2,6-difluorophenyl)-4-methyl-8-(trifluoromethyl)-4H-imidazo[1,2-a][1,4]benzodiazepin-2-yl]methanol;

(4S)-7-chloro-6-(2,6-difluorophenyl)-4-methyl-8-(trifluoromethyl)-4H-imidazo[1,2-a][1,4]benzodiazepine;

[(4S)-7-chloro-6-(3-fluoro-2-pyridyl)-4-methyl-8-(trifluoromethyl)-4H-imidazo[1,2-a][1,4]benzodiazepin-1-yl]methanol;

(4S)-7-chloro-N-(2-fluoroethyl)-6-(3-fluoro-2-pyridyl)-4-methyl-8-(trifluoromethyl)-4H-[1,2,4]triazolo[1,5-a][1,4]benzodiazepine-2-carboxamide;

[(4S)-7-chloro-6-(3-fluoro-2-pyridyl)-4-methyl-8-(trifluoromethyl)-4H-imidazo[1,2-a][1,4]benzodiazepin-2-yl]methanol;

(4S)-7-chloro-6-(3-fluoro-2-pyridyl)-N-(2-hydroxyethyl)-1,4-dimethyl-8-(trifluoromethyl)-4H-imidazo[1,2-a][1,4]benzodiazepine-2-carboxamide;

(4S)-7-chloro-6-(3-fluoro-2-pyridyl)-N-[(2S)-2-hydroxypropyl]-4-methyl-8-(trifluoromethyl)-4H-imidazo[1,2-a][1,4]benzodiazepine-2-carboxamide;

[(4S)-7-chloro-6-(3-fluoro-2-pyridyl)-4-methyl-8-(trifluoromethyl)-4H-imidazo[1,2-a][1,4]benzodiazepin-2-yl]-[3-(difluoromethyl)azetidin-1-yl]methanone;

(4S)-7-chloro-6-(3-fluoro-2-pyridyl)-N-[(2R)-2-hydroxy-propyl]-4-methyl-8-(trifluoromethyl)-4H-imidazo[1,2-a][1,4]benzodiazepine-2-carboxamide;
[(4S)-7-chloro-6-(3-fluoro-2-pyridyl)-4-methyl-8-(trifluoromethyl)-4H-imidazo[1,2-a][1,4]benzodiazepin-2-yl]-(3-ethoxyazetidin-1-yl)methanone;
(4S)-7-chloro-6-(3-fluoro-2-pyridyl)-N-(2-hydroxy-2-methyl-propyl)-4-methyl-8-(trifluoromethyl)-4H-imidazo[1,2-a][1,4]benzodiazepine-2-carboxamide;
[(4S)-7-chloro-6-(3-fluoro-2-pyridyl)-4-methyl-8-(trifluoromethyl)-4H-imidazo[1,2-a][1,4]benzodiazepin-2-yl]-(3-hydroxy-3-methyl-azetidin-1-yl)methanone;
[(4S)-7-chloro-6-(3-fluoro-2-pyridyl)-4-methyl-8-(trifluoromethyl)-4H-imidazo[1,2-a][1,4]benzodiazepin-2-yl]-(3-fluoroazetidin-1-yl)methanone;
(4S)-7-chloro-6-(3-fluoro-2-pyridyl)-N-[(2R)-2-hydroxypropyl]-1,4-dimethyl-8-(trifluoromethyl)-4H-imidazo[1,2-a][1,4]benzodiazepine-2-carboxamide;
(3-methylazetidin-1-yl)-[(4S)-7-chloro-6-(3-fluoro-2-pyridyl)-4-methyl-8-(trifluoromethyl)-4H-imidazo[1,2-a][1,4]benzodiazepin-2-yl]methanone;
(4S)-7-chloro-6-(3-fluoro-2-pyridyl)-N-[(1-hydroxycyclopropyl)methyl]-4-methyl-8-(trifluoromethyl)-4H-imidazo[1,2-a][1,4]benzodiazepine-2-carboxamide;
(4S)-7-chloro-6-(3-fluoro-2-pyridyl)-N-(3-hydroxycyclobutyl)-4-methyl-8-(trifluoromethyl)-4H-imidazo[1,2-a][1,4]benzodiazepine-2-carboxamide; and
(4S)-7-chloro-6-(3-fluoro-2-pyridyl)-N-(3-hydroxycyclobutyl)-4-methyl-8-(trifluoromethyl)-4H-imidazo[1,2-a][1,4]benzodiazepine-2-carboxamide.

In a particularly preferred embodiment, the present invention provides a compound of formula (I) as described herein, or a pharmaceutically acceptable salt thereof, wherein said compound of formula (I) is selected from:
azetidin-1-yl-[(4S)-7-chloro-6-(3-fluoro-2-pyridyl)-4-methyl-8-(trifluoromethyl)-4H-[1,2,4]triazolo[1,5-a][1,4]benzodiazepin-2-yl]methanone;
(4S)-7-chloro-6-(2,6-difluorophenyl)-N-[(2R)-2-hydroxypropyl]-4-methyl-8-(trifluoromethyl)-4H-[1,2,4]triazolo[1,5-a][1,4]benzodiazepine-2-carboxamide;
(4S)-7-chloro-6-(2,6-difluorophenyl)-N-(2-hydroxyethyl)-4-methyl-8-(trifluoromethyl)-4H-[1,2,4]triazolo[1,5-a][1,4]benzodiazepine-2-carboxamide;
(4S)-7-chloro-6-(2,6-difluorophenyl)-N-[(2S)-2-hydroxypropyl]-4-methyl-8-(trifluoromethyl)-4H-[1,2,4]triazolo[1,5-a][1,4]benzodiazepine-2-carboxamide;
[(4S)-7-chloro-6-(2,6-difluorophenyl)-4-methyl-8-(trifluoromethyl)-4H-[1,2,4]triazolo[1,5-a][1,4]benzodiazepin-2-yl]-(1,1-dioxo-1,4-thiazinan-4-yl)methanone;
(4S)-7-chloro-6-(2,6-difluorophenyl)-N',N',4-trimethyl-8-(trifluoromethyl)-4H-[1,2,4]triazolo[1,5-a][1,4]benzodiazepine-2-carbohydrazide;
[(4S)-7-chloro-6-(3-fluoro-2-pyridyl)-4-methyl-8-(trifluoromethyl)-4H-[1,2,4]triazolo[1,5-a][1,4]benzodiazepin-2-yl]-(3-ethoxyazetidin-1-yl)methanone.

In a particularly preferred embodiment, the present invention provides a compound of formula (I) as described herein, or a pharmaceutically acceptable salt thereof, wherein said compound of formula (I) is azetidin-1-yl-[(4S)-7-chloro-6-(3-fluoro-2-pyridyl)-4-methyl-8-(trifluoromethyl)-4H-[1,2,4]triazolo[1,5-a][1,4]benzodiazepin-2-yl]methanone.

In a particularly preferred embodiment, the present invention provides a compound of formula (I) as described herein, or a pharmaceutically acceptable salt thereof, wherein said compound of formula (I) is (4S)-7-chloro-6-(2,6-difluorophenyl)-N-[(2R)-2-hydroxypropyl]-4-methyl-8-(trifluoromethyl)-4H-[1,2,4]triazolo[1,5-a][1,4]benzodiazepine-2-carboxamide.

In a particularly preferred embodiment, the present invention provides a compound of formula (I) as described herein, or a pharmaceutically acceptable salt thereof, wherein said compound of formula (I) is (4S)-7-chloro-6-(2,6-difluorophenyl)-N-(2-hydroxyethyl)-4-methyl-8-(trifluoromethyl)-4H-[1,2,4]triazolo[1,5-a][1,4]benzodiazepine-2-carboxamide.

In a particularly preferred embodiment, the present invention provides a compound of formula (I) as described herein, or a pharmaceutically acceptable salt thereof, wherein said compound of formula (I) is (4S)-7-chloro-6-(2,6-difluorophenyl)-N-[(2S)-2-hydroxypropyl]-4-methyl-8-(trifluoromethyl)-4H-[1,2,4]triazolo[1,5-a][1,4]benzodiazepine-2-carboxamide.

In a particularly preferred embodiment, the present invention provides a compound of formula (I) as described herein, or a pharmaceutically acceptable salt thereof, wherein said compound of formula (I) is [(4S)-7-chloro-6-(2,6-difluorophenyl)-4-methyl-8-(trifluoromethyl)-4H-[1,2,4]triazolo[1,5-a][1,4]benzodiazepin-2-yl]-(1,1-dioxo-1,4-thiazinan-4-yl)methanone.

In a particularly preferred embodiment, the present invention provides a compound of formula (I) as described herein, or a pharmaceutically acceptable salt thereof, wherein said compound of formula (I) is (4S)-7-chloro-6-(2,6-difluorophenyl)-N',N',4-trimethyl-8-(trifluoromethyl)-4H-[1,2,4]triazolo[1,5-a][1,4]benzodiazepine-2-carbohydrazide.

In a particularly preferred embodiment, the present invention provides a compound of formula (I) as described herein, or a pharmaceutically acceptable salt thereof, wherein said compound of formula (I) is [(4S)-7-chloro-6-(3-fluoro-2-pyridyl)-4-methyl-8-(trifluoromethyl)-4H-[1,2,4]triazolo[1,5-a][1,4]benzodiazepin-2-yl]-(3-ethoxyazetidin-1-yl) methanone.

In one embodiment, the present invention provides pharmaceutically acceptable salts of the compounds of formula (I) as described herein, especially pharmaceutically acceptable salts selected from hydrochlorides, fumarates, lactates (in particular derived from L-(+)-lactic acid), tartrates (in particular derived from L-(+)-tartaric acid) and trifluoroacetates. In yet a further particular embodiment, the present invention provides compounds according to formula (I) as described herein (i.e., as "free bases" or "free acids", respectively).

In some embodiments, the compounds of formula (I) are isotopically-labeled by having one or more atoms therein replaced by an atom having a different atomic mass or mass number. Such isotopically-labeled (i.e., radiolabeled) compounds of formula (I) are considered to be within the scope of this disclosure. Examples of isotopes that can be incorporated into the compounds of formula (I) include isotopes of hydrogen, carbon, nitrogen, oxygen, phosphorous, sulfur, fluorine, chlorine, and iodine, such as, but not limited to, $^{2}$H, $^{3}$H, $^{11}$C, $^{13}$C, $^{14}$C, $^{13}$N, $^{15}$N, $^{15}$O, $^{17}$O, $^{18}$O, $^{31}$P, $^{32}$P, $^{35}$, $^{18}$F, $^{36}$Cl, $^{123}$I, and $^{125}$I, respectively. Certain isotopically-labeled compounds of formula (I), for example, those incorporating a radioactive isotope, are useful in drug and/or substrate tissue distribution studies. The radioactive isotopes tritium, i.e. $^{3}$H, and carbon-14, i.e., $^{14}$C, are particularly useful for this purpose in view of their ease of incorporation and ready means of detection. For example, a compound of formula (I) can be enriched with 1, 2, 5, 10, 25, 50, 75, 90, 95, or 99 percent of a given isotope.

Substitution with heavier isotopes such as deuterium, i.e. $^{2}$H, may afford certain therapeutic advantages resulting from greater metabolic stability, for example, increased in vivo half-life or reduced dosage requirements.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of formula (I) can generally be prepared by conventional techniques known to those skilled in the art or by processes analogous to those described in the Examples as set out below using an appropriate isotopically-labeled reagent in place of the non-labeled reagent previously employed.

Processes of Manufacturing

Processes for the manufacture of the compound of formula (I) as described herein are also an object of the invention.

The preparation of compounds of formula (I) of the present invention may be carried out in sequential or convergent synthetic routes. Syntheses of the compounds of the invention are shown in the following schemes. The skills required for carrying out the reactions and purifications of the resulting products are known to those skilled in the art. The substituents and indices used in the following description of the processes have the significance given herein before and in the claims, unless indicated to the contrary. In more detail, the compounds of formula (I) can be manufactured by the methods given below, by the methods given in the examples or by analogous methods. Appropriate reaction conditions for the individual reaction steps are known to a person skilled in the art. Also, for reaction conditions described in literature affecting the described reactions see for example: *Comprehensive Organic Transformations: A Guide to Functional Group Preparations*, 3rd Edition, Richard C. Larock. John Wiley & Sons, New York, N.Y. 2018). It is convenient to carry out the reactions in the presence or absence of a solvent. There is no particular restriction on the nature of the solvent to be employed, provided that it has no adverse effect on the reaction or the reagents involved and that it can dissolve the reagents, at least to some extent. The described reactions can take place over a wide range of temperatures, and the precise reaction temperature is not critical to the invention. It is convenient to carry out the described reactions in a temperature range between −78° C. to reflux temperature. The time required for the reaction may also vary widely, depending on many factors, notably the reaction temperature and the nature of the reagents. However, a period of from 0.5 h to several days will usually suffice to yield the described intermediates and compounds. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The preparation of compounds of formula (I) of the present invention may be carried out in sequential or convergent synthetic routes. Syntheses of the invention are shown in the following general schemes. The skills required for carrying out the reactions and purifications of the resulting products are known to those skilled in the art. The substituents and indices used in the following description of the processes have the significance given herein before unless indicated to the contrary.

In more detail, the compounds of formula (I) can be manufactured by the methods given below, by the methods given in the examples or by analogous methods. Appropriate reaction conditions for the individual reaction steps are known to a person skilled in the art. The reaction sequence is not limited to the one displayed in schemes 1-9, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula (I) and their pharmaceutically acceptable salts can be prepared by the process described in the following Schemes without in particular being restricted to the routes and conditions illustrated.

Imidazoles of formulas (I) can be prepared by a process described below (Scheme 1).

Thiolactams (III) are prepared by reaction of lactams (II) (building blocks A, C, D, L, M, N, V, X) with Lawesson's reagent or $P_2S_5$. Their reaction with ammonia yields amidines of formula (IV) that are reacted with ethyl bromopyruvate and an organic base such as DIPEA to form compounds (V). Ring closure of (V) occurs upon heating in acetic acid to form imidazole-esters of formula (VI). If desired, these compounds can be directly reacted with amines $HNR^8R^9$, preferably alkyl amines or ammonia, to produce amides of formula (I). Furthermore, compounds (VI) can be saponified using a base such as sodium hydroxide or lithium hydroxide in a mixture of water and methanol or tetrahydrofuran to yield carboxylic acids (VII) which, in turn, can be reacted with the amines $HNR^8R^9$ using an amide coupling reagent such as HATU, EDC/HOBt, BOP-Cl or PyBOP in presence of a suitable base such as DIPEA or triethylamine to form compounds (I) of the invention.

Scheme 1 Synthesis of imidazoles (I) as described above and in the claims

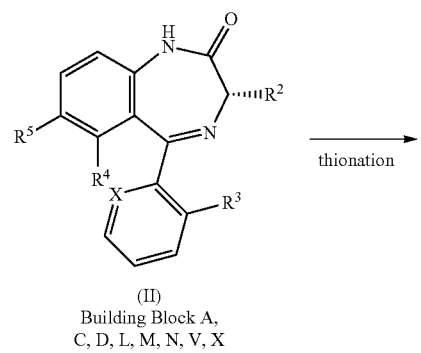

(II)
Building Block A,
C, D, L, M, N, V, X thionation

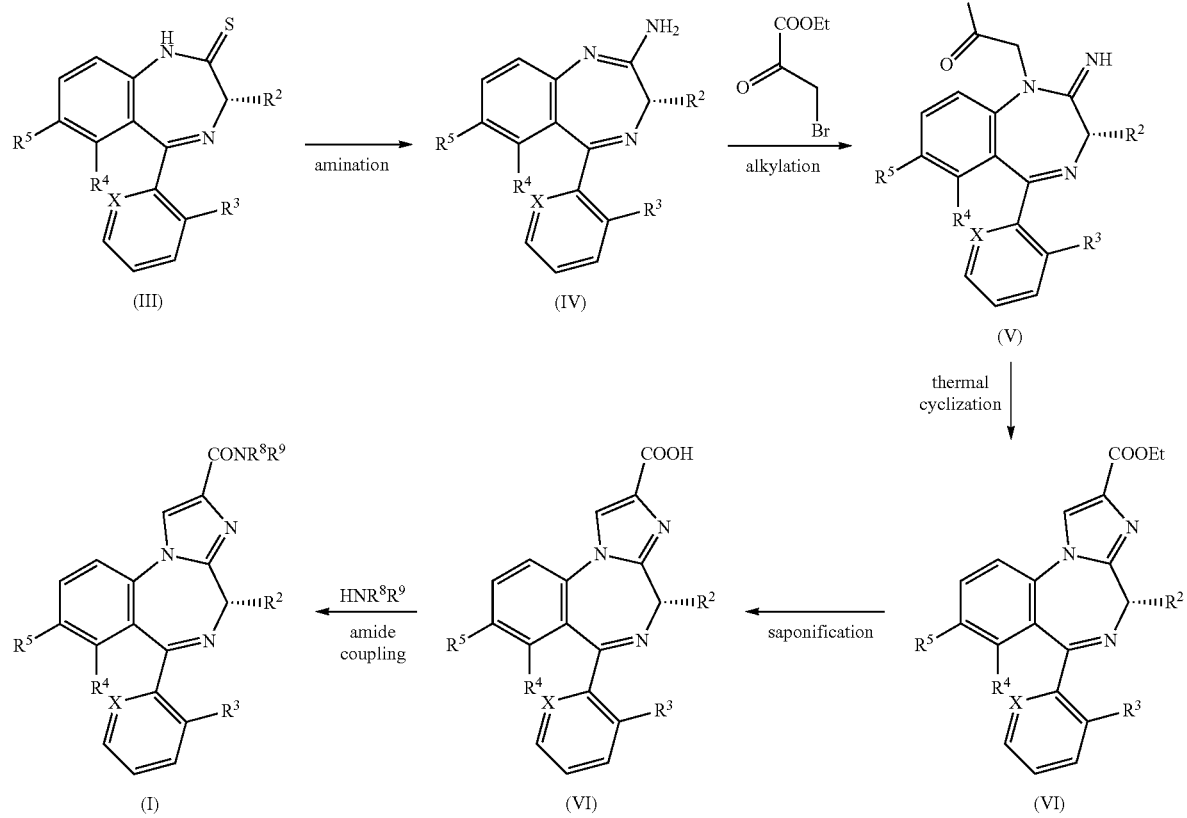

In further embodiments of the invention, according to Scheme 2, carboxylic acids (VII) can be converted into their corresponding Weinreb amides (VIII) by coupling with N,O-dimethylhydroxylamine hydrochloride and a coupling reagent such as EDC/HOBt and a base.

Reduction of (VIII) to aldehydes of formula (IX) can be accomplished by treatment with diisobutylaluminium hydride. Finally, aldehydes (IX) can be fluorinated using N,N-diethylaminosulfur trifluoride or a similar fluorinating reagent to form final derivatives (I).

Scheme 2 Synthesis of imidazoles (I) as described above and in the claims

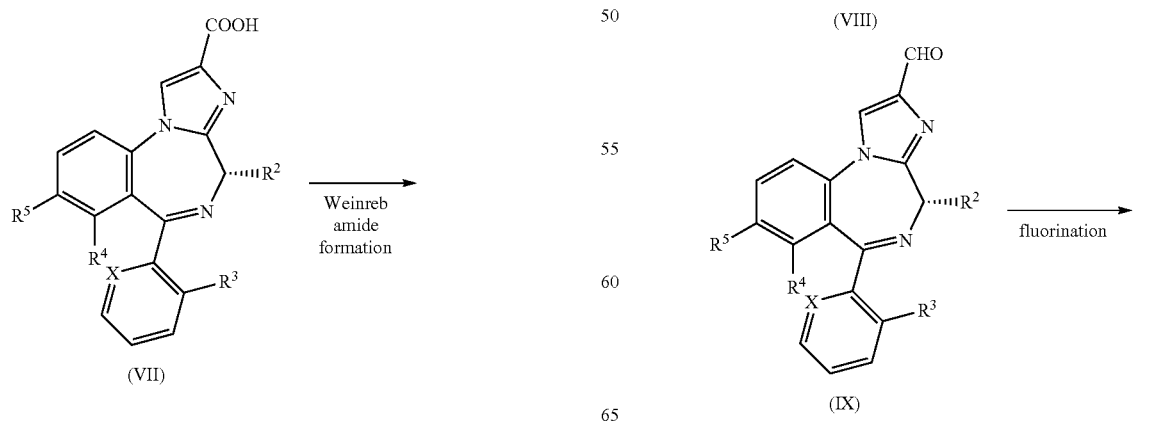

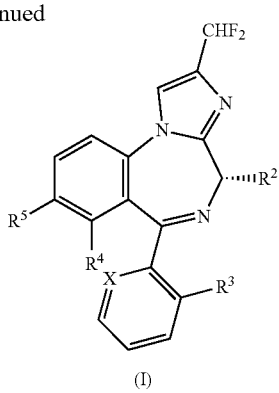

In a further embodiment of the invention, imidazoles of formula (I) can be prepared by a process described in Scheme 3.

Reaction of intermediates (IV) with 1,3-dichloroacetone and sodium bicarbonate leads to formation of the chloromethylimidazoles (X). These can be treated with aqueous bases such as sodium hydroxide to yield primary alcohols of formula (I). Synthesis of methoxymethyl-imidazoles (I) can be accomplished by reaction of chloromethyl-imidazoles (X) with sodium methoxide, while synthesis of disubstituted imidazole (I) can be achieved by reaction of compounds (X) with tert-butyl (2-hydroxyethyl)carbamate and sodium hydride in a suitable solvent such as dimethylformamide.

In further embodiments of the invention, triazoles of formulas (I) can be prepared by a process described below (Scheme 4).

Scheme 3 Synthesis of compounds (I) as described above and in the claims

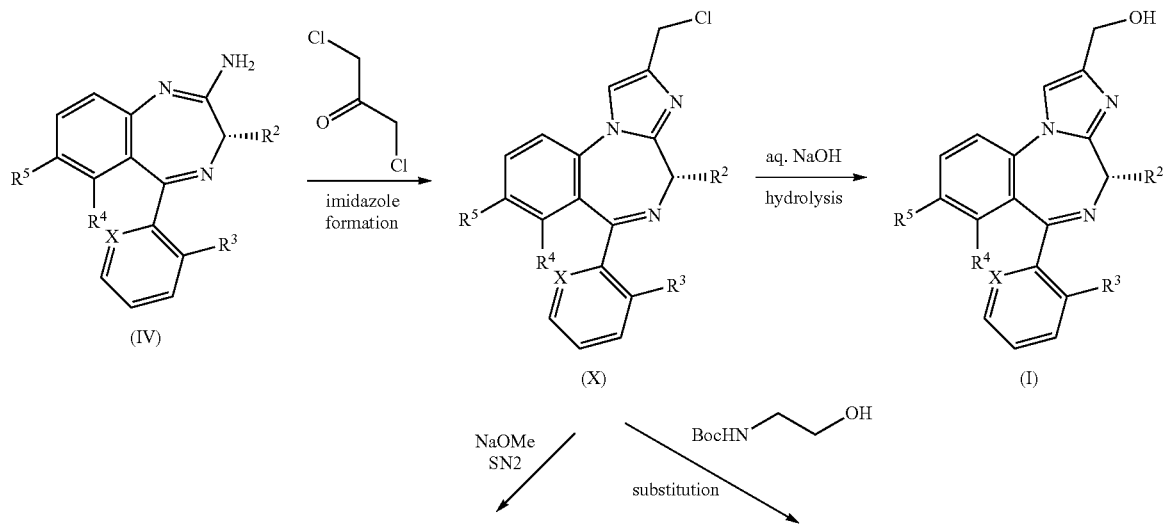

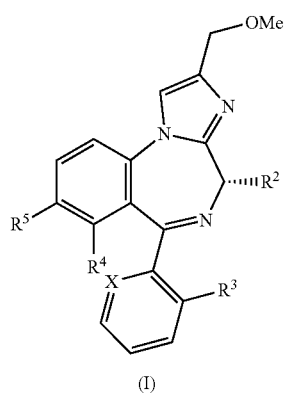

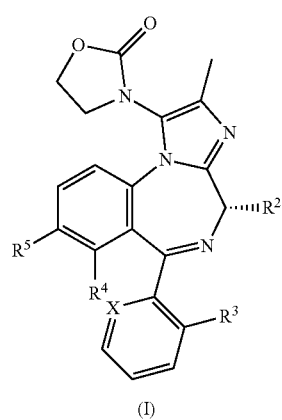

Scheme 4 Synthesis of triazoles (I) as described above and in the claims

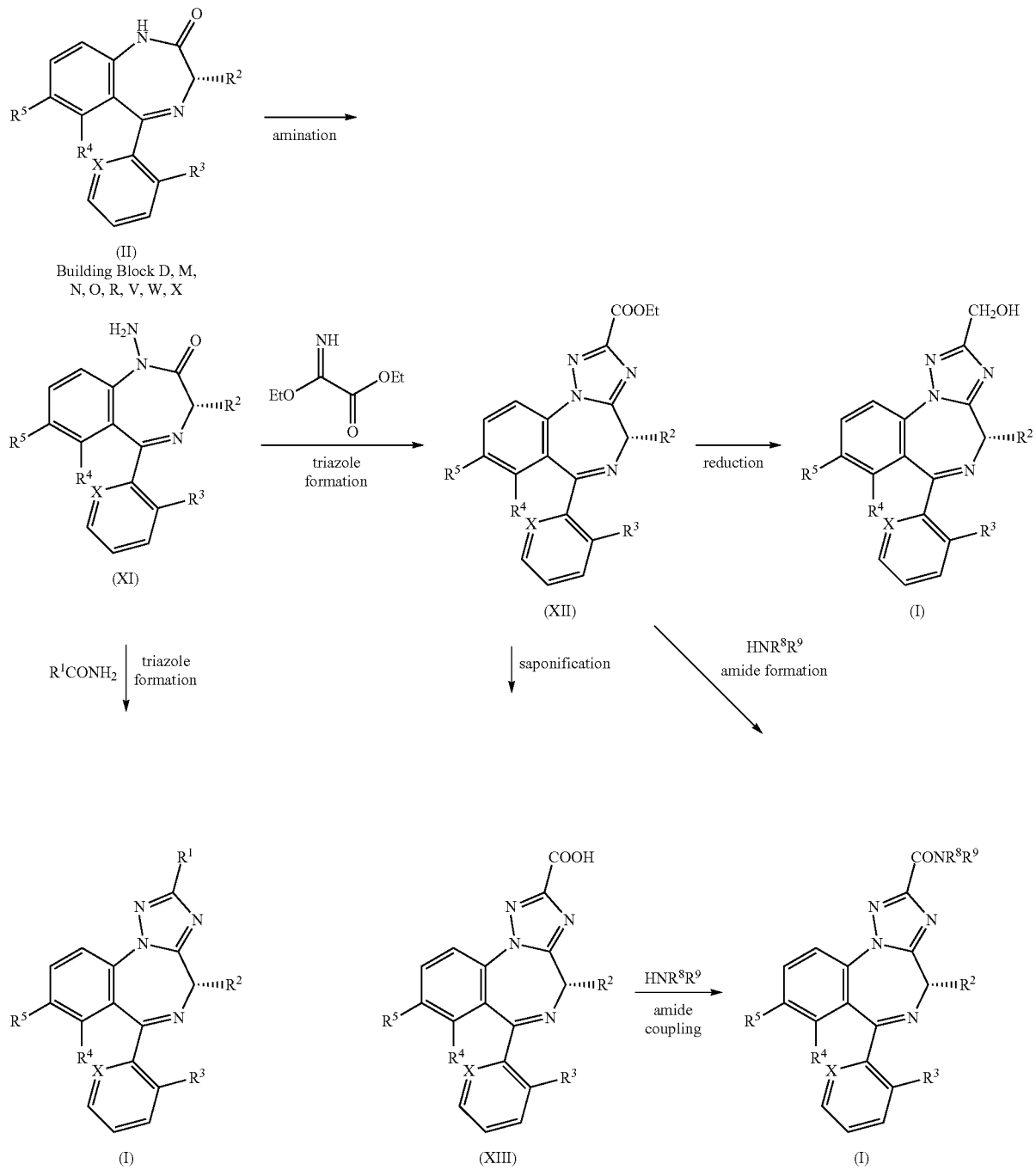

Synthesis of compounds (XI) can be accomplished by N-amination of lactams (II) (building blocks D, M, N, O, R, V, W, X) with O-(diphenylphosphinyl)hydroxylamine in presence of a base such as cesium carbonate. Ring closure to form triazole-esters (XII) can be achieved by reaction of compounds (XI) with ethyl 2-ethoxy-2-iminoacetate in ethanol. Ethyl esters (XII) can be reduced with sodium borohydride or lithium borohydride to the corresponding primary alcohols (I). If desired, ethyl esters (XII) can be directly reacted with amines $HNR^8R^9$, preferably alkyl amines or ammonia, to produce triazole-amides (I). Furthermore, esters (XII) can be saponified using a base such as sodium hydroxide or lithium hydroxide in a mixture of water and methanol or tetrahydrofuran to yield carboxylic acids (XIII) which, in turn, can be reacted with amines $HNR^8R^9$ using an amide coupling reagent such as HATU, EDC/HOBt, BOP-Cl or PyBOP in presence of a suitable base such as DIPEA or triethylamine or POCl3 in pyridine to form compounds of formula (I).

In further embodiments of the invention, triazoles of formulas (I) can be prepared by a process described below (Scheme 5).

Scheme 5 Synthesis of compounds (I) as described above and in the claims

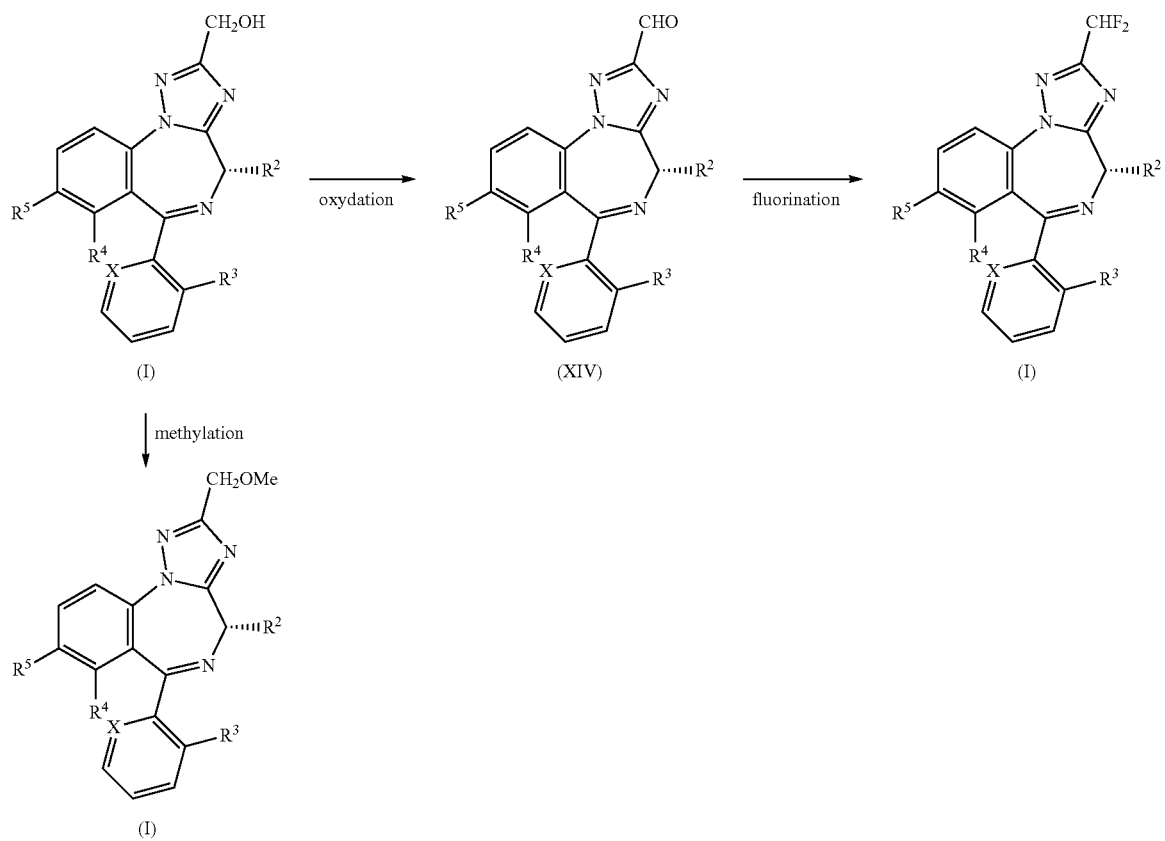

According to Scheme 5, aldehydes of formula (XIV) can be accomplished by reaction of alcohols (I) with an oxydating agent such as manganese dioxide or Dess-Martin reagent. Following a fluorination reaction using N,N-diethylaminosulfur trifluoride or a similar fluorinating reagent, aldehydes (XIV) are converted to corresponding difluoromethyl derivatives (I). Furthermore, alcohols (I) can be reacted with a methylating agent such as iodomethane in presence of silver carbonate to form methyl ethers of formula (I).

In a further embodiment of the invention, triazoles of formulas (I) can be prepared by a process described below (Scheme 6).

Scheme 6 Synthesis of compounds (I) as described above and in the claims

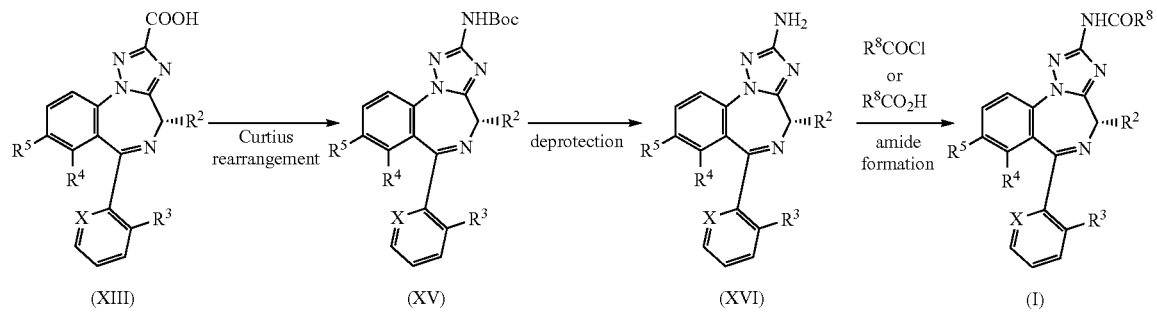

-continued

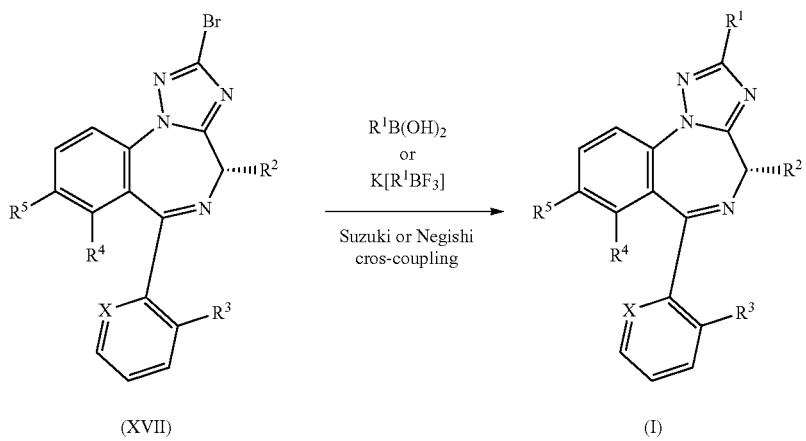

According to Scheme 6, carboxylic acids (XIII) can be converted to N-Boc protected amines (XV) by Curtius rearrangement using diphenylphosphoryl azide followed by treatment with tert-butanol. Subsequent deprotection reaction to form amines (XVI) can be accomplished by treatment with an acid such as hydrochloric acid in 1,4-dioxane. Amides of general formula (I) can be obtained by treatment of amines (XVI) with an acylating reagent such as an acid chloride or an organic anhydride. In case the reaction undergoes formation of double acylation product, one acyl group can be removed by treatment with ammonia in methanol to form pure mono acylated compounds (I). Furthermore, compounds (XVI) can be transformed into bromoderivatives (XVII) by a Sandmeyer reaction, using for example tert-butyl nitrite in presence of copper(II) bromide. These bromides (XVII) are appropriate starting materials for a Suzuki type reaction with alkyl boron compounds in presence of a palladium catalyst and a ligand to form compounds of formula (I). Such boron compounds include boronic acids, boronic acid esters and trifluoroborates.

The synthesis of building blocks (A, C, D, H, N, W) of formula (II) is highlighted in Scheme 7.

Scheme 7 Synthesis of building blocks (A, C, D, H, N) wherein $R^5$ is Cl, Br or I and $R^2$ is H; all other definitions are as described above and in the claims

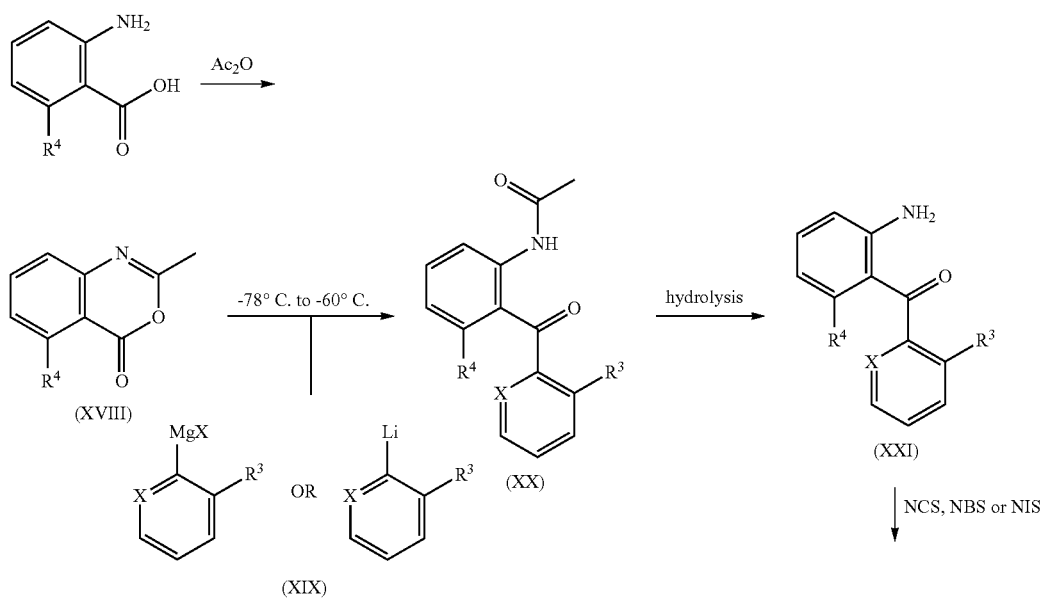

-continued

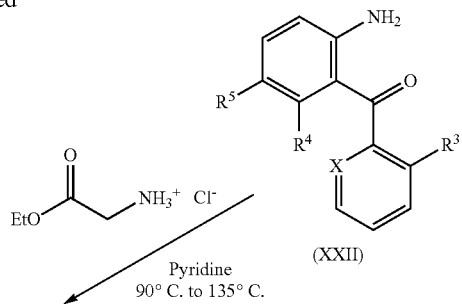

(XXII)

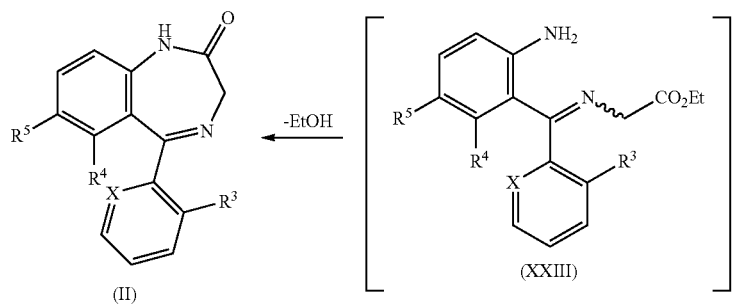

(II)        (XXIII)

Commercially available 2-amino-6-chlorobenzoic acid can be heated in acetic anhydride to form 5-chloro-2-methyl-3,1-benzoxazin-4-one (XVIII). Grignard or organo-lithium reagents of formula (XIX) (prepared by metalation reaction from corresponding aryl bromide or via kinetic deprotonation) can be reacted with benzoxazin-4-ones (electrophiles) at controlled temperatures to provide ketones of formula (XX). Compounds of formula (XX) are deacetylated and turned into anilines (XXI) by hydrolysis under acidic conditions (HCl). Conveniently, at this junction, halogens at $R^5$ can be installed by treatment with N-chlorosuccinimide (NCS), N-bromosuccinimide (NBS) or N-iodosuccinimide (NIS) to yield intermediates of formula (XXII). Final thermal cyclisation reaction with ethyl 2-aminoacetate hydrochloride in pyridine yields the desired benzodiazepines (II), presumably via formation of imine intermediate (XXIII).

In further embodiments of the invention, mainly where $R^2$ is alkyl or substituted alkyl, but not restricted to those compounds, an alternative process is envisaged and detailed in Scheme 8.

In such a case, compounds of formula (XXIV) can be prepared by amide coupling reaction between anilines (XXII) and N-Boc protected L-amino acids upon exposure to phosphoryl chloride ($POCl_3$), or by other methods known to those skilled in the art. Removal of N-Boc protecting group can be effected with mineral acids (e.g. HCl) or organic acids (e.g. trifluoroacetic acid) to yield amines of formula (XXV). Final intramolecular condensation reaction promoted by acidic media (e.g. silica or acetic acid) and heat (80-110° C.) provides the desired benzodiazepine building blocks of formula (II).

Scheme 8 Synthesis of building blocks (L, M, O, R, S, X) wherein $R^5$ is Cl, Br or I and $R^2$ is alkyl or substituted alkyl; all other definitions are as described above and in the claims

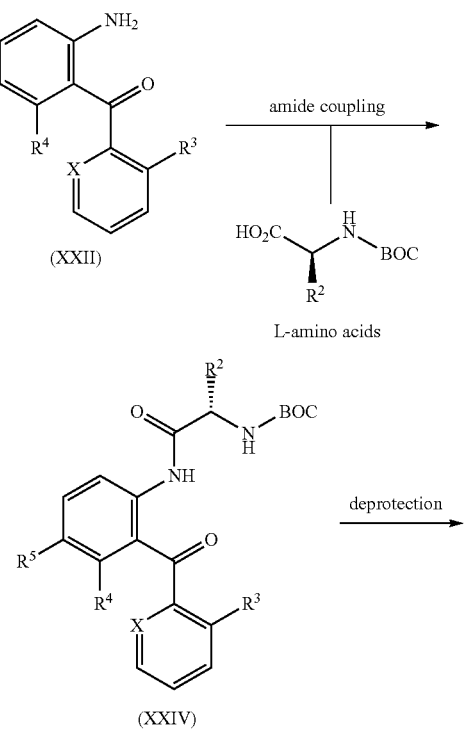

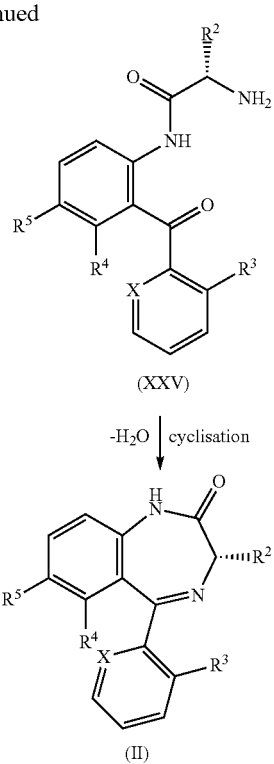

Furthermore, as described in Scheme 9, trifluoromethyl derivatives (II) can be synthesized from aryl iodides (II) using trifluoromethylation reagents such as methyl 2,2-difluoro-2-(fluorosulfonyl)acetate in presence of copper(I)-iodide.

Scheme 9 Synthesis of building blocks (V, W) wherein $R^5$ is $CF_3$; all other definitions are as described above and in the claims

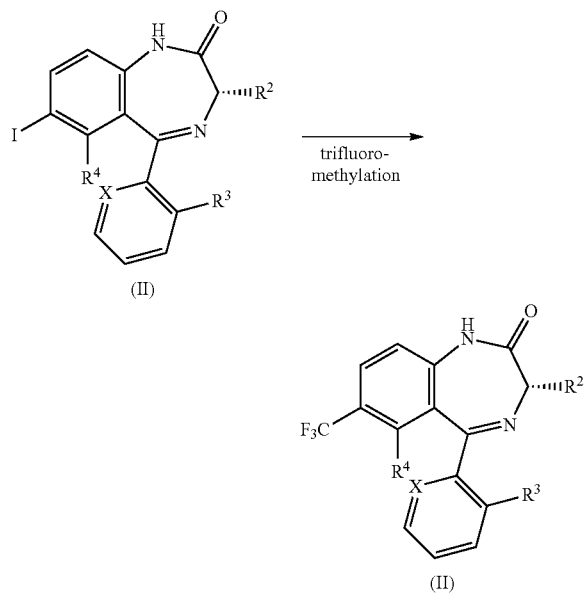

Notably, partial racemisation of the chiral center may occur depending on specific reaction conditions adopted. As a result, chiral purification (e.g. by HPLC or SFC) of final derivatives of formula (I) is required to obtain final derivatives with enantiomeric excess (ee) above 97%.

In one aspect, the present invention provides a process of manufacturing the compounds of formula (I) described herein, wherein said process is as described in any one of Schemes 1 to 9 above.

In a further aspect, the present invention provides a compound of formula (I) as described herein, or a pharmaceutically acceptable salt thereof, when manufactured according to the processes disclosed herein.

Using the Compounds of the Invention

As explained in the background section and illustrated in the experimental section, the compounds of formula (I) and their pharmaceutically acceptable salts possess valuable pharmacological properties that make them useful for the treatment or prevention of diseases or conditions that are associated with the GABAA γ1 receptor.

In one aspect, the present invention provides a compound of formula (I) as described herein, or a pharmaceutically acceptable salt thereof, for use as therapeutically active substance.

In a further aspect, the present invention provides a method for treating or preventing acute neurological disorders, chronic neurological disorders and/or cognitive disorders in a subject, said method comprising administering an effective amount of a compound of formula (I) as described herein, or a pharmaceutically acceptable salt thereof, or a pharmaceutical composition described herein, to the subject.

In a further aspect, the present invention provides the use of a compound of formula (I) as described herein, or a pharmaceutically acceptable salt thereof, or a pharmaceutical composition described herein, in a method for treating or preventing acute neurological disorders, chronic neurological disorders and/or cognitive disorders in a subject.

In a further aspect, the present invention provides a compound of formula (I) as described herein, or a pharmaceutically acceptable salt thereof, or a pharmaceutical composition described herein, for use in a method for treating or preventing acute neurological disorders, chronic neurological disorders and/or cognitive disorders in a subject.

In a further aspect, the present invention provides the use of a compound of formula (I) as described herein, or a pharmaceutically acceptable salt thereof, for the manufacture of a medicament for the treatment of prevention of acute neurological disorders, chronic neurological disorders and/or cognitive disorders.

In one embodiment, said acute neurological disorders, chronic neurological disorders and/or cognitive disorders are selected from autism spectrum disorders (ASD), Angelman syndrome, age-related cognitive decline, Rett syndrome, Prader-Willi syndrome, amyotrophic lateral sclerosis (ALS), fragile-X disorder, negative and/or cognitive symptoms associated with schizophrenia, tardive dyskinesia, anxiety, social anxiety disorder (social phobia), panic disorder, agoraphobia, generalized anxiety disorder, disruptive, impulse-control and conduct disorders, Tourette's syndrome (TS), obsessive-compulsive disorder (OCD), acute stress disorder, post-traumatic stress disorder (PTSD), attention deficit hyperactivity disorder (ADHD), sleep disorders, Parkinson's disease (PD), Huntington's chorea, Alzheimer's disease (AD), mild cognitive impairment (MCI), dementia, behavioral and psychological symptoms (BPS) in neurodegenerative conditions, multi-infarct dementia, agitation, psychosis, substance-induced psychotic disorder, aggression, eating disorders, depression, chronic apathy, anhedonia, chronic fatigue, seasonal affective disorder, postpartum depression, drowsiness, sexual dysfunction, bipolar disorders, epilepsy and pain.

In one embodiment, said acute neurological disorders, chronic neurological disorders and/or cognitive disorders are selected from Alzheimer's disease, mild cognitive impairment (MCI), age-related cognitive decline, negative and/or cognitive symptoms associated with schizophrenia, bipolar disorders, autism spectrum disorder (ASD), Angelman syndrome, Rett syndrome, Prader-Willi syndrome, epilepsy, post-traumatic stress disorder (PTSD), amyotrophic lateral sclerosis (ALS), and fragile-X disorder.

In a preferred embodiment, said acute neurological disorders, chronic neurological disorders and/or cognitive disorders are selected from autism spectrum disorder (ASD), Angelman syndrome, Alzheimer's disease, negative and/or cognitive symptoms associated with schizophrenia and post-traumatic stress disorder (PTSD).

In a preferred embodiment, said acute neurological disorders, chronic neurological disorders and/or cognitive disorders are selected from autism spectrum disorder (ASD), Rett syndrome, post-traumatic stress disorder and fragile-X disorder.

In a preferred embodiment, said acute neurological disorders, chronic neurological disorders and/or cognitive disorders are selected from autism spectrum disorder (ASD) and Angelman syndrome.

In a particularly preferred embodiment, said acute neurological disorders, chronic neurological disorders and/or cognitive disorders are Angelman syndrome.

In a particularly preferred embodiment, said acute neurological disorders, chronic neurological disorders and/or cognitive disorders are autism spectrum disorder (ASD).

In a further particularly preferred embodiment, said acute neurological disorders, chronic neurological disorders and/or cognitive disorders are autism spectrum disorder (ASD), targeting core symptoms and associated comorbidities, such as anxiety and irritability, social anxiety disorder (social phobia) and generalized anxiety disorder.

Pharmaceutical Compositions and Administration

In one aspect, the present invention provides pharmaceutical compositions comprising compounds of formula (I) or their pharmaceutically acceptable salts as defined herein and one or more pharmaceutically acceptable excipients. Exemplary pharmaceutical compositions are described in the Example section below.

In a further aspect, the present invention relates to pharmaceutical compositions comprising compounds of formula (I) or their pharmaceutically acceptable salts as defined above and one or more pharmaceutically acceptable excipients for the treatment or prevention of acute neurological disorders, chronic neurological disorders and/or cognitive disorders.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions or infusion solutions).

The compounds of formula (I) and their pharmaceutically acceptable salts can be processed with pharmaceutically inert, inorganic or organic excipients for the production of tablets, coated tablets, dragées and hard gelatin capsules. Lactose, corn starch or derivatives thereof, talc, stearic acid or its salts etc. can be used, for example, as such excipients for tablets, dragées and hard gelatin capsules.

Suitable excipients for soft gelatin capsules are, for example, vegetable oils, waxes, fats, semi-solid substances and liquid polyols, etc.

Suitable excipients for the production of solutions and syrups are, for example, water, polyols, saccharose, invert sugar, glucose, etc.

Suitable excipients for injection solutions are, for example, water, alcohols, polyols, glycerol, vegetable oils, etc.

Suitable excipients for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given herein can be exceeded when this is shown to be indicated.

EXAMPLES

The invention will be more fully understood by reference to the following examples. The claims should not, however, be construed as limited to the scope of the examples.

In case the preparative examples are obtained as a mixture of enantiomers, the pure enantiomers can be separated by methods described herein or by methods known to the man skilled in the art, such as e.g., chiral chromatography (e.g., chiral SFC) or crystallization.

All reaction examples and intermediates were prepared under an argon atmosphere if not specified otherwise.

Building Block Syntheses

The building blocks can be produced according to the following synthetic procedures.

Building Block A 7-bromo-6-chloro-5-(2,6-difluorophenyl)-1,3-dihydro-1,4-benzodiazepin-2-one

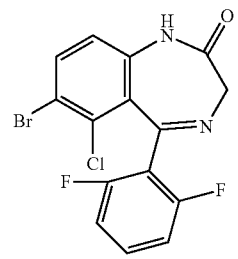 [SMILES: O=C1CN=C(c2c(F)cccc2F)c2c(ccc(Br)c2Cl)N1]

a) 5-chloro-2-methyl-3,1-benzoxazin-4-one

A solution of 2-amino-6-chlorobenzoic acid (250 g, 1.46 mol) in acetic anhydride (1250 mL) was stirred at 140° C. for 2 h. The reaction mixture was concentrated in vacuo. The resulting crude residue was suspended in ethyl acetate (1000 mL), stirred for 30 min, filtered and dried in vacuo to afford the title compound (238 g, 84%) as a grey solid. $^1$H NMR (DMSO-d$_6$, 400 MHz) δ: 7.80 (app t, J=8.0 Hz, 1H), 7.62 (d, J=8.0 Hz, 1H), 7.49 (d, J=7.6 Hz, 1H), 2.36 (s, 3H).

b) N-[3-chloro-2-(2,6-difluorobenzoyl)phenyl]acetamide

To a solution of 5-chloro-2-methyl-3,1-benzoxazin-4-one (100 g, 511.2 mmol) and 2-bromo-1,3-difluorobenzene (118.4 g, 613.5 mmol) in tetrahydrofuran (1000 mL) was added dropwise i-PrMgCl·LiCl (1.3 m, 500 mL, 650 mmol) at −70° C. under nitrogen. The mixture was allowed to warm up to room temperature within 1 h, quenched with saturated aqueous ammonium chloride (1500 mL) and extracted with ethyl acetate (2×1500 mL). The combined organic layers were washed with brine (2000 mL), dried (Na$_2$SO$_4$) and concentrated in vacuo. The residue was suspended in ethyl acetate (150 mL). The resulting suspension was stirred at room temperature for 20 min, filtered and dried in vacuo to afford the title compound (113 g, 71%) as an off-white solid. $^1$H NMR (DMSO-d$_6$, 400 MHz) δ: 9.85 (s, 1H), 7.65-7.45 (m, 1H), 7.40 (t, J=7.2 Hz, 1H), 7.38-7.34 (m, 2H), 7.16 (t, J=8.8 Hz, 2H), 1.85 (s, 3H).

c) (2-amino-6-chloro-phenyl)(2,6-difluorophenyl)methanone

To a solution of N-[3-chloro-2-(2,6-difluorobenzoyl)phenyl]acetamide (113 g, 364.9 mmol) in ethanol (250 mL) was added aqueous hydrochloric acid (12 m, 200 mL). The reaction mixture was stirred at 100° C. for 1 h, then diluted with ethyl acetate (1100 mL). The organic layer was washed with water (1100 mL), saturated aqueous sodium bicarbonate (1100 mL) and brine (1100 mL), dried (Na$_2$SO$_4$) and concentrated in vacuo. Petroleum ether (120 mL) was added to the crude and the suspension was stirred at room temperature for 20 min. The solid was filtered and dried to afford the title compound (88 g, 90%) as a yellow solid. $^1$H NMR (DMSO-d$_6$, 400 MHz) δ: 7.62-7.56 (m, 1H), 7.21-7.15 (m, 3H), 6.83 (d, J=7.6 Hz, 1H), 6.74 (s, 2H), 6.58 (d, J=7.6 Hz, 1H).

d) (6-amino-3-bromo-2-chloro-phenyl)-(2,6-difluorophenyl)methanone

To a solution of (2-amino-6-chloro-phenyl)-(2,6-difluorophenyl)methanone (88.0 g, 328.8 mmol) in dichloromethane (225 mL) and N,N-dimethylformamide (225 mL) was added 1-bromopyrrolidine-2,5-dione (64.4 g, 362 mmol) at 0° C. The reaction mixture was stirred at 30° C. for 1 h. The mixture was diluted with dichloromethane (600 mL) and washed with water (500 mL) and brine (4×500 mL), dried (Na$_2$SO$_4$) and concentrated in vacuo. The residue was purified by flash column chromatography (silica, petroleum ether/ethyl acetate, 1:0 to 2:1). The solid was suspended in petroleum ether (200 mL) and stirred at room temperature for 20 min. The suspension was filtered and the solid was dried in vacuo to afford the title compound (96.0 g, 84%) as a yellow solid. MS: 345.9 ([{$^{79}$Br, $^{35}$Cl} M+H]$^+$), 347.8 ([{$^{81}$Br, $^{35}$Cl or $^{79}$Br, $^{37}$Cl} M+H]$^+$), ESI pos.

e) 7-bromo-6-chloro-5-(2,6-difluorophenyl)-1,3-dihydro-1,4-benzodiazepin-2-one To a solution of (6-amino-3-bromo-2-chloro-phenyl)-(2,6-difluorophenyl)methanone (25.0 g, 72.1 mmol) in pyridine (625 mL) was added ethyl 2-aminoacetate hydrochloride (70.5 g, 505 mmol). The reaction mixture was stirred at 135° C. for 36 h. The reaction mixture was concentrated in vacuo to remove pyridine. The residue was diluted with ethyl acetate (2000 mL) and washed with aqueous hydrochloric acid (1.0 m, 3×1500 mL), water (2000 mL) and brine (2×1000 mL), dried (Na$_2$SO$_4$), filtered and concentrated in vacuo. The crude product was purified by flash column chromatography (silica, petroleum ether/ethyl acetate 10:1 to 2:1) to afford the title compound (10.1 g, 12%) as an off-white solid. MS: 385.0 ([{$^{79}$Br, $^{35}$Cl} M+H]$^+$), ESI pos.

Building Block C 6,7-dichloro-5-(2-fluorophenyl)-1,3-dihydro-1,4-benzodiazepin-2-one

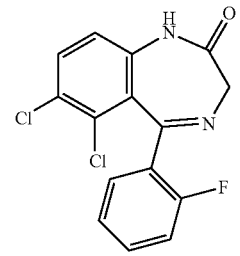 [SMILES: O=C1CN=C(c2ccccc2F)c2c(ccc(Cl)c2Cl)N1]

a) N-[3-chloro-2-(2-fluorobenzoyl)phenyl]acetamide

To a solution of 5-chloro-2-methyl-3,1-benzoxazin-4-one (17.8 g, 91 mmol) and 1-bromo-2-fluorobenzene (15.9 g, 9.95 mL, 91 mmol) in tetrahydrofuran (500 mL) was added dropwise n-butyllithium (1.6 m, 68.3 mL, 109 mmol) at −70° C. under nitrogen. The mixture was allowed to warm up to room temperature within 1 h, then filtered to give a solid (19.95 g). The filtrate was concentrated in vacuo (7.29 g). The solids were combined, diluted with ethyl acetate (70 mL) and heated up to 80° C. The red solution was allowed to cool down to room temperature. The suspension was filtered to give a white solid (9.01 g). The filtrate was purified by flash column chromatography (silica, 0-70% ethyl acetate in heptane) to give a light yellow solid (6.89 g). The solids were combined and dried in vacuo to afford the title compound (14.67 g, 55%) as a light yellow solid. MS: 292.2 ([{$^{35}$Cl} M+H]$^+$), ESI pos.

b) (2-amino-6-chloro-phenyl)-(2-fluorophenyl)methanone

In analogy to experiment of building block A c, N-[3-chloro-2-(2-fluorobenzoyl)phenyl]acetamide was converted into the title compound (393 mg, 92%) which was obtained as a yellow solid. MS: 250.2 ([{$^{35}$Cl} M+H]$^+$), ESI pos.

c) (6-amino-2,3-dichloro-phenyl)-(2-fluorophenyl)methanone

In analogy to experiment of building block A d, (2-amino-6-chloro-phenyl)-(2-fluorophenyl)methanone using 1-chloropyrrolidine-2,5-dione was converted into the title compound (234 mg, 53%) which was obtained as an orange yellow solid. MS: 284.0 ([{$^{35}$Cl, $^{35}$Cl} M+H]$^+$), ESI pos.

d) 6,7-dichloro-5-(2-fluorophenyl)-1,3-dihydro-1,4-benzodiazepin-2-one

In analogy to experiment of building block A e, (6-amino-2,3-dichloro-phenyl)-(2-fluorophenyl)methanone was converted into the title compound (193 mg, 74%) which was obtained as a grey solid. MS: 323.2 ([{$^{35}$Cl, $^{35}$Cl} M+H]$^+$), ESI pos.
Building Block D 6,7-dichloro-5-(2,6-difluorophenyl)-1,3-dihydro-1,4-benzodiazepin-2-one

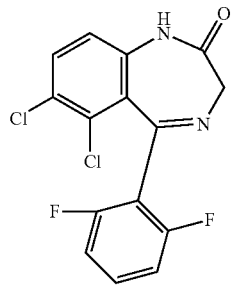 [SMILES: O=C1CN=C(c2c(F)cccc2F)c2c(ccc(Cl)c2Cl)N1]

a) (6-amino-2,3-chloro-phenyl)-(2,6-difluorophenyl) methanone

In analogy to experiment of building block A d, (2-amino-6-chloro-phenyl)-(2,6-difluorophenyl)methanone using 1-chloropyrrolidine-2,5-dione was converted into the title compound (3.44 g, 47%) which was obtained as a yellow solid. MS: 302.0 ([{$^{35}$Cl, $^{35}$Cl} M+H]$^+$), ESI pos.

b) 6,7-dichloro-5-(2,6-difluorophenyl)-1,3-dihydro-1,4-benzodiazepin-2-one

In analogy to experiment of building block A e, (6-amino-2,3-dichloro-phenyl)-(2,6-difluorophenyl)methanone was converted into the title compound (2.6 g, 53%) which was obtained as a yellow solid. MS: 341.0 ([{$^{35}$Cl, $^{35}$Cl} M+H]$^+$), ESI pos.
Building Block H 6-chloro-5-(2-fluorophenyl)-7-iodo-1,3-dihydro-1,4-benzodiazepin-2-one

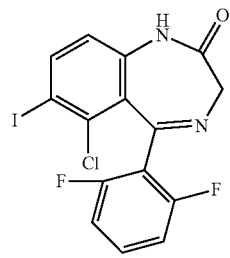

a) (6-amino-2-chloro-3-iodo-phenyl)-(2,6-difluorophenyl)methanone

In analogy to experiment of building block A d, (2-amino-6-chloro-phenyl)-(2,6-difluorophenyl)methanone using 1-iodopyrrolidine-2,5-dione was converted into the title compound (7.1 g, 85%) which was obtained as a yellow solid. MS: 393.8 ([{$^{35}$Cl} M+H]$^+$), 395.8 ([{$^{35}$Cl} M+H]$^+$), ESI pos.

b) 6-chloro-5-(2,6-difluorophenyl)-7-iodo-1,3-dihydro-1,4-benzodiazepin-2-one

In analogy to experiment of building block A e, (6-amino-2-chloro-3-iodo-phenyl)-(2,6-difluorophenyl)methanone was converted into the title compound (2.7 g, 68%) which was obtained as a yellow solid. MS: 432.8 ([{$^{35}$Cl} M+H]$^+$), 434.8 ([{$^{35}$Cl} M+H]$^+$), ESI pos.
Building Block M (3S)-6,7-dichloro-5-(2,6-difluorophenyl)-3-methyl-1,3-dihydro-1,4-benzodiazepin-2-one

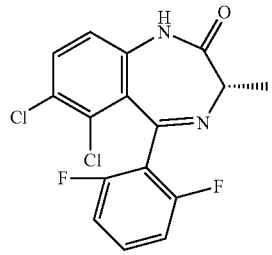 [SMILES: C[C@@H]1N=C(c2c(F)cccc2F)c2c(ccc(Cl)c2Cl)NC1=O]

a) tert-butyl N-[(1S)-2-[3,4-dichloro-2-(2,6-difluorobenzoyl)anilino]-1-methyl-2-oxo-ethyl]carbamate To a solution of (6-amino-2,3-dichloro-phenyl)-(2,6-difluorophenyl)methanone (10.0 g, 33.1 mmol) and 2-(tert-butoxycarbonylamino)propanoic acid (9.39 g, 49.65 mmol) in pyridine (100 mL) was slowly added phosphoryl chloride (4.63 mL, 49.65 mmol) at −5° C. The reaction mixture was stirred at −5° C. for 1 h, then slowly poured into water (300 mL) and stirred for 10 min. The suspension was filtered, washed with water (2×100 mL) and dried in vacuo to afford the title compound (11.0 g, 69%) as a yellow solid. MS: 373.2 ([{$^{35}$Cl, $^{35}$Cl} M−C$_4$H$_8$—CO$_2$+H]$^+$), ESI pos.

b) (2S)-2-amino-N-[3,4-dichloro-2-(2,6-difluorobenzoyl)phenyl]propanamide

To a solution of (tert-butyl N-[(1S)-2-[3,4-dichloro-2-(2,6-difluorobenzoyl)anilino]-1-methyl-2-oxo-ethyl]carbamate (11.0 g, 23.24 mmol) in ethyl acetate (50 mL) was slowly added hydrochloric acid (4 m in 1,4-dioxane, 58.1 mL, 232.41 mmol). The reaction mixture was stirred at 25° C. for 2 h. Saturated aqueous sodium bicarbonate (250 mL) was slowly added, then the mixture was extracted with ethyl acetate (3×100 mL). The combined organic layers were washed with brine (2×100 mL), dried (Na$_2$SO$_4$) and concentrated in vacuo to afford the title compound (8.0 g, 92%) as a yellow oil. MS: 373.0 ([{$^{35}$Cl, $^{35}$Cl} M+H]$^+$), ESI pos.

c) (3S)-6,7-dichloro-5-(2,6-difluorophenyl)-3-methyl-1,3-dihydro-1,4-benzodiazepin-2-one To a solution of (2S)-2-amino-N-[3,4-dichloro-2-(2,6-difluorobenzoyl)phenyl]propanamide (8.0 g, 21.44 mmol) in toluene (150 mL) was added silica (138 mg, 667 mmol). The reaction mixture was stirred at 90° C. for 16 h, then concentrated in vacuo. The residue was purified by flash column chromatography (petroleum ether/ethyl acetate 5:1 to 3:1) to afford the title compound (7.0 g, 92%) as a light yellow solid. MS: 355.0 ([$\{^{35}Cl, ^{35}Cl\}$ M+H]$^+$), ESI pos.

Building Block L

(3S)-7-bromo-6-chloro-5-(2,6-difluorophenyl)-3-methyl-1,3-dihydro-1-benzodiazepin-2-one

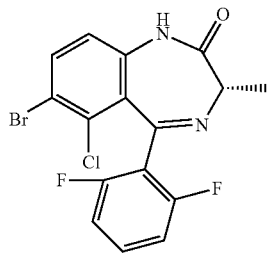

a) tert-butyl N-[(1S)-2-[4-bromo-3-chloro-2-(2,6-difluorobenzoyl)anilino]-1-methyl-2-oxo-ethyl]carbamate In analogy to experiment of building block M a, (6-amino-3-bromo-2-chloro-phenyl)-(2,6-difluorophenyl)methanone using (2S)-2-(tert-butoxycarbonylamino)propanoic acid was converted into the title compound (1.50 g, 98%) which was obtained as a yellow solid. MS: 418.7 ([$\{^{81}Br, ^{35}Cl$ or $^{79}Br, ^{37}Cl\}$ M–$C_4H_8$–$CO_2$+H]$^+$), 540.7 ([$\{^{81}Br, ^{35}Cl$ or $^{79}Br, ^{37}Cl\}$ M+Na]), ESI pos.

b) (2S)-2-amino-N-[4-bromo-3-chloro-2-(2,6-difluorobenzoyl)phenyl]propanamide In analogy to experiment of building block M b, tert-butyl N-[(1S)-2-[4-bromo-3-chloro-2-(2,6-difluorobenzoyl)anilino]-1-methyl-2-oxo-ethyl]carbamate was converted into the title compound (1.1 g, 94%) which was obtained as a yellow oil, which was used in the following step without further characterization.

c) (3S)-7-bromo-6-chloro-5-(2,6-difluorophenyl)-3-methyl-1,3-dihydro-1,4-benzodiazepin-2-one To a solution of (2S)-2-amino-N-[4-bromo-3-chloro-2-(2,6-difluorobenzoyl)phenyl]propanamide (960 mg, 2.30 mmol) in toluene (9.19 mL) was added silica (138 mg, 2.30 mmol). The reaction mixture was stirred at 90° C. for 15 h, then concentrated in vacuo. The residue was purified by flash column chromatography (petroleum ether/ethyl acetate 3:1) to afford the title compound (920 mg, 95%) as a yellow solid. MS: 399.1 ([$\{^{79}Br, ^{35}Cl\}$ M+H]$^+$), 401.1 ([$\{^{81}Br, ^{35}Cl$ or $^{79}Br, ^{37}Cl\}$ M+H]$^+$), ESI pos.

Building Block N

6,7-dichloro-5-(3-fluoro-2-pyridyl)-1,3-dihydro-1,4-benzodiazepin-2-one

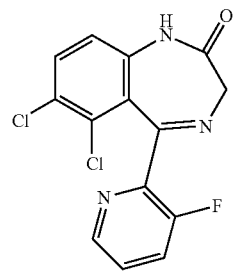 [SMILES: O=C1CN=C(c2ncccc2F)c2c(ccc(Cl)c2Cl)N1]

a) N-[3-chloro-2-(3-fluoropyridine-2-carbonyl)phenyl]acetamide

To a stirred solution of 2-bromo-3-fluoropyridine (26.99 g, 153.37 mmol) in tert-butyl methyl ether (1000 mL) was slowly added n-butyllithium (2.5 m, 55.21 mL, 138.04 mmol) at −60° C. The mixture was stirred at −60° C. for 1 h, then a solution of 5-chloro-2-methyl-3,1-benzoxazin-4-one (15.0 g, 76.69 mmol) in tetrahydrofuran (500 mL) was added dropwise. The mixture was stirred at −60° C. for 1 h. Saturated aqueous ammonium chloride (100 mL) was added and the mixture was warmed up slowly, then diluted with water (200 mL). The reaction mixture was filtered and the filtrate was extracted with ethyl acetate (3×100 mL). The combined organic layers were washed with brine (100 mL), dried ($Na_2SO_4$) and concentrated in vacuo. The residue was purified (together with another 17 parallel batchs) by flash column chromatography (silica, dichloromethane/methanol 50:1 to 10:1) and dried in vacuo to give a yellow solid (260 g) which was re-purified by trituration to afford the title compound (82 g, 18%, 88% purity) as a white solid and another second batch (160 g, 24%, 61% purity) as a yellow solid. MS: 292.9 ([$\{^{35}Cl\}$ M+H]$^+$), ESI pos.

b) N-[3,4-dichloro-2-(3-fluoropyridine-2-carbonyl)phenyl]acetamide

In analogy to experiment of building block A d, N-[3-chloro-2-(3-fluoropyridine-2-carbonyl)phenyl]acetamide using 1-chloropyrrolidine-2,5-dione was converted into the title compound (36 g, 84%) which was obtained as a white solid. MS: 327.0 ([$\{^{35}Cl, ^{35}Cl\}$ M+H]$^+$), ESI pos.

c) (6-amino-2,3-dichloro-phenyl)-(3-fluoro-2-pyridyl)methanone

To a stirred suspension of N-[3,4-dichloro-2-(3-fluoropyridine-2-carbonyl)phenyl]acetamide (20.0 g, 61.14 mmol) in methanol (100 mL) was slowly added hydrochloric acid (4 m in methanol, 152.8 mL, 611.4 mmol). The reaction mixture was stirred at 40° C. for 24 h. The reaction mixture (together with other three batches, totally using 70 g of N-[3,4-dichloro-2-(3-fluoropyridine-2-carbonyl)phenyl]acetamide) was cooled, slowly poured into a stirred mixture of saturated aqueous sodium bicarbonate (2.0 L) and ice. Saturated aqueous sodium bicarbonate was added to basify to pH 8-9 and the mixture was stirred at 20° C. for 10 min, then extracted with ethyl acetate (3×1.0 L). The combined organic layers were filtered. The filtrate was washed with brine (2×500 mL), dried (Na$_2$SO$_4$) and concentrated in vacuo. The residue was purified by trituration (petroleum ether/ethyl acetate 1:1, 100 mL) and dried in vacuo to afford the title compound (44.5 g, 99% purity) as a yellow solid and a second batch (11.0 g, 85% purity) as an orange solid (total 55.5 g, 88%). MS: 285.0 ([{$^{35}$Cl, $^{35}$Cl} M+H]$^+$), ESI pos.

d) 6,7-dichloro-5-(3-fluoro-2-pyridyl)-1,3-dihydro-1,4-benzodiazepin-2-one

In analogy to experiment of building block A e, (6-amino-2,3-dichloro-phenyl)-(3-fluoro-2-pyridyl)methanone was converted into the title compound (3.76 g, 28%) which was obtained as a white solid. MS: 323.7 ([{$^{35}$Cl, $^{35}$Cl} M+H]$^+$), ESI pos.

Building Block O (3S)-6,7-dichloro-5-(3-fluoro-2-pyridyl)-3-methyl-1,3-dihydro-1,4-benzodiazepin-2-one

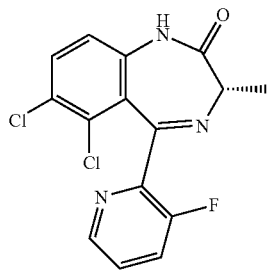 [SMILES: C[C@@H]1N=C(c2ncccc2F)c2c(ccc(Cl)c2Cl)NC1=O]

a) tert-butyl N-[(1S)-2-[3,4-dichloro-2-(3-fluoro-pyridine-2-carbonyl)anilino]-1-methyl-2-oxo-ethyl]carbamate In analogy to experiment of building block M a, (6-amino-2,3-dichloro-phenyl)-(3-fluoro-2-pyridyl)methanone was converted into the title compound (8.6 g, 67%) which was obtained as a white solid. MS: 456.0 ([{$^{35}$Cl, $^{35}$Cl} M+H]$^+$), ESI pos.

b) (2S)-2-amino-N-[3,4-dichloro-2-(3-fluoropyridine-2-carbonyl)phenyl]propanamide In analogy to experiment of building block M b, tert-butyl N-[(1S)-2-[3,4-dichloro-2-(3-fluoropyridine-2-carbonyl)anilino]-1-methyl-2-oxo-ethyl]carbamate was converted into the title compound (6.6 g, 100%) which was obtained as a yellow solid. MS: 356.0 ([{$^{35}$Cl, $^{35}$Cl} M+H]$^+$), ESI pos.

c) (3S)-6,7-dichloro-5-(3-fluoro-2-pyridyl)-3-methyl-1,3-dihydro-1,4-benzodiazepin-2-one In analogy to experiment of building block M c, (2S)-2-amino-N-[3,4-dichloro-2-(3-fluoropyridine-2-carbonyl)phenyl]propanamide was converted into the title compound (5.5 g, 88%) which was obtained as a yellow solid. MS: 338.0 ([{$^{35}$Cl, $^{35}$Cl} M+H]$^+$), ESI pos.

Building Block R (3S)-7-bromo-6-chloro-5-(3-fluoro-2-pyridyl-3-methyl-1,3-dihydro-1,4-benzodiazepin-2-one

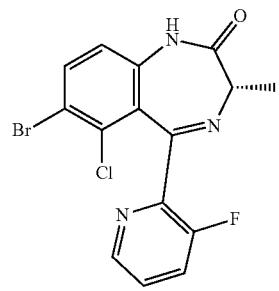 [SMILES: C[C@@H]1N=C(c2ncccc2F)c2c(ccc(Br)c2Cl)NC1=O]

a) (2-amino-6-chloro-phenyl)-(3-fluoro-2-pyridyl)methanone

In analogy to experiment of building block N c, N-[3-chloro-2-(3-fluoropyridine-2-carbonyl)phenyl]acetamide was converted into the title compound (4.1 g, 96%) which was obtained as a yellow solid. MS: 250.9 ([{$^{35}$Cl} M+H]$^+$), ESI pos.

b) (6-amino-3-bromo-2-chloro-phenyl)-(3-fluoro-2-pyridyl)methanone

In analogy to experiment of building block A d, (2-amino-6-chloro-phenyl)-(3-fluoro-2-pyridyl)methanone using 1-bromopyrrolidine-2,5-dione was converted into the title compound (1.1 g, 84%) which was obtained as a yellow solid. MS: 330.9 ([{$^{79}$Br, $^{35}$Cl} M+H]$^+$), ESI pos.

c) tert-butyl N-[(1S)-2-[4-bromo-3-chloro-2-(3-fluoropyridine-2-carbonyl)anilino]-1-methyl-2-oxo-ethyl]carbamate In analogy to experiment of building block M a, (6-amino-3-bromo-2-chloro-phenyl)-(3-fluoro-2-pyridyl)methanone using (2S)-2-(tert-butoxycarbonylamino)propanoic acid was converted into the title compound (1.4 g, 97%) which was obtained as a yellow foam. The crude was used as such in the following step without further characterization.

d) (2S)-2-amino-N-[4-bromo-3-chloro-2-(3-fluoropyridine-2-carbonyl)phenyl]propanamide In analogy to experiment of building block M b, tert-butyl N-[(1S)-2-[4-bromo-3-chloro-2-(3-fluoropyridine-2-carbonyl)anilino]-1-methyl-2-oxo-ethyl]carbamate was converted into the title compound (1.1 g, 98%) which was obtained as a yellow oil. The crude was used as such in the following step without further characterization.

e) (3S)-7-bromo-6-chloro-5-(3-fluoro-2-pyridyl)-3-methyl-1,3-dihydro-1,4-benzodiazepin-2-one In analogy to experiment of building block M c, (2S)-2-amino-N-[4-bromo-3-chloro-2-(3-fluoropyridine-2-carbonyl)phenyl]propanamide was converted into the title compound (430 mg, 40%) which was obtained as a yellow solid.

MS: 381.9 ([{$^{79}$Br, $^{35}$Cl} M+H]$^+$), 383.9 ([{$^{81}$Br, $^{35}$Cl or $^{79}$Br, $^{37}$Cl} M+H]$^+$), ESI pos.

Building Block S (3S)-6-chloro-5-(2,6-difluorophenyl)-7-iodo-3-methyl-1,3-dihydro-1,4-benzodiazepin-2-one

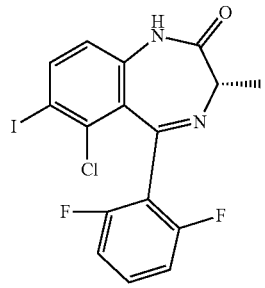 [SMILES: C[C@@H]1N=C(c2c(F)cccc2F)c2c(ccc(I)c2Cl)NC1=O]

a) tert-butyl N-[(1S)-2-[3-chloro-2-(2,6-difluorobenzoyl)-4-iodo-anilino]-1-methyl-2-oxo-ethyl]carbamate In analogy to experiment of building block M a, (6-amino-2-chloro-3-iodo-phenyl)-(2,6-difluorophenyl)methanone using (2S)-2-(tert-butoxycarbonylamino)propanoic acid was converted into the title compound (5.8 g, 81%) which was obtained as a yellow solid. MS: 465.0 ([M−C$_4$H$_8$—CO$_2$+H]$^+$), 509.0 ([M−C$_4$H$_8$+H]$^+$), ESI pos.

b) (2S)-2-amino-N-[3-chloro-2-(2,6-difluorobenzoyl)-4-iodo-phenyl]propanamide

In analogy to experiment of building block M b, tert-butyl N-[(1S)-2-[3-chloro-2-(2,6-difluorobenzoyl)-4-iodo-anilino]-1-methyl-2-oxo-ethyl]carbamate was converted into the title compound (4.7 g, 99%) which was obtained as a yellow solid. The crude was used as such in the following step without further characterization.

c) (3S)-6-chloro-5-(2,6-difluorophenyl)-7-iodo-3-methyl-1,3-dihydro-1,4-benzodiazepin-2-one In analogy to experiment of building block M c, (2S)-2-amino-N-[3-chloro-2-(2,6-difluorobenzoyl)-4-iodo-phenyl]propanamide was converted into the title compound (3.8 g, 94%) which was obtained as a yellow solid. MS: 446.8 ({$^{35}$Cl} [M+H]$^+$), ESI pos.

Building Block V (3S)-6-chloro-5-(2,6-difluorophenyl)-3-methyl-7-(trifluoromethyl)-1,3-dihydro-1,4-benzodiazepin-2-one

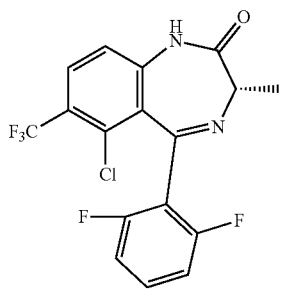 [SMILES: C[C@@H]1N=C(c2c(F)cccc2F)c2c(ccc(C(F)(F)F)c2Cl)NC1=O]

A mixture of (3S)-6-chloro-5-(2,6-difluorophenyl)-7-iodo-3-methyl-1,3-dihydro-1,4-benzodiazepin-2-one (building block S, 14.0 g, 31.35 mmol), methyl 2,2-difluoro-2-(fluorosulfonyl)acetate (18.1 g, 94.0 mmol) and copper (I) iodide (11.9 g, 62.7 mmol) in N,N-dimethylformamide (140 mL) and hexamethylphosphoric triamide (70 mL) was stirred under nitrogen at 70° C. for 16 h. The reaction mixture was poured into ice-water (150 mL) and the aqueous layer was extracted with ethyl acetate (4×150 mL). The combined organic layers were dried (Na$_2$SO$_4$) and concentrated in vacuo. The residue was purified by preparative HPLC (Phenomenex luna C18, water containing 0.1% trifluoroacetic acid/acetonitrile) followed by chiral SFC (Daicel Chiralcel OJ, ethanol containing 0.1% aqueous ammonia) to afford the title compound (4.2 g, 33%) as a yellow solid. MS: 389.1 ([{$^{35}$Cl} M+H]$^+$), ESI pos. $^1$H NMR (CDCl$_3$, 400 MHz) δ: 8.71 (s, 1H), 7.81 (d, J=8.6 Hz, 1H), 7.34 (tt, J=6.3, 8.4 Hz, 1H), 7.18 (d, J=8.5 Hz, 1H), 7.08-6.58 (m, 2H), 3.97 (q, J=6.4 Hz, 1H), 1.79 (d, J=6.4 Hz, 3H).

Building Block W 6-chloro-5-(2,6-difluorophenyl)-7-(trifluoromethyl)-1,3-dihydro-1,4-benzodiazepin-2-one

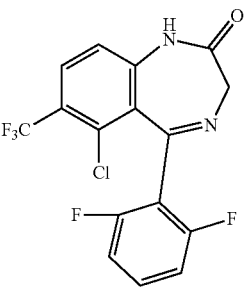 [SMILES: O=C1CN=C(c2c(F)cccc2F)c2c(ccc(C(F)(F)F)c2Cl)N1]

In analogy to experiment of building block V, 6-chloro-5-(2,6-difluorophenyl)-7-iodo-1,3-dihydro-1,4-benzodiazepin-2-one (building block H) was converted into the title compound (1.9 g, 55%) which was obtained as a white solid. MS: 375.2 ([{$^{35}$Cl} M+H]$^+$), ESI pos.

Building Block X (3S)-6-chloro-5-(3-fluoro-2-pyridyl)-3-methyl-7-(trifluoromethyl)-1,3-dihydro-1,4-benzodiazepin-2-one

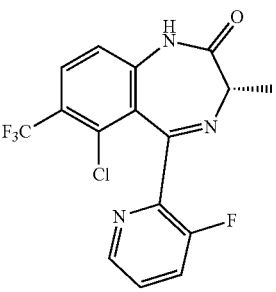 [SMILES: C[C@@H]1N=C(c2ncccc2F)c2c(ccc(C(F)(F)F)c2Cl)NC1=O]

a) [6-bromo-2-chloro-3-(trifluoromethyl)phenyl]-(3-fluoro-2-pyridyl)methanol To a solution of 4-bromo-2-chloro-1-(trifluoromethyl)benzene (100.00 g, 385.43 mmol) in dry tetrahydrofuran (1000 mL) was added LDA (231 mL, 462.5 mmol) dropwise. The mixture was stirred for 45 min at −60° C. under nitrogen atmosphere. A solution of 3-fluoropyridine-2-carbaldehyde (67.50 g, 539.6 mmol) in tetrahydrofuran (200 mL) was added and the reaction mixture was warmed up to 0° C., stirred for another 2 h. The reaction mixture was quenched with saturated ammonium chloride solution (500 mL), diluted with water (500 mL) and extracted with ethyl acetate (3×1.0 L). The combined organic layers were washed with brine (1.0 L), dried ($Na_2SO_4$) and concentrated in vacuo. The residue was purified by flash column chromatography (silica, petroleum ether/ethyl acetate 3:1) to afford the title compound (140 g, 95%) as a yellow oil. MS: 385.9 ([$\{^{79}Br, ^{35}Cl\}$ M+H]$^+$), 387.9 ([$\{^{81}Br, ^{35}Cl$ or $^{79}Br, ^{37}Cl\}$ M+H]$^+$), ESI pos. $^1$H NMR (CDCl$_3$, 400 MHz) δ: 8.53-8.41 (m, 1H), 7.65 (d, J=8.4 Hz, 1H), 7.51 (d, J=8.6 Hz, 1H), 7.42-7.32 (m, 2H), 6.81 (d, J=3.2 Hz, 1H), 5.93 (d, J=4.2 Hz, 1H).

b) [6-bromo-2-chloro-3-(trifluoromethyl)phenyl]-4-(3-fluoro-2-pyridyl)methanone A mixture of [6-bromo-2-chloro-3-(trifluoromethyl)phenyl]-(3-fluoro-2-pyridyl)methanol (140.0 g, 364.1 mmol) and manganese dioxide (158.2 g, 1820 mmol) in dichloromethane (1000 mL) was stirred at 25° C. for 48 h. The reaction mixture was filtered and the filtrate was concentrated in vacuo to afford the title compound (120 g, 86%) as an off-white solid which was used in the following step without further purification. MS: 383.9 ([$\{^{79}Br, ^{35}Cl\}$ M+H]$^+$), 385.9 ([$\{^{81}Br, ^{35}Cl$ or $^{79}Br, ^{37}Cl\}$ M+H]$^+$), ESI pos.

c) [6-(benzhydrlideneamino)-2-chloro-3-(trifluoromethyl)phenyl]-(3-fluoro-2-pyridyl)methanone A mixture of [6-bromo-2-chloro-3-(trifluoromethyl)phenyl]-(3-fluoro-2-pyridyl)methanone (40.0 g, 104.6 mmol), diphenylmethanimine (37.9 g, 209.1 mmol), cesium carbonate (68.14 g, 209.13 mmol), 2,2'-bis(diphenylphosphino)-1,1'-binaphthalene (13.01 g, 20.91 mmol) and tris(dibenzylideneacetone)dipalladium(0) (4.79 g, 5.23 mmol) in N,N-dimethylformamide (400 mL) was stirred under nitrogen at 100° C. for 12 h. The reaction mixture was cooled, diluted with water (800 mL) and extracted with ethyl acetate (3×500 mL). The combined organic layers were washed with brine (2×500 mL), dried ($Na_2SO_4$) and concentrated in vacuo. The residue (together with another two parallel batches) was purified by flash column chromatography (silica, petroleum ether/ethyl acetate, 3:1) to afford the title compound (88 g, 58%) as a yellow solid. MS: 483.1 ([$\{^{35}Cl\}$ M+H]$^+$), 485.1 ([$\{^{37}Cl\}$ M+H]$^+$), ESI pos.

d) [6-amino-2-chloro-3-(trifluoromethyl)phenyl]-(3-fluoro-2-pyridyl)methanone To a solution of [6-(benzhydrylideneamino)-2-chloro-3-(trifluoromethyl)phenyl]-(3-fluoro-2-pyridyl)methanone (88.0 g, 182.2 mmol) in tetrahydrofuran (500 mL) and water (500 mL), was added concentrated aqueous hydrochloric acid (200 mL). The mixture was stirred at 20° C. for 1 h. Sodium carbonate was added slowly until pH>7. The mixture was extracted with ethyl acetate (3×500 mL). The combined organic layers were washed with brine (500 mL), dried ($Na_2SO_4$) and concentrated in vacuo. The residue was purified by flash column chromatography (petroleum ether/ethyl acetate: 1:1) to afford the title compound (46 g, 79%) as a yellow solid. MS: 319.0 ([$\{^{35}Cl\}$ M+H]$^+$), 321.0 ([$\{^{37}Cl\}$ M+H]$^+$), ESI pos.

e) tert-butyl N-[(1S)-2-[3-chloro-2-(3-fluoropyridine-2-carbonyl)-4-(trifluoromethyl)anilino]-1-methyl-2-oxo-ethyl]carbamate In analogy to experiment of building block M a, [6-amino-2-chloro-3-(trifluoromethyl)phenyl]-(3-fluoro-2-pyridyl)methanone was converted into the title compound (15 g, 62%) which was obtained as a yellow solid. MS: 434.0 ([$\{^{35}Cl\}$ M−C$_4$H$_8$+H]$^+$), 436.0 ([$\{^{37}Cl\}$ M−C$_4$H$_8$+H]$^+$), ESI pos.

f) (2S)-2-amino-N-[3-chloro-2-(3-fluoropyridine-2-carbonyl)-4-(trifluoromethyl)phenyl]propanamide In analogy to experiment of building block M b, tert-butyl N-[(1S)-2-[3-chloro-2-(3-fluoropyridine-2-carbonyl)-4-(trifluoromethyl)anilino]-1-methyl-2-oxo-ethyl]carbamate was converted into the title compound (32 g, 97%) which was obtained as a brown oil. MS: 389.9 ([$\{^{35}Cl\}$ M+H]$^+$), 391.9 ([$\{^{35}Cl\}$ M+H]$^+$), ESI pos.

g) (3S)-6-chloro-5-(3-fluoro-2-pyridyl)-3-methyl-7-(trifluoromethyl)-1,3-dihydro-1,4-benzodiazepin-2-one In analogy to experiment of building block M c, (2S)-2-amino-N-[3-chloro-2-(3-fluoropyridine-2-carbonyl)-4-(trifluoromethyl)phenyl]propanamide was converted into the title compound (13 g, 36%) which was obtained as a red solid. MS: 372.1 ([$\{^{35}Cl\}$ M+H]$^+$), 374.1 ([$\{^{35}Cl\}$ M+H]$^+$), ESI pos.

EXAMPLES

Example 1

(7,8-dichloro-6-(2-fluorophenyl)-4H-benzo[f]imidazo[1,2-a][1,4]diazepin-2-yl)(3-methoxyazetidin-1-yl)methanone

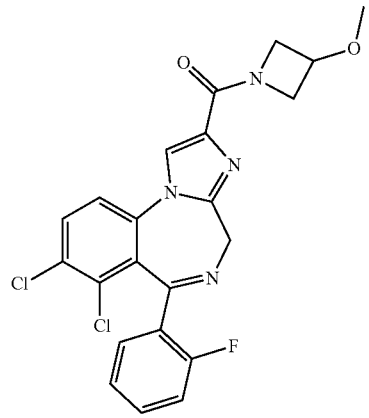 [SMILES: COC1CN(C(=O)c2cn3c(n2)CN=C(c2ccccc2F)c2c-3ccc(Cl)c2Cl)C1]

a) 6,7-dichloro-5-(2-fluorophenyl)-1,3-dihydro-1,4-benzodiazepine-2-thione

To a solution of 6,7-dichloro-5-(2-fluorophenyl)-1,3-dihydro-1,4-benzodiazepin-2-one (building block C, 3.22 g, 9.96 mmol) in diglyme (40 mL) was added phosphorus pentasulfide (3.32 g, 14.9 mmol) and sodium bicarbonate (2.51 g, 29.9 mmol). The reaction mixture was stirred at 80° C. for 4 d and then poured into ice (200 mL), stirred for 30 min and extracted with ethyl acetate (2×125 mL). The combined organic layers were washed with aqueous sodium bicarbonate (1.0 m, 125 mL) and brine (125 mL), dried (Na$_2$SO$_4$) and concentrated in vacuo. The crude material was purified by flash column chromatography (silica, heptane/ethyl acetate 1:0 to 3:1) to afford the title compound (2.62 g, 78%) as an orange solid. MS: 339.0 ([{$^{35}$Cl, $^{35}$Cl} M+H]$^+$), 341.0 ([{$^{35}$Cl, $^{37}$Cl} M+H]$^+$), ESI pos.

b) 6,7-dichloro-5-(2-fluorophenyl)-3H-1,4-benzodiazepin-2-amine

To a solution of aqueous ammonia (25%, 21.1 g, 23.4 mL, 310 mmol) in methanol (7 mL) was added a solution of 6,7-dichloro-5-(2-fluorophenyl)-1,3-dihydro-1,4-benzodiazepine-2-thione (1.4 g, 4.13 mmol) in tetrahydrofuran (28 mL). The reaction mixture was stirred at room temperature for 5 d. The organic solvents were removed in vacuo, the precipitated solid was filtered, washed with water (3×20 mL) and dried in vacuo to afford the title compound (1.30 g, 98%) as a brown solid. MS: 322.1 ([{$^{35}$Cl, $^{35}$Cl} M+H]$^+$), 324.1 ([{$^{35}$Cl, $^{37}$Cl} M+H]$^+$), ESI pos.

c) ethyl 3-[6,7-dichloro-5-(2-fluorophenyl)-2-imino-3H-1,4-benzodiazepin-1-yl]-2-oxo-propanoate To a solution of 6,7-dichloro-5-(2-fluorophenyl)-3H-1,4-benzodiazepin-2-amine (1.20 g, 3.71 mmol) in tetrahydrofuran (27 mL) was added N,N-diisopropylethylamine (960 mg, 1.3 mL, 7.42 mmol) followed by ethyl 3-bromo-2-oxopropanoate (1.61 g, 1.04 mL, 7.42 mmol). The reaction mixture was stirred at room temperature for 3 d, then treated with saturated aqueous sodium bicarbonate (100 mL) and extracted with ethyl acetate (2×100 mL). The combined organic layers were washed with half-concentrated brine (100 mL), dried (Na$_2$SO$_4$), filtered and concentrated in vacuo. The residue was purified by flash column chromatography (silica, heptane/ethyl acetate 4:6 to 1:0, then dichloromethane/methanol 1:0 to 9:1) to afford the title compound (371 mg, 23%) as a light brown solid. MS: 436.2 ([{$^{35}$Cl, $^{35}$Cl} M+H]$^+$), 438.2 ([{$^{35}$Cl, $^{37}$Cl} M+H]$^+$), ESI pos.

d) ethyl 7,8-dichloro-6-(2-fluorophenyl)-4H-benzo[f]imidazo[1,2-a][1,4]diazepine-2-carboxylate A solution of ethyl 3-[6,7-dichloro-5-(2-fluorophenyl)-2-imino-3H-1,4-benzodiazepin-1-yl]-2-oxo-propanoate (317 mg, 0.727 mmol) in acetic acid (6 mL) was stirred at 118° C. for 45 min. The reaction mixture was concentrated in vacuo. The residue was treated with saturated aqueous sodium bicarbonate (20 mL) and extracted with ethyl acetate (2×20 mL). The combined organic layers were dried (Na$_2$SO$_4$), filtered and concentrated in vacuo. The residue was purified by flash column chromatography (silica, heptane/ethyl acetate 4:1 to 1:9) followed by preparative HPLC (YMC-Triart C18, water containing 0.1% triethylamine/acetonitrile) to afford the title compound (151 mg, 50%) as a white solid. MS: 418.2 ([{$^{35}$Cl, $^{35}$Cl} M+H]$^+$), 420.2 ([{$^{35}$Cl, $^{37}$Cl} M+H]$^+$), ESI pos.

e) 7,8-dichloro-6-(2-fluorophenyl-4H-benzo[f]imidazo[1,2-a][1,4]diazepine-2-carboxylic acid To a suspension of ethyl 7,8-dichloro-6-(2-fluorophenyl)-4H-benzo[f]imidazo[1,2-a][1,4]diazepine-2-carboxylate (130 mg, 0.311 mmol) in methanol (1.5 mL) and tetrahydrofuran (3 mL) was added aqueous lithium hydroxide (1.0 m, 0.47 mL, 0.47 mmol). The reaction mixture was stirred at room temperature for 24 h. The reaction mixture was quenched with aqueous hydrochloric acid (1.0 m, 0.78 mL, 0.78 mmol). The solvent was concentrated in vacuo and the residue was suspended in water (4 mL). The suspension was filtered, washed with water (2×3 mL) and dried in vacuo to afford the title compound (117 mg, 97%) as a white solid. MS: 388.2 ([{$^{35}$Cl, $^{35}$Cl} M–H]$^-$), 390.2 ([{$^{35}$Cl, $^{37}$Cl} M–H]$^-$), ESI neg.

f) (7,8-dichloro-6-(2-fluorophenyl-4H-benzo[f]imidazo[1,2-a][1,4]diazepin-2-yl)(3-methoxyazetidin-1-yl)methanone To a suspension of 7,8-dichloro-6-(2-fluorophenyl)-4H-benzo[f]imidazo[1,2-a][1,4]diazepine-2-carboxylic acid (35 mg, 0.090 mmol) in dichloromethane (0.7 mL) was added triethylamine (27.2 mg, 37.5 µl, 0.269 mmol), followed by N-(3-dimethylaminopropyl)-N'-ethylcarbodiimide hydrochloride (18.9 mg, 0.099 mmol) and 1-hydroxybenzotriazole hydrate (15.1 mg, 0.099 mmol). The reaction mixture was stirred at room temperature for 30 min. Then, 3-methoxyazetidine hydrochloride (13.3 mg, 0.108 mmol) was added and the reaction mixture was stirred at room temperature for 24 h, then quenched with aqueous hydrochloric acid (1.0 m, 10 mL) and extracted with dichloromethane (3×10 mL). The combined organic layers were washed with aqueous sodium carbonate (10%, 10 mL), dried (Na$_2$SO$_4$), filtered and concentrated in vacuo. The residue was purified by flash column chromatography (silica, heptane/ethyl acetate 1:1 to 0:1) to afford the title compound (21 mg, 51%) as a white solid. MS: 459.3 ([{$^{35}$Cl, $^{35}$Cl} M+H]$^+$), 461.3 ([{$^{35}$Cl, $^{35}$Cl} M+H]$^+$), ESI pos.

Example 2

(7,8-dichloro-6-(2,6-difluorophenyl)-4H-benzo[f]imidazo[1,2-a][1,4]diazepin-2-yl)(3-methoxyazetidin-1-yl)methanone

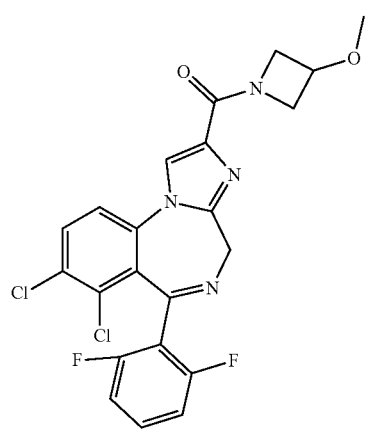 [SMILES: COC1CN(C(=O)c2cn3c(n2)CN=C(c2c(F)cccc2F)c2c-3ccc(Cl)c2Cl)C1]

a) 6,7-dichloro-5-(2,6-difluorophenyl)-1,3-dihydro-1,4-benzodiazepin-2-thione

In analogy to experiment of example 1 a, 6,7-dichloro-5-(2,6-difluorophenyl)-1,3-dihydro-1,4-benzodiazepin-2-one (building block D) was converted into the title compound (2.1 g, quantitative) which was obtained as a red oil. MS: 357.0 ([{$^{35}$Cl, $^{35}$Cl} M+H]$^+$), 359.0 ([{$^{35}$Cl, $^{37}$Cl} M+H]$^+$), ESI pos.

b) 6,7-dichloro-5-(2,6-difluorophenyl)-3H-1,4-benzodiazepin-2-amine

In analogy to experiment of example 1 b, 6,7-dichloro-5-(2,6-difluorophenyl)-1,3-dihydro-1,4-benzodiazepin-2-thione was converted into the title compound (215 mg, 63%) which was obtained as a brown solid. MS: 340.2 ([{$^{35}$Cl, $^{35}$Cl} M+H]$^+$), 342.2 ([{$^{35}$Cl, $^{35}$Cl} M+H]$^+$), ESI pos.

c) ethyl 3-[6,7-dichloro-5-(2,6-difluorophenyl)-2-imino-3H-1,4-benzodiazepin-1-yl]-2-oxo-propanoate In analogy to experiment of example 1 c, 6,7-dichloro-5-(2,6-difluorophenyl)-3H-1,4-benzodiazepin-2-amine was converted into the title compound (76 mg, 27%) which was obtained as an orange foam. MS: 454.1 ([{$^{35}$Cl, $^{35}$Cl} M+H]$^+$), 456.1 ([{$^{35}$Cl, $^{37}$Cl} M+H]$^+$), ESI pos.

d) ethyl 7,8-dichloro-6-(2,6-difluorophenyl)-4H-benzo[f]imidazo[1,2-a][1,4]diazepine-2-carboxylate In analogy to experiment of example 1 d, ethyl 3-[6,7-dichloro-5-(2,6-difluorophenyl)-2-imino-3H-1,4-benzodiazepin-1-yl]-2-oxo-propanoate was converted into the title compound (348 mg. 73%) which was obtained as an off-white solid. MS: 436.2 ([{$^{35}$Cl, $^{35}$Cl} M+H]$^+$), 438.2 ([{$^{35}$Cl, $^{35}$Cl} M+H]$^+$), ESI pos.

e) 7,8-dichloro-6-(2,6-difluorophenyl)-4H-benzo[f]imidazo[1,2-a][1,4]diazepine-2-carboxylic acid In analogy to experiment of example 1 e, ethyl 7,8-dichloro-6-(2,6-difluorophenyl)-4H-benzo[f]imidazo[1,2-a][1,4]diazepine-2-carboxylate was converted into the title compound (296 mg, 91%) which was obtained as an off-white solid. MS: 408.2 ([{$^{35}$Cl, $^{35}$Cl} M+H]$^+$), 410.2 ([{$^{35}$Cl, $^{37}$Cl} M+H]$^+$), ESI pos.

f) (7,8-dichloro-6-(2,6-difluorophenyl)-4H-benzo[f]imidazo[1,2-a][1,4]diazepin-2-yl)(3-methoxyazetidin-1-yi)methanone In analogy to experiment of example 1 f, 7,8-dichloro-6-(2,6-difluorophenyl)-4H-benzo[f]imidazo[1,2-a][1,4]diazepine-2-carboxylic acid was converted into the title compound (33 mg, 40%) which was obtained as a white solid. MS: 477.3 ([{$^{35}$Cl, $^{35}$Cl} M+H]$^+$), 479.3 ([{$^{35}$Cl, $^{35}$Cl} M+H]$^+$), ESI pos.

Example 3

8-bromo-7-chloro-2-(difluoromethyl)-6-(2,6-difluorophenyl)-4H-benzo[f]imidazo[1,2-a][1,4]diazepine

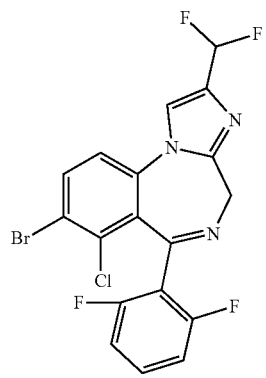 [SMILES: Fc1cccc(F)c1C1=NCc2nc(C(F)F)cn2-c2ccc(Br)c(Cl)c21]

a) 7-bromo-6-chloro-5-(2,6-difluorophenyl)-1,3-dihydro-1,4-benzodiazepine-2-thione To a solution of 7-bromo-6-chloro-5-(2,6-difluorophenyl)-1,3-dihydro-1,4-benzodiazepin-2-one (building block A, 777 mg, 2.02 mmol) in toluene (14 mL) was added Lawesson's reagent (489 mg, 1.21 mmol). The reaction mixture was stirred at 120° C. for 3 h, then concentrated in vacuo. The crude material was purified by flash column chromatography (silica, heptane/ethyl acetate 1:0 to 4:1) to afford the title compound (510 mg, 63%) as a light yellow powder. MS: 403.1 ([{$^{79}$Br, $^{35}$Cl} M+H]$^+$), 405.0 ([{$^{81}$Br, $^{35}$Cl or $^{79}$Br, $^{35}$Cl} M+H]$^+$), ESI pos.

b) 7-bromo-6-chloro-5-(2,6-difluorophenyl)-3H-1,4-benzodiazepin-2-amine

In analogy to experiment of example 1 b, 7-bromo-6-chloro-5-(2,6-difluorophenyl)-1,3-dihydro-1,4-benzodiazepine-2-thione was converted into the title compound (236 mg, 82%) which was obtained as a light yellow powder. MS: 386.0 ([{$^{79}$Br, $^{35}$Cl} M+H]$^+$), 388.1 ([{$^{81}$Br, $^{35}$Cl or $^{79}$Br, $^{37}$Cl} M+H]$^+$), ESI pos.

c) ethyl 3-[7-bromo-6-chloro-5-(2,6-difluorophenyl)-2-imino-3H-1,4-benzodiazepin-1-yl]-2-oxo-propanoate In analogy to experiment of example 1 c, 7-bromo-6-chloro-5-(2,6-difluorophenyl)-3H-1,4-benzodiazepin-2-amine was converted into the title compound (80 mg, 13%) which was obtained as a light yellow powder. MS: 500.1 ([{$^{79}$Br, $^{35}$Cl} M+H]$^+$), 502.1 ([{$^{81}$Br, $^{35}$Cl or $^{79}$Br, $^{37}$Cl} M+H]$^+$), ESI pos.

d) ethyl 8-bromo-7-chloro-6-(2,6-difluorophenyl)-4H-benzo[f]imidazo[1,2-a][1,4]diazepine-2-carboxylate In analogy to experiment of example 1 d, ethyl 3-[7-bromo-6-chloro-5-(2,6-difluorophenyl)-2-imino-3H-1,4-benzodiazepin-1-yl]-2-oxo-propanoate was converted into the title compound (15 mg, 45%) which was obtained as a white powder. MS: 482.1 ([{$^{79}$Br, $^{35}$Cl} M+H]$^+$), 484.1 ([{$^{81}$Br, $^{35}$Cl or $^{79}$Br, $^{37}$Cl} M+H]$^+$), ESI pos.

e) 8-bromo-7-chloro-6-(2,6-difluorophenyl)-4H-benzo[f]imidazo[1,2-a][1,4]diazepine-2-carboxylic acid To a suspension of ethyl 8-bromo-7-chloro-6-(2,6-difluorophenyl)-4H-benzo[f]imidazo[1,2-a][1,4]diazepine-2-carboxylate (20 mg, 0.042 mmol) in methanol (0.3 mL) was added aqueous sodium hydroxide (1.0 m, 0.125 mL, 0.125 mmol). The reaction mixture was stirred at 50° C. for 2 h. The mixture was cooled and treated with aqueous hydrochloric acid (1.0 m, 0.51 mL, 0.51 mmol). The resulting suspension was stirred at room temperature for 20 min, filtered and the solid was dried in vacuo to afford the title compound (17 mg, 90%) as a light yellow powder. MS: 453.0 ([{$^{79}$Br, $^{35}$Cl} M+H]$^+$), 455.0 ([{$^{81}$Br, $^{35}$Cl or $^{79}$Br, $^{37}$Cl} M+H]$^+$), ESI pos.

f) 8-bromo-7-chloro-6-(2,6-difluorophenyl-N-methoxy-N-methyl-4H-benzo[f]imidazo[1,2-a][1,4]diazepine-2-carboxamide In analogy to experiment of example 1 f, 8-bromo-7-chloro-6-(2,6-difluorophenyl)-4H-benzo[f]imidazo[1,2-a][1,4]diazepine-2-carboxylic acid using N,O-dimethylhydroxylamine hydrochloride was converted into the title compound (26 mg, 89%) which was obtained as a light yellow viscous oil and used as such without further purification. MS: 497.1 ([{$^{79}$Br, $^{35}$Cl} M+H]$^+$), 499.1 ([{$^{81}$Br, $^{35}$Cl or $^{79}$Br, $^{37}$Cl} M+H]$^+$), ESI pos.

g) 8-bromo-7-chloro-6-(2,6-difluorophenyl)-4H-benzo[f]imidazo[1,2-a][1,4]diazepine-2-carbaldehyde A solution of 8-bromo-7-chloro-6-(2,6-difluorophenyl)-N-methoxy-N-methyl-4H-benzo[f]imidazo[1,2-a][1,4]diazepine-2-carboxamide (26.4 mg, 0.053 mmol) in tetrahydrofuran (0.5 mL) was cooled to −78° C. Diisobutylaluminium hydride solution (1.0 m, 0.48 mL, 0.48 mmol) was added dropwise. The reaction mixture was stirred at −78° C. over 30 min and then quenched with aqueous potassium sodium tartrate tetrahydrate (20%). The mixture was stirred at room temperature overnight. The aqueous solution was extracted with ethyl acetate (3×10 mL). The combined organic layers were washed with brine (20 mL), dried (Na$_2$SO$_4$), filtered and concentrated in vacuo to afford the title compound (17 mg, 73%) as an orange waxy solid. MS: 434.3 ([{$^{79}$Br, $^{35}$Cl} M−H]$^+$), ESI neg.

h) 8-bromo-7-chloro-2-(difluoromethyl)-6-(2,6-difluorophenyl)-4H-benzo[f]imidazo[1,2-a][1,4]diazepine To a solution of 8-bromo-7-chloro-6-(2,6-difluorophenyl)-4H-benzo[f]imidazo[1,2-a][1,4]diazepine-2-carbaldehyde (17 mg, 0.039 mmol) in dichloromethane (1 mL) was added N,N-diethylaminosulfur trifluoride (9.9 mg, 8.1 µL, 0.058 mmol). The mixture was stirred at room temperature for 2 days. Another portion of N,N-diethylaminosulfur trifluoride (19 mg, 16 µL, 0.117 mmol) was added and the reaction mixture was stirred at room temperature for another day. The reaction mixture was quenched with water, followed by addition of an aqueous sodium bicarbonate solution. The aqueous layer was extracted with dichloromethane (2×10 mL). The combined organic layers were washed with brine (15 mL), dried (Na$_2$SO$_4$) and concentrated in vacuo. The crude material was purified by flash column chromatography (silica, heptane/ethyl acetate 1:0 to 1:1). A second purification with the same conditions was needed to afford the title compound (18 mg, 23%) as a yellow viscous oil. MS: 460.0 ([{$^{79}$Br, $^{35}$Cl} M+H]$^+$), 462.1 ([{$^{81}$Br, $^{35}$Cl or $^{79}$Br, $^{37}$Cl} M+H]$^+$), ESI pos.

Example 4

(8-bromo-7-chloro-6-(2,6-difluorophenyl)-4H-benzo[f]imidazo[1,2-a][1,4]diazepin-2-yl)methanol

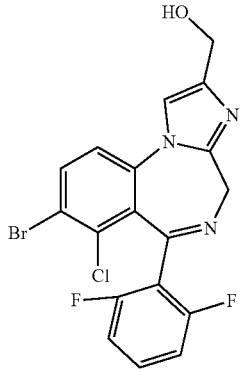 [SMILES: OCc1cn2c(n1)CN=C(c1c(F)cccc1F)c1c-2ccc(Br)c1Cl]

To a suspension of 7-bromo-6-chloro-5-(2,6-difluorophenyl)-3H-1,4-benzodiazepin-2-amine (100 mg, 0.260 mmol) and 1,3-dichloropropan-2-one (38.2 mg, 0.286 mmol) in 1,4-dioxane (1.5 mL) was added sodium bicarbonate (21.8 mg, 0.260 mmol). The reaction mixture was stirred at 100° C. for 6 h. Aqueous sodium hydroxide (1.0 m, 0.65 mL, 0.65 mmol) was added dropwise and the mixture was stirred at 100° C. for another hour, then concentrated in vacuo. Water was added and the aqueous layer was extracted with dichloromethane. The combined organic layers were dried (Na$_2$SO$_4$), concentrated in vacuo and the crude material was purified by flash column chromatography (silica, dichloromethane/methanol 1:0 to 19:1) to afford the title compound (15 mg, 13%) as an orange powder. MS: 440.1 [M+H]+, ESI pos. MS: 440.0 ([{$^{79}$Br, $^{35}$Cl} M+H]$^+$), 442.1 ([{$^{81}$Br, $^{35}$Cl or $^{79}$Br, $^{37}$Cl} M+H]$^+$), ESI pos.

Example 5

7,8-dichloro-6-(2,6-difluorophenyl)-2-(methoxymethyl)-4H-benzo[f]imidazo[1,2-a][1,4]diazepine

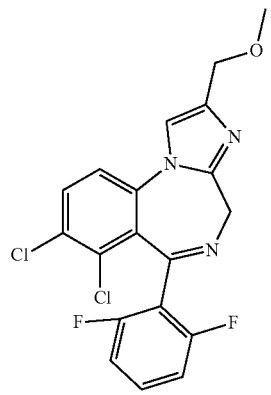 [SMILES: COCc1cn2c(n1)CN=C(c1c(F)cccc1F)c1c-2ccc(Cl)c1Cl]

a) 7,8-dichloro-2-(chloromethyl)-6-(2,6-difluorophenyl)-4H-benzo[f]imidazo[1,2-a][1,4]diazepine To a suspension of 6,7-dichloro-5-(2,6-difluorophenyl)-3H-1,4-benzodiazepin-2-amine (250 mg, 0.735 mmol) and 1,3-dichloropropan-2-one (118 mg, 0.882 mmol) in 1,4-dioxane (3.75 mL) was added sodium bicarbonate (67.9 mg, 0.808 mmol) and the mixture was stirred at 100° C. for 16 h. The reaction mixture was concentrated in vacuo. Water was added and the aqueous layer was extracted with dichloromethane. The combined organic layers were dried ($Na_2SO_4$) and concentrated in vacuo. The crude material was purified by flash column chromatography (silica, dichloromethane/methanol 1:0 to 97:3) to afford the title compound (90 mg, 30%) as a light brown solid. MS: 413.8 ($[\{^{35}Cl, ^{35}Cl, ^{35}Cl\}$ M+H]$^+$), 416.0 ($[\{^{35}Cl, ^{35}Cl, ^{37}Cl\}$ M+H]$^+$).

b) 7,8-dichloro-6-(2,6-difluorophenyl)-2-(methoxymethyl)-4H-benzo[f]imidazo[1,2-a][1,4]diazepine A solution of 7,8-dichloro-2-(chloromethyl)-6-(2,6-difluorophenyl)-4H-benzo[f]imidazo[1,2-a][1,4]diazepine (10 mg, 24.2 µmol) in methanol (0.300 mL) and aqueous ammonia (25%, 0.084 mL, 0.969 mmol) was heated in the microwave at 100° C. for 30 min. The reaction mixture was concentrated in vacuo and purified by flash column chromatography (silica, heptane/ethyl acetate 1:0 to 3:7) to afford the title compound (3 mg, 30%) as a white powder. MS: 408.1 ($[\{^{35}Cl, ^{35}Cl\}$ M+H]$^+$), 410.1 ($[\{^{35}Cl, ^{37}Cl\}$ M+H]$^+$), ESI pos.

Example 6

7,8-dichloro-6-(2,6-difluorophenyl)-N-methyl-4H-[1,2,4]triazolo[1,5-a][1,4]benzodiazepine-2-carboxamide

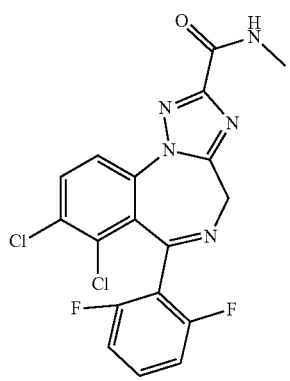 [SMILES: CNC(=O)c1nc2n(n1)-c1ccc(Cl)c(Cl)c1C(c1c(F)cccc1F)=NC2]

a) 1-amino-6,7-dichloro-5-(2,6-difluorophenyl)-3H-1,4-benzodiazepin-2-one

To a solution of 6,7-dichloro-5-(2,6-difluorophenyl)-1,3-dihydro-1,4-benzodiazepin-2-one (building block D, 500 mg, 1.47 mmol) in N,N-dimethylformamide (10 mL) was added sodium hydride (60% in mineral oil, 88 mg, 2.2 mmol) portionwise at 0-5° C. After 15 min stirring at that temperature, O-diphenylphosphinyl hydroxylamine (513 mg, 2.2 mmol) was added portionwise and the reaction mixture was stirred at 20° C. for 16 h, then filtered and washed with acetonitrile (10 mL). The filtrate was concentrated in vacuo to afford the title compound (500 mg, 96%) as a yellow solid which was used in the following step without further purification. MS: 355.8 ($[\{^{35}Cl, ^{35}Cl\}$ M−H]$^-$), ESI neg.

b) ethyl 7,8-dichloro-6-(2,6-difluorophenyl)-4H-[1,2,4]triazolo[1,5-a][1,4]benzodiazepine-2-carboxylate A mixture of 1-amino-6,7-dichloro-5-(2,6-difluorophenyl)-3H-1,4-benzodiazepin-2-one (400 mg, 1.12 mmol) and ethyl 2-amino-2-thioxo-acetate (449 mg, 3.37 mmol) in toluene (8 mL) and acetic acid (0.8 mL) was stirred at 120° C. for 12 h. The reaction mixture was cooled and concentrated in vacuo. The residue was purified by flash column chromatography (petroleum ether/ethyl acetate 5:1) followed by preparative HPLC (Phenomenex luna C18, water containing 0.1% trifluoroacetic acid/acetonitrile) to afford the title compound (100 mg, 20%) as a light pink solid. MS: 437.0 ($[\{^{35}Cl, ^{35}Cl\}$ M+H]$^+$), 439.0 ($[\{^{35}Cl, ^{37}Cl\}$ M+H]$^+$), ESI pos.

c) 7,8-dichloro-6-(2,6-difluorophenyl)-4H-[1,2,4]triazolo[1,5-a][1,4]benzodiazepine-2-carboxylic acid To a stirred solution of ethyl 7,8-dichloro-6-(2,6-difluorophenyl)-4H-[1,2,4]triazolo[1,5-a][1,4]benzodiazepine-2-carboxylate (50 mg, 0.11 mmol) in methanol (1 mL) was slowly added aqueous sodium hydroxide (1.0 m, 0.34 mL, 0.34 mmol). The reaction mixture was stirred at 20° C. for 1 h. Aqueous hydrochloric acid (1.0 m) was added slowly until pH 4-5. The suspension was filtered, washed with water (2×5 mL) and lyophilized to afford the title compound (36 mg, 76%) as a white solid. MS: 409.0 ($[\{^{35}Cl, ^{35}Cl\}$ M+H]$^+$), 411.0 ($[\{^{35}Cl, ^{37}Cl\}$ M+H]$^+$), ESI pos.

d) 7,8-dichloro-6-(2,6-difluorophenyl-N-methyl-4H-[1,2,4]triazolo[1,5-a][1,4]benzodiazepine-2-carboxamide A mixture of 7,8-dichloro-6-(2,6-difluorophenyl)-4H-[1,2,4]triazolo[1,5-a][1,4]benzodiazepine-2-carboxylic acid (50 mg, 0.12 mmol), methylamine hydrochloride (25 mg, 0.37 mmol), 1-[bis(dimethylamino)methylene]-1H-1,2,3-triazolo[4,5-b]pyridinium 3-oxide hexafluorophosphate (70 mg, 0.18 mmol) and N,N-diisopropylethylamine (0.11 mL, 0.61 mmol) in N,N-dimethylformamide (1 mL) was stirred at 20° C. for 2 h. The reaction mixture was diluted with acetonitrile (1 mL), purified by preparative HPLC (Waters Xbridge, water containing 0.05% ammonium hydroxyde/acetonitrile) and then lyophilized to afford the title compound (23 mg, 44%) as a white solid. MS: 422.1 ($[\{^{35}Cl, ^{35}Cl\}$ M+H]$^+$), 424.1 ($[\{^{35}Cl, ^{37}Cl\}$ M+H]$^+$), ESI pos.

Example 7

7,8-dichloro-6-(2,6-difluorophenyl)-N-(trideuteriomethyl)-4H-[1,2,4]triazolo[1,5-a][1,4]benzodiazepine-2-carboxamide

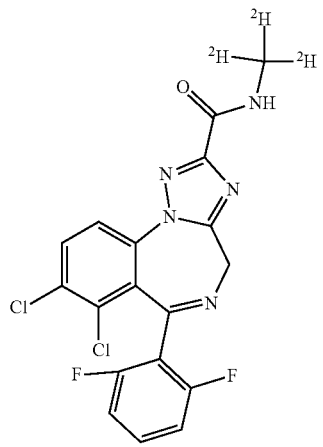 [SMILES: [2H]C([2H])([2H])NC(=O)c1nc2n(n1)-c1ccc(Cl)c(Cl)c1C(c1c(F)cccc1F)=NC2]

In analogy to experiment of example 6 d, 7,8-dichloro-6-(2,6-difluorophenyl)-4H-[1,2,4]triazolo[1,5-a][1,4]benzodiazepine-2-carboxylic acid using trideuteriomethanamine hydrochloride was converted into the title compound (32 mg, 59%) which was obtained as a white solid. MS: 425.0 ([{$^{35}$Cl, $^{35}$Cl} M+H]$^+$), 427.0 ([{$^{35}$Cl, $^{37}$Cl} M+H]$^+$), ESI pos.

Example 8 azetidin-1-yl-[7,8-dichloro-6-(2,6-difluorophenyl)-4H-[1,2,4]triazolo[1,5-a][1,4]benzodiazepin-2-yl]methanone

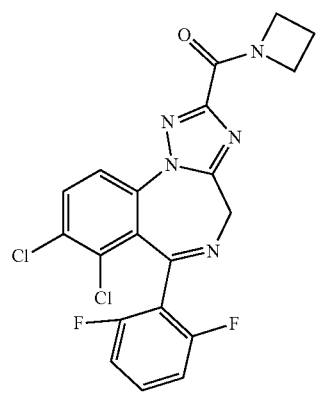 [SMILES: O=C(c1nc2n(n1)-c1ccc(Cl)c(Cl)c1C(c1c(F)cccc1F)=NC2)N1CCC1]

In analogy to experiment of example 6 d, 7,8-dichloro-6-(2,6-difluorophenyl)-4H-[1,2,4]triazolo[1,5-a][1,4]benzodiazepine-2-carboxylic acid using azetidine hydrochloride was converted into the title compound (11 mg, 20%) which was obtained as a white solid. MS: 448.1 ([{$^{35}$Cl, $^{35}$Cl} M+H]$^+$), 450.0 ([{$^{35}$Cl, $^{37}$Cl} M+H]$^+$), ESI pos.

Example 9

7,8-dichloro-6-(2,6-difluorophenyl)-N,N-dimethyl-4H-[1,2,4]triazolo[1,5-a][1,4]benzodiazepine-2-carboxamide

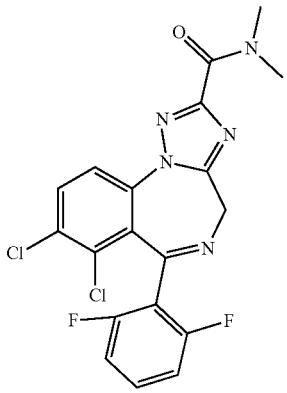 [SMILES: CN(C)C(=O)c1nc2n(n1)-c1ccc(Cl)c(Cl)c1C(c1c(F)cccc1F)=NC2]

In analogy to experiment of example 6 d, 7,8-dichloro-6-(2,6-difluorophenyl)-4H-[1,2,4]triazolo[1,5-a][1,4]benzodiazepine-2-carboxylic acid using dimethylamine hydrochloride was converted into the title compound (19 mg, 36%) which was obtained as a white solid. MS: 435.9 ([{$^{35}$Cl, $^{35}$Cl} M+H]$^+$), 437.9 ([{$^{35}$Cl, $^{37}$Cl} M+H]$^+$), ESI pos.

Example 10

7,8-dichloro-6-(2,6-difluorophenyl)-N-(oxetan-3-yl)-4H-[1,2,4]triazolo[1,5-a][1,4]benzodiazepine-2-carboxamide

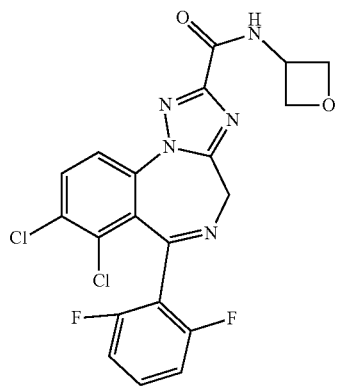 [SMILES: O=C(NC1COC1)c1nc2n(n1)-c1ccc(Cl)c(Cl)c1C(c1c(F)cccc1F)=NC2]

In analogy to experiment of example 6 d, 7,8-dichloro-6-(2,6-difluorophenyl)-4H-[1,2,4]triazolo[1,5-a][1,4]benzodiazepine-2-carboxylic acid using 3-aminooxetane was converted into the title compound (17 mg, 30%) which was obtained as a grey solid. MS: 463.9 ([{$^{35}$Cl, $^{35}$Cl} M+H]$^+$), 465.9 ([{$^{35}$Cl, $^{37}$Cl} M+H]$^+$), ESI pos.

Example 11

[7,8-dichloro-6-(2,6-difluorophenyl)-4H-[1,2,4]triazolo[1,5-a][1,4]benzodiazepin-2-yl]-(3-methoxyazetidin-1-yl)methanone

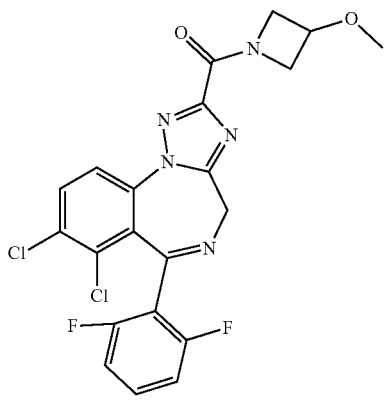 [SMILES: COC1CN(C(=O)c2nc3n(n2)-c2ccc(Cl)c(Cl)c2C(c2c(F)cccc2F)=NC3)C1]

A mixture of 3-methoxyazetidin (0.37 mL, 0.370 mmol), triethylamine (0.03 mL, 0.240 mmol), 7,8-dichloro-6-(2,6-difluorophenyl)-4H-[1,2,4]triazolo[1,5-a][1,4]benzodiazepine-2-carboxylic acid (50 mg, 0.120 mmol) and bis(2-oxo-3-oxazolidinyl)phosphinic chloride (62 mg, 0.240 mmol) in N,N-dimethylformamide (2 mL) was stirred at 20° C. for 16 h. The mixture was diluted with ethyl acetate (100 mL), washed with water (30 mL) and brine (30 mL), dried (Na$_2$SO$_4$) and concentrated in vacuo. The residue was purified by preparative HPLC (Phenomenex luna C18, water containing 0.1% trifluoroacetic acid/acetonitrile) to afford the title compound (21 mg, 36%) as a grey solid. MS: 478.0 ([{$^{35}$Cl, $^{35}$Cl} M+H]$^+$), 480.0 ([{$^{35}$Cl, $^{37}$Cl} M+H]$^+$), ESI pos.

Example 12

7,8-dichloro-6-(3-fluoro-2-pyridyl)-N-methyl-4H-imidazo[1,2-a][1,4]benzodiazepine-2-carboxamide

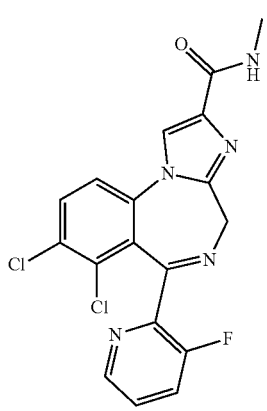 [SMILES: CNC(=O)c1cn2c(n1)CN=C(c1ncccc1F)c1c-2ccc(Cl)c1Cl]

a) 6,7-dichloro-5-(3-fluoro-2-pyridyl-1,3-dihydro-1,4-benzodiazepine-2-thione

In analogy to experiment of example 3 a, 6,7-dichloro-5-(3-fluoro-2-pyridyl)-1,3-dihydro-1,4-benzodiazepin-2-one (building block N) was converted into the title compound (108 mg, 52%) which was obtained as a yellow solid. MS: 340.0 ([{$^{35}$Cl, $^{35}$Cl} M+H]$^+$), 342.0 ([{$^{35}$Cl, $^{37}$Cl} M+H]$^+$), ESI pos.

b) 6,7-dichloro-5-(3-fluoro-2-pyridyl)-3H-1,4-benzodiazepin-2-amine

In analogy to experiment of example 1 b, 6,7-dichloro-5-(3-fluoro-2-pyridyl)-1,3-dihydro-1,4-benzodiazepine-2-thione was converted into the title compound (162 mg, 79%) which was obtained as a light yellow solid. MS: 323.0 ([{$^{35}$Cl, $^{35}$Cl} M+H]$^+$), 325.0 ([{$^{35}$Cl, $^{37}$Cl} M+H]$^+$), ESI pos.

c) methyl 7,8-dichloro-6-(3-fluoro-2-pyridyl)-4H-imidazo[1,2-a][1,4]benzodiazepine-2-carboxylate A solution of 6,7-dichloro-5-(3-fluoro-2-pyridyl)-3H-1,4-benzodiazepin-2-amine (160 mg, 0.50 mmol), methyl bromopyruvate (90 mg, 0.50 mmol) and sodium bicarbonate (42 mg, 0.50 mmol) in acetonitrile (36 mL) was stirred at 60° C. for 5 h. The solution was filtered through Celite. The filtrate was concentrated in vacuo and the residue was purified by preparative thin layer chromatography (ethyl acetate) to afford the title compound (12 mg, 6%) as a light yellow solid. MS: 405.0 ([{$^{35}$Cl, $^{35}$Cl} M+H]$^+$), 407.0 ([{$^{35}$Cl, $^{37}$Cl} M+H]$^+$), ESI pos.

d) 7,8-dichloro-6-(3-fluoro-2-pyridyl)-N-methyl-4H-imidazo[1,2-a][1,4]benzodiazepine-2-carboxamide To a solution of methylamine (1.0 m in tetrahydrofuran, 0.69 mL, 0.690 mmol) and methyl 7,8-dichloro-6-(3-fluoro-2-pyridyl)-4H-imidazo[1,2-a][1,4]benzodiazepine-2-carboxylate (28 mg, 0.070 mmol) in methanol (2 mL) was added cesium carbonate (68 mg, 0.210 mmol). The reaction mixture was stirred at 70° C. for 16 h, then concentrated in vacuo. The residue was purified by preparative TLC (dichloromethane/methanol 10:1) to afford the title compound (12 mg, 41%) as an off-white solid. MS: 404.0 ([{$^{35}$Cl, $^{35}$Cl} M+H]$^+$), 406.0 ([{$^{35}$Cl, $^{37}$Cl} M+H]$^+$), ESI pos.

Example 13

[(4S)-7,8-dichloro-6-(2,6-difluorophenyl)-4-methyl-4H-[1,2,4]triazolo[1,5-a][1,4]benzodiazepin-2-yl]methanol

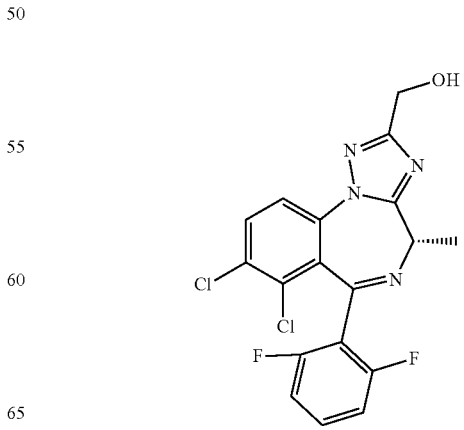

a) (3S)-1-amino-6,7-dichloro-5-(2,6-difluorophenyl)-3-methyl-3H-1,4-benzodiazepin-2-one In analogy to experiment of example 6 a, (3S)-6,7-dichloro-5-(2,6-difluorophenyl)-3-methyl-1,3-dihydro-1,4-benzodiazepin-2-one (building block M) was converted into the title compound (1.5 g, 83%) which was obtained as a light yellow oil. MS: 370.1 ([{$^{35}$Cl, $^{35}$Cl} M+H]$^+$), 372.1 ([{$^{35}$Cl, $^{35}$Cl} M+H]$^+$), ESI pos.

b) ethyl (4S)-7,8-dichloro-6-(2,6-difluorophenyl)-4-methyl-4H-[1,2,4]triazolo[1,5-a][1,4]benzodiazepine-2-carboxylate A mixture of (3S)-1-amino-6,7-dichloro-5-(2,6-difluorophenyl)-3-methyl-3H-1,4-benzodiazepin-2-one (1.5 g, 4.05 mmol) and ethyl 2-ethoxy-2-imino-acetate (1.47 g, 10.1 mmol) in 1,4-dioxane (15 mL) was stirred at 100° C. for 4 h and at 120° C. for 24 h. The mixture was cooled and another portion of ethyl 2-ethoxy-2-imino-acetate (1.47 g, 10.1 mmol) was added. The reaction was stirred at 120° C. for another 24 h, then cooled and concentrated in vacuo. The residue was purified by flash column chromatography (silica, petroleum ether/ethyl acetate 3:1) followed by preparative HPLC (Phenomenex Synergi Max-RP, water containing 0.1% trifluoroacetic acid/acetonitrile). The pure fraction was basified by addition of saturated aqueous sodium bicarbonate to pH>8 and concentrated in vacuo. The residue was extracted with ethyl acetate (3×50 mL). The combined organic layers were washed with brine (100 mL), dried (Na$_2$SO$_4$) and concentrated in vacuo to afford the title compound (800 mg, 44%) as a white solid. MS: 451.2 ([{$^{35}$Cl, $^{35}$Cl} M+H]$^+$), 453.2 ([{$^{35}$Cl, $^{37}$Cl} M+H]$^+$), ESI pos.

c) [(4S)-7,8-dichloro-6-(2,6-difluorophenyl)-4-methyl-4H-[1,2,4]triazolo[1,5-a][1,4]benzodiazepin-2-yl]methanol To a solution of ethyl (4S)-7,8-dichloro-6-(2,6-difluorophenyl)-4-methyl-4H-[1,2,4]triazolo[1,5-a][1,4]benzodiazepine-2-carboxylate (200 mg, 0.44 mmol) in tetrahydrofuran (2 mL) and methanol (2 mL) was added sodium borohydride (51 mg, 2.22 mmol) portionwise. The reaction mixture was stirred under nitrogen at 25° C. for 2 h. Saturated aqueous ammonium chloride (5 mL) was added slowly. The mixture was diluted with water (5 mL) and extracted with ethyl acetate (3×5 mL).

The combined organic layers were washed with brine (5 mL), dried (Na$_2$SO$_4$) and concentrated in vacuo. The residue was purified by chiral SFC (Daicel Chiralpak AD, ethanol containing 0.1% aqueous ammonia). The pure fraction was extracted with ethyl acetate (3×10 mL). The combined organic layers were washed with brine (10 mL), dried (Na$_2$SO$_4$) and concentrated in vacuo. The solid (100 mg) was further purified by chiral SFC (Daicel Chiralpak AD, ethanol containing 0.1% aqueous ammonia) to afford the enantiopure (−)-title compound (49 mg, 49%) as a white solid. MS: 409.0 ([{$^{35}$Cl, $^{35}$Cl} M+H]$^+$), 411.0 ([{$^{35}$Cl, $^{37}$Cl} M+H]$^+$), ESI pos.

Example 14 azetidin-1-yl-[(4S)-7,8-dichloro-6-(2,6-difluorophenyl)-4-methyl-4H-[1,2,4]triazolo[1,5-a][1,4]benzodiazepin-2-yl]methanone

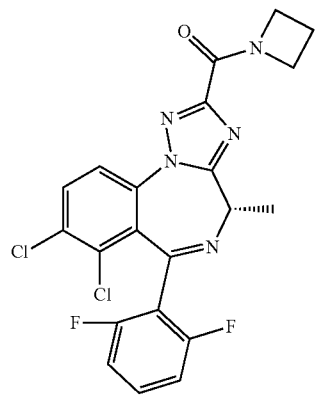 [SMILES: C[C@@H]1N=C(c2c(F)cccc2F)c2c(ccc(Cl)c2Cl)-n2nc(C(=O)N3CCC3)nc21]

a) (4S)-7,8-dichloro-6-(2,6-difluorophenyl)-4-methyl-4H-[1,2,4]triazolo[1,5-a][1,4]benzodiazepine-2-carboxylic acid In analogy to experiment of example 6 c, ethyl (4S)-7,8-dichloro-6-(2,6-difluorophenyl)-4-methyl-4H-[1,2,4]triazolo[1,5-a][1,4]benzodiazepine-2-carboxylate was converted into the title compound (140 mg, 73%) which was obtained as a white solid. MS: 423.0 ([{$^{35}$Cl, $^{35}$Cl} M+H]$^+$), 425.0 ([{$^{35}$Cl, $^{35}$Cl} M+H]$^+$), ESI pos.

b) azetidin-1-yl-[(4S)-7,8-dichloro-6-(2,6-difluorophenyl)-4-methyl-4H-[1,2,4]triazolo[1,5-a][1,4]benzodiazepin-2-yl]methanone In analogy to experiment of example 6 d, (4S)-7,8-dichloro-6-(2,6-difluorophenyl)-4-methyl-4H-[1,2,4]triazolo[1,5-a][1,4]benzodiazepine-2-carboxylic using azetidine hydrochloride was converted into the enantiopure (−)-title compound (8 mg, 13%) which was obtained as a white solid. MS: 462.0 ([{$^{35}$Cl, $^{35}$Cl} M+H]$^+$), 464.0 ([{$^{35}$Cl, $^{37}$Cl} M+H]$^+$), ESI pos.

Example 15

(4S)-7,8-dichloro-6-(2,6-difluorophenyl)-4-methyl-4H-[1,2,4]triazolo[1,5-a][1,4]benzodiazepine

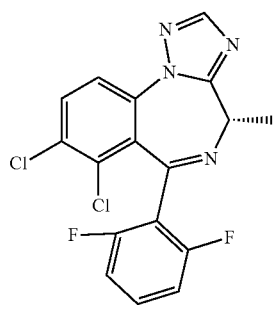 [SMILES: C[C@@H]1N=C(c2c(F)cccc2F)c2c(ccc(Cl)c2Cl)-n2ncnc21]

A mixture of 1-amino-6,7-dichloro-5-(2,6-difluorophenyl)-3-methyl-3H-1,4-benzodiazepin-2-one (300 mg, 0.81 mmol), zinc chloride (331 mg, 2.43 mmol) and formamide (1.83 g, 40.5 mmol) was stirred at 150° C. for 2 h. The reaction mixture was cooled, diluted with water (10 mL) and extracted with ethyl acetate (3×20 mL). The combined organic layers were washed with brine (20 mL), dried (Na$_2$SO$_4$) and concentrated in vacuo. The residue was purified by flash column chromatography (silica, petroleum ether/ethyl acetate 3:1) followed by preparative HPLC (Uni-Sil 3-100 C18 Ultra, water containing 0.225% formic acid/acetonitrile) and, finally, by chiral SFC (Daicel Chiralcel OJ, ethanol containing 0.1% aqueous ammonia) to afford the enantiopure (−)-title compound (46 mg, 46%) as a white solid. MS: 379.0 ([{$^{35}$Cl, $^{35}$Cl} M+H]$^+$), 381.0 ([{$^{35}$Cl, $^{37}$Cl} M+H]$^+$), ESI pos.

Example 16

[(4S)-7,8-dichloro-6-(2,6-difluorophenyl)-4-methyl-4H-[1,2,4]triazolo[1,5-a][1,4]benzodiazepin-2-yl]-(3-methoxyazetidin-1-yl)methanone

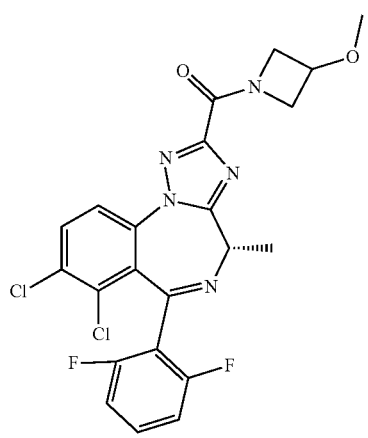 [SMILES: COC1CN(C(=O)c2nc3n(n2)-c2ccc(Cl)c(Cl)c2C(c2c(F)cccc2F)=N[C@H]3C)C1]

To a solution of (4S)-7,8-dichloro-6-(2,6-difluorophenyl)-4-methyl-4H-[1,2,4]triazolo[1,5-a][1,4]benzodiazepine-2-carboxylic acid (15 mg, 0.35 mmol) and 3-methoxyazetidine hydrochloride (219 mg, 1.77 mmol) in pyridine (3 mL) was added phosphoryl trichloride (163 mg, 1.06 mmol) portionwise at 0° C. The reaction mixture was stirred under nitrogen at 0° C. for 2 h. The reaction mixture was slowly poured into water (10 mL) and stirred for 10 min, then extracted with ethyl acetate (3×10 mL). The combined organic layers were washed with brine (2×10 mL), dried (Na$_2$SO$_4$) and concentrated in vacuo. The residue was purified by preparative HPLC (Waters Xbridge, water containing 0.05% ammonium hydroxyde/acetonitrile), followed by chiral SFC (Daicel Chiralcel OJ, methanol containing 0.1% aqueous ammonia) to afford the enantiopure (−)-title compound (33 mg, 54%) as a white solid. MS: 492.0 ([{$^{35}$Cl, $^{35}$Cl} M+H]$^+$), 494.0 ([{$^{35}$Cl, $^{37}$Cl} M+H]$^+$), ESI pos.

Example 17

[(4S)-7,8-dichloro-6-(2,6-difluorophenyl)-4-methyl-4H-[1,2,4]triazolo[1,5-a][1,4]benzodiazepin-2-yl]-[3-(trideuteriomethoxy)azetidin-1-yl]methanone

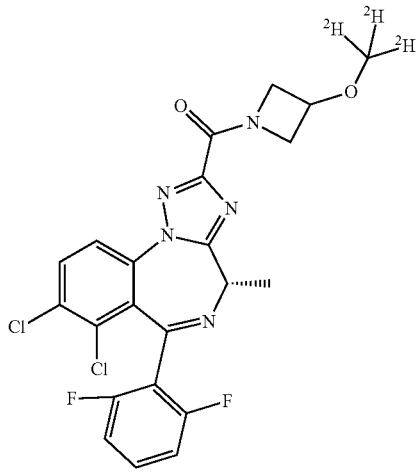 [SMILES: [2H]C([2H])([2H])OC1CN(C(=O)c2nc3n(n2)-c2ccc(Cl)c(Cl)c2C(c2c(F)cccc2F)=N[C@H]3C)C1]

A solution of (4S)-7,8-dichloro-6-(2,6-difluorophenyl)-4-methyl-4H-[1,2,4]triazolo[1,5-a][1,4]benzodiazepine-2-carboxylic acid (100 mg, 0.24 mmol) and (benzotriazol-1-yloxy)tripyrrolidinophosphonium hexafluorophosphate (184 mg, 0.35 mmol) in N,N-dimethylformamide (2 mL) was stirred at 20° C. for 15 min. 3-(trideuteriomethoxy)-azetidine trifluoroacetate (145 mg, 0.71 mmol) and N,N-diisopropylethylamine (153.0 mg, 1.18 mmol) were added and the reaction mixture was stirred at 20° C. for 2 h, then poured into ice-water (10 mL) and extracted with ethyl acetate (3×10 mL). The combined organic layers were washed with brine (2×2 mL), dried (Na$_2$SO$_4$) and concentrated in vacuo. The residue was purified by preparative HPLC (Waters Xbridge, water containing 0.05% ammonium hydroxyde/acetonitrile) followed by chiral SFC (Daicel Chiralpak IC, methanol containing 0.1% aqueous ammonia) to afford the enantiopure (−)-title compound (14 mg, 28%) as a white solid. MS: 495.2 ([{$^{35}$Cl, $^{35}$Cl} M+H]$^+$), 497.2 ([{$^{35}$Cl, $^{37}$Cl} M+H]$^+$), ESI pos.

Example 18

(4S)-7,8-dichloro-2-(difluoroethyl)-6-(2,6-difluorophenyl)-4-methyl-4H-[1,2,4]triazolo[1,5-a][1,4]benzodiazepine

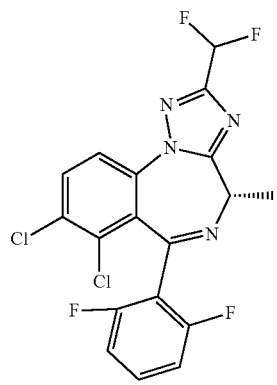 [SMILES: C[C@@H]1N=C(c2c(F)cccc2F)c2c(ccc(Cl)c2Cl)-n2nc(C(F)F)nc21]

a) (4S)-7,8-dichloro-6-(2,6-difluorophenyl)-4-methyl-4H-[1,2,4]triazolo[1,5-a][1,4]benzodiazepine-2-carbaldehyde A mixture of [(4S)-7,8-dichloro-6-(2,6-difluorophenyl)-4-methyl-4H-[1,2,4]triazolo[1,5-a][1,4]benzodiazepin-2-yl]methanol (410 mg, 1 mmol) and Dess-Martin periodinane (1.27 g, 3.01 mmol) in dichloroethane (10 mL) was stirred at 80° C. for 2 h. The mixture was cooled, filtered and concentrated in vacuo. The residue was purified by chromatography (silica, dichloromethane/methanol 20:1) to afford the title compound (300 mg, 74%) as a white solid. $^1$H NMR (CDCl$_3$, 400 MHz) δ: 10.10 (s, 1H) 7.96 (d, J=8.8 Hz, 1H), 7.82 (d, J=8.9 Hz, 1H), 7.33 (tt, J=8.4, 6.3 Hz, 1H), 6.60-7.09 (m, 2H), 4.44 (q, J=6.6 Hz, 1H), 2.15 (d, J=6.7 Hz, 3H).

b) (4S)-7,8-dichloro-2-(difluoromethyl)-6-(2,6-difluorophenyl)-4-methyl-4H-[1,2,4]triazolo[1,5-a][1,4]benzodiazepine To a solution of (4S)-7,8-dichloro-6-(2,6-difluorophenyl)-4-methyl-4H-imidazo[1,2-a][1,4]benzodiazepine-2-carbaldehyde (200 mg, 0.49 mmol) in dichloromethane (4 mL) was added diethylaminosulfur trifluoride (238 mg, 1.47 mmol) slowly at −70° C. The reaction mixture was stirred at −70° C. for 10 min, warmed up to 0° C. and stirred at that temperature for 1 h. Saturated aqueous sodium bicarbonate (5 mL) was added slowly. The mixture was diluted with water (5 mL) and extracted with dichloromethane (3×10 mL). The combined organic layers were washed with brine (20 mL), dried (Na$_2$SO$_4$) and concentrated in vacuo. The residue was purified by preparative HPLC (Phenomenex Gemini-NX C18, water containing 0.1% trifluoroacetic acid/acetonitrile) followed by chiral SFC (Daicel Chiralcel OJ, methanol containing 0.1% aqueous ammonia) to afford the enantiopure (−)-title compound (27 mg, 54%) as a white solid. MS: 429.0 ([{$^{35}$Cl, $^{35}$Cl} M+H]$^+$), 431.0 ([{$^{35}$Cl, $^{37}$Cl} M+H]$^+$), ESI pos.

Example 19

(4S)-7,8-dichlor-6-(2,6-difluorophenyl)-4-methyl-N,N-bis(trideuteriomethyl)-4H-[1,2,4]triazolo[1,5-a][1,4]benzodiazepine-2-carboxamide

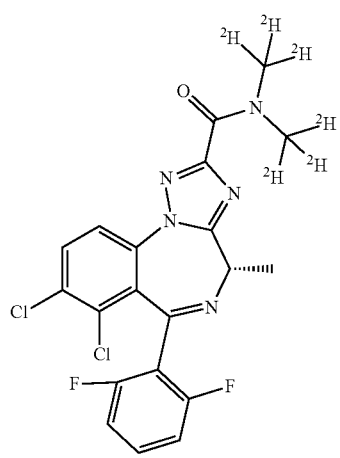 [SMILES: [2H]C([2H])([2H])N(C(=O)c1nc2n(n1)-c1ccc(Cl)c(Cl)c1C(c1c(F)cccc1F)=N[C@H]2C)C([2H])([2H])[2H]]

In analogy to experiment of example 6 d, (4S)-7,8-dichloro-6-(2,6-difluorophenyl)-4-methyl-4H-[1,2,4]triazolo[1,5-a][1,4]benzodiazepine-2-carboxylic acid using dimethylamine-d$_6$ hydrochloride was converted into the enantiopure (−)-title compound (8 mg, 8%) which was obtained as a white solid. MS: 456.0 ([{$^{35}$Cl, $^{35}$Cl} M+H]$^+$), 458.1 ([{$^{35}$Cl, $^{37}$Cl} M+H]$^+$), ESI pos.

Example 20

(4S)-7,8-dichloro-6-(2,6-difluorophenyl)-4-methyl-N-(trideuteriomethyl)-4H-[1,2,4]triazolo[1,5-a][1,4]benzodiazepine-2-carboxamide

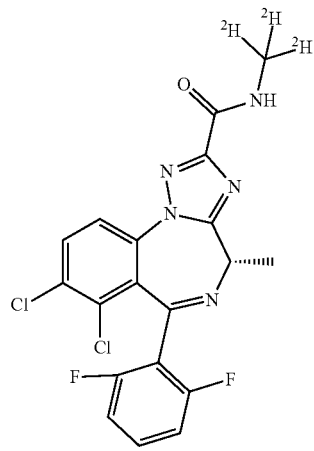 [SMILES: [2H]C([2H])([2H])NC(=O)c1nc2n(n1)-c1ccc(Cl)c(Cl)c1C(c1c(F)cccc1F)=N[C@H]2C]

In analogy to experiment of example 6 d, (4S)-7,8-dichloro-6-(2,6-difluorophenyl)-4-methyl-4H-[1,2,4]triazolo[1,5-a][1,4]benzodiazepine-2-carboxylic acid using methylamine-d$_3$ hydrochloride was converted into the enantiopure (−)-title compound (7 mg, 9%) which was obtained as a white solid. MS: 439.1 ([{$^{35}$Cl, $^{35}$Cl} M+H]$^+$), 441.0 ([{$^{35}$Cl, $^{37}$Cl} M+H]$^+$), ESI pos. $^1$H NMR (CDCl$_3$, 400 MHz) δ: 8.02 (d, J=8.8 Hz, 1H), 7.79 (d, J=8.8 Hz, 1H), 7.29-7.38 (m, 1H), 7.26 (br s, 1H), 6.56-7.09 (m, 2H), 4.38 (q, J=6.7 Hz, 1H), 2.09 (d, J=6.7 Hz, 3H).

Example 21

(4S)-7,8-dichloro-6-(2,6-difluorophenyl)-2,4-dimethyl-4H-[1,2,4]triazolo[1,5-a][1,4]benzodiazepine

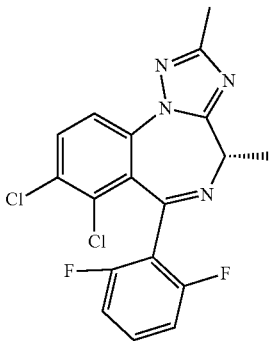 [SMILES: Cc1nc2n(n1)-c1ccc(Cl)c(Cl)c1C(c1c(F)cccc1F)=N[C@H]2C]

A mixture of (3S)-1-amino-6,7-dichloro-5-(2,6-difluorophenyl)-3-methyl-3H-1,4-benzodiazepin-2-one (200 mg, 0.54 mmol) and acetamide (160 mg, 2.7 mmol) in polyphosphoric acid (2.0 mL) was stirred at 120° C. for 2 h and at 150° C. for 6 h. The mixture was cooled and poured slowly into water (20 mL). The suspension was extracted with ethyl acetate (3×20 mL). The combined organic layers were washed with brine (20 mL), dried (Na$_2$SO$_4$) and concentrated in vacuo. The residue was purified by preparative HPLC (Phenomenex luna C18, water containing 0.1% trifluoroacetic acid/acetonitrile) followed by chiral SFC (Daicel Chiralpak AD, methanol) to afford the enantiopure (−)-title compound (18 mg, 15%) as a white solid. MS: 393.0 ([{$^{35}$Cl, $^{35}$Cl} M+H]$^+$), 395.0 ([{$^{35}$Cl, $^{37}$Cl} M+H]$^+$), ESI pos.

Example 22

(4S)-7-chloro-6-(2,6-difluorophenyl)-4-methyl-8-(trifluoromethyl)-4H-[1,2,4]triazolo[1,5-a][1,4]benzodiazepine

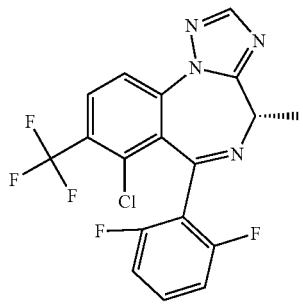 [SMILES: C[C@@H]1N=C(c2c(F)cccc2F)c2c(ccc(C(F)(F)F)c2Cl)-n2ncnc21]

a) (3S)-1-amino-6-chloro-5-(2,6-difluorophenyl)-3-methyl-7-(trifluoromethyl)-3H-1,4-benzodiazepin-2-one To a solution of (3S)-6-chloro-5-(2,6-difluorophenyl)-3-methyl-7-(trifluoromethyl)-1,3-dihydro-1,4-benzodiazepin-2-one (building block V, 500.0 mg, 1.29 mmol) in N,N-dimethylformamide (10 mL) was added cesium carbonate (838 mg, 2.57 mmol) and 0-(diphenylphosphinyl)hydroxylamine (330 mg, 1.41 mmol) at 0° C. The reaction mixture was stirred at 0° C. for 1 h, then poured into ice-water (20 mL). The aqueous layer was extracted with ethyl acetate (3×20 mL). The combined organic layers were washed with brine (2×10 mL), dried (Na$_2$SO$_4$) and concentrated in vacuo. The residue was purified by flash column chromatography (silica, petroleum ether/ethyl acetate 5:1 to 3:1) to afford the title compound (400 mg, 76%) as a yellow oil. MS: 403.9 ([{$^{35}$Cl} M+H]$^+$), ESI pos.

b) (4S)-7-chloro-6-(2,6-difluorophenyl)-4-methyl-8-(trifluoromethyl)-4H-[1,2,4]triazolo[1,5-a][1,4]benzodiazepine In analogy to experiment of example 15, (3S)-1-amino-6-chloro-5-(2,6-difluorophenyl)-3-methyl-7-(trifluoromethyl)-3H-1,4-benzodiazepin-2-one was converted into the enantiopure (−)-title compound (9 mg, 29%) which was obtained as a white solid. MS: 413.0 ([{$^{35}$Cl, $^{35}$Cl} M+H]$^+$), 415.0 ([{$^{35}$Cl, $^{37}$Cl} M+H]$^+$), ESI pos.

Example 23

[(4S)-7-chloro-6-(2,6-difluorophenyl)-4-methyl-8-(trifluoroethyl)-4H-[1,2,4]triazolo[1,5-a][1,4]benzodiazepin-2-yl]-(3-methoxyazetidin-1-yl)methanone

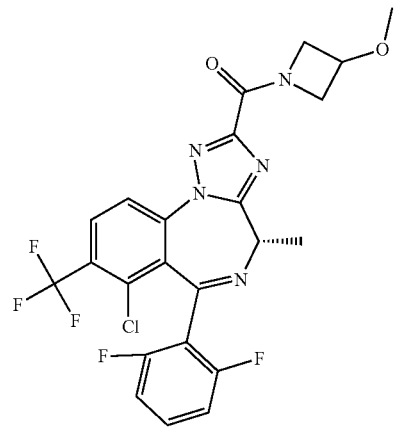 [SMILES: COC1CN(C(=O)c2nc3n(n2)-c2ccc(C(F)(F)F)c(Cl)c2C(c2c(F)cccc2F)=N[C@H]3C)C1]

a) ethyl (4S)-7-chloro-6-(2,6-difluorophenyl)-4-methyl-8-(trifluoromethyl)-4H-[1,2,4]triazolo[1,5-a][1,4]benzodiazepine-2-carboxylate In analogy to experiment of example 13 b, (3S)-1-amino-6-chloro-5-(2,6-difluorophenyl)-3-methyl-7-(trifluoromethyl)-3H-1,4-benzodiazepin-2-one was converted into the title compound (490 mg, 41%) which was obtained as a yellow solid. MS: 485.0 ([{$^{35}$Cl} M+H]$^+$), ESI pos.

b) (4S)-7-chloro-6-(2,6-difluorophenyl)-4-methyl-8-(trifluoromethyl)-4H-[1,2,4]triazolo[1,5-a][1,4]benzodiazepine-2-carboxylic acid In analogy to experiment of example 6 c, ethyl (4S)-7-chloro-6-(2,6-difluorophenyl)-4-methyl-8-(trifluoromethyl)-4H-[1,2,4]triazolo[1,5-a][1,4]benzodiazepine-2-carboxylate was converted into the title compound (119 mg, 83%) which was obtained as a white solid. MS: 457.0 ([{$^{35}$Cl} M+H]$^+$), ESI pos.

c) [(4S)-7-chloro-6-(2,6-difluorophenyl)-4-methyl-8-(trifluoromethyl)-4H-[1,2,4]triazolo[1,5-a][1,4]benzodiazepin-2-yl]-(3-methoxyazetidin-1-yl)methanone In analogy to experiment of example 17, (4S)-7-chloro-6-(2,6-difluorophenyl)-4-methyl-8-(trifluoromethyl)-4H-[1,2,4]triazolo[1,5-a][1,4]benzodiazepine-2-carboxylic acid using 3-methoxyazetidine hydrochloride was converted into the enantiopure (−)-title compound (28 mg, 46%) which was obtained as a white solid. MS: 526.1 ([{$^{35}$Cl} M+H]$^+$), ESI pos.

Example 24

[7,8-dichloro-6-(2,6-difluorophenyl)-4H-[1,2,4]triazolo[1,5-a][1,4]benzodiazepin-2-yl]-(3-hydroxyazetidin-1-yl)methanone

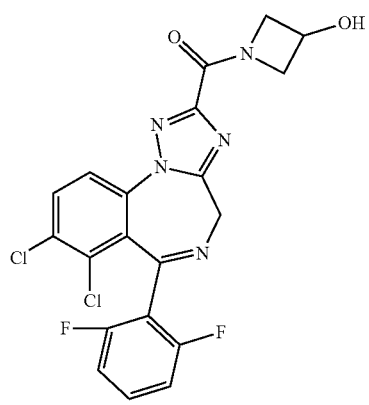 [SMILES: O=C(c1nc2n(n1)-c1ccc(Cl)c(Cl)c1C(c1c(F)cccc1F)=NC2)N1CC(O)C1]

In analogy to experiment of example 16, 7,8-dichloro-6-(2,6-difluorophenyl)-4H-[1,2,4]triazolo[1,5-a][1,4]benzodiazepine-2-carboxylic acid using 3-hydroxyazetidine hydrochloride was converted into the title compound (34 mg, 59%) which was obtained as a white solid. MS: 464.0 ([{$^{35}$Cl, $^{35}$Cl} M+H]$^+$), 466.0 ([{$^{35}$Cl, $^{37}$Cl} M+H]$^+$), ESI pos.

Example 25

[(4S)-7,8-dichloro-6-(2,6-difluorophenyl)-4-methyl-4H-[1,2,4]triazolo[1,5-a][1,4]benzodiazepin-2-yl]-(3-hydroxyazetidin-1-yl)methanone

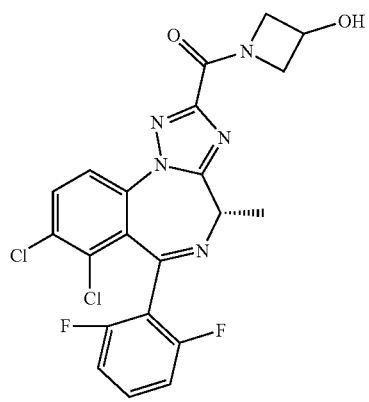 [SMILES: C[C@@H]1N=C(c2c(F)cccc2F)c2c(ccc(Cl)c2Cl)-n2nc(C(=O)N3CC(O)C3)nc21]

In analogy to experiment of example 17, (4S)-7,8-dichloro-6-(2,6-difluorophenyl)-4-methyl-4H-[1,2,4]triazolo[1,5-a][1,4]benzodiazepine-2-carboxylic acid using 3-hydroxyazetidine hydrochloride was converted into the enantiopure (−)-title compound (31 mg, 43%) which was obtained as a white solid. MS: 478.0 ([{$^{35}$Cl, $^{35}$Cl} M+H]$^+$), 480.0 ([{$^{35}$Cl, $^{37}$Cl} M+H]$^+$), ESI pos.

Example 26 azetidin-1-yl-[(4S)-7-chloro-6-(2,6-difluorophenyl)-4-methyl-8-(trifluoromethyl)-4H-[1,2,4]triazolo[1,5-a][1,4]benzodiazepin-2-yl]methanone

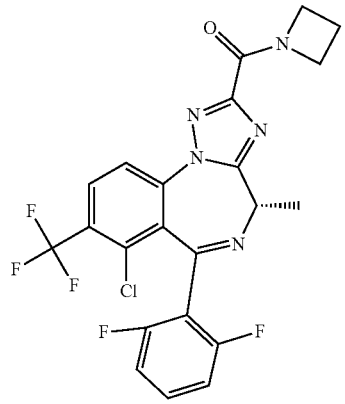 [SMILES: C[C@@H]1N=C(c2c(F)cccc2F)c2c(ccc(C(F)(F)F)c2Cl)-n2nc(C(=O)N3CCC3)nc21]

In analogy to experiment of example 6 d, (4S)-7-chloro-6-(2,6-difluorophenyl)-4-methyl-8-(trifluoromethyl)-4H-[1,2,4]triazolo[1,5-a][1,4]benzodiazepine-2-carboxylic acid using azetidine hydrochloride was converted into the enantiopure (−)-title compound (20 mg, 22%) which was obtained as a white solid. MS: 496.0 ([{$^{35}$Cl} M+H]$^+$), ESI pos.

Example 27

(4S)-7,8-dichloro-6-(2,6-difluorophenyl)-2-(methoxymethyl)-4-methyl-4H-[1,2,4]triazolo[1,5-a][1,4]benzodiazepine

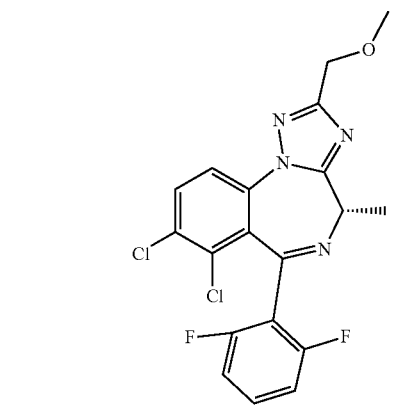 [SMILES: COCc1nc2n(n1)-c1ccc(Cl)c(Cl)c1C(c1c(F)cccc1F)=N[C@H]2C]

To a stirred mixture of [(4S)-7,8-dichloro-6-(2,6-difluorophenyl)-4-methyl-4H-[1,2,4]triazolo[1,5-a][1,4]benzodiazepin-2-yl]methanol (100 mg, 0.24 mmol) and silver carbonate (135 mg, 0.49 mmol) in acetonitrile (2 mL) was slowly added iodomethane (173 mg, 1.22 mmol). The reaction mixture was stirred at 20° C. for 16 h. The reaction mixture was filtered and the filtrate was concentrated in vacuo. The residue was purified by preparative HPLC (Phenomenex Gemini-NX C18, water containing 0.1% trifluoroacetic acid/acetonitrile) followed by chiral SFC (Daicel Chiralpak AD, isopropanol containing 0.1% aqueous ammonia) to afford the enantiopure (−)-title compound (20 mg, 49%) as a white solid. MS: 423.0 ([{$^{35}$Cl, $^{35}$Cl} M+H]$^+$), 425.1 ([{$^{35}$Cl, $^{35}$Cl} M+H]$^+$), ESI pos.

Example 28

(4S)-7,8-dichloro-6-(2,6-difluorophenyl)-N-(2-methoxyethyl)-4-methyl-4H-[1,2,4]triazolo[1,5-a][1,4]benzodiazepine-2-carboxamide

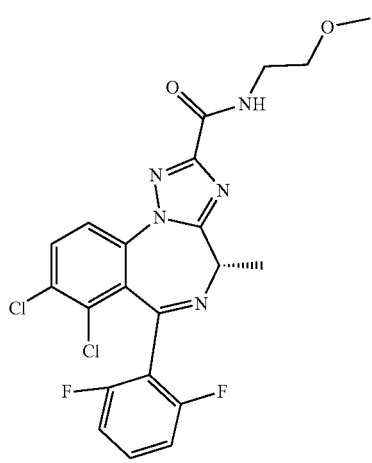 [SMILES: COCCNC(=O)c1nc2n(n1)-c1ccc(Cl)c(Cl)c1C(c1c(F)cccc1F)=N[C@H]2C]

In analogy to experiment of example 16, (4S)-7,8-dichloro-6-(2,6-difluorophenyl)-4-methyl-4H-[1,2,4]triazolo[1,5-a][1,4]benzodiazepine-2-carboxylic using 2-methoxyethylamine was converted into the enantiopure (−)-title compound (21 mg, 21%) which was obtained as a white solid. MS: 480.0 ([{$^{35}$Cl, $^{35}$Cl} M+H]$^+$), 482.0 ([{$^{35}$Cl, $^{37}$Cl} M+H]$^+$), ESI pos.

Example 29

(4S)-7-chloro-6-(2,6-difluorophenyl)-2,4-dimethyl-8-(trifluoromethyl)-4H-[1,2,4]triazolo[1,5-a][1,4]benzodiazepine

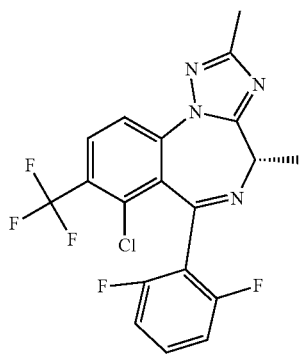 [SMILES: Cc1nc2n(n1)-c1ccc(C(F)(F)F)c(Cl)c1C(c1c(F)cccc1F)=N[C@H]2C]

In analogy to experiment of example 15, (3S)-1-amino-6-chloro-5-(2,6-difluorophenyl)-3-methyl-7-(trifluoromethyl)-3H-1,4-benzodiazepin-2-one using thioacetamide was converted into enantiopure (−)-title compound (12 mg, 38%) which was obtained as a white solid. MS: 427.0 ([{35Cl} M+H]$^+$), 429.0 ([{37Cl} M+H]$^+$), ESI pos.

Example 30

(4S)-7,8-dichloro-6-(2,6-difluorophenyl)-N-(2-fluoroethyl)-4-methyl-4H-[1,2,4]triazolo[1,5-a][1,4]benzodiazepine-2-carboxamide

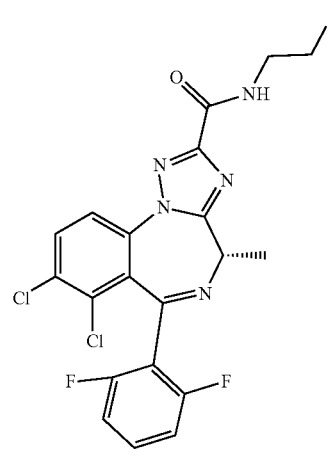

In analogy to experiment of example 16, (4S)-7,8-dichloro-6-(2,6-difluorophenyl)-4-methyl-4H-[1,2,4]triazolo[1,5-a][1,4]benzodiazepine-2-carboxylic using 2-fluoroethylamine hydrochloride was converted into the enantiopure (−)-title compound (14 mg, 17%) which was obtained as a white solid. MS: 468.0 ([{$^{35}$Cl, $^{35}$Cl} M+H]$^+$), 470.0 ([{$^{35}$Cl, $^{37}$Cl} M+H]$^+$), ESI pos.

Example 31

[(4S)-7,8-dichloro-6-(2,6-difluorophenyl)-4-methyl-4H-[1,2,4]triazolo[1,5-a][1,4]benzodiazepin-2-yl]-[3-(difluoromethoxy)azetidin-1-yl]methanone

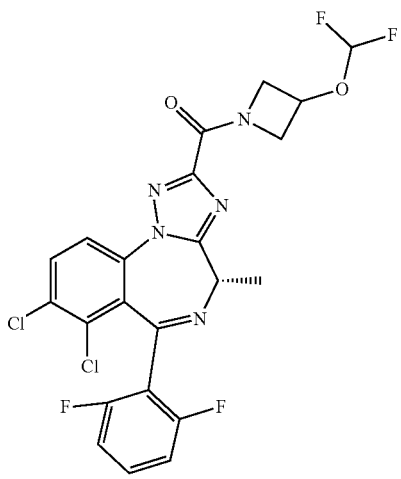 [SMILES: C[C@@H]1N=C(c2c(F)cccc2F)c2c(ccc(Cl)c2Cl)-n2nc(C(=O)N3CC(OC(F)F)C3)nc21]

In analogy to experiment of example 17, (4S)-7,8-dichloro-6-(2,6-difluorophenyl)-4-methyl-4H-[1,2,4]triazolo[1,5-a][1,4]benzodiazepine-2-carboxylic using 3-(difluoromethoxy)azetidine trifluoroacetate was converted into the enantiopure (−)-title compound (18 mg, 20%) which was obtained as a white solid. MS: 528.0 ([{$^{35}$Cl, $^{35}$Cl} M+H]$^+$), 530.0 ([{$^{35}$Cl, $^{37}$Cl} M+H]$^+$), ESI pos.

Example 32

7,8-dichloro-6-(2,6-difluorophenyl)-2-methyl-4H-[1,2,4]triazolo[1,5-a][1,4]benzodiazepine

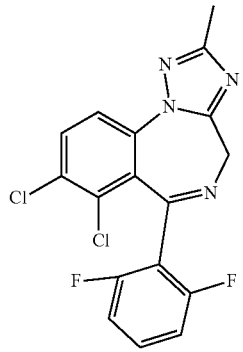 [SMILES: Cc1nc2n(n1)-c1ccc(Cl)c(Cl)c1C(c1c(F)cccc1F)=NC2]

In analogy to experiment of example 21, 1-amino-6,7-dichloro-5-(2,6-difluorophenyl)-3H-1,4-benzodiazepin-2-one was converted into the title compound (5.5 mg, 3%) which was obtained as a yellow solid. MS: 379.0 ([{$^{35}$Cl, $^{35}$Cl} M+H]$^+$), 381.0 ([{$^{35}$Cl, $^{37}$Cl} M+H]$^+$), ESI pos.

Example 33

7,8-dichloro-2-(difluoromethyl)-6-(2,6-difluorophenyl)-4H-[1,2,4]triazolo[1,5-a][1,4]benzodiazepine

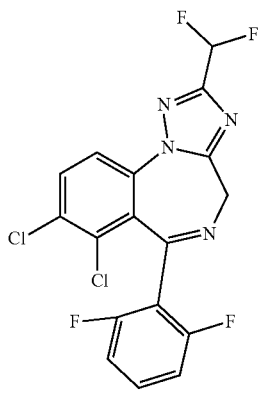 [SMILES: Fc1cccc(F)c1C1=NCc2nc(C(F)F)nn2-c2ccc(Cl)c(Cl)c21]

a) [7,8-dichloro-6-(2,6-difluorophenyl)-4H-[1,2,4]triazolo[1,5-a][1,4]benzodiazepin-2-yl]methanol In analogy to experiment of example 13 c, ethyl 7,8-dichloro-6-(2,6-difluorophenyl)-4H-[1,2,4]triazolo[1,5-a][1,4]benzodiazepine-2-carboxylate was converted into the title compound (426 mg, 89%) which was obtained as a white solid. MS: 395.0 ([{$^{35}$Cl, $^{35}$Cl} M+H]$^+$), 397.0 ([{$^{35}$Cl, $^{35}$Cl} M+H]$^+$), ESI pos.

b) 7,8-dichloro-6-(2,6-difluorophenyl)-4H-[1,2,4]triazolo[1,5-a][1,4]benzodiazepine-2-carbaldehyde A mixture of [7,8-dichloro-6-(2,6-difluorophenyl)-4H-[1,2,4]triazolo[1,5-a][1,4]benzodiazepin-2-yl]methanol (316 mg, 0.80 mmol) and manganese oxide (1.39 g, 16.0 mmol) in dichloroethane (4 mL) was stirred at 50° C. for 16 h. The solvent was removed in vacuo and the residue was purified by chromatography (silica, petroleum ether/ethyl acetate 3:1) to afford the title compound (153 mg, 49%) as a yellow solid. $^1$H NMR (CDCl$_3$, 400 MHz) δ: 10.09 (s, 1H) 7.97 (d, J=8.8 Hz, 1 H) 7.83 (d, J=8.9 Hz, 1H) 7.34 (tt, J=8.4, 6.3 Hz, 1H) 6.66-7.08 (m, 2H) 5.67 (d, J=12.7 Hz, 1H) 4.34 (d, J=12.7 Hz, 1H).

c) 7,8-dichloro-2-(difluoromethyl)-6-(2,6-difluorophenyl)-4H-[1,2,4]triazolo[1,5-a][1,4]benzodiazepine In analogy to experiment of example 18 b, 7,8-dichloro-6-(2,6-difluorophenyl)-4H-[1,2,4]triazolo[1,5-a][1,4]benzodiazepine-2-carbaldehyde was converted into the title compound (29 mg, 18%) which was obtained as a white solid. MS: 415.0 ([{$^{35}$Cl, $^{35}$Cl} M+H]$^+$), 417.0 ([{$^{35}$C, $^{37}$Cl} M+H]$^+$), ESI pos.

Example 34

(4S)-7-chloro-6-(2,6-difluorophenyl)-4-methyl-N-(trideuteriomethyl)-8-(trifluoromethyl)-4H-[1,2,4]triazolo[1,5-a][1,4]benzodiazepine-2-carboxamide

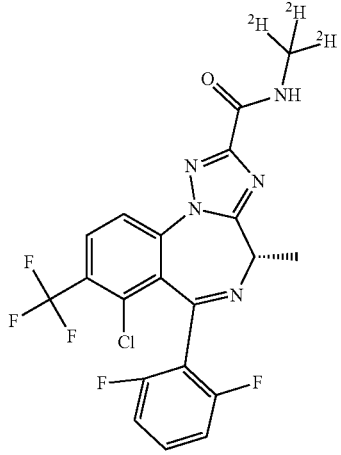 [SMILES: [2H]C([2H])([2H])NC(=O)c1nc2n(n1)-c1ccc(C(F)(F)F)c(Cl)c1C(c1c(F)cccc1F)=N[C@H]2C]

In analogy to experiment of example 6 d, (4S)-7-chloro-6-(2,6-difluorophenyl)-4-methyl-8-(trifluoromethyl)-4H-[1,2,4]triazolo[1,5-a][1,4]benzodiazepine-2-carboxylic acid using trideuteriomethanamine hydrochloride was converted into the enantiopure (−)-title compound (16 mg, 54%) which was obtained as a white solid. MS: 473.1 ([{$^{35}$Cl} M+H]$^+$), ESI pos.

Example 35

(4S)-7,8-dichloro-6-(2,6-difluorophenyl)-4-methyl-4H-[1,2,4]triazolo[1,5-a][1,4]benzodiazepine-2-carboxamide

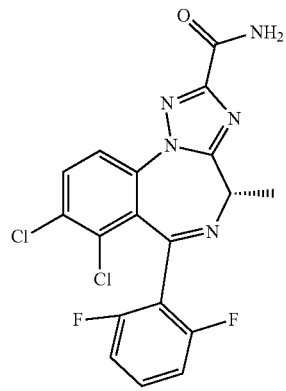 [SMILES: C[C@@H]1N=C(c2c(F)cccc2F)c2c(ccc(Cl)c2Cl)-n2nc(C(N)=O)nc21]

To a mixture of ethyl (4S)-7,8-dichloro-6-(2,6-difluorophenyl)-4-methyl-4H-[1,2,4]triazolo[1,5-a][1,4]benzodiazepine-2-carboxylate (400 mg, 0.89 mmol) in methanol (4 mL) was added aqueous ammonia (25%, 2.0 mL, 0.89 mmol). The reaction mixture was stirred at 80° C. for 15 h and then cooled to room temperature. The suspension was filtered and dried in vacuo. The residue was purified by chiral SFC (Daicel Chiralpak AD, methanol containing 0.1% aqueous ammonia) to afford the enantiopure (−)-title compound (30 mg, 49%) as a white solid. MS: 422.0 ([$\{^{35}Cl, ^{35}Cl\}$ M+H]$^+$), 424.0 ([$\{^{35}Cl, ^{37}Cl\}$ M+H]$^+$), ESI pos.

Example 36

[(4S)-7,8-dichloro-6-(2,6-difluorophenyl)-4-methyl-4H-[1,2,4]triazolo[1,5-a][1,4]benzodiazepin-2-yl]-(1,1-dioxo-1,4-thiazinan-4-yl)methanone

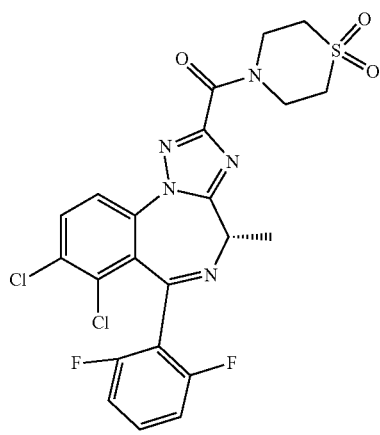 [SMILES: C[C@@H]1N=C(c2c(F)cccc2F)c2c(ccc(Cl)c2Cl)-n2nc(C(=O)N3CCS(=O)(=O)CC3)nc21]

In analogy to experiment of example 6 d, (4S)-7,8-dichloro-6-(2,6-difluorophenyl)-4-methyl-4H-[1,2,4]triazolo[1,5-a][1,4]benzodiazepine-2-carboxylic acid using thiomorpholine-1,1-dioxide was converted into the enantiopure (−)-title compound (48 mg, 78%) which was obtained as a white solid. MS: 540.2 ([$\{^{35}Cl, ^{35}Cl\}$ M+H]$^+$), 542.2 ([$\{^{35}Cl, ^{37}Cl\}$ M+H]$^+$), ESI pos.

Example 37

[7-chloro-6-(2,6-difluorophenyl)-8-(trifluoromethyl)-4H-[1,2,4]triazolo[1,5-a][1,4]benzodiazepin-2-yl]-(3-methoxyazetidin-1-yl)methanone

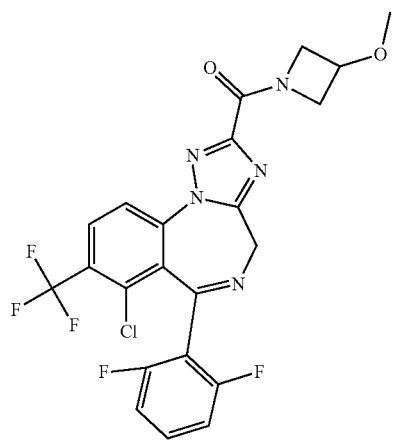 [SMILES: COC1CN(C(=O)c2nc3n(n2)-c2ccc(C(F)(F)F)c(Cl)c2C(c2c(F)cccc2F)=NC3)C1]

a) 1-amino-6-chloro-5-(2,6-difluorophenyl)-3-methyl-7-(trifluoromethyl)-3H-1,4-benzodiazepin-2-one In analogy to experiment of example 22 a, 6-chloro-5-(2,6-difluorophenyl)-7-(trifluoromethyl)-1,3-dihydro-1,4-benzodiazepin-2-one (building block W) was converted into the title compound (660 mg, 88%) which was obtained as a white solid. MS: 390.0 ([$\{^{35}Cl\}$ M+H]$^+$), ESI pos.

b) ethyl 7-chloro-6-(2,6-difluorophenyl)-8-(trifluoromethyl)-4H-[1,2,4]triazolo[1,5-a][1,4]benzodiazepine-2-carboxylate In analogy to experiment of example 13 b, 1-amino-6-chloro-5-(2,6-difluorophenyl)-3-methyl-7-(trifluoromethyl)-3H-1,4-benzodiazepin-2-one was converted into the title compound (300 mg, 34%) which was obtained as a yellow solid. MS: 471.0 ([$\{^{35}Cl\}$ M+H]$^+$), ESI pos.

c) 7-chloro-6-(2,6-difluorophenyl)-8-(trifluoromethyl)-4H-[1,2,4]triazolo[1,5-a][1,4]benzodiazepine-2-carboxylic acid In analogy to experiment of example 6 c, ethyl 7-chloro-6-(2,6-difluorophenyl)-8-(trifluoromethyl)-4H-[1,2,4]triazolo[1,5-a][1,4]benzodiazepine-2-carboxylate was converted into the title compound (200 mg, 72%) which was obtained as a white solid. MS: 443.1 ([$\{^{35}Cl\}$ M+H]$^+$), ESI pos.

d) [7-chloro-6-(2,6-difluorophenyl)-8-(trifluoromethyl)-4H-[1,2,4]triazolo[1,5-a][1,4]benzodiazepin-2-yl]-(3-methoxyazetidin-1-yl)methanone In analogy to experiment of example 17, 7-chloro-6-(2,6-difluorophenyl)-8-(trifluoromethyl)-4H-[1,2,4]triazolo[1, 5-a][1,4]benzodiazepine-2-carboxylic acid using 3-methoxyazetidine hydrochloride was converted into the title compound (24 mg, 20%) which was obtained as a white solid. MS: 512.1 ([{$^{35}$Cl} M+H]$^+$), ESI pos.

Example 38

[(4S)-7,8-dichloro-6-(3-fluoro-2-pyridyl)-4-methyl-4H-[1,2,4]triazolo[1,5-a][1,4]benzodiazepin-2-yl]-(3-methoxyazetidin-1-yl)methanone

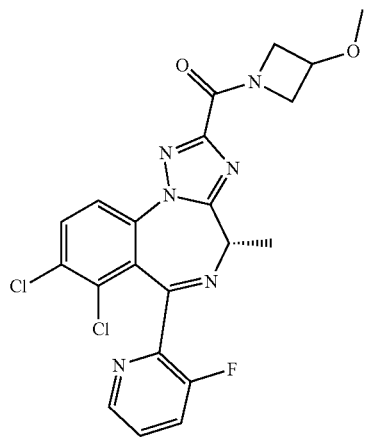 [SMILES: COC1CN(C(=O)c2nc3n(n2)-c2ccc(Cl)c(Cl)c2C(c2ncccc2F)=N[C@H]3C)C1]

a) 1-amino-6,7-dichloro-5-(3-fluoro-2-pyridyl)-3-methyl-3H-1,4-benzodiazepin-2-one In analogy to experiment of example 22 a, (3S)-6,7-dichloro-5-(3-fluoro-2-pyridyl)-3-methyl-1,3-dihydro-1,4-benzodiazepin-2-one (building block O) was converted into the title compound (610 mg, 64%) which was obtained as a yellow solid. MS: 353.0 ([{$^{35}$Cl, $^{35}$Cl} M+H]$^+$), 355.0 ([{$^{35}$Cl, $^{37}$Cl} M+H]$^+$), ESI pos.

b) ethyl 7,8-dichloro-6-(3-fluoro-2-pyridyl)-4-methyl-4H-[1,2,4]triazolo[1,5-a][1,4]benzodiazepine-2-carboxylate A mixture of 1-amino-6,7-dichloro-5-(3-fluoro-2-pyridyl)-3-methyl-3H-1,4-benzodiazepin-2-one (610 mg, 1.73 mmol) and ethyl 2-ethoxy-2-iminoacetate (610 mg, 4.2 mmol) in ethanol (7 mL) was stirred at 80° C. for 2 h and at 100° C. for 24 h. The reaction mixture was cooled and another portion of ethyl 2-ethoxy-2-iminoacetate (610 mg, 4.2 mmol) was added. The reaction was stirred at 100° C. for another 24 h, then cooled and concentrated in vacuo. The residue was purified by flash column chromatography (silica, petroleum ether/ethyl acetate 1:1) to afford the title compound (690 mg, 85%) as a yellow solid. MS: 434.2 ([{$^{35}$Cl, $^{35}$Cl} M+H]$^+$), 436.2 ([{$^{35}$Cl, $^{35}$Cl} M+H]$^+$), ESI pos.

c) 7,8-dichloro-6-(3-fluoro-2-pyridyl)-4-methyl-4H-[1,2,4]triazolo[1,5-a][1,4]benzodiazepine-2-carboxylic acid In analogy to experiment of example 6 c, ethyl 7,8-dichloro-6-(3-fluoro-2-pyridyl)-4-methyl-4H-[1,2,4]triazolo[1,5-a][1,4]benzodiazepine-2-carboxylate was converted into the title compound (390 mg, 58%) which was obtained as a yellow solid. MS: 406.0 ([{$^{35}$Cl, $^{35}$Cl} M+H]$^+$), 408.0 ([{$^{35}$Cl, $^{37}$Cl} M+H]$^+$), ESI pos.

d) [(4S)-7,8-dichloro-6-(3-fluoro-2-pyridyl)-4-methyl-4H-[1,2,4]triazolo[1,5-a][1,4]benzodiazepin-2-yl]-(3-methoxyazetidin-1-yl)methanone In analogy to experiment of example 17, 7,8-dichloro-6-(3-fluoro-2-pyridyl)-4-methyl-4H-[1,2,4]triazolo[1,5-a][1,4]benzodiazepine-2-carboxylic acid using 3-methoxyazetidine hydrochloride was converted into the enantiopure (+)-title compound (37 mg, 32%) which was obtained as a white solid. MS: 475.0 ([{$^{35}$Cl, $^{35}$Cl} M+H]$^+$), 477.0 ([{$^{35}$Cl, $^{37}$Cl} M+H]$^+$), ESI pos.

Example 39

[(4S)-7,8-dichloro-6-(3-fluoro-2-pyridyl)-4-methyl-4H-[1,2,4]triazolo[1,5-a][1,4]benzodiazepin-2-yl]-[3-(trideuteriomethoxy)azetidin-1-yl]methanone

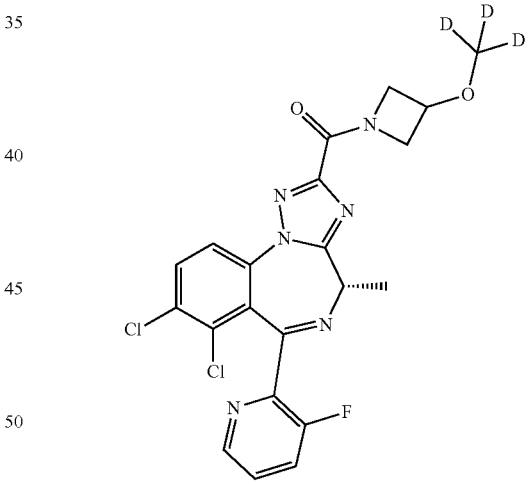

In analogy to experiment of example 17, 7,8-dichloro-6-(3-fluoro-2-pyridyl)-4-methyl-4H-[1,2,4]triazolo[1,5-a][1,4]benzodiazepine-2-carboxylic acid using 3-trideuteriomethoxyazetidine hydrochloride was converted into the enantiopure (−)-title compound (40 mg, 28%) which was obtained as a white solid. MS: 478.2 ([{$^{35}$Cl, $^{35}$Cl} M+H]$^+$), 480.2 ([{$^{35}$Cl, $^{37}$Cl} M+H]$^+$), ESI pos.

Example 40

[(4S)-7,8-dichloro-6-(2,6-difluorophenyl)-4-methyl-4H-[1,2,4]triazolo[1,5-a][1,4]benzodiazepin-2-yl]-(3-fluoroazetidin-1-yl)methanone

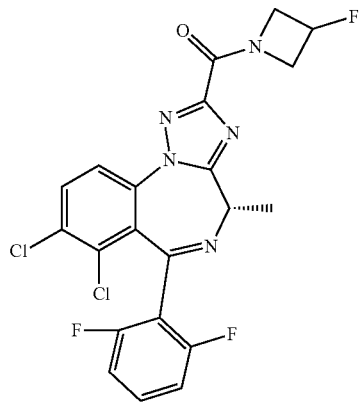 [SMILES: C[C@@H]1N=C(c2c(F)cccc2F)c2c(ccc(Cl)c2Cl)-n2nc(C(=O)N3CC(F)C3)nc21]

In analogy to experiment of example 17, (4S)-7,8-dichloro-6-(2,6-difluorophenyl)-4-methyl-4H-[1,2,4]triazolo[1,5-a][1,4]benzodiazepine-2-carboxylic acid using 3-fluoroazetidine hydrochloride was converted into the enantiopure (−)-title compound (22 mg, 44%) which was obtained as a white solid. MS: 480.0 ([{$^{35}$Cl, $^{35}$Cl} M+H]$^+$), 482.0 ([{$^{35}$Cl, $^{37}$Cl} M+H]$^1$), ESI pos.

Example 41

1-[(4S)-7,8-dichloro-6-(2,6-difluorophenyl)-4-methyl-4H-[1,2,4]triazolo[1,5-a][1,4]benzodiazepine-2-carbonyl]azetidine-3-carbonitrile

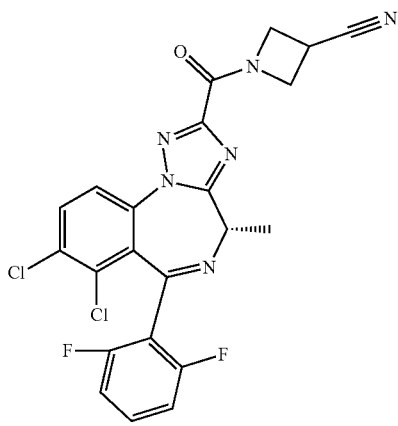 [SMILES: C[C@@H]1N=C(c2c(F)cccc2F)c2c(ccc(Cl)c2Cl)-n2nc(C(=O)N3CC(C#N)C3)nc21]

In analogy to experiment of example 17, (4S)-7,8-dichloro-6-(2,6-difluorophenyl)-4-methyl-4H-[1,2,4]triazolo[1,5-a][1,4]benzodiazepine-2-carboxylic acid using azetidine-3-carbonitrile was converted into the enantiopure (−)-title compound (29 mg, 42%) which was obtained as a white solid. MS: 487.0 ([{$^{35}$Cl, $^{35}$Cl} M+H]$^+$), 489.0 ([{$^{35}$Cl, $^{37}$Cl} M+H]$^+$), ESI pos.

Example 42 azetidin-1-yl-[(4S)-7,8-dichloro-6-(3-fluoro-2-pyridyl)-4-methyl-4H-[1,2,4]triazolo[1,5-a][1,4]benzodiazepin-2-yl]methanone

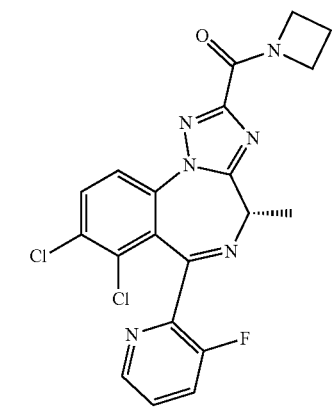 [SMILES: C[C@@H]1N=C(c2ncccc2F)c2c(ccc(Cl)c2Cl)-n2nc(C(=O)N3CCC3)nc21]

In analogy to experiment of example 17, 7,8-dichloro-6-(3-fluoro-2-pyridyl)-4-methyl-4H-[1,2,4]triazolo[1,5-a][1,4]benzodiazepine-2-carboxylic acid using azetidine hydrochloride was converted into the enantiopure (+)-title compound (12 mg, 29%) which was obtained as a white solid. MS: 445.0 ([{$^{35}$Cl, $^{35}$Cl} M+H]$^+$), 447.0 ([{$^{35}$Cl, $^{37}$Cl} M+H]$^+$), ESI pos.

Example 43

[(4S)-7,8-dichloro-6-(2,6-difluorophenyl)-4-methyl-4H-[1,2,4]triazolo[1,5-a][1,4]benzodiazepin-2-yl]-[(3S)-3-hydroxypyrrolidin-1-yl]methanone

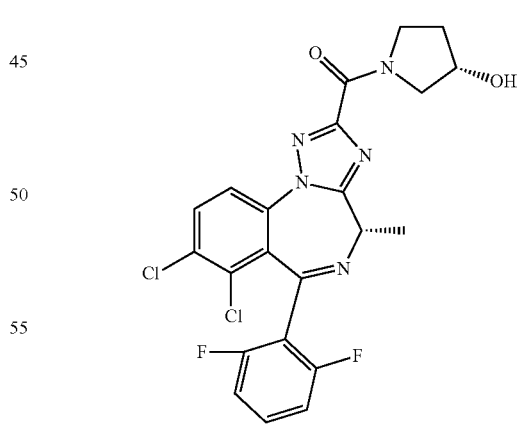

In analogy to experiment of example 17, (4S)-7,8-dichloro-6-(2,6-difluorophenyl)-4-methyl-4H-[1,2,4]triazolo[1,5-a][1,4]benzodiazepine-2-carboxylic acid using (S)-3-hydroxypyrrolidine hydrochloride was converted into the enantiopure (−)-title compound (48 mg, 47%) which was obtained as a white solid. MS: 492.1 ([{$^{35}$Cl, $^{35}$Cl} M+H]$^+$), 494.0 ([{$^{35}$Cl, $^{37}$Cl} M+H]$^+$), ESI pos.

Example 44

[(4S)-7,8-dichloro-6-(3-fluoro-2-pyridyl)-4-methyl-4H-[1,2,4]triazolo[1,5-a][1,4]benzodiazepin-2-yl]-(3-hydroxyazetidin-1-yl)methanone

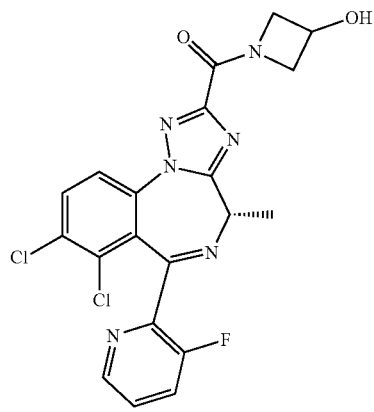 [SMILES: C[C@@H]1N=C(c2ncccc2F)c2c(ccc(Cl)c2Cl)-n2nc(C(=O)N3CC(O)C3)nc21]

In analogy to experiment of example 17, 7,8-dichloro-6-(3-fluoro-2-pyridyl)-4-methyl-4H-[1,2,4]triazolo[1,5-a][1,4]benzodiazepine-2-carboxylic acid using 3-hydroxyazetidine hydrochloride was converted into the enantiopure (+)-title compound (13 mg, 31%) which was obtained as a white solid. MS: 461.1 ([{$^{35}$Cl, $^{35}$Cl} M+H]$^{+}$), 463.1 ([{$^{35}$Cl, $^{37}$Cl} M+H]$^{+}$), ESI pos.

Example 45

[(4S)-7,8-dichloro-6-(2,6-difluorophenyl)-4-methyl-4H-[1,2,4]triazolo[1,5-a][1,4]benzodiazepin-2-yl]-[(3S)-3-methoxypyrrolidin-1-yl]methanone

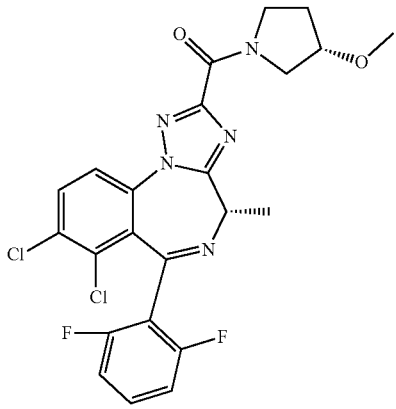 [SMILES: CO[C@H]1CCN(C(=O)c2nc3n(n2)-c2ccc(Cl)c(Cl)c2C(c2c(F)cccc2F)=N[C@H]3C)C1]

In analogy to experiment of example 17, (4S)-7,8-dichloro-6-(2,6-difluorophenyl)-4-methyl-4H-[1,2,4]triazolo[1,5-a][1,4]benzodiazepine-2-carboxylic acid using (3S)-3-methoxypyrrolidine hydrochloride was converted into the enantiopure (−)-title compound (27 mg, 34%) which was obtained as a white solid. MS: 506.1 ([{$^{35}$Cl, $^{35}$Cl} M+H]$^{+}$), 508.1 ([{$^{35}$Cl, $^{37}$Cl} M+H]$^{+}$), ESI pos.

Example 46

[(4S)-7,8-dichloro-6-(2,6-difluorophenyl)-4-methyl-4H-[1,2,4]triazolo[1,5-a][1,4]benzodiazepin-2-yl]-[(3R)-3-methoxypyrrolidin-1-yl]methanone

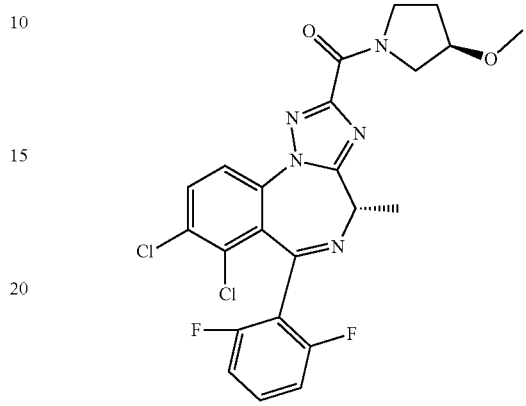

In analogy to experiment of example 17, (4S)-7,8-dichloro-6-(2,6-difluorophenyl)-4-methyl-4H-[1,2,4]triazolo[1,5-a][1,4]benzodiazepine-2-carboxylic acid using (3R)-3-methoxypyrrolidine hydrochloride was converted into the enantiopure (−)-title compound (19 mg, 31%) which was obtained as a white solid. MS: 506.1 ([{$^{35}$Cl, $^{35}$Cl} M+H]$^{+}$), 508.1 ([{$^{35}$Cl, $^{37}$Cl} M+H]$^{+}$), ESI pos.

Example 47

[(4S)-7,8-dichloro-6-(2,6-difluorophenyl)-4-methyl-4H-[1,2,4]triazolo[1,5-a][1,4]benzodiazepin-2-yl]-[(3R)-3-hydroxypyrrolidin-1-yl]methanone

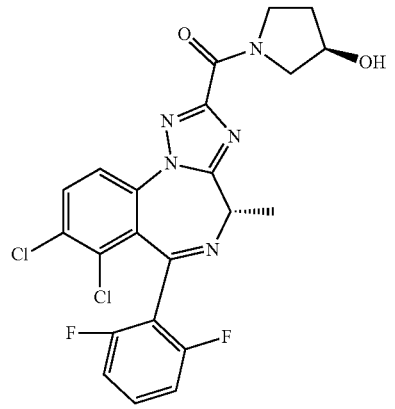 [SMILES: C[C@@H]1N=C(c2c(F)cccc2F)c2c(ccc(Cl)c2Cl)-n2nc(C(=O)N3CC[C@@H](O)C3)nc21]

In analogy to experiment of example 17, (4S)-7,8-dichloro-6-(2,6-difluorophenyl)-4-methyl-4H-[1,2,4]triazolo[1,5-a][1,4]benzodiazepine-2-carboxylic acid using (3R)-3-hydroxypyrrolidine hydrochloride was converted into the enantiopure (−)-title compound (27 mg, 44%) which was obtained as a white solid. MS: 492.1 ([{$^{35}$Cl, $^{35}$Cl} M+H]$^{+}$), 494.1 ([{$^{35}$Cl, $^{37}$Cl} M+H]$^{+}$), ESI pos.

Example 48 azetidin-1-yl-[(4S)-8-bromo-7-chloro-6-(3-fluoro-2-pyridyl)-4-methyl-4H-[1,2,4]triazolo[1,5-a][1,4]benzodiazepin-2-yl]methanone

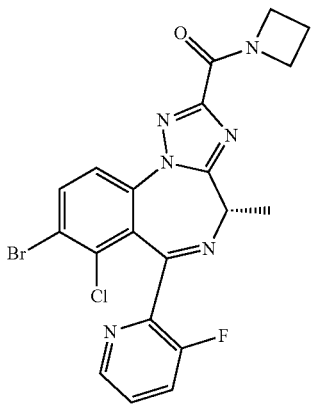

a) 1-amino-7-bromo-6-chloro-5-(3-fluoro-2-pyridyl)-3-methyl-3H-1,4-benzodiazepin-2-one In analogy to experiment of example 22 a, (3S)-7-bromo-6-chloro-5-(3-fluoro-2-pyridyl)-3-methyl-1,3-dihydro-1,4-benzodiazepin-2-one (building block R) was converted into the title compound (3.2 g, 88%) which was obtained as a pink solid. MS: 397.0 ([{$^{79}$Br, $^{35}$Cl} M+H]$^+$), 399.0 ([{$^{81}$Br, $^{35}$Cl or $^{79}$Br, $^{37}$Cl} M+H]$^+$), ESI pos.

b) ethyl-8-bromo-7-chloro-6-(3-fluoro-2-pyridyl-4-methyl-4H-[1,2,4]triazolo[1,5-a][1,4]benzodiazepine-2-carboxylate A mixture of 1-amino-7-bromo-6-chloro-5-(3-fluoro-2-pyridyl)-3-methyl-3H-1,4-benzodiazepin-2-one (3.2 g, 22.0 mmol) and ethyl 2-ethoxy-2-imino-acetate (3.2 g, 8.05 mmol) in ethanol (1 mL) was stirred at 80° C. for 2 h and at 120° C. for 16 h. The mixture was cooled and another portion of ethyl 2-ethoxy-2-imino-acetate (3.2 g, 8.05 mmol) was added. The reaction was stirred at 120° C. for another 16 h, then cooled and concentrated in vacuo. The residue was purified by flash column chromatography (silica, petroleum ether/ethyl acetate 3:1) followed by preparative HPLC (Phenomenex luna C18, water containing 0.1% trifluoroacetic acid/acetonitrile). The pure fraction was basified by addition of saturated aqueous sodium bicarbonate to pH>8 and concentrated in vacuo. The residue was extracted with ethyl acetate (3×100 mL). The combined organic layers were washed with brine (50 mL), dried (Na$_2$SO$_4$) and concentrated in vacuo to afford the title compound (2.4 g, 62%) as a pink solid. MS: 478.0 ([{$^{79}$Br, $^{35}$Cl} M+H]$^+$), 480.0 ([{$^{81}$Br, $^{35}$Cl or $^{79}$Br, $^{37}$Cl} M+H]$^+$), ESI pos.

c) 8-bromo-7-chloro-6-(3-fluoro-2-pyridyl-4-methyl-4H-[1,2,4]triazolo[1,5-a][1,4]benzodiazepine-2-carboxylic acid In analogy to experiment of example 6 c, ethyl-8-bromo-7-chloro-6-(3-fluoro-2-pyridyl)-4-methyl-4H-[1,2,4]triazolo[1,5-a][1,4]benzodiazepine-2-carboxylate was converted into the title compound (770 mg, 78%) which was obtained as a yellow solid. MS: 450.0 ([{$^{79}$Br, $^{35}$Cl} M+H]$^+$), 452.0 ([{$^{81}$Br, $^{35}$Cl or $^{79}$Br, $^{37}$Cl} M+H]$^+$), ESI pos.

d) azetidin-1-yl-[(4S)-8-bromo-7-chloro-6-(3-fluoro-2-pyridyl)-4-methyl-4H-[1,2,4]triazolo[1,5-a][1,4]benzodiazepin-2-yl]methanone In analogy to experiment of example 17, 8-bromo-7-chloro-6-(3-fluoro-2-pyridyl)-4-methyl-4H-[1,2,4]triazolo[1,5-a][1,4]benzodiazepine-2-carboxylic acid using azetidine hydrochloride was converted into the enantiopure (−)-title compound (27 mg, 10%) which was obtained as a white solid. MS: 491.1 ([{$^{79}$Br, $^{35}$Cl} M+H]$^+$), 493.1 ([{$^{81}$Br, $^{35}$Cl or $^{79}$Br, $^{37}$Cl} M+H]$^+$), ESI pos.

Example 49

(4S)-7,8-dichloro-2-cyclopropyl-6-(2,6-difluorophenyl)-4-methyl-4H-[1,2,4]triazolo[1,5-a][1,4]benzodiazepine

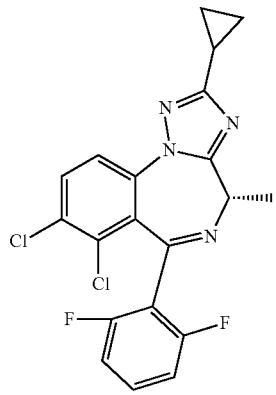 [SMILES: C[C@@H]1N=C(c2c(F)cccc2F)c2c(ccc(Cl)c2Cl)-n2nc(C3CC3)nc21]

a) tert-butyl N-[7,8-dichloro-6-(2,6-difluorophenyl)-4-methyl-4H-[1,2,4]triazolo[1,5-a][1,4]benzodiazepin-2-yl]carbamate To a mixture of 7,8-dichloro-6-(2,6-difluorophenyl)-4-methyl-4H-[1,2,4]triazolo[1,5-a][1,4]benzodiazepine-2-carboxylic acid (1.00 g, 2.36 mmol) and triethylamine (717 mg, 7.09 mmol) in 1,4-dioxane (10 mL) was added diphenylphosphoryl azide (1.95 g, 7.09 mmol) slowly. The mixture was stirred at 15° C. for 30 min and at 50° C. for 2 h. Then tert-butanol (10 mL) was added and the mixture was stirred at 100° C. for 16 h. The mixture was cooled and concentrated in vacuo. The residue was purified by flash column chromatography (silica, petroleum ether/ethyl acetate 10:1) to afford the title compound (1.00 g, 86%) as a yellow solid which was used in the following step without further purification. MS: 494.2 ([{$^{35}$Cl, $^{35}$Cl} M+H]$^+$), 496.2 ([{$^{35}$Cl, $^{35}$Cl} M+H]$^+$), ESI pos.

b) 7,8-dichloro-6-(2,6-difluorophenyl)-4-methyl-4H-[1,2,4]triazolo[1,5-a][1,4]benzodiazepin-2-amine To a solution of tert-butyl N-[7,8-dichloro-6-(2,6-difluorophenyl)-4-methyl-4H-[1,2,4]triazolo[1,5-a][1,4]benzodiazepin-2-yl]carbamate (1.0 g, 2.02 mmol) in dichloromethane (5 mL) was slowly added hydrochloric acid (4 m in 1,4-dioxane, 2.5 mL, 10.1 mmol). The reaction mixture was stirred at 15° C. for 16 h. Saturated aqueous sodium bicarbonate (250 mL) was slowly added until pH 8, then the mixture was extracted with dichloromethane (3×30 mL). The combined organic layers were washed with brine (30 mL), dried (Na$_2$SO$_4$) and concentrated in vacuo to afford the title compound (900 mg, 81%) as a yellow oil which was used in the following step without further purification. MS: 393.9 ([$\{^{35}Cl, ^{35}Cl\}$ M–C$_4$H$_8$—CO$_2$+H]$^+$), 395.9 ([$\{^{35}Cl, ^{37}Cl\}$ M–C$_4$H$_8$—CO$_2$+H]$^+$), ESI pos.

c) 2-bromo-7,8-dichloro-6-(2,6-difluorophenyl)-4-methyl-4H-[1,2,4]triazolo[1,5-a][1,4]benzodiazepine To a mixture of copper (II) bromide (734 mg, 3.29 mmol) and tert-butyl nitrite (509 mg, 4.93 mmol) in acetonitrile (9 mL) was added a suspension of 7,8-dichloro-6-(2,6-difluorophenyl)-4-methyl-4H-[1,2,4]triazolo[1,5-a][1,4]benzodiazepin-2-amine (0.9 g, 1.64 mmol) in acetonitrile (9 mL) at 50° C. slowly. The reaction mixture was stirred at 70° C. for 2 h, then cooled and concentrated in vacuo. The residue was purified by chromatography (silica, petroleum ether/ethyl acetate 5:1) to afford the title compound (450 mg, 58%) as a light yellow solid. MS: 458.8 ([$\{^{35}Cl, ^{35}Cl\}$ M+H]$^+$), 460.8 ([$\{^{35}Cl, ^{37}Cl\}$ M+H]$^+$), ESI pos.

d) (4S)-7,8-dichloro-2-cyclopropyl-6-(2,6-difluorophenyl)-4-methyl-4H-[1,2,4]triazolo[1,5-a][1,4]benzodiazepine A mixture of potassium cyclopropyltrifluoroborate (323 mg, 2.18 mmol), cesium carbonate (427 mg, 1.31 mmol), 2-bromo-7,8-dichloro-6-(2,6-difluorophenyl)-4-methyl-4H-[1,2,4]triazolo[1,5-a][1,4]benzodiazepine (200 mg, 0.44 mmol) and [1,1'-bis(diphenylphosphino) ferrocene]dichloropalladium(II) (64 mg, 0.09 mmol) in toluene (3.2 mL) and water (0.8 mL) was stirred under nitrogen at 80° C. for 16 h. The reaction mixture was cooled, diluted with water (10 mL) and extracted with ethyl acetate (3×10 mL). The combined organic layers were washed with brine (10 mL), dried (Na$_2$SO$_4$) and concentrated in vacuo. The residue was purified by flash column chromatography (silica, petroleum ether/ethyl acetate 5:1) followed by preparative HPLC (Waters Xbridge, water containing 10 mM ammonium bicarbonate/acetonitrile) and, finally, by chiral SFC (Daicel Chiralpak AD, ethanol containing 0.1% aqueous ammonia) to afford the enantiopure (−)-title compound (26 mg, 34%) as a white solid. MS: 419.0 ([$\{^{35}Cl, ^{35}Cl\}$ M+H]$^+$), 421.0 ([$\{^{35}Cl, ^{37}Cl\}$ M+H]$^+$), ESI pos.

Example 50

1-[(4S)-7,8-dichloro-6-(2,6-difluorophenyl)-4-methyl-4H-[1,2,4]triazolo[1,5-a][1,4]benzodiazepin-2-yl]pyrrolidin-2-one

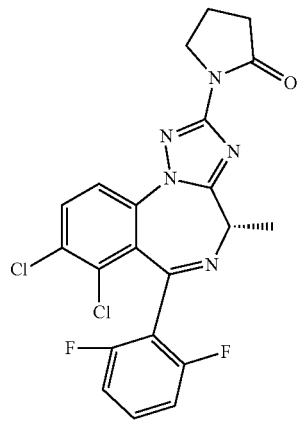 [SMILES: C[C@@H]1N=C(c2c(F)cccc2F)c2c(ccc(Cl)c2Cl)-n2nc(N3CCCC3=O)nc21]

a) 4-chloro-N-[7,8-dichloro-6-(2,6-difluorophenyl)-4-methyl-4H-[1,2,4]triazolo[1,5-a][1,4]benzodiazepin-2-yl]butanamide To a stirred solution of 7,8-dichloro-6-(2,6-difluorophenyl)-4-methyl-4H-[1,2,4]triazolo[1,5-a][1,4]benzodiazepin-2-amine (300 mg, 0.76 mmol) and pyridine (180 mg, 2.28 mmol) in acetonitrile (3 mL) was added 4-chlorobutyryl chloride (215 mg, 1.52 mmol) slowly at −20° C. The mixture was stirred at −20° C. for 30 min. The mixture was diluted with water (10 mL) and extracted with ethyl acetate (3×10 mL). The combined organic layers were washed with brine (10 mL), dried (Na$_2$SO$_4$) and concentrated in vacuo to afford the title compound (250 mg, 66%) as a yellow oil which was used in the following step without further characterization.

b) 1-[(4S)-7,8-dichloro-6-(2,6-difluorophenyl)-4-methyl-4H-[1,2,4]triazolo[1,5-a][1,4]benzodiazepin-2-yl]pyrrolidin-2-one To a stirred solution of 4-chloro-N-[7,8-dichloro-6-(2,6-difluorophenyl)-4-methyl-4H-[1,2,4]triazolo[1,5-a][1,4]benzodiazepin-2-yl]butanamide (250 mg, 0.41 mmol) in N,N-dimethylformamide (4 mL) was added sodium methylate (98 mg, 1.23 mmol) slowly. The mixture was stirred at 60° C. for 4 h. The reaction mixture was cooled, diluted with water (5 mL) and extracted with ethyl acetate (3×10 mL). The combined organic layers were washed with brine (10 mL), dried (Na$_2$SO$_4$) and concentrated in vacuo. The residue was purified by preparative TLC (silica, petroleum ether/ethyl acetate 1:2) followed by preparative HPLC (Waters Xbridge, water containing 10 mM ammonium bicarbonate/acetonitrile) and, finally, by chiral SFC (Daicel Chiralpak AD, ethanol containing 0.1% aqueous ammonia) to afford the enantiopure (−)-title compound (21 mg, 26%) as a white solid. MS: 462.1 ([$\{^{35}Cl, ^{35}Cl\}$ M+H]$^+$), 464.1 ([$\{^{35}Cl, ^{37}Cl\}$ M+H]$^+$), ESI pos.

Example 51

[3-(difluoromethoxy)azetidin-1-yl]-[(4S)-7-chloro-6-(2,6-difluorophenyl)-4-methyl-8-(trifluoromethyl)-4H-[1,2,4]triazolo[1,5-a][1,4]benzodiazepin-2-yl]methanone

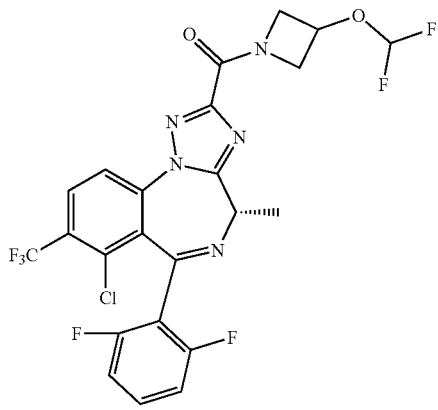 [SMILES: C[C@@H]1N=C(c2c(F)cccc2F)c2c(ccc(C(F)(F)F)c2Cl)-n2nc(C(=O)N3CC(OC(F)F)C3)nc21]

In analogy to experiment of example 17, 7-chloro-6-(2,6-difluorophenyl)-4-methyl-8-(trifluoromethyl)-4H-[1,2,4]triazolo[1,5-a][1,4]benzodiazepine-2-carboxylic acid using 3-(difluoromethoxy)azetidine hydrochloride was converted into the enantiopure (−)-title compound (20 mg, 29%) which was obtained as a white solid. MS: 562.2 ([{$^{35}$Cl} M+H]$^+$), ESI pos.

Example 52

4-[(4S)-7,8-dichloro-6-(2,6-difluorophenyl)-4-methyl-4H-[1,2,4]triazolo[1,5-a][1,4]benzodiazepin-2-yl]-1,4-thiazinane 1,1-dioxide

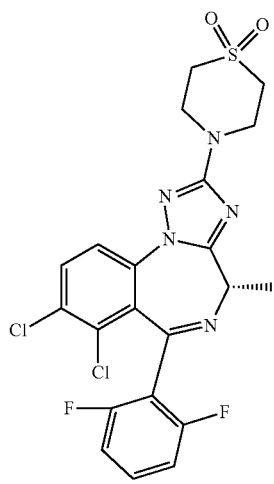 [SMILES: C[C@@H]1N=C(c2c(F)cccc2F)c2c(ccc(Cl)c2Cl)-n2nc(N3CCS(=O)(=O)CC3)nc21]

A mixture of 2-bromo-7,8-dichloro-6-(2,6-difluorophenyl)-4-methyl-4H-[1,2,4]triazolo[1,5-a][1,4]benzodiazepine (200 mg, 0.44 mmol) and thiomorpholine 1,1-dioxide hydrochloride (90 mg, 0.52 mmol), XantPhos-Pd-G3 (45 mg, 0.04 mmol) and cesium carbonate (427 mg, 1.31 mmol) in 1,4-dioxane (3 mL) was stirred under nitrogen at 90° C. for 16 h. The reaction mixture was cooled and poured into water (10 mL), then extracted with ethyl acetate (3×10 mL). The combined organic layers were washed with brine (10 mL), dried (Na$_2$SO$_4$) and concentrated in vacuo. The residue was purified by preparative TLC (silica, petroleum ether/ethyl acetate 1:2) followed by preparative HPLC (Waters Xbridge, water containing 10 mM ammonium bicarbonate/acetonitrile) and, finally, by chiral SFC (Daicel Chiralpak IG, isopropanol containing 0.1% aqueous ammonia) to afford the enantiopure (−)-title compound (15 mg, 13%) as a white solid. MS: 512.1 ([{$^{35}$Cl, $^{35}$Cl} M+H]$^+$), 514.1 ([{$^{35}$Cl, $^{35}$Cl} M+H]$^+$), ESI pos.

Example 53

(4S)-7,8-dichloro-6-(2,6-difluorophenyl)-4-methyl-4H-[1,2,4]triazolo[1,5-a][1,4]benzodiazepine-2-carbonitrile

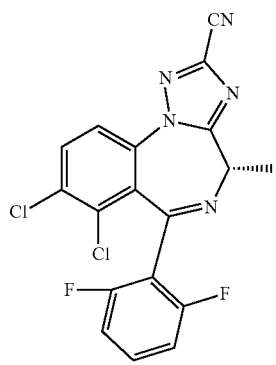 [SMILES: C[C@@H]1N=C(c2c(F)cccc2F)c2c(ccc(Cl)c2Cl)-n2nc(C#N)nc21]

a) (4S)-7,8-dichloro-6-(2,6-difluorophenyl)-4-methyl-4H-[1,2,4]triazolo[1,5-a][1,4]benzodiazepine-2-carboxamide A mixture of ethyl (4S)-7,8-dichloro-6-(2,6-difluorophenyl)-4-methyl-4H-[1,2,4]triazolo[1,5-a][1,4]benzodiazepine-2-carboxylate (200 mg, 0.440 mmol) in methanol (2 mL) was stirred at 20° C. for 15 min, then aqueous ammonia (25%, 1 mL) was added. The mixture was stirred at 60° C. for 15 h. The resulting suspension was filtered and the residue was purified by chiral SFC (Daicel Chiralpak IG, isopropanol containing 0.1% aqueous ammonia) to afford the enantiopure (−)-title compound (60 mg, 40%) as a white solid. MS: 422.0 ([{$^{35}$Cl, $^{35}$Cl} M+H]$^+$), 424.0 ([{$^{35}$Cl, $^{35}$Cl} M+H]$^+$), ESI pos.

b) (4S)-7,8-dichloro-6-(2,6-difluorophenyl)-4-methyl-4H-[1,2,4]triazolo[1,5-a][1,4]benzodiazepine-2-carbonitrile A mixture of (4S)-7,8-dichloro-6-(2,6-difluorophenyl)-4-methyl-4H-[1,2,4]triazolo[1,5-a][1,4]benzodiazepine-2-carboxamide (50 mg, 0.12 mmol) and trifluoroacetic anhydride (50 mg, 0.24 mmol) in tetrahydrofuran (1 mL) was stirred at 20° C. for 15 min. Triethylamine (0.05 mL, 0.36 mmol) was added. The mixture was stirred at 20° C. for 3 h, then purified by preparative HPLC (Phenomenex Gemini NX-C18, water containing 10 mM ammonium bicarbonate/acetonitrile) to afford the enantiopure (−)-title compound (18 mg, 38%) as a white solid. MS: 404.1 ([{$^{35}$Cl, $^{35}$Cl} M+H]$^+$), 406.1 ([{$^{35}$Cl, $^{37}$Cl} M+H]$^+$), ESI pos.

Example 54

(4S)-7,8-dichloro-6-(2,6-difluorophenyl)-N-(2-hydroxyethyl)-4-methyl-4H-[1,2,4]triazolo[1,5-a][1,4]benzodiazepine-2-carboxamide

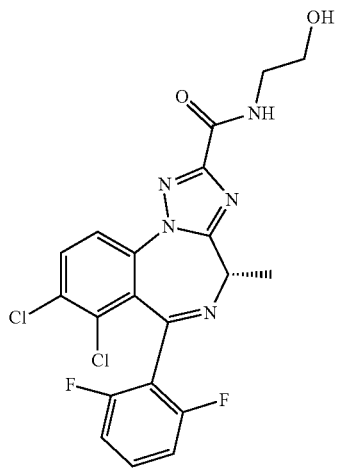 [SMILES: C[C@@H]1N=C(c2c(F)cccc2F)c2c(ccc(Cl)c2Cl)-n2nc(C(=O)NCCO)nc21]

In analogy to experiment of example 17, (4S)-7,8-dichloro-6-(2,6-difluorophenyl)-4-methyl-4H-[1,2,4]triazolo[1,5-a][1,4]benzodiazepine-2-carboxylic acid using 2-aminoethanol was converted into the enantiopure (−)-title compound (35 mg, 21%) which was obtained as a white solid. MS: 466.1 ([{$^{35}$Cl, $^{35}$Cl} M+H]$^+$), 468.1 ([{$^{35}$Cl, $^{37}$Cl} M+H]$^+$), ESI pos.

Example 55

(4S)-7,8-dichloro-6-(2,6-difluorophenyl)-4-methyl-N-(oxetan-3-yl)-4H-[1,2,4]triazolo[1,5-a][1,4]benzodiazepine-2-carboxamide

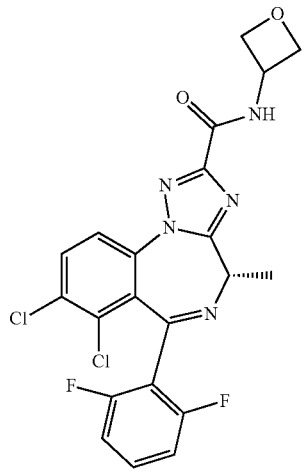 [SMILES: C[C@@H]1N=C(c2c(F)cccc2F)c2c(ccc(Cl)c2Cl)-n2nc(C(=O)NC3COC3)nc21]

In analogy to experiment of example 17, (4S)-7,8-dichloro-6-(2,6-difluorophenyl)-4-methyl-4H-[1,2,4]triazolo[1,5-a][1,4]benzodiazepine-2-carboxylic acid using oxetan-3-amine was converted into the enantiopure (−)-title compound (39 mg, 20%) which was obtained as a white solid. MS: 478.1 ([{$^{35}$Cl, $^{35}$Cl} M+H]$^+$), 480.1 ([{$^{35}$Cl, $^{37}$Cl} M+H]$^+$), ESI pos.

Example 56

(4S)-7,8-dichloro-N-(cyanomethyl)-6-(2,6-difluorophenyl)-4-methyl-4H-[1,2,4]triazolo[1,5-a][1,4]benzodiazepine-2-carboxamide

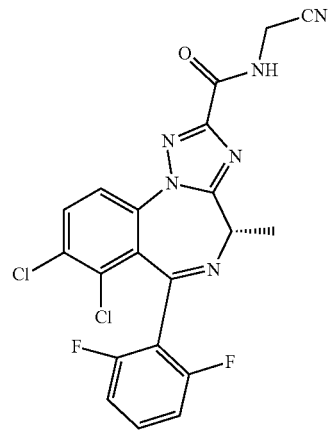 [SMILES: C[C@@H]1N=C(c2c(F)cccc2F)c2c(ccc(Cl)c2Cl)-n2nc(C(=O)NCC#N)nc21]

In analogy to experiment of example 17, (4S)-7,8-dichloro-6-(2,6-difluorophenyl)-4-methyl-4H-[1,2,4]triazolo[1,5-a][1,4]benzodiazepine-2-carboxylic acid using 2-aminoacetonitrile was converted into the enantiopure (−)-title compound (31 mg, 21%) which was obtained as a white solid. MS: 461.1 ([{$^{35}$Cl, $^{35}$Cl} M+H]$^+$), 463.1 ([{$^{35}$Cl, $^{37}$Cl} M+H]$^+$), ESI pos.

Example 57

3-fluoro-N-[(4S)-7,8-dichloro-6-(2,6-difluorophenyl)-4-methyl-4H-[1,2,4]triazolo[1,5-a][1,4]benzodiazepin-2-yl]azetidine-1-carboxamide

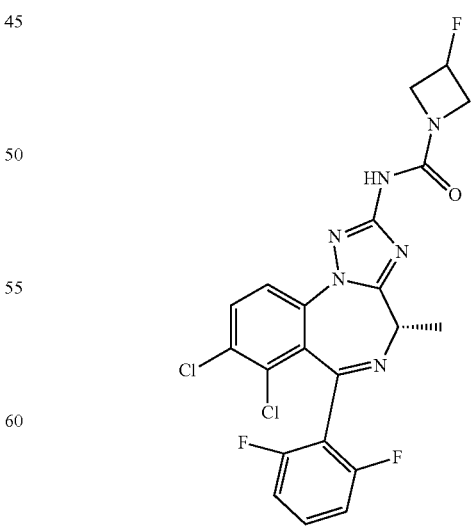

To a mixture of 7,8-dichloro-6-(2,6-difluorophenyl)-4-methyl-4H-[1,2,4]triazolo[1,5-a][1,4]benzodiazepin-2- amine (150 mg, 0.380 mmol), 3-fluoroazetidine hydrochloride (90 mg, 0.810 mmol), triethylamine (0.3 mL, 1.91 mmol) in tetrahydrofuran (4 mL) was added bis(trichloromethyl) carbonate (125 mg, 0.420 mmol) at 0° C. The mixture was stirred at 20° C. for 2 h. The reaction was quenched with water (30 mL) and extracted with ethyl acetate (100 mL). The organic layer was washed with brine (30 mL), dried (Na$_2$SO$_4$) and concentrated in vacuo. The residue was purified by preparative HPLC (Phenomenex Synergi C18, water containing 0.1% trifluoroacetic acid/acetonitrile), followed by SFC (Daicel Chiralcel OJ, methanol containing 0.1% aqueous ammonia) to afford the enantiopure (−)-title compound (22 mg, 15%) as a white solid. MS: 495.0 ([{$^{35}$Cl, $^{35}$Cl} M+H]$^+$), 497.0 ([{$^{35}$Cl, $^{37}$Cl} M+H]$^+$), ESI pos.

Example 58

(3-hydroxyazetidin-1-yl)-[(4S)-7-chloro-6-(2,6-difluorophenyl)-4-methyl-8-(trifluoromethyl)-4H-[1,2,4]triazolo[1,5-a][1,4]benzodiazepin-2-yl]methanone

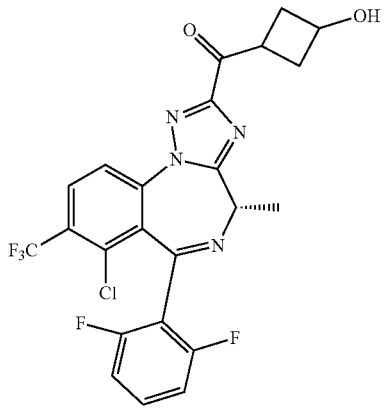 [SMILES: C[C@@H]1N=C(c2c(F)cccc2F)c2c(ccc(C(F)(F)F)c2Cl)-n2nc(C(=O)C3CC(O)C3)nc21]

In analogy to experiment of example 17, 7-chloro-6-(2,6-difluorophenyl)-4-methyl-8-(trifluoromethyl)-4H-[1,2,4]triazolo[1,5-a][1,4]benzodiazepine-2-carboxylic acid using azetidin-3-ol hydrochloride was converted into the enantiopure (−)-title compound (44 mg, 26%) which was obtained as a white solid. MS: 511.9 ([{$^{35}$Cl} M+H]$^+$), ESI pos.

Example 59

(4S)-7,8-dichloro-N-(2,2-difluoroethyl)-6-(2,6-difluorophenyl)-4-methyl-4H-[1,2,4]triazolo[1,5-a][1,4]benzodiazepine-2-carboxamide

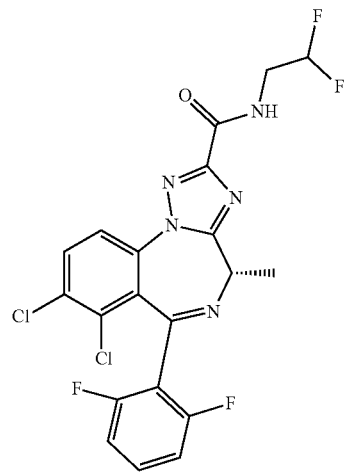 [SMILES: C[C@@H]1N=C(c2c(F)cccc2F)c2c(ccc(Cl)c2Cl)-n2nc(C(=O)NCC(F)F)nc21]

In analogy to experiment of example 17, (4S)-7,8-dichloro-6-(2,6-difluorophenyl)-4-methyl-4H-[1,2,4]triazolo[1,5-a][1,4]benzodiazepine-2-carboxylic acid using 2,2-difluoroethanamine was converted into the enantiopure (−)-title compound (49 mg, 28%) which was obtained as a white solid. MS: 486.1 ([{$^{35}$Cl, $^{35}$Cl} M+H]$^+$), 488.1 ([{$^{35}$Cl, $^{37}$Cl} M+H]$^+$), ESI pos.

Example 60

3-methoxy-N-[(4S)-7,8-dichloro-6-(2,6-difluorophenyl)-4-methyl-4H-[1,2,4]triazolo[1,5-a][1,4]benzodiazepin-2-yl]azetidine-1-carboxamide

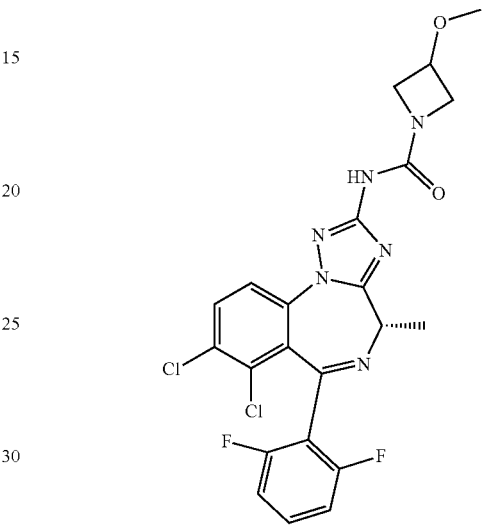

In analogy to experiment of example 57, 7,8-dichloro-6-(2,6-difluorophenyl)-4-methyl-4H-[1,2,4]triazolo[1,5-a][1,4]benzodiazepin-2-amine using 3-methoxyazetidine hydrochloride was converted into the enantiopure (−)-title compound (26 mg, 15%) which was obtained as a white solid. MS: 507.1 ([{$^{35}$Cl, $^{35}$Cl} M+H]$^+$), 509.1 ([{$^{35}$Cl, $^{37}$Cl} M+H]$^+$), ESI pos.

Example 61

(4S)-7,8-dichloro-N-(1-cyanocyclopropyl)-6-(2,6-difluorophenyl)-4-methyl-4H-[1,2,4]triazolo[1,5-a][1,4]benzodiazepine-2-carboxamide

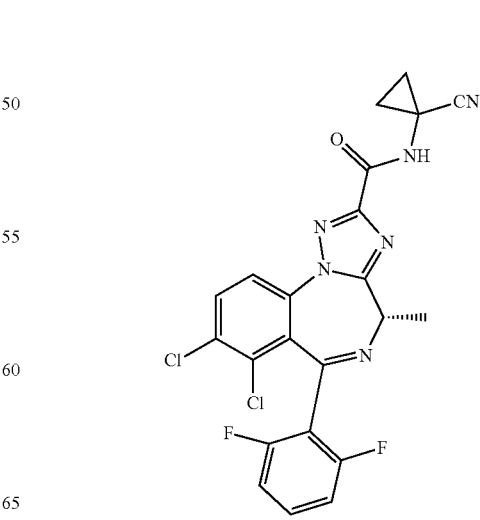

In analogy to experiment of example 16, (4S)-7,8-dichloro-6-(2,6-difluorophenyl)-4-methyl-4H-[1,2,4]triazolo[1,5-a][1,4]benzodiazepine-2-carboxylic acid using 1-aminocyclopropanecarbonitrile was converted into the enantiopure (−)-title compound (27 mg, 23%) which was obtained as a white solid. MS: 487.1 ([$\{^{35}Cl, ^{35}Cl\}$ M+H]$^+$), 489.1 ([$\{^{35}Cl, ^{37}Cl\}$ M+H]$^+$), ESI pos.

Example 62

[7,8-dichloro-6-(3-fluoro-2-pyridyl)-4H-[1,2,4]triazolo[1,5-a][1,4]benzodiazepin-2-yl]-(3-methoxyazetidin-1-yl)methanone

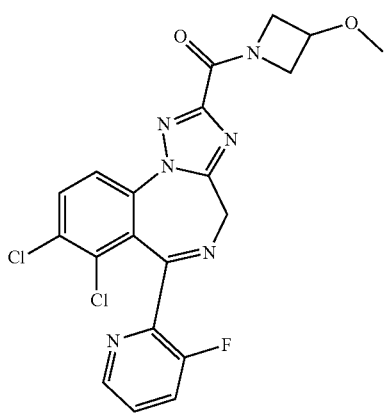 [SMILES: COC1CN(C(=O)c2nc3n(n2)-c2ccc(Cl)c(Cl)c2C(c2ncccc2F)=NC3)C1]

a) 1-amino-6,7-dichloro-5-(3-fluoro-2-pyridyl)-3H-1,4-benzodiazepin-2-one

In analogy to experiment of example 22 a, 6,7-dichloro-5-(3-fluoro-2-pyridyl)-1,3-dihydro-1,4-benzodiazepin-2-one (building block N) was converted into the title compound (360 mg, 86%) which was obtained as a yellow solid. MS: 338.8 ([$\{^{35}Cl, ^{35}Cl\}$ M+H]$^+$), 340.8 ([$\{^{35}Cl, ^{35}Cl\}$ M+H]$^+$), ESI pos.

b) ethyl 7,8-dichloro-6-(3-fluoro-2-pyridyl)-4H-[1,2,4]triazolo[1,5-a][1,4]benzodiazepine-2-carboxylate In analogy to experiment of example 48 b, 1-amino-6,7-dichloro-5-(3-fluoro-2-pyridyl)-3H-1,4-benzodiazepin-2-one was converted into the title compound (50 mg, 10%) which was obtained as a yellow solid. MS: 420.0 ([$\{^{35}Cl, ^{35}Cl\}$ M+H]$^+$), 422.0 ([$\{^{35}Cl, ^{37}Cl\}$ M+H]$^+$), ESI pos.

c) 7,8-dichloro-6-(3-fluoro-2-pyridyl-4H-[1,2,4]triazolo[1,5-a][1,4]benzodiazepine-2-carboxylic acid In analogy to experiment of example 6 c, ethyl 7,8-dichloro-6-(3-fluoro-2-pyridyl)-4H-[1,2,4]triazolo[1,5-a][1,4]benzodiazepine-2-carboxylate was converted into the title compound (40 mg, 83%) which was obtained as a yellow solid and used as such in the following step without further purification. MS: 392.0 ([$\{^{35}Cl, ^{35}Cl\}$ M−H]$^−$), 394.0 ([$\{^{35}Cl, ^{37}Cl\}$ M−H]$^−$), ESI neg.

d) [7,8-dichloro-6-(3-fluoro-2-pyridyl)-4H-[1,2,4]triazolo[1,5-a][1,4]benzodiazepin-2-yl]-(3-methoxyazetidin-1-yl)methanone In analogy to experiment of example 17, 7,8-dichloro-6-(3-fluoro-2-pyridyl)-4H-[1,2,4]triazolo[1,5-a][1,4]benzodiazepine-2-carboxylic acid using 3-methoxyazetidine hydrochloride was converted into the title compound (18 mg, 38%) which was obtained as a white solid. MS: 461.2 ([$\{^{35}Cl, ^{35}Cl\}$ M+H]$^+$), 463.2 ([$\{^{35}Cl, ^{37}Cl\}$ M+H]$^+$), ESI pos.

Example 63

(4S)-7,8-dichloro-6-(2,6-difluorophenyl)-4-methyl-N-[(2S)-2-hydroxypropyl]-4H-[1,2,4]triazolo[1,5-a][1,4]benzodiazepine-2-carboxamide

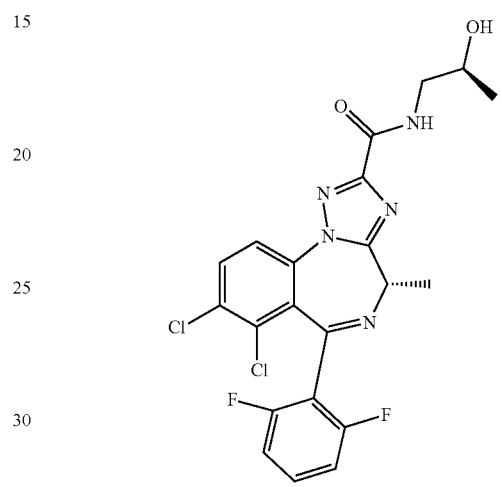

In analogy to experiment of example 6 d, (4S)-7,8-dichloro-6-(2,6-difluorophenyl)-4-methyl-4H-[1,2,4]triazolo[1,5-a][1,4]benzodiazepine-2-carboxylic acid using (2S)-1-aminopropan-2-ol was converted into the enantiopure (−)-title compound (29 mg, 25%) which was obtained as a white solid. MS: 480.2 ([$\{^{35}Cl, ^{35}Cl\}$ M+H]$^+$), 482.2 ([$\{^{35}Cl, ^{35}Cl\}$ M+H]$^+$), ESI pos.

Example 64

(4S)-7,8-dichloro-6-(2,6-difluorophenyl)-N-ethyl-4-methyl-4H-[1,2,4]triazolo[1,5-a][1,4]benzodiazepine-2-carboxamide

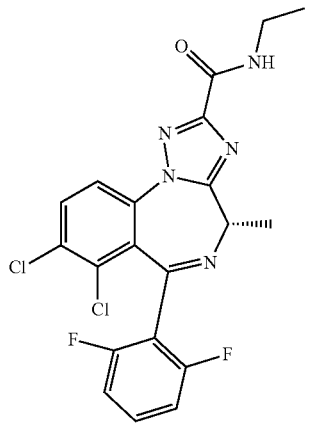 [SMILES: CCNC(=O)c1nc2n(n1)-c1ccc(Cl)c(Cl)c1C(c1c(F)cccc1F)=N[C@H]2C]

In analogy to experiment of example 17, (4S)-7,8-dichloro-6-(2,6-difluorophenyl)-4-methyl-4H-[1,2,4]triazolo[1,5-a][1,4]benzodiazepine-2-carboxylic acid using ethylamine hydrochloride was converted into the enantiopure (−)-title compound (36 mg, 22%) which was obtained as a white solid. MS: 450.0 ([{$^{35}$Cl, $^{35}$Cl} M+H]$^+$), ESI pos.

Example 65

(4S)-7,8-dichloro-6-(2,6-difluorophenyl)-4-methyl-N-[(2R)-2-hydroxypropyl]-4H-[1,2,4]triazolo[1,5-a][1,4]benzodiazepine-2-carboxamide

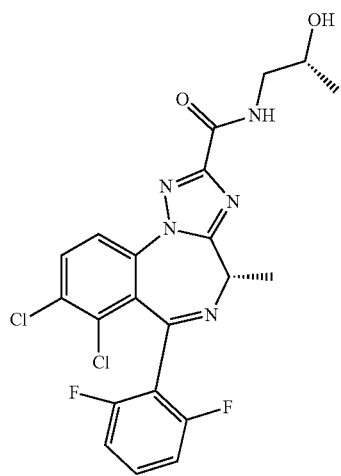 [SMILES: C[C@@H]1N=C(c2c(F)cccc2F)c2c(ccc(Cl)c2Cl)-n2nc(C(=O)NC[C@@H](C)O)nc21]

In analogy to experiment of example 6 d, (4S)-7,8-dichloro-6-(2,6-difluorophenyl)-4-methyl-4H-[1,2,4]triazolo[1,5-a][1,4]benzodiazepine-2-carboxylic acid using (2R)-1-aminopropan-2-ol was converted into the enantiopure (−)-title compound (11 mg, 9%) which was obtained as a white solid. MS: 480.1 ([{$^{35}$Cl, $^{35}$Cl} M+H]$^+$), 482.1 ([{$^{35}$Cl, $^{37}$Cl} M+H]$^+$), ESI pos.

Example 66

1-[(4S)-7,8-dichloro-6-(2,6-difluorophenyl)-4-methyl-4H-[1,2,4]triazolo[1,5-a][1,4]benzodiazepin-2-yl]azetidin-3-ol

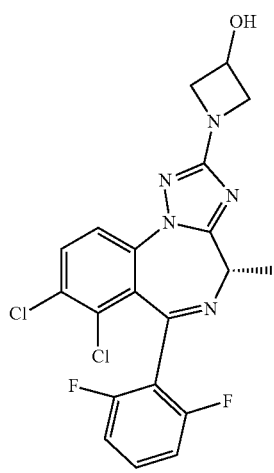 [SMILES: C[C@@H]1N=C(c2c(F)cccc2F)c2c(ccc(Cl)c2Cl)-n2nc(N3CC(O)C3)nc21]

In analogy to experiment of example 52, 2-bromo-7,8-dichloro-6-(2,6-difluorophenyl)-4-methyl-4H-[1,2,4]triazolo[1,5-a][1,4]benzodiazepine using azetidin-3-ol hydrochloride was converted into the enantiopure (−)-title compound (5.4 mg, 3%) which was obtained as a white solid. MS: 450.1 ([{$^{35}$Cl, $^{35}$Cl} M+H]$^+$), 452.1 ([{$^{35}$Cl, $^{37}$Cl} M+H]$^+$), ESI pos.

Example 67

N-[[(4S)-7,8-dichloro-6-(2,6-difluorophenyl)-4-methyl-4H-[1,2,4]triazolo[1,5-a][1,4]benzodiazepin-2-yl]methyl]acetamide

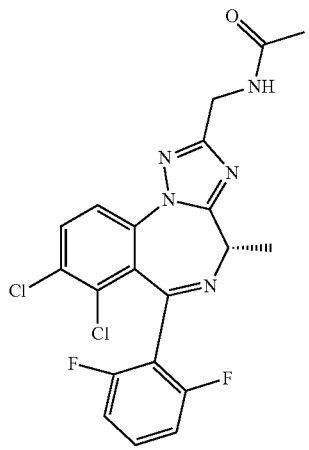 [SMILES: CC(=O)NCc1nc2n(n1)-c1ccc(Cl)c(Cl)c1C(c1c(F)cccc1F)=N[C@H]2C]

a) [7,8-dichloro-6-(2,6-difluorophenyl)-4-methyl-4H-[1,2,4]triazolo[1,5-a][1,4]benzodiazepin-2-yl] methyl methanesulfonate To a solution of [7,8-dichloro-6-(2,6-difluorophenyl)-4-methyl-4H-[1,2,4]triazolo[1,5-a][1,4]benzodiazepin-2-yl] methanol (300 mg, 0.73 mmol) and triethylamine (225 mg, 2.23 mmol) in dichloromethane (5.0 mL) was added methanesulfonyl chloride (0.09 mL, 1.18 mmol) at 0° C. The reaction mixture was stirred for 30 min at 0° C., then poured into saturated aqueous ammonium chloride (50 mL). The aqueous layer was extracted with dichloromethane (2×50 mL). The combined organic layers were washed with brine (2×20 mL), dried (Na$_2$SO$_4$) and concentrated in vacuo. The residue was purified by flash column chromatography (silica, petroleum ether/ethyl acetate 5:1 to 1:1) to afford the title compound (180 mg, 50%) as a yellow oil. MS: 487.0 ([{$^{35}$Cl, $^{35}$Cl} M+H]$^+$), 489.0 ([{$^{35}$Cl, $^{37}$Cl} M+H]$^+$), ESI pos.

b) [7,8-dichloro-6-(2,6-difluorophenyl)-4-methyl-4H-[1,2,4]triazolo[1,5-a][1,4]benzodiazepin-2-yl] methanamine To a solution of [7,8-dichloro-6-(2,6-difluorophenyl)-4-methyl-4H-[1,2,4]triazolo[1,5-a][1,4]benzodiazepin-2-yl] methyl methanesulfonate (180 mg, 0.37 mmol) in ethanol (2 mL) was added aqueous ammonia (25%, 1.0 mL, 33 mmol) at 0° C. The reaction mixture was stirred for 3 h at 20° C., then poured into water (10 mL) and extracted with ethyl acetate (2×20 mL). The combined organic layers were dried (Na$_2$SO$_4$), filtered and concentrated in vacuo. The residue (150 mg) was used as such in the following step without further purification. MS: 408.0 ([$\{^{35}Cl, ^{35}Cl\}$ M+H]$^+$), 410.0 ([$\{^{35}Cl, ^{37}Cl\}$ M+H]$^+$), ESI pos.

c) N-[[(4S)-7,8-dichloro-6-(2,6-difluorophenyl)-4-methyl-4H-[1,2,4]triazolo[1,5-a][1,4]benzodiazepin-2-yl]methyl]acetamide To a solution of [7,8-dichloro-6-(2,6-difluorophenyl)-4-methyl-4H-[1,2,4]triazolo[1,5-a][1,4]benzodiazepin-2-yl]methanamine (150 mg, 0.37 mmol) and N-ethyl-N-isopropyl-propan-2-amine (142 mg, 1.1 mmol) in dichloromethane (2.0 mL) was added acetic anhydride (56 mg, 0.55 mmol) at 0° C. The reaction mixture was stirred for 2 h at 25° C., then concentrated in vacuo. The residue was purified by preparative HPLC (Waters Xbridge, water containing 10 mM ammonium bicarbonate/acetonitrile) followed by chiral SFC (Daicel Chiralcel AD, isopropanol containing 0.1% aqueous ammonia) to afford the enantiopure (−)-title compound (49 mg, 29%) as a white solid. MS: 450.3 ([$\{^{35}Cl, ^{35}Cl\}$ M+H]$^+$), 452.3 ([$\{^{35}Cl, ^{37}Cl\}$ M+H]$^+$), ESI pos.

Example 68

(3-hydroxyazetidin-1-yl)-[(4S)-7,8-dichloro-6-(2,6-difluorophenyl)-4-methyl-4H-imidazo[1,2-a][1,4]benzodiazepin-2-yl]methanone

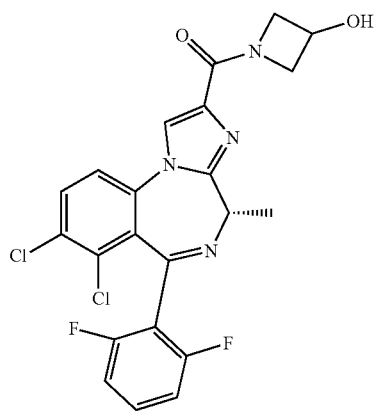 [SMILES: C[C@@H]1N=C(c2c(F)cccc2F)c2c(ccc(Cl)c2Cl)-n2cc(C(=O)N3CC(O)C3)nc21]

a) 6,7-dichloro-5-(2,6-difluorophenyl)-3-methyl-1,3-dihydro-1,4-benzodiazepine-2-thione In analogy to experiment of example 3 a, 6,7-dichloro-5-(2,6-difluorophenyl)-3-methyl-1,3-dihydro-1,4-benzodiazepin-2-one (building block M) was converted into the title compound (390 mg, 77%) which was obtained as a light yellow solid. MS: 371.0 ([$\{^{35}Cl, ^{35}Cl\}$ M+H]$^+$), 373.0 ([$\{^{35}Cl, ^{37}Cl\}$ M+H]$^+$), ESI pos.

b) 6,7-dichloro-5-(2,6-difluorophenyl)-3-methyl-3H-1,4-benzodiazepin-2-amine

In analogy to experiment of example 1 b, 6,7-dichloro-5-(2,6-difluorophenyl)-3-methyl-1,3-dihydro-1,4-benzodiazepine-2-thione was converted into the title compound (390 mg, 77%) which was obtained as a light yellow solid. MS: 352.0 ([$\{^{35}Cl, ^{35}Cl\}$ M−H]$^−$), 354.0 ([$\{^{35}Cl, ^{37}Cl\}$ M−H]$^−$), ESI neg.

c) ethyl 7,8-dichloro-6-(2,6-difluorophenyl)-4-methyl-4H-imidazo[1,2-a][1,4]benzodiazepine-2-carboxylate To a solution of 6,7-dichloro-5-(2,6-difluorophenyl)-3-methyl-3H-1,4-benzodiazepin-2-amine (10.0 g, 2.82 mmol) in tetrahydrofuran (100 mL) was added potassium carbonate (1.17 g, 8.47 mmol) followed by ethyl 3-bromo-2-oxopropanoate (1.65 g, 8.47 mmol). The reaction mixture was stirred at 20° C. for 16 h, then concentrated in vacuo. The crude was dissolved in ethanol (23 mL) and the reaction mixture was stirred at 90° C. for 48 h. The reaction mixture was cooled and concentrated in vacuo. The residue was purified by preparative HPLC (Phenomenex luna C18, water containing 0.1% trifluoroacetic acid/acetonitrile) to afford the title compound (2.8 g, 26%) as a white solid. MS: 450.0 ([$\{^{35}Cl, ^{35}Cl\}$ M+H]$^+$), 452.0 ([$\{^{35}Cl, ^{37}Cl\}$ M+H]$^+$), ESI pos.

d) 7,8-dichloro-6-(2,6-difluorophenyl)-4-methyl-4H-imidazo[1,2-a][1,4]benzodiazepine-2-carboxylic acid In analogy to experiment of example 3 e, ethyl 7,8-dichloro-6-(2,6-difluorophenyl)-4-methyl-4H-imidazo[1,2-a][1,4]benzodiazepine-2-carboxylate was converted into the title compound (300 mg, 62%) which was obtained as a yellow solid. MS: 422.2 ([$\{^{35}Cl, ^{35}Cl\}$ M+H]$^+$), 424.2 ([$\{^{35}Cl, ^{37}Cl\}$ M+H]$^+$), ESI pos.

e) (3-hydroxyazetidin-1-yl)-[(4S)-7,8-dichloro-6-(2,6-difluorophenyl)-4-methyl-4H-imidazo[1,2-a][1,4]benzodiazepin-2-yl]methanone In analogy to experiment of example 6 d, 7,8-dichloro-6-(2,6-difluorophenyl)-4-methyl-4H-imidazo[1,2-a][1,4]benzodiazepine-2-carboxylic acid using azetidin-3-ol was converted into the enantiopure (−)-title compound (31 mg, 28%) which was obtained as a white solid. MS: 476.9 ([$\{^{35}Cl, ^{35}Cl\}$ M+H]$^+$), 478.9 ([$\{^{35}Cl, ^{37}Cl\}$ M+H]$^+$), ESI pos.

Example 69

(4S)-7,8-dichloro-6-(2,6-difluorophenyl)-4-methyl-4H-[1,2,4]triazolo[1,5-a][1,4]benzodiazepine-2-sulfonamide

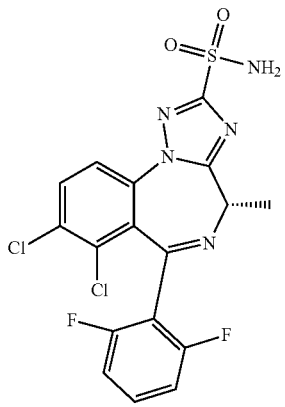 [SMILES: C[C@@H]1N=C(c2c(F)cccc2F)c2c(ccc(Cl)c2Cl)-n2nc(S(N)(=O)=O)nc21]

a) 2-benzylsulfanyl-7,8-dichloro-6-(2,6-difluorophenyl)-4-methyl-4H-[1,2,4]triazolo[1,5-a][1,4]benzodiazepine To a solution of 2-bromo-7,8-dichloro-6-(2,6-difluorophenyl)-4-methyl-4H-[1,2,4]triazolo[1,5-a][1,4]benzodiazepine (500 mg, 1.09 mmol) in 1,4-dioxane (5 mL) was added phenylmethanethiol (271 mg, 2.18 mmol), Xantphos (126 mg, 0.22 mmol), Pd$_2$(dba)$_3$ (99 mg, 0.11 mmol) and DIPEA (0.6 mL, 3.27 mmol). The mixture was stirred under nitrogen at 100° C. for 16 h, then purified by flash column chromatography (silica, petroleum ether/ethyl acetate 5:1) to afford the title compound (500 mg, 90%) as a yellow oil. MS: 501.3 ([{$^{35}$Cl, $^{35}$Cl} M+H]$^+$), 503.3 ([{$^{35}$Cl, $^{37}$Cl} M+H]$^+$), ESI pos.

b) 7,8-dichloro-6-(2,6-difluorophenyl)-4-methyl-4H-[1,2,4]triazolo[1,5-a][1,4]benzodiazepine-2-sulfonyl chloride To a solution of 2-benzylsulfanyl-7,8-dichloro-6-(2,6-difluorophenyl)-4-methyl-4H-[1,2,4]triazolo[1,5-a][1,4]benzodiazepine (130 mg, 0.26 mmol) in acetonitrile (1.3 mL) was added 1-chloropyrrolidine-2,5-dione (138 mg, 1.04 mmol) and aqueous hydrochloric acid (2 m, 0.6 mL, 1.04 mmol) at 0° C. The reaction mixture was stirred at 25° C. for 2 h. The reaction mixture was diluted with water (10 mL) and extracted with ethyl acetate (3×10 mL). The combined organic layers were washed with brine (2×10 mL), dried (Na$_2$SO$_4$) and concentrated in vacuo to afford the title compound (150 mg, 69%) as a yellow solid. MS: 477.2 ([{$^{35}$Cl, $^{35}$Cl} M+H]$^+$), 479.2 ([{$^{35}$Cl, $^{37}$Cl} M+H]$^+$), ESI pos.

c) (4S)-7,8-dichloro-6-(2,6-difluorophenyl)-4-methyl-4H-[1,2,4]triazolo[1,5-a][1,4]benzodiazepine-2-sulfonamide A mixture of 7,8-dichloro-6-(2,6-difluorophenyl)-4-methyl-4H-[1,2,4]triazolo[1,5-a][1,4]benzodiazepine-2-sulfonyl chloride (200 mg, 0.420 mmol) and aqueous ammonia (25%, 44 mg, 1.26 mmol) in tetrahydrofuran (2 mL) was stirred at 25° C. for 2 h. The reaction mixture was cooled and concentrated in vacuo. The residue was purified by preparative HPLC (Phenomenex Gemini-NX C18, water containing 0.05% ammonium hydroxide/acetonitrile), followed by SFC (Daicel Chiralpak IG, isopropanol containing 0.1% aqueous ammonia) to afford the enantiopure (−)-title compound (8.4 mg, 28%) as a white solid. MS: 458.1 ([{$^{35}$Cl, $^{35}$Cl} M+H]$^+$), 460.1 ([{$^{35}$Cl, $^{37}$Cl} M+H]$^+$), ESI pos.

Example 70 azetidin-1-yl-[(4S)-7,8-dichloro-6-(2,6-difluorophenyl)-4-methyl-4H-imidazo[1,2-a][1,4]benzodiazepin-2-yl]methanone

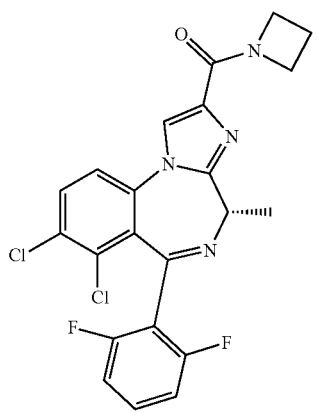 [SMILES: C[C@@H]1N=C(c2c(F)cccc2F)c2c(ccc(Cl)c2Cl)-n2cc(C(=O)N3CCC3)nc21]

In analogy to experiment of example 17, 7,8-dichloro-6-(2,6-difluorophenyl)-4-methyl-4H-imidazo[1,2-a][1,4]benzodiazepine-2-carboxylic acid using azetidine hydrochloride was converted into the enantiopure (−)-title compound (20 mg, 39%) which was obtained as a white solid. MS: 461.1 ([{$^{35}$Cl, $^{35}$Cl} M+H]$^+$), 463.1 ([{$^{35}$Cl, $^{37}$Cl} M+H]$^+$), ESI pos.

Example 71

1-[(4S)-7,8-dichloro-6-(2,6-difluorophenyl)-4-methyl-4H-imidazo[1,2-a][1,4]benzodiazepine-2-carbonyl]azetidine-3-carbonitrile

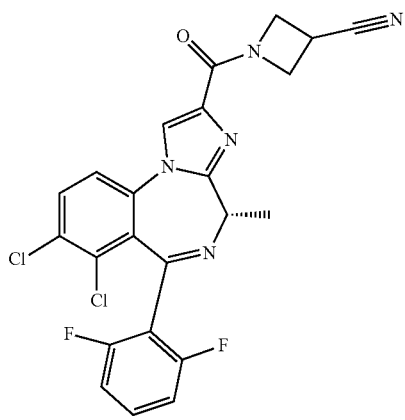 [SMILES: C[C@@H]1N=C(c2c(F)cccc2F)c2c(ccc(Cl)c2Cl)-n2cc(C(=O)N3CC(C#N)C3)nc21]

In analogy to experiment of example 17, 7,8-dichloro-6-(2,6-difluorophenyl)-4-methyl-4H-imidazo[1,2-a][1,4]benzodiazepine-2-carboxylic acid using azetidine-3-carbonitrile hydrochloride was converted into the enantiopure (−)-title compound (19 mg, 37%) which was obtained as a white solid. MS: 486.0 ([{$^{35}$Cl, $^{35}$Cl} M+H]$^+$), 488.0 ([{$^{35}$Cl, $^{37}$Cl} M+H]$^+$), ESI pos.

Example 72

[3-(fluoromethyl)azetidin-1-yl]-[(4S)-7,8-dichloro-6-(2,6-difluorophenyl)-4-methyl-4H-[1,2,4]triazolo[1,5-a][1,4]benzodiazepin-2-yl]methanone

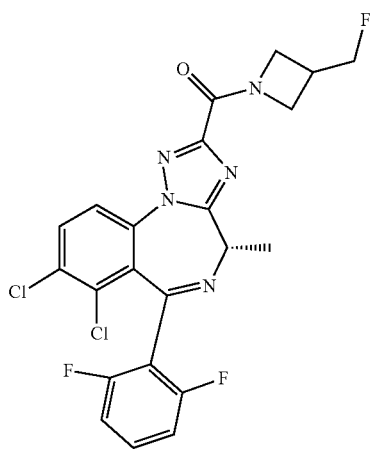 [SMILES: C[C@@H]1N=C(c2c(F)cccc2F)c2c(ccc(Cl)c2Cl)-n2nc(C(=O)N3CC(CF)C3)nc21]

In analogy to experiment of example 17, (4S)-7,8-dichloro-6-(2,6-difluorophenyl)-4-methyl-4H-[1,2,4]triazolo[1,5-a][1,4]benzodiazepine-2-carboxylic acid using 3-(fluoromethyl)azetidine hydrochloride was converted into the enantiopure (−)-title compound (20 mg, 17%) which was obtained as an off-white solid. MS: 494.1 ([{$^{35}$Cl, $^{35}$Cl} M+H]$^{+}$), 496.1 ([{$^{35}$Cl, $^{37}$Cl} M+H]$^{+}$), ESI pos.

Example 73

(4S)-7,8-dichloro-6-(2,6-difluorophenyl)-N,4-dimethyl-4H-[1,2,4]triazolo[1,5-a][1,4]benzodiazepine-2-sulfonamide

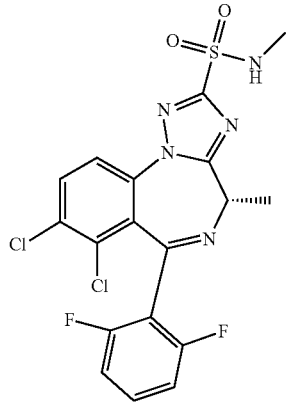 [SMILES: CNS(=O)(=O)c1nc2n(n1)-c1ccc(Cl)c(Cl)c1C(c1c(F)cccc1F)=N[C@H]2C]

A mixture of 7,8-dichloro-6-(2,6-difluorophenyl)-4-methyl-4H-[1,2,4]triazolo[1,5-a][1,4]benzodiazepine-2-sulfonyl chloride (200 mg, 0.42 mmol) and methanamine in tetrahydrofuran (2 m, 65 mg, 2.09 mmol) in tetrahydrofuran (2 mL) was stirred at 25° C. for 2 h. The reaction mixture was cooled and concentrated in vacuo. The residue was purified by preparative HPLC (Phenomenex Gemini-NX C18, water containing 0.05% ammonium hydroxide/acetonitrile) followed by chiral SFC (Daicel Chiralpak IG, methanol containing 0.1% aqueous ammonia) to afford the enantiopure (−)-title compound (17 mg, 9%) as a white solid. MS: 471.9 ([{$^{35}$Cl, $^{35}$Cl} M+H]$^{+}$), 473.9 ([{$^{35}$Cl, $^{37}$Cl} M+H]$^{+}$), ESI pos.

Example 74

(4S)-7,8-dichloro-6-(2,6-difluorophenyl)-4-methyl-4H-imidazo[1,2-a][1,4]benzodiazepine-2-carbonitrile

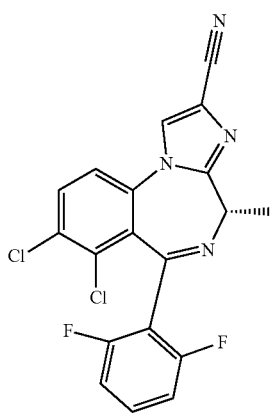 [SMILES: C[C@@H]1N=C(c2c(F)cccc2F)c2c(ccc(Cl)c2Cl)-n2cc(C#N)nc21]

a) 7,8-dichloro-6-(2,6-difluorophenyl)-4-methyl-4H-imidazo[1,2-a][1,4]benzodiazepine-2-carboxamide To a mixture of ethyl 7,8-dichloro-6-(2,6-difluorophenyl)-4-methyl-4H-imidazo[1,2-a][1,4]benzodiazepine-2-carboxylate (299 mg, 0.66 mmol) in ethanol (0.5 mL) was added ammonium hydroxide (0.2 mL, 0.70 mmol). The mixture was stirred at 80° C. for 24 h, then concentrated in vacuo. The residue (120 mg) was used as such in the following step without further purification. MS: 421.0 ([{$^{35}$Cl, $^{35}$Cl} M+H]$^{+}$), 423.0 ([{$^{35}$Cl, $^{37}$Cl} M+H]$^{+}$), ESI pos b) (4S)-7,8-dichloro-6-(2,6-difluorophenyl)-4-methyl-4H-imidazo[1,2-a][1,4]benzodiazepine-2-carbonitrile To a mixture of 7,8-dichloro-6-(2,6-difluorophenyl)-4-methyl-4H-imidazo[1,2-a][1,4]benzodiazepine-2-carboxamide (110.0 mg, 0.260 mmol) in dichloromethane (0.500 mL) was added trifluoroacetic anhydride (0.06 mL, 0.390 mmol). The reaction mixture was stirred at 25° C. for 3 h. The reaction mixture was concentrated in vacuo. The residue was purified by flash column chromatography (silica, petroleum ether/ethyl acetate 10:1 to 5:1 to 3:1) followed by chiral SFC (Daicel Chiralpak IC, methanol containing 0.1% aqueous ammonia) to afford the enantiopure (−)-title compound (28 mg, 27%) as a white solid. MS: 403.0 ([{$^{35}$Cl, $^{35}$Cl} M+H]$^{+}$), 405.0 ([{$^{35}$Cl, $^{37}$Cl} M+H]$^{+}$), ESI pos.

Example 75

[3-(difluoromethyl)azetidin-1-yl]-[(4S)-7,8-dichloro-6-(2,6-difluorophenyl)-4-methyl-4H-[1,2,4]triazolo[1,5-a][1,4]benzodiazepin-2-yl]methanone

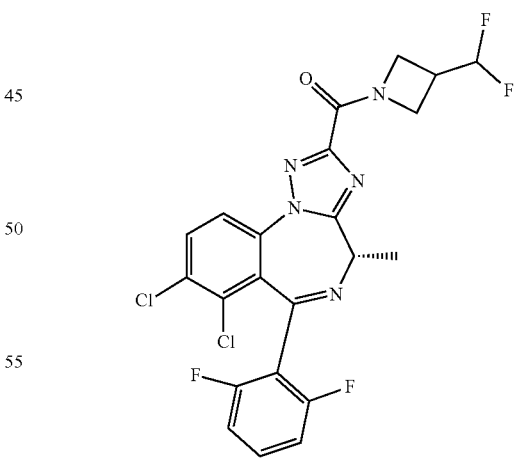

In analogy to experiment of example 17, (4S)-7,8-dichloro-6-(2,6-difluorophenyl)-4-methyl-4H-[1,2,4]triazolo[1,5-a][1,4]benzodiazepine-2-carboxylic acid using 3-(difluoromethyl)azetidine hydrochloride was converted into the enantiopure (−)-title compound (21 mg, 17%) which was obtained as a white solid. MS: 512.1 ([{$^{35}$Cl, $^{35}$Cl} M+H]$^{+}$), 514.1 ([{$^{35}$Cl, $^{37}$Cl} M+H]$^{+}$), ESI pos.

Example 76

[(4S)-7,8-dichloro-6-(2,6-difluorophenyl)-4-methyl-4H-[1,2,4]triazolo[1,5-a][1,4]benzodiazepin-2-yl]-[(3R)-3-fluoropyrrolidin-1-yl]methanone

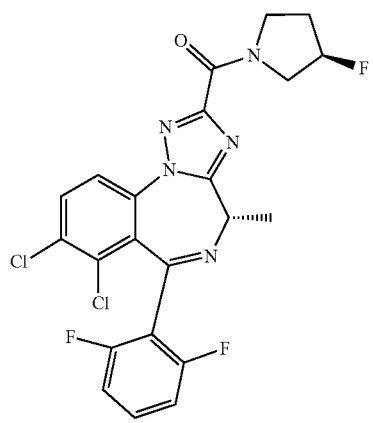 [SMILES: C[C@@H]1N=C(c2c(F)cccc2F)c2c(ccc(Cl)c2Cl)-n2nc(C(=O)N3CC[C@@H](F)C3)nc21]

In analogy to experiment of example 17, (4S)-7,8-dichloro-6-(2,6-difluorophenyl)-4-methyl-4H-[1,2,4]triazolo[1,5-a][1,4]benzodiazepine-2-carboxylic acid using (3R)-3-fluoropyrrolidine hydrochloride was converted into the enantiopure (−)-title compound (27 mg, 15%) which was obtained as a white solid. MS: 493.9 ([$\{^{35}Cl, ^{35}Cl\}$ M+H]$^+$), 495.9 ([$\{^{35}Cl, ^{37}Cl\}$ M+H]$^+$), ESI pos.

Example 77

1-[(4S)-7,8-dichloro-6-(2,6-difluorophenyl)-4-methyl-4H-[1,2,4]triazolo[1,5-a][1,4]benzodiazepin-2-yl]azetidine-3-carbonitrile

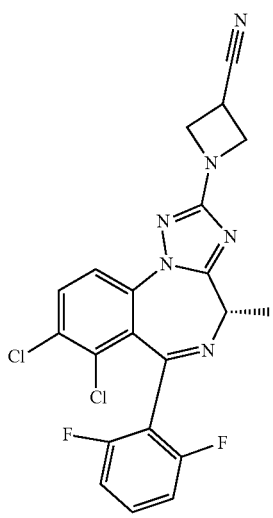 [SMILES: C[C@@H]1N=C(c2c(F)cccc2F)c2c(ccc(Cl)c2Cl)-n2nc(N3CC(C#N)C3)nc21]

In analogy to experiment of example 52, 2-bromo-7,8-dichloro-6-(2,6-difluorophenyl)-4-methyl-4H-[1,2,4]triazolo[1,5-a][1,4]benzodiazepine using azetidine-3-carbonitrile hydrochloride was converted into the enantiopure (+)-title compound (20 mg, 18%) which was obtained as an off-white solid. MS: 459.1 ([$\{^{35}Cl, ^{35}Cl\}$ M+H]$^+$), 461.1 ([$\{^{35}Cl, ^{37}Cl\}$ M+H]$^+$), ESI pos.

Example 78

[(4S)-7,8-dichloro-6-(3-fluoro-2-pyridyl)-4-methyl-4H-[1,2,4]triazolo[1,5-a][1,4]benzodiazepin-2-yl]-[(3R)-3-fluoropyrrolidin-1-yl]methanone

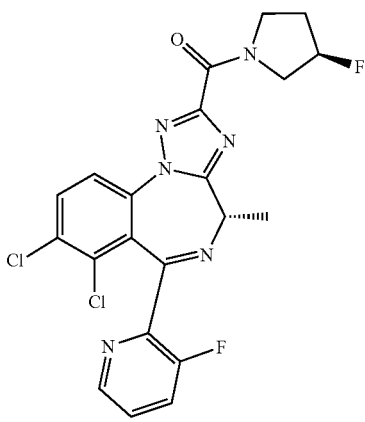 [SMILES: C[C@@H]1N=C(c2ncccc2F)c2c(ccc(Cl)c2Cl)-n2nc(C(=O)N3CC[C@@H](F)C3)nc21]

In analogy to experiment of example 17, 7,8-dichloro-6-(3-fluoro-2-pyridyl)-4-methyl-4H-[1,2,4]triazolo[1,5-a][1,4]benzodiazepine-2-carboxylic acid using (3R)-3-fluoropyrrolidine hydrochloride was converted into the enantiopure (−)-title compound (18 mg, 9%) which was obtained as a white solid. MS: 477.3 ([$\{^{35}Cl, ^{35}Cl\}$ M+H]$^+$), 479.3 ([$\{^{35}Cl, ^{37}Cl\}$ M+H]$^+$), ESI pos.

Example 79

[(4S)-7,8-dichloro-6-(3-fluoro-2-pyridyl)-4-methyl-4H-[1,2,4]triazolo[1,5-a][1,4]benzodiazepin-2-yl]-[(3S)-3-fluoropyrrolidin-1-yl]methanone

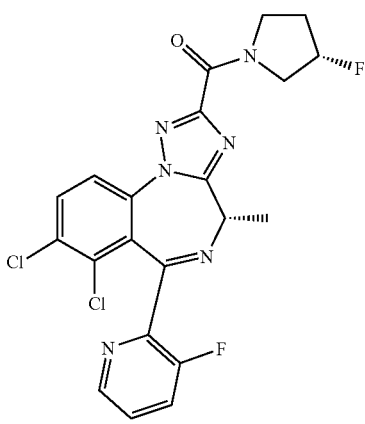 [SMILES: C[C@@H]1N=C(c2ncccc2F)c2c(ccc(Cl)c2Cl)-n2nc(C(=O)N3CC[C@H](F)C3)nc21]

In analogy to experiment of example 17, 7,8-dichloro-6-(3-fluoro-2-pyridyl)-4-methyl-4H-[1,2,4]triazolo[1,5-a][1,4]benzodiazepine-2-carboxylic acid using (3S)-3-fluoropyrrolidine hydrochloride was converted into the enantiopure (+)-title compound (24 mg, 11%) which was obtained as a white solid. MS: 477.1 ([{$^{35}$Cl, $^{35}$Cl} M+H]$^+$), 479.1 ([{$^{35}$Cl, $^{37}$Cl} M+H]$^+$), ESI pos.

Example 80

[(4S)-7,8-dichloro-6-(2,6-difluorophenyl)-4-methyl-4H-[1,2,4]triazolo[1,5-a][1,4]benzodiazepin-2-yl]-[(3S)-3-fluoropyrrolidin-1-yl]methanone

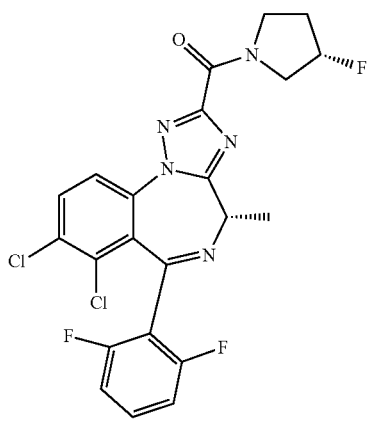 [SMILES: C[C@@H]1N=C(c2c(F)cccc2F)c2c(ccc(Cl)c2Cl)-n2nc(C(=O)N3CC[C@H](F)C3)nc21]

In analogy to experiment of example 17, (4S)-7,8-dichloro-6-(2,6-difluorophenyl)-4-methyl-4H-[1,2,4]triazolo[1,5-a][1,4]benzodiazepine-2-carboxylic acid using (3S)-3-fluoropyrrolidine hydrochloride was converted into the enantiopure (−)-title compound (47 mg, 42%) which was obtained as a white solid. MS: 494.1 ([{$^{35}$Cl, $^{35}$Cl} M+H]$^+$), 496.1 ([{$^{35}$Cl, $^{37}$Cl} M+H]$^+$), ESI pos.

Example 81

(4S)-7,8-dichloro-6-(2,6-difluorophenyl)-4-methyl-2-(oxetan-3-yl)-4H-[1,2,4]triazolo[1,5-a][1,4]benzodiazepine

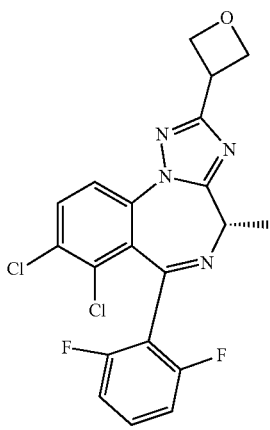 [SMILES: C[C@@H]1N=C(c2c(F)cccc2F)c2c(ccc(Cl)c2Cl)-n2nc(C3COC3)nc21]

A mixture of 2-bromo-7,8-dichloro-6-(2,6-difluorophenyl)-4-methyl-4H-[1,2,4]triazolo[1,5-a][1,4]benzodiazepine (100 mg, 0.22 mmol), sodium iodide (8.2 mg, 0.05 mmol), zinc (28.5 mg, 0.44 mmol), pyridine-2-carboxamidine (2.6 mg, 0.02 mmol), iodonickel (4.1 mg, 0.02 mmol), N,N-dimethylacetamide (3 mL), trifluoroacetic acid (2.5 mg, 0.02 mmol) and 3-bromooxetane (44.9 mg, 0.33 mmol) was flushed with nitrogen and the reaction mixture was stirred at 60° C. for 16 h. This set up was repeated 3 times. The 3 reaction tubes were combined and diluted with water (20 mL) and ethyl acetate (20 mL). The layers were separated. The aqueous layer was extracted with ethyl acetate (2×20 mL). The combined organic layers were washed with brine (3×20 mL), dried (Na$_2$SO$_4$), filtered and concentrated in vacuo. The residue was purified by preparative TLC (petroleum ether/ethyl acetate 1:1) followed by preparative HPLC (Waters Xbridge, water containing 10 mM ammonium bicarbonate/acetonitrile) and, finally, by chiral SFC (Daicel Chiralcel OJ, 20% methanol containing 0.1% aqueous ammonia) to afford the enantiopure (−)-title compound (23.1 mg, 34%) as a off-white solid. MS: 435.1 ([{$^{35}$Cl, $^{35}$Cl} M+H]$^+$), 437.1 ([{$^{35}$Cl, $^{37}$Cl} M+H]$^+$), ESI pos.

Example 82

(4S)-7,8-dichloro-6-(2,6-difluorophenyl)-4-methyl-2-methylsulfonyl-4H-[1,2,4]triazolo[1,5-a][1,4]benzodiazepine

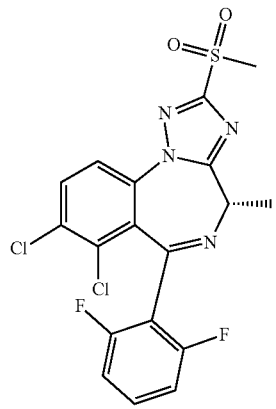 [SMILES: C[C@@H]1N=C(c2c(F)cccc2F)c2c(ccc(Cl)c2Cl)-n2nc(S(C)(=O)=O)nc21]

a) 7,8-dichloro-6-(2,6-difluorophenyl)-2-iodo-4-methyl-4H-[1,2,4]triazol[1,5-a][1,4]benzodiazepine In analogy to experiment of example 49 c, 7,8-dichloro-6-(2,6-difluorophenyl)-4-methyl-4H-[1,2,4]triazolo[1,5-a][1,4]benzodiazepin-2-amine was converted into the title compound (600 mg, 94%) which was obtained as a white solid. MS: 505.2 ([{$^{35}$Cl, $^{35}$Cl} M+H]$^+$), 507.2 ([{$^{35}$Cl, $^{37}$Cl} M+H]$^+$), ESI pos.

b) 7,8-dichloro-6-(2,6-difluorophenyl)-4-methyl-2-methylsulfanyl-4H-[1,2,4]triazolo[1,5-a][1,4]benzodiazepine In analogy to experiment of example 69 a, 7,8-dichloro-6-(2,6-difluorophenyl)-2-iodo-4-methyl-4H-[1,2,4]triazolo[1,5-a][1,4]benzodiazepine using methylsulfanylsodium was converted into the title compound (150 mg, 84%) which was obtained as a yellow oil. MS: 424.8 ([{$^{35}$Cl, $^{35}$Cl} M+H]$^+$), 426.8 ([{$^{35}$Cl, $^{37}$Cl} M+H]$^+$), ESI pos.

c) (4S)-7,8-dichloro-6-(2,6-difluorophenyl)-4-methyl-2-methylsulfonyl-4H-[1,2,4]triazolo[1,5-a][1,4]benzodiazepine To a mixture of 7,8-dichloro-6-(2,6-difluorophenyl)-4-methyl-2-methylsulfanyl-4H-[1,2,4]triazolo[1,5-a][1,4]benzodiazepine (150 mg, 0.35 mmol) in dichloromethane (1.5 mL) was added m-CPBA (179 mg, 0.88 mmol). The reaction mixture was stirred at 25° C. for 1 h, then quenched with a solution of sodium thiosulfate. The reaction mixture was diluted with water (20 mL) and extracted with ethyl acetate (3×20 mL). The combined organic layers were washed with brine (2×10 mL), dried (Na$_2$SO$_4$) and concentrated in vacuo. The residue was purified by preparative HPLC (Phenomenex Gemini-NX C18, water containing 0.05% ammonium hydroxide/acetonitrile) followed by chiral SFC (Daicel Chiralpak IG, methanol containing 0.1% aqueous ammonia) to afford the enantiopure (−)-title compound (21 mg, 13%) as a white solid. MS: 457.3 ([{$^{35}$Cl, $^{35}$Cl} M+H]$^+$), 459.3 ([{$^{35}$Cl, $^{37}$Cl} M+H]$^+$), ESI pos.

Example 83

(4S)-7-chloro-6-(3-fluoro-2-pyridyl)-2,4-dimethyl-8-(trifluoromethyl)-4H-[1,2,4]triazolo[1,5-a][1,4]benzodiazepine

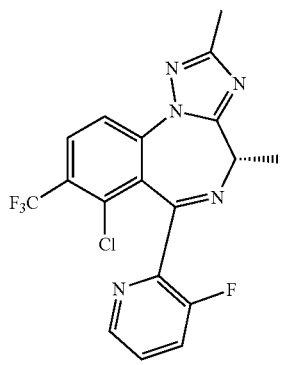 [SMILES: Cc1nc2n(n1)-c1ccc(C(F)(F)F)c(Cl)c1C(c1ncccc1F)=N[C@H]2C]

a) (3S)-1-amino-6-chloro-5-(3-fluoro-2-pyridyl)-3-methyl-7-(trifluoromethyl)-3H-1,4-benzodiazepin-2-one In analogy to experiment of example 22 a, (3S)-6-chloro-5-(3-fluoro-2-pyridyl)-3-methyl-7-(trifluoromethyl)-1,3-dihydro-1,4-benzodiazepin-2-one (building block X) was converted into the title compound (300 mg, 66%) which was obtained as a yellow solid. MS: 387.2 ([{$^{35}$Cl} M+H]$^+$), 389.2 ([{$^{35}$Cl} M+H]$^+$), ESI pos.

b) (4S)-7-chloro-6-(3-fluoro-2-pyridyl)-2,4-dimethyl-8-(trifluoromethyl)-4H-[1,2,4]triazolo[1,5-a][1,4]benzodiazepine A mixture of (3S)-1-amino-6-chloro-5-(3-fluoro-2-pyridyl)-3-methyl-7-(trifluoromethyl)-3H-1,4-benzodiazepin-2-one (70 mg, 0.18 mmol) and ethyl ethanimidate (67.11 mg, 0.54 mmol) in pyridine (1 mL) was stirred at 50° C. for 2 h. The reaction mixture was diluted with water (10 mL) and extracted with ethyl acetate (3×10 mL). The combined organic layers were washed with brine (2×10 mL), dried (Na$_2$SO$_4$) and concentrated in vacuo. The residue was purified by preparative TLC (petroleum ether/ethyl acetate 1:1) followed by chiral SFC (Daicel Chiralpak IG, methanol containing 0.1% aqueous ammonia) to afford the enantiopure (+)-title compound (8 mg, 11%) as a white solid. MS: 410.1 ([{$^{35}$Cl} M+H]$^+$), 412.1 ([{$^{37}$Cl} M+H]$^+$), ESI pos.

Example 84

(4S)-7,8-dichloro-6-(3-fluoro-2-pyridyl)-2,4-dimethyl-4H-[1,2,4]triazolo[1,5-a][1,4]benzodiazepine

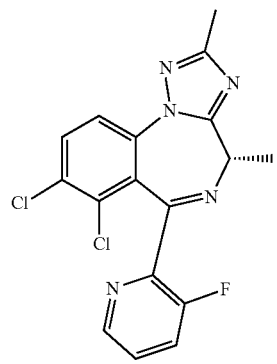 [SMILES: Cc1nc2n(n1)-c1ccc(Cl)c(Cl)c1C(c1ncccc1F)=N[C@H]2C]

In analogy to experiment of example 83 b, 1-amino-6,7-dichloro-5-(3-fluoro-2-pyridyl)-3-methyl-3H-1,4-benzodiazepin-2-one was converted into the enantiopure (+)-title compound (66 mg, 31%) which was obtained as a white solid. MS: 376.0 ([{$^{35}$Cl, $^{35}$Cl} M+H]$^+$), 378.0 ([{$^{35}$Cl, $^{37}$Cl} M+H]$^+$), ESI pos.

Example 85 azetidin-1-yl-[(4S)-7-chloro-6-(3-fluoro-2-pyridyl)-4-methyl-8-(trifluoromethyl)-4H-[1,2,4]triazolo[1,5-a][1,4]benzodiazepin-2-yl]methanone

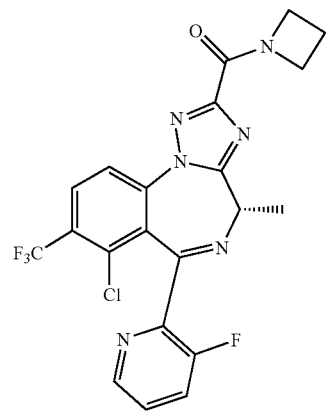 [SMILES: C[C@@H]1N=C(c2ncccc2F)c2c(ccc(C(F)(F)F)c2Cl)-n2nc(C(=O)N3CCC3)nc21]

a) ethyl (4S)-7-chloro-6-(3-fluoro-2-pyridyl)-4-methyl-8-(trifluoromethyl)-4H-[1,2,4]triazolo[1,5-a][1,4]benzodiazepine-2-carboxylate In analogy to experiment of example 48 b, (3S)-1-amino-6-chloro-5-(3-fluoro-2-pyridyl)-3-methyl-7-(trifluoromethyl)-3H-1,4-benzodiazepin-2-one using toluene was converted into the title compound (45 mg, 52%) which was b) azetidin-1-yl-[(4S)-7-chloro-6-(3-fluoro-2-pyridyl)-4-methyl-8-(trifluoromethyl)-4H-[1,2,4]triazolo[1,5-a][1,4]benzodiazepin-2-yl]methanone To a solution of i-PrMgCl (0.21 mL, 0.43 mmol) and azetidine (48.8 mg, 0.86 mmol) in tetrahydrofuran (0.5 mL) at 0° C., was added ethyl (4S)-7-chloro-6-(3-fluoro-2-pyridyl)-4-methyl-8-(trifluoromethyl)-4H-[1,2,4]triazolo[1,5-a][1,4]benzodiazepine-2-carboxylate (40 mg, 0.09 mmol) at 0° C. The reaction mixture was stirred at 0° C. for 30 min, then concentrated in vacuo. The residue was purified by preparative TLC (ethyl acetate) followed by chiral SFC (Daicel Chiralpak AS, methanol containing 0.1% aqueous ammonia) to afford the enantiopure (+)-title compound (15 mg, 17%) as a white solid. MS: 479.1 ([{$^{35}$Cl} M+H]$^+$), 481.1 ([{$^{37}$Cl} M+H]$^+$), ESI pos.

Example 86

(3-ethoxyazetidin-1-yl)-[(4S)-7,8-dichloro-6-(3-fluoro-2-pyridyl)-4-methyl-4H-[1,2,4]triazolo[1,5-a][1,4]benzodiazepin-2-yl]methanone

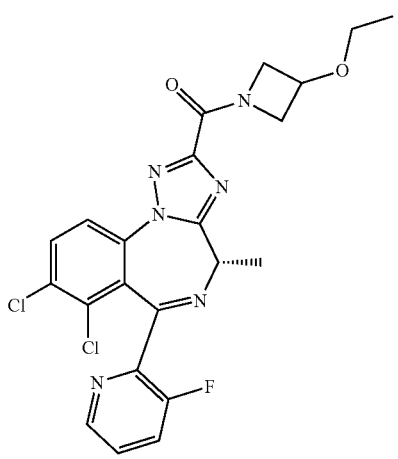 [SMILES: CCOC1CN(C(=O)c2nc3n(n2)-c2ccc(Cl)c(Cl)c2C(c2ncccc2F)=N[C@H]3C)C1]

In analogy to experiment of example 17, 7,8-dichloro-6-(3-fluoro-2-pyridyl)-4-methyl-4H-[1,2,4]triazolo[1,5-a][1,4]benzodiazepine-2-carboxylic acid using 3-ethoxyazetidine was converted into the enantiopure (+)-title compound (36 mg, 22%) which was obtained as a light yellow solid. MS: 489.3 ([{$^{35}$Cl, $^{35}$Cl} M+H]$^+$), 491.3 ([{$^{35}$Cl, $^{37}$Cl} M+H]$^+$), ESI pos.

Example 87

[(4S)-7,8-dichloro-6-(3-fluoro-2-pyridyl)-4-methyl-4H-[1,2,4]triazolo[1,5-a][1,4]benzodiazepin-2-yl]-(3-methylazetidin-1-yl)methanone

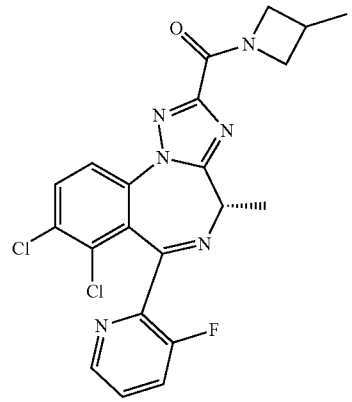 [SMILES: CC1CN(C(=O)c2nc3n(n2)-c2ccc(Cl)c(Cl)c2C(c2ncccc2F)=N[C@H]3C)C1]

In analogy to experiment of example 17, 7,8-dichloro-6-(3-fluoro-2-pyridyl)-4-methyl-4H-[1,2,4]triazolo[1,5-a][1,4]benzodiazepine-2-carboxylic acid using 3-methylazetidine was converted into enantiopure (+)-title compound (22 mg, 17%) which was obtained as a white solid. MS: 459.1 ([{$^{35}$Cl, $^{35}$Cl} M+H]$^+$), 461.1 ([{$^{35}$Cl, $^{37}$Cl} M+H]$^+$), ESI pos.

Example 88

(4S)-7,8-dichloro-N-cyclopropyl-6-(3-fluoro-2-pyridyl)-4-methyl-4H-[1,2,4]triazolo[1,5-a][1,4]benzodiazepine-2-carboxamide

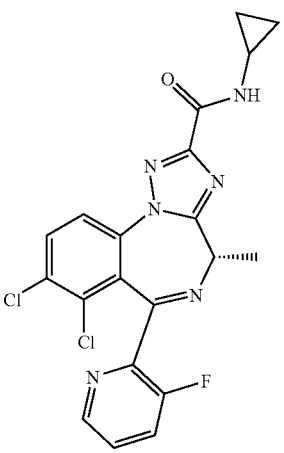 [SMILES: C[C@@H]1N=C(c2ncccc2F)c2c(ccc(Cl)c2Cl)-n2nc(C(=O)NC3CC3)nc21]

In analogy to experiment of example 17, 7,8-dichloro-6-(3-fluoro-2-pyridyl)-4-methyl-4H-[1,2,4]triazolo[1,5-a][1,4]benzodiazepine-2-carboxylic acid using cyclopropylamine was converted into the enantiopure (−)-title compound (25 mg, 19%) which was obtained as a white solid. MS: 445.2 ([{$^{35}$Cl, $^{35}$Cl} M+H]$^+$), 447.2 ([{$^{35}$Cl, $^{37}$Cl} M+H]$^+$), ESI pos.

Example 89

[(4S)-7,8-dichloro-6-(3-fluoro-2-pyridyl)-4-methyl-4H-[1,2,4]triazolo[1,5-a][1,4]benzodiazepin-2-yl]-[(3S)-3-methoxypyrrolidin-1-yl]methanone

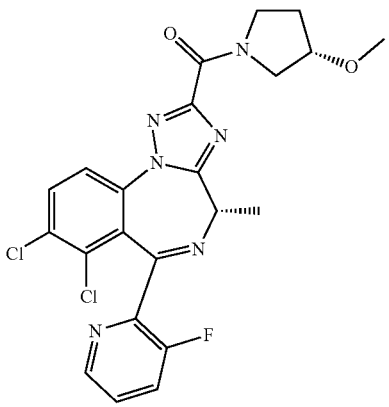 [SMILES: CO[C@H]1CCN(C(=O)c2nc3n(n2)-c2ccc(Cl)c(Cl)c2C(c2ncccc2F)=N[C@H]3C)C1]

In analogy to experiment of example 17, 7,8-dichloro-6-(3-fluoro-2-pyridyl)-4-methyl-4H-[1,2,4]triazolo[1,5-a][1,4]benzodiazepine-2-carboxylic acid using (3S)-3-methoxypyrrolidine was converted into the enantiopure (+)-title compound (25 mg, 21%) which was obtained as a white solid. MS: 489.1 ([{$^{35}$Cl, $^{35}$Cl} M+H]$^+$), 491.1 ([{$^{35}$Cl, $^{37}$Cl} M+H]$^+$), ESI pos.

Example 90

[(4S)-7,8-dichloro-6-(3-fluoro-2-pyridyl)-4-methyl-4H-[1,2,4]triazolo[1,5-a][1,4]benzodiazepin-2-yl]-[3-(difluoromethoxy)azetidin-1-yl]methanone

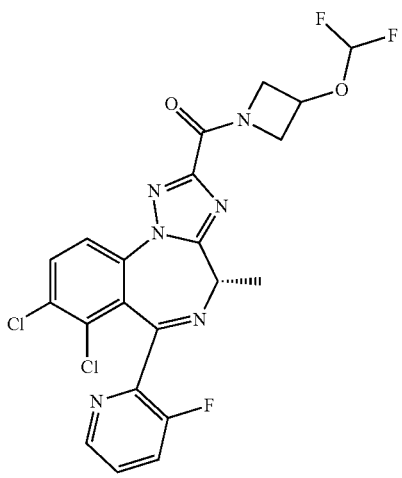 [SMILES: C[C@@H]1N=C(c2ncccc2F)c2c(ccc(Cl)c2Cl)-n2nc(C(=O)N3CC(OC(F)F)C3)nc21]

a) 3-(difluoromethoxy)azetidine

To a solution of tert-butyl 3-(difluoromethoxy)azetidine-1-carboxylate (200 mg, 0.90 mmol) in dichloromethane (2 mL) was added trifluoroacetic acid (0.5 mL, 6.49 mmol) slowly at 0° C. The mixture was stirred at 25° C. for 2 h, then concentrated in vacuo to afford the title compound (210 mg, 98%) as a colorless oil. The crude was used as such in the following step without further characterization.

b) [(4S)-7,8-dichloro-6-(3-fluoro-2-pyridyl)-4-methyl-4H-[1,2,4]triazolo[1,5-a][1,4]benzodiazepin-2-yl]-[3-(difluoromethoxy)azetidin-1-yl]methanone In analogy to experiment of example 17, 7,8-dichloro-6-(3-fluoro-2-pyridyl)-4-methyl-4H-[1,2,4]triazolo[1,5-a][1,4]benzodiazepine-2-carboxylic acid using 3-(difluoromethoxy)azetidine was converted into the enantiopure (+)-title compound (24 mg, 16%) which was obtained as a white solid. MS: 511.0 ([{$^{35}$Cl, $^{35}$Cl} M+H]$^+$), 513.0 ([{$^{35}$Cl, $^{37}$Cl} M+H]$^+$), ESI pos.

Example 91

(4S)-7,8-dichloro-6-(2,6-difluorophenyl)-2-methoxy-4-methyl-4H-[1,2,4]triazolo[1,5-a][1,4]benzodiazepine

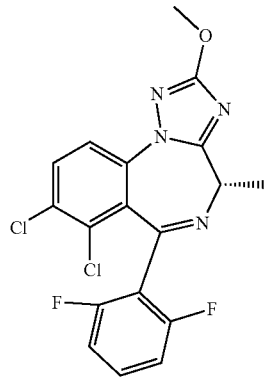 [SMILES: COc1nc2n(n1)-c1ccc(Cl)c(Cl)c1C(c1c(F)cccc1F)=N[C@H]2C]

a) [6,7-dichloro-5-(2,6-difluorophenyl)-3-methyl-2-oxo-3H-1-benzazepin-1-yl]urea To a solution of 1-amino-6,7-dichloro-5-(2,6-difluorophenyl)-3-methyl-3H-1,4-benzodiazepin-2-one (2.0 g, 5.4 mmol) in dichloromethane (2 mL) was added isocyanatosodium (3.51 g, 54.0 mmol) and trifluoroacetic acid (6.11 g, 54.0 mmol). The reaction mixture was stirred at 25° C. for 3 h, then quenched by addition of water (10 mL). The aqueous layer was extracted with dichloromethane (2×20 mL). The combined organic layers were washed with brine (2×10 mL) and concentrated in vacuo. The residue was purified by flash column chromatography (silica, petroleum ether/ethyl acetate 3:1 to 1:1) to afford the title compound (1.6 g, 72%) as a white solid. MS: 413.2 ([{$^{35}$Cl, $^{35}$Cl} M+H]$^+$), 415.2 ([{$^{35}$Cl, $^{37}$Cl} M+H]$^+$), ESI pos.

b) 7,8-dichloro-6-(2,6-difluorophenyl)-4-methyl-1,4-dihydro-[1,2,4]triazolo[1,5-a][1]benzazepin-2-one To a solution of [6,7-dichloro-5-(2,6-difluorophenyl)-3-methyl-2-oxo-3H-1-benzazepin-1-yl]urea (300 mg, 0.73 mmol) in ethanol (5 mL) was added t-BuOK in tetrahydrofuran (1.0 m, 3.0 mL, 3 mmol) at 60° C. The reaction mixture was stirred at 60° C. for 1 h, then combined with three other batches to work up. The reaction mixture was diluted with dichloromethane (100 mL). The organic layer was washed with water (50 mL), dried (Na$_2$SO$_4$) and concentrated in vacuo. The residue was purified by flash column chromatography (silica, petroleum ether/ethyl acetate 5:1 to 1:1) to afford the title compound (400 mg, 37%) as a yellow solid. MS: 395.0 ([{$^{35}$Cl, $^{35}$Cl} M+H]$^+$), 397.0 ([{$^{35}$Cl, $^{37}$Cl} M+H]$^+$), ESI pos.

c) (4S)-7,8-dichloro-6-(2,6-difluorophenyl)-2-methoxy-4-methyl-4H-[1,2,4]triazolo[1,5-a][1,4]benzodiazepine To a solution of 7,8-dichloro-6-(2,6-difluorophenyl)-4-methyl-1,4-dihydro-[1,2,4]triazolo[1,5-a][1]benzazepin-2-one (100 mg, 0.25 mmol) in toluene (2 mL) was added methyl iodide (180 mg, 1.27 mmol) and silver(II) oxide (94 mg, 0.76 mmol). The reaction mixture was stirred at 25° C. for 15 h, then concentrated in vacuo. The residue was purified by flash column chromatography (silica, ethyl acetate) followed by preparative HPLC (Waters Xbridge, water containing 10 mM ammonium bicarbonate/acetonitrile) and, finally, by chiral SFC (Daicel Chiralcel OJ, methanol containing 0.1% aqueous ammonia) to afford the enantiopure (−)-title compound (22 mg, 21%) as a white solid. MS: 409.2 ([{$^{35}$Cl, $^{35}$Cl} M+H]$^+$), 411.2 ([{$^{35}$Cl, $^{37}$Cl} M+H]$^+$), ESI pos.

Example 92

(4S)-7,8-dichloro-6-(2,6-difluorophenyl)-4-methyl-2-(oxetan-3-yloxy)-4H-[1,2,4]triazolo[1,5-a][1,4]benzodiazepine

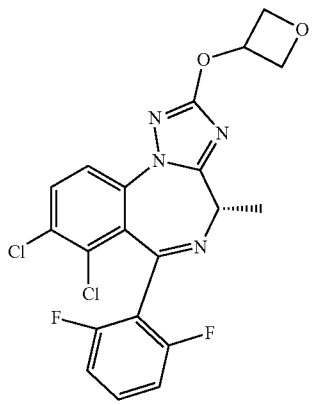 [SMILES: C[C@@H]1N=C(c2c(F)cccc2F)c2c(ccc(Cl)c2Cl)-n2nc(OC3COC3)nc21]

In analogy to experiment of example 91 c, 7,8-dichloro-6-(2,6-difluorophenyl)-4-methyl-1,4-dihydro-[1,2,4]triazolo[1,5-a][1]benzazepin-2-one using 3-iodooxetane was converted into the enantiopure (−)-title compound (12 mg, 12%) which was obtained as a white solid. MS: 451.0 ([{$^{35}$Cl, $^{35}$Cl} M+H]$^+$), 453.0 ([{$^{35}$Cl, $^{37}$Cl} M+H]$^+$), ESI pos.

Example 93

[(4S)-7,8-dichloro-6-(2,6-difluorophenyl)-4-methyl-4H-[1,2,4]triazolo[1,5-a][1,4]benzodiazepin-2-yl]-(2-oxa-6-azaspiro[3.3]heptan-6-yl)methanone

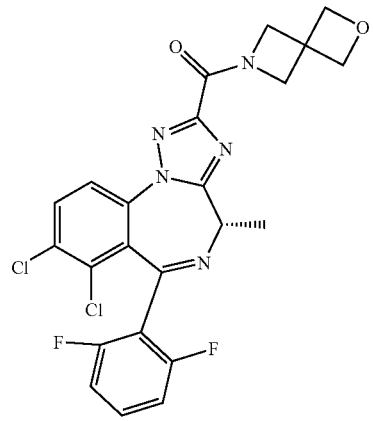 [SMILES: C[C@@H]1N=C(c2c(F)cccc2F)c2c(ccc(Cl)c2Cl)-n2nc(C(=O)N3CC4(COC4)C3)nc21]

In analogy to experiment of example 17, (4S)-7,8-dichloro-6-(2,6-difluorophenyl)-4-methyl-4H-[1,2,4]triazolo[1,5-a][1,4]benzodiazepine-2-carboxylic acid using 2-oxa-6-azaspiro[3.3]heptane was converted into the enantiopure (−)-title compound (7.7 mg, 4%) which was obtained as an off-white solid. MS: 504.2 ([{$^{35}$Cl, $^{35}$Cl} M+H]$^+$), 506.2 ([{$^{35}$Cl, $^{37}$Cl} M+H]$^+$), ESI pos.

Example 94

[(4S)-7,8-dichloro-6-(2,6-difluorophenyl)-4-methyl-4H-[1,2,4]triazolo[1,5-a][1,4]benzodiazepin-2-yl]-(1-oxa-6-azaspiro[3.3]heptan-6-yl)methanone

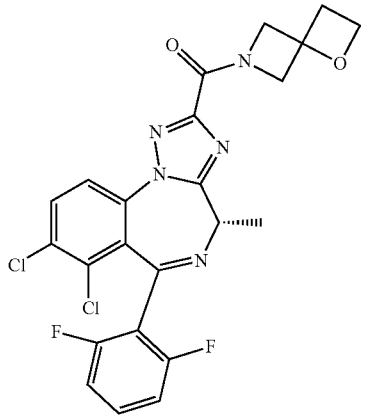 [SMILES: C[C@@H]1N=C(c2c(F)cccc2F)c2c(ccc(Cl)c2Cl)-n2nc(C(=O)N3CC4(CCO4)C3)nc21]

In analogy to experiment of example 17, (4S)-7,8-dichloro-6-(2,6-difluorophenyl)-4-methyl-4H-[1,2,4]triazolo[1,5-a][1,4]benzodiazepine-2-carboxylic acid using 1-oxa-6-azaspiro[3.3]heptane oxalate was converted into the enantiopure (−)-title compound (11 mg, 11%) which was obtained as an off-white solid. MS: 504.2 ([{$^{35}$Cl, $^{35}$Cl} M+H]$^+$), 506.2 ([{$^{35}$Cl, $^{37}$Cl} M+H]$^+$), ESI pos.

Example 95

7-oxa-2-azaspiro[3.5]nonan-2-yl-[(4S)-7,8-dichloro-6-(3-fluoro-2-pyridyl)-4-methyl-4H-[1,2,4]triazolo[1,5-a][1,4]benzodiazepin-2-yl]methanone

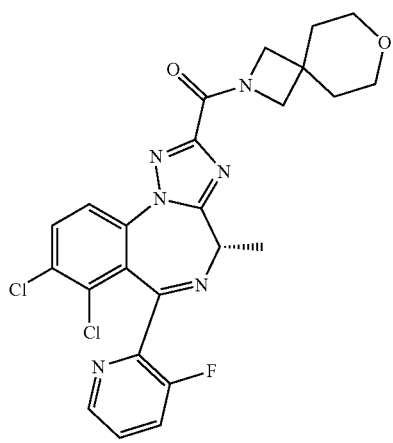 [SMILES: C[C@@H]1N=C(c2ncccc2F)c2c(ccc(Cl)c2Cl)-n2nc(C(=O)N3CC4(CCOCC4)C3)nc21]

In analogy to experiment of example 17, 7,8-dichloro-6-(3-fluoro-2-pyridyl)-4-methyl-4H-[1,2,4]triazolo[1,5-a][1,4]benzodiazepine-2-carboxylic acid using 7-oxa-2-azaspiro[3.5]nonane was converted into the enantiopure (−)-title compound (12 mg, 10%) which was obtained as a white solid. MS: 515.1 ([{$^{35}$Cl, $^{35}$Cl} M+H]$^+$), 517.1 ([{$^{35}$Cl, $^{37}$Cl} M+H]$^+$), ESI pos.

Example 96

[(4S)-7,8-dichloro-6-(2,6-difluorophenyl)-4-methyl-4H-[1,2,4]triazolo[1,5-a][1,4]benzodiazepin-2-yl]-(5-oxa-2-azaspiro[3.5]nonan-2-yl)methanone

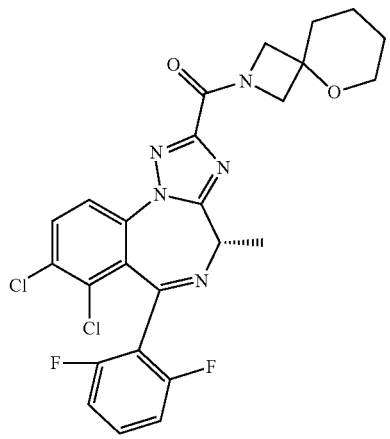 [SMILES: C[C@@H]1N=C(c2c(F)cccc2F)c2c(ccc(Cl)c2Cl)-n2nc(C(=O)N3CC4(CCCCO4)C3)nc21]

In analogy to experiment of example 17, (4S)-7,8-dichloro-6-(2,6-difluorophenyl)-4-methyl-4H-[1,2,4]triazolo[1,5-a][1,4]benzodiazepine-2-carboxylic acid using 5-oxa-2-azaspiro[3.5]nonane hemioxalate was converted into the enantiopure (−)-title compound (15 mg, 13%) which was obtained as a white solid. MS: 532.0 ([{$^{35}$Cl, $^{35}$Cl} M+H]$^+$), 534.0 ([{$^{35}$Cl, $^{37}$Cl} M+H]$^+$), ESI pos.

Example 97

[(4S)-7,8-dichloro-6-(3-fluoro-2-pyridyl)-4-methyl-4H-[1,2,4]triazolo[1,5-a][1,4]benzodiazepin-2-yl]-(5-oxa-2-azaspiro[3.4]octan-2-yl)methanone

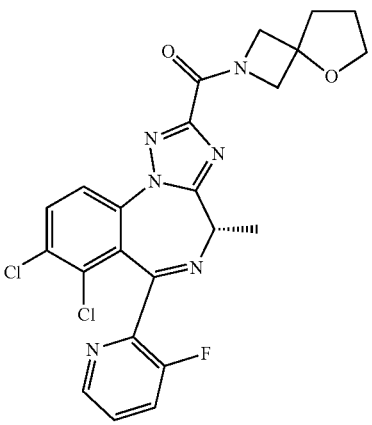 [SMILES: C[C@@H]1N=C(c2ncccc2F)c2c(ccc(Cl)c2Cl)-n2nc(C(=O)N3CC4(CCCO4)C3)nc21]

In analogy to experiment of example 17, 7,8-dichloro-6-(3-fluoro-2-pyridyl)-4-methyl-4H-[1,2,4]triazolo[1,5-a][1,4]benzodiazepine-2-carboxylic acid using 5-oxa-2-azaspiro[3.4]octane hydrochloride was converted into the enantiopure (+)-title compound (36 mg, 19%) which was obtained as a white solid. MS: 501.1 ([{$^{35}$Cl, $^{35}$Cl} M+H]$^+$), 503.1 ([{$^{35}$Cl, $^{37}$Cl} M+H]$^+$), ESI pos.

Example 98

[(4S)-7,8-dichloro-6-(3-fluoro-2-pyridyl)-4-methyl-4H-[1,2,4]triazolo[1,5-a][1,4]benzodiazepin-2-yl]-(1-oxa-6-azaspiro[3.3]heptan-6-yl)methanone

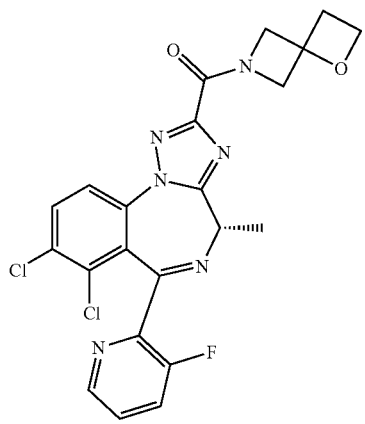 [SMILES: C[C@@H]1N=C(c2ncccc2F)c2c(ccc(Cl)c2Cl)-n2nc(C(=O)N3CC4(CCO4)C3)nc21]

In analogy to experiment of example 17, 7,8-dichloro-6-(3-fluoro-2-pyridyl)-4-methyl-4H-[1,2,4]triazolo[1,5-a][1,4]benzodiazepine-2-carboxylic acid using 1-oxa-6-azaspiro[3.3]heptane oxalate was converted into the enantiopure (+)-title compound (2.2 mg, 1%) which was obtained as a white solid. MS: 487.0 ([{$^{35}$Cl, $^{35}$Cl} M+H]$^+$), 489.0 ([{$^{35}$Cl, $^{37}$Cl} M+H]$^+$), ESI pos.

Example 99

[(4S)-7,8-dichloro-6-(2,6-difluorophenyl)-4-methyl-4H-[1,2,4]triazolo[1,5-a][1,4]benzodiazepin-2-yl]-(7-oxa-2-azaspiro[3.5]nonan-2-yl)methanone

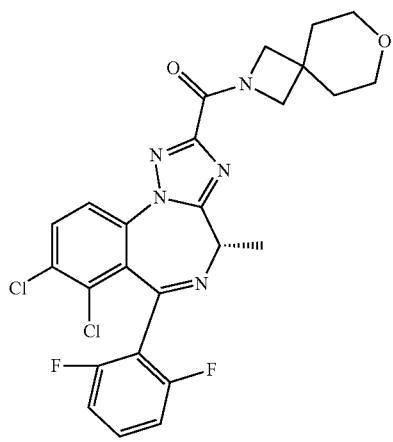 [SMILES: C[C@@H]1N=C(c2c(F)cccc2F)c2c(ccc(Cl)c2Cl)-n2nc(C(=O)N3CC4(CCOCC4)C3)nc21]

In analogy to experiment of example 17, (4S)-7,8-dichloro-6-(2,6-difluorophenyl)-4-methyl-4H-[1,2,4]triazolo[1,5-a][1,4]benzodiazepine-2-carboxylic acid using 7-oxa-2-azaspiro[3.5]nonane was converted into the enantiopure (−)-title compound (12 mg, 10%) which was obtained as an off-white solid. MS: 532.2 ([$\{^{35}Cl, ^{35}Cl\}$ M+H]$^+$), 534.2 ([$\{^{35}Cl, ^{37}Cl\}$ M+H]$^+$), ESI pos.

Example 100

[(4S)-7,8-dichloro-6-(3-fluoro-2-pyridyl)-4-methyl-4H-[1,2,4]triazolo[1,5-a][1,4]benzodiazepin-2-yl]-(6-oxa-2-azaspiro[3.4]octan-2-yl)methanone

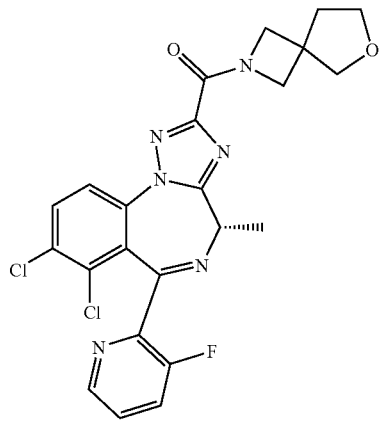 [SMILES: C[C@@H]1N=C(c2ncccc2F)c2c(ccc(Cl)c2Cl)-n2nc(C(=O)N3CC4(CCOC4)C3)nc21]

In analogy to experiment of example 17, 7,8-dichloro-6-(3-fluoro-2-pyridyl)-4-methyl-4H-[1,2,4]triazolo[1,5-a][1,4]benzodiazepine-2-carboxylic acid using 6-oxa-2-azaspiro[3.4]octane was converted into the enantiopure (+)-title compound (15 mg, 10%) which was obtained as a white solid. MS: 501.1 ([$\{^{35}Cl, ^{35}Cl\}$ M+H]$^+$), 503.1 ([$\{^{35}Cl, ^{37}Cl\}$ M+H]$^+$), ESI pos.

Example 101

[(4S)-7,8-dichloro-6-(3-fluoro-2-pyridyl)-4-methyl-4H-[1,2,4]triazolo[1,5-a][1,4]benzodiazepin-2-yl]-(5-oxa-2-azaspiro[3.5]nonan-2-yl)methanone

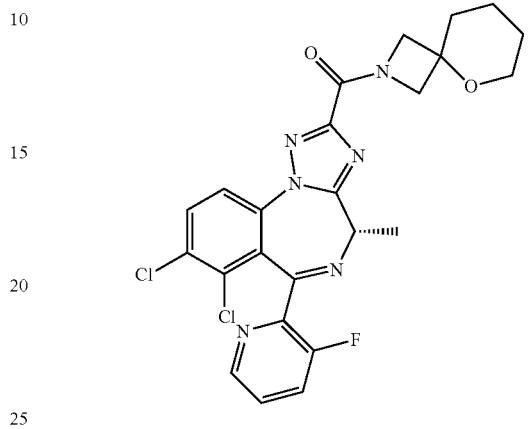

In analogy to experiment of example 17, 7,8-dichloro-6-(3-fluoro-2-pyridyl)-4-methyl-4H-[1,2,4]triazolo[1,5-a][1,4]benzodiazepine-2-carboxylic acid using 5-oxa-2-azaspiro[3.5]nonane hemioxalate was converted into the enantiopure (+)-title compound (10 mg, 7%) which was obtained as a white solid. MS: 515.1 ([$\{^{35}Cl, ^{35}Cl\}$ M+H]$^+$), 517.1 ([$\{^{35}Cl, ^{37}Cl\}$ M+H]$^+$), ESI pos.

Example 102

[(4S)-7,8-dichloro-6-(3-fluoro-2-pyridyl)-4-methyl-4H-[1,2,4]triazolo[1,5-a][1,4]benzodiazepin-2-yl]-(2-oxa-6-azaspiro[3.3]heptan-6-yl)methanone

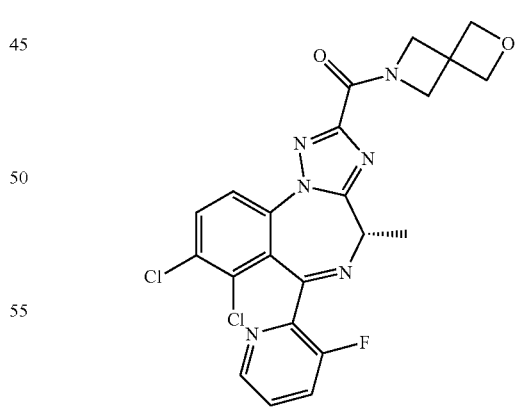

In analogy to experiment of example 17, 7,8-dichloro-6-(3-fluoro-2-pyridyl)-4-methyl-4H-[1,2,4]triazolo[1,5-a][1,4]benzodiazepine-2-carboxylic acid using 2-oxa-6-azaspiro[3.3]heptane was converted into the enantiopure (+)-title compound (21 mg, 9%) which was obtained as a white solid. MS: 487.0 ([$\{^{35}Cl, ^{35}Cl\}$ M+H]$^+$), 489.0 ([$\{^{35}Cl, ^{37}Cl\}$ M+H]$^+$), ESI pos.

Example 103

[(4S)-7-chloro-6-(3-fluoro-2-pyridyl)-4-methyl-8-(trifluoromethyl)-4H-[1,2,4]triazolo[1,5-a][1,4]benzodiazepin-2-yl]-(3-methoxyazetidin-1-yl)methanone

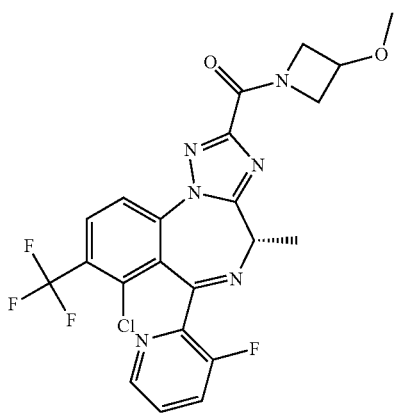 [SMILES: COC1CN(C(=O)c2nc3n(n2)-c2ccc(C(F)(F)F)c(Cl)c2C(c2ncccc2F)=N[C@H]3C)C1]

In analogy to experiment of example 85 b, ethyl (4S)-7-chloro-6-(3-fluoro-2-pyridyl)-4-methyl-8-(trifluoromethyl)-4H-[1,2,4]triazolo[1,5-a][1,4]benzodiazepine-2-carboxylate using 3-methoxyazetidine hydrochloride was converted into the enantiopure (+)-title compound (54 mg, 33%) which was obtained as a white solid. MS: 509.2 ([{$^{35}$Cl} M+H]$^+$), 511.2 ([{$^{35}$Cl} M+H]$^+$), ESI pos.

Example 104

[(4S)-7-chloro-6-(3-fluor-2-pyridyl)-4-methyl-8-(trifluoromethyl)-4H-[1,2,4]triazolo[1,5-a][1,4]benzodiazepin-2-yl]-[3-(trideuteriomethoxy)azetidin-1-yl]methanone

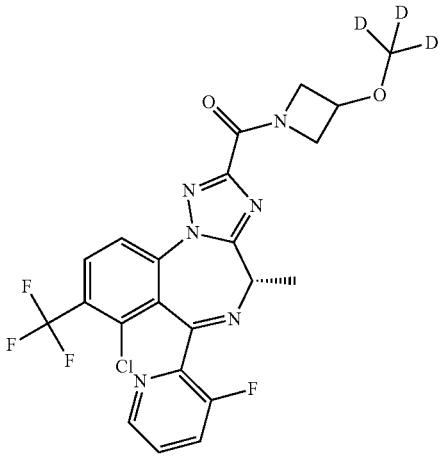 [SMILES: [2H]C([2H])([2H])OC1CN(C(=O)c2nc3n(n2)-c2ccc(C(F)(F)F)c(Cl)c2C(c2ncccc2F)=N[C@H]3C)C1]

a) 7-chloro-6-(3-fluoro-2-pyridyl)-4-methyl-8-(trifluoromethyl)-4H-[1,2,4]triazolo[1,5-a][1,4]benzodiazepine-2-carboxylic acid To a solution of ethyl (4S)-7-chloro-6-(3-fluoro-2-pyridyl)-4-methyl-8-(trifluoromethyl)-4H-[1,2,4]triazolo[1,5-a][1,4]benzodiazepine-2-carboxylate (300 mg, 0.64 mmol) in methanol (3 mL) was added sodium hydroxide (77 mg, 1.92 mmol). The reaction mixture was stirred at 25° C. for 0.5 h, diluted with water (10 mL) and extracted with ethyl acetate (3×10 mL). The combined organic layers were washed with brine (2×10 mL), dried (Na$_2$SO$_4$), filtered and concentrated in vacuo to afford the title compound (230 mg, 73%) as a yellow solid. MS: 440.0 ([{$^{35}$Cl} M+H]$^+$), 442.0 ([{$^{35}$Cl} M+H]$^+$), ESI pos.

b) [(4S)-7-chloro-6-(3-fluoro-2-pyridyl)-4-methyl-8-(trifluoromethyl)-4H-[1,2,4]triazolo[1,5-a][1,4]benzodiazepin-2-yl]-[3-(trideuteriomethoxy)azetidin-1-yl]methanone In analogy to experiment of example 17, 7-chloro-6-(3-fluoro-2-pyridyl)-4-methyl-8-(trifluoromethyl)-4H-[1,2,4]triazolo[1,5-a][1,4]benzodiazepine-2-carboxylic acid using 3-(trideuteriomethoxy)azetidine was converted into the enantiopure (+)-title compound (15 mg, 12%) which was obtained as a white solid. MS: 512.1 ([{$^{35}$Cl} M+H]$^+$), 514.1 ([{$^{35}$Cl} M+H]$^+$), ESI pos.

Example 105

(4S)-7-chloro-6-(2,6-difluorophenyl)-N-[(2R)-2-hydroxypropyl]-4-methyl-8-(trifluoromethyl)-4H-[1,2,4]triazolo[1,5-a][1,4]benzodiazepine-2-carboxamide

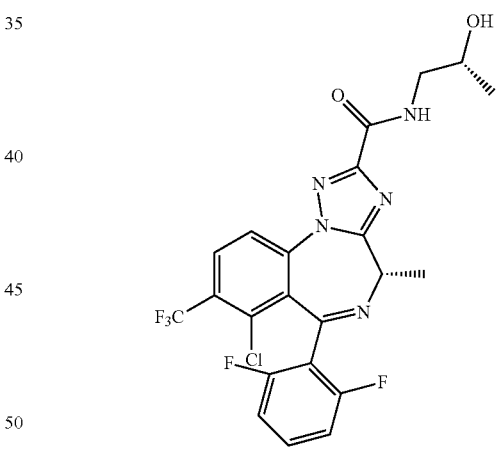

In analogy to experiment of example 17, (4S)-7-chloro-6-(2,6-difluorophenyl)-4-methyl-8-(trifluoromethyl)-4H-[1,2,4]triazolo[1,5-a][1,4]benzodiazepine-2-carboxylic acid using (2R)-1-aminopropan-2-ol was converted into the enantiopure (−)-title compound (10.0 mg, 9%) which was obtained as a white solid. MS: 514.0 ([{$^{35}$Cl} M+H]$^+$), 516.0 ([{$^{37}$Cl} M+H]$^+$), ESI pos.

Example 106

(4S)-7-chloro-6-(2,6-difluorophenyl)-N-(2-fluoro-ethyl)-4-methyl-8-(trifluoromethyl)-4H-[1,2,4]triazolo[1,5-a][1,4]benzodiazepine-2-carboxamide

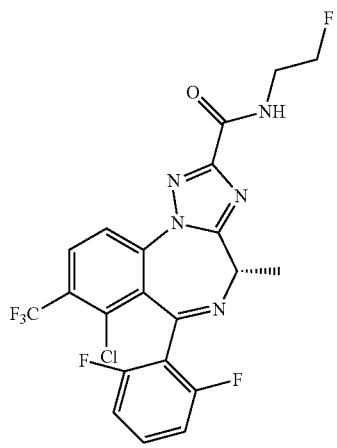 [SMILES: C[C@@H]1N=C(c2c(F)cccc2F)c2c(ccc(C(F)(F)F)c2Cl)-n2nc(C(=O)NCCF)nc21]

In analogy to experiment of example 17, (4S)-7-chloro-6-(2,6-difluorophenyl)-4-methyl-8-(trifluoromethyl)-4H-[1,2,4]triazolo[1,5-a][1,4]benzodiazepine-2-carboxylic acid using 2-fluoroethanamine was converted into the enantiopure (−)-title compound (10 mg, 9%) which was obtained as a white solid. MS: 502.0 ([{$^{35}$Cl} M+H]$^+$), 504.0 ([{$^{35}$Cl} M+H]$^+$), ESI pos.

Example 107

(4S)-7-chloro-6-(2,6-difluorophenyl)-N-(2-hydroxyethyl)-4-methyl-8-(trifluoromethyl)-4H-[1,2,4]triazolo[1,5-a][1,4]benzodiazepine-2-carboxamide

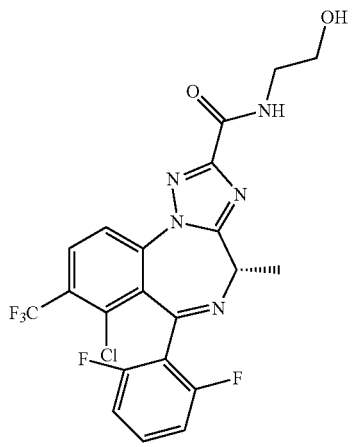 [SMILES: C[C@@H]1N=C(c2c(F)cccc2F)c2c(ccc(C(F)(F)F)c2Cl)-n2nc(C(=O)NCCO)nc21]

In analogy to experiment of example 17, (4S)-7-chloro-6-(2,6-difluorophenyl)-4-methyl-8-(trifluoromethyl)-4H-[1,2,4]triazolo[1,5-a][1,4]benzodiazepine-2-carboxylic acid using 2-aminoethanol was converted into the enantiopure (−)-title compound (10 mg, 8%) which was obtained as a white solid. MS: 500.0 ([{$^{35}$Cl} M+H]$^+$), 502.0 ([{$^{37}$Cl} M+H]$^+$), ESI pos.

Example 108

[(4S)-7,8-dichloro-6-(2,6-difluorophenyl)-4-methyl-4H-[1,2,4]triazolo[1,5-a][1,4]benzodiazepin-2-yl]-(5-oxa-2-azaspiro[3.4]octan-2-yl)methanone

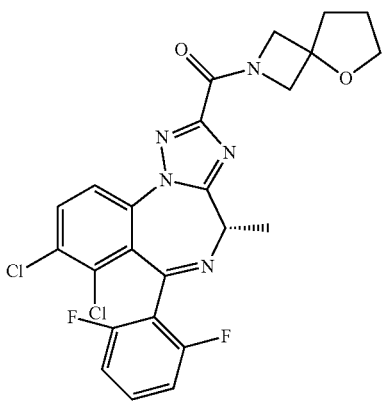 [SMILES: C[C@@H]1N=C(c2c(F)cccc2F)c2c(ccc(Cl)c2Cl)-n2nc(C(=O)N3CC4(CCCO4)C3)nc21]

In analogy to experiment of example 17, (4S)-7,8-dichloro-6-(2,6-difluorophenyl)-4-methyl-4H-[1,2,4]triazolo[1,5-a][1,4]benzodiazepine-2-carboxylic acid using 5-oxa-2-azaspiro[3.4]octane hydrochloride was converted into the enantiopure (−)-title compound (8.5 mg, 8%) which was obtained as an off-white solid. MS: 518.3 ([{$^{35}$Cl, $^{35}$Cl} M+H]$^+$), 520.3 ([{$^{35}$Cl, $^{37}$Cl} M+H]$^+$), ESI pos.

Example 109

(4S)-7-chloro-6-(2,6-difluorophenyl)-N-[(2S)-2-hydroxypropyl]-4-methyl-8-(trifluoromethyl)-4H-[1,2,4]triazolo[1,5-a][1,4]benzodiazepine-2-carboxamide

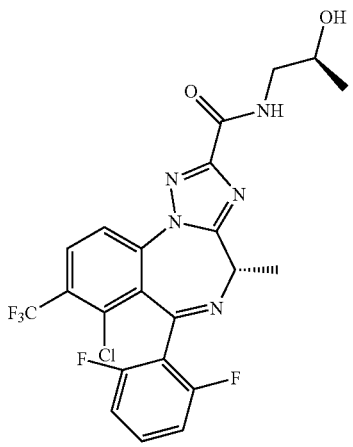 [SMILES: C[C@H](O)CNC(=O)c1nc2n(n1)-c1ccc(C(F)(F)F)c(Cl)c1C(c1c(F)cccc1F)=N[C@H]2C]

In analogy to experiment of example 17, (4S)-7-chloro-6-(2,6-difluorophenyl)-4-methyl-8-(trifluoromethyl)-4H-[1,2,4]triazolo[1,5-a][1,4]benzodiazepine-2-carboxylic acid using (2S)-1-aminopropan-2-ol was converted into the enantiopure (−)-title compound (20 mg, 15%) which was obtained as an off-white solid. MS: 514.0 ([{$^{35}$Cl} M+H]$^+$), 516.0 ([{$^{35}$Cl} M+H]$^+$), ESI pos.

Example 110

(4S)-7-chlor-N-(cyanomethyl)-6-(2,6-difluorophenyl)-4-methyl-8-(trifluoromethyl)-4H-[1,2,4]triazolo[1,5-a][1,4]benzodiazepine-2-carboxamide

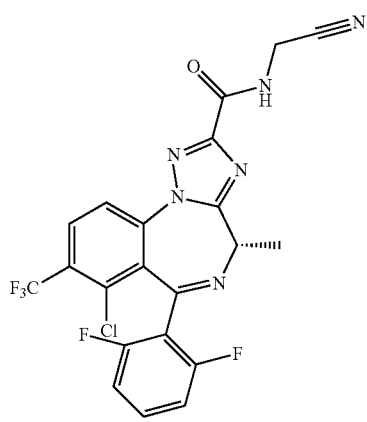 [SMILES: C[C@@H]1N=C(c2c(F)cccc2F)c2c(ccc(C(F)(F)F)c2Cl)-n2nc(C(=O)NCC#N)nc21]

In analogy to experiment of example 17, 7-chloro-6-(2,6-difluorophenyl)-4-methyl-8-(trifluoromethyl)-4H-[1,2,4]triazolo[1,5-a][1,4]benzodiazepine-2-carboxylic acid using 2-aminoacetonitrile hydrochloride was converted into the enantiopure (−)-title compound (14 mg, 11%) which was obtained as an off-white solid. MS: 495.1 ([{$^{35}$Cl} M+H]$^+$), 497.1 ([{$^{37}$Cl} M+H]$^+$), ESI pos.

Example 111

(4S)-7,8-dichloro-6-(2,6-difluorophenyl)-1,4-dimethyl-4H-imidazo[1,2-a][1,4]benzodiazepine

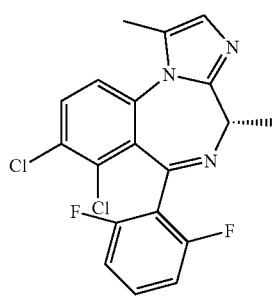 [SMILES: Cc1cnc2n1-c1ccc(Cl)c(Cl)c1C(c1c(F)cccc1F)=N[C@H]2C]

A mixture of 6,7-dichloro-5-(2,6-difluorophenyl)-3-methyl-3H-1,4-benzodiazepin-2-amine (132 mg, 0.374 mmol), propargylamine (103 mg, 0.120 mL, 1.87 mmol) and p-toluenesulfonic acid monohydrate (7.1 mg, 0.037 mmol) in 1-butanol (5 mL) was stirred at 110° C. for 18 h. The reaction mixture was concentrated in vacuo. The residue was dissolved in dichloromethane and washed with saturated aqueous sodium bicarbonate. The organic layer was dried (Na$_2$SO$_4$) and concentrated in vacuo. The residue was purified by flash column chromatography (silica, methanol/dichloromethane 1:99) followed by chiral SFC (IC, 25% methanol) to afford the enantiopure (−)-title compound (27 mg, 18%) as a white foam. MS: 392.3 ([{$^{35}$Cl, $^{35}$Cl} M+H]$^+$), 394.3 ([{$^{35}$Cl, $^{37}$Cl} M+H]$^+$), ESI pos.

Example 112

[(4S)-7-chloro-6-(3-fluoro-2-pyridyl)-4-methyl-8-(trifluoromethyl)-4H-[1,2,4]triazolo[1,5-a][1,4]benzodiazepin-2-yl]-(2-oxa-6-azaspiro[3.3]heptan-6-yl)methanone

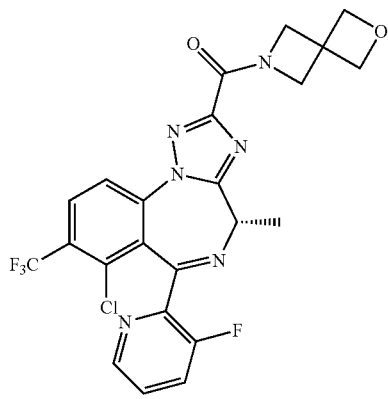 [SMILES: C[C@@H]1N=C(c2ncccc2F)c2c(ccc(C(F)(F)F)c2Cl)-n2nc(C(=O)N3CC4(COC4)C3)nc21]

In analogy to experiment of example 85 b, ethyl (4S)-7-chloro-6-(3-fluoro-2-pyridyl)-4-methyl-8-(trifluoromethyl)-4H-[1,2,4]triazolo[1,5-a][1,4]benzodiazepine-2-carboxylate using 2-oxa-6-azaspiro[3.3]heptane was converted into the enantiopure (+)-title compound (31 mg, 18%) which was obtained as a white solid. MS: 521.1 ([{$^{35}$Cl} M+H]$^+$), 523.1 ([{$^{37}$Cl} M+H]$^+$), ESI pos.

Example 113

[(4S)-7-chloro-6-(3-fluoro-2-pyridyl)-4-methyl-8-(trifluoromethyl)-4H-[1,2,4]triazolo[1,5-a][1,4]benzodiazepin-2-yl]-(5-oxa-2-azaspiro[3,4]octan-2-yl)methanone

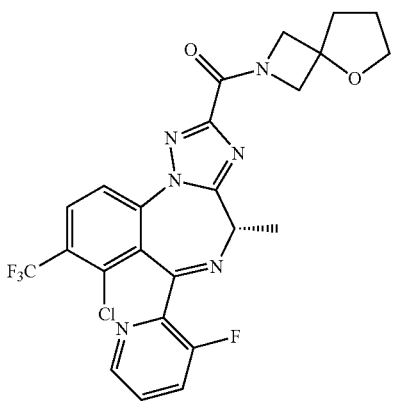 [SMILES: C[C@@H]1N=C(c2ncccc2F)c2c(ccc(C(F)(F)F)c2Cl)-n2nc(C(=O)N3CC4(CCCO4)C3)nc21]

In analogy to experiment of example 85 b, ethyl (4S)-7-chloro-6-(3-fluoro-2-pyridyl)-4-methyl-8-(trifluoromethyl)-4H-[1,2,4]triazolo[1,5-a][1,4]benzodiazepine-2-carboxylate using 5-oxa-2-azaspiro[3.4]octane hydrochloride was converted into the enantiopure (+)-title compound (32 mg, 18%) which was obtained as a white solid. MS: 535.1 ([{$^{35}$Cl} M+H]$^+$), 537.1 ([{$^{37}$Cl} M+H]$^+$), ESI pos.

Example 114

[(4S)-7-chloro-6-(2,6-difluorophenyl)-4-methyl-8-(trifluoromethyl)-4H-[1,2,4]triazolo[1,5-a][1,4]benzodiazepin-2-yl]-(1,1-dioxo-1,4-thiazinan-4-yl)methanone

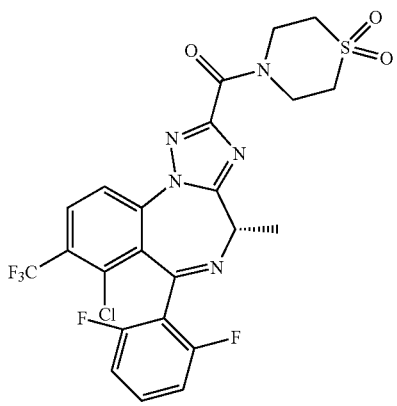 [SMILES: C[C@@H]1N=C(c2c(F)cccc2F)c2c(ccc(C(F)(F)F)c2Cl)-n2nc(C(=O)N3CCS(=O)(=O)CC3)nc21]

In analogy to experiment of example 17, 7-chloro-6-(2,6-difluorophenyl)-4-methyl-8-(trifluoromethyl)-4H-[1,2,4]triazolo[1,5-a][1,4]benzodiazepine-2-carboxylic acid using thiomorpholine 1,1-dioxide hydrochloride was converted into the enantiopure (−)-title compound (8.1 mg, 6%) which was obtained as an off-white solid. MS: 574.2 ([{$^{35}$Cl} M+H]$^+$), 576.2 ([{$^{35}$Cl} M+H]$^+$), ESI pos.

Example 115

(4S)-7-chloro-6-(2,6-difluorophenyl)-1,4-dimethyl-8-(trifluoromethyl)-4H-imidazo[1,2-a][1,4]benzodiazepine

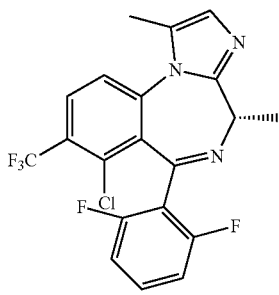 [SMILES: Cc1cnc2n1-c1ccc(C(F)(F)F)c(Cl)c1C(c1c(F)cccc1F)=N[C@H]2C]

a) 6-chloro-5-(2,6-difluorophenyl)-3-methyl-7-(trifluoromethyl)-1,3-dihydro-1,4-benzodiazepine-2-thione In analogy to experiment of example 3 a, (3S)-6-chloro-5-(2,6-difluorophenyl)-3-methyl-7-(trifluoromethyl)-1,3-dihydro-1,4-benzodiazepin-2-one (building block V) was converted into the title compound (288 mg, 79%) which was obtained as a yellow solid. MS: 403.2 ([{$^{35}$Cl} M+H]$^+$), 405.2 ([{$^{37}$Cl} M+H]$^+$), ESI pos.

b) 6-chloro-5-(2,6-difluorophenyl)-3-methyl-7-(trifluoromethyl)-3H-1,4-benzodiazepin-2-amine In analogy to experiment of example 1 b, 6-chloro-5-(2,6-difluorophenyl)-3-methyl-7-(trifluoromethyl)-1,3-dihydro-1,4-benzodiazepine-2-thione was converted into the title compound (230 mg, 83%) which was obtained as a yellow solid. MS: 388.3 ([{$^{35}$Cl} M+H]$^+$), 390.3 ([{$^{35}$Cl} M+H]$^+$), ESI pos.

c) (4S)-7-chloro-6-(2,6-difluorophenyl)-1,4-dimethyl-8-(trifluoromethyl)-4H-imidazo[1,2-a][1,4]benzodiazepine In analogy to experiment of example 111, 6-chloro-5-(2,6-difluorophenyl)-3-methyl-7-(trifluoromethyl)-3H-1,4-benzodiazepin-2-amine was converted into the enantiopure (−)-title compound (15 mg, 11%) which was obtained as a light yellow solid. MS: 426.3 ([{$^{35}$Cl} M+H]$^+$), 428.3 ([{$^{35}$Cl} M+H]$^+$), ESI pos.

Example 116

(4S)-8-bromo-7-chloro-6-(2,6-difluorophenyl)-1,4-dimethyl-4H-imidazo[1,2-a][1,4]benzodiazepine

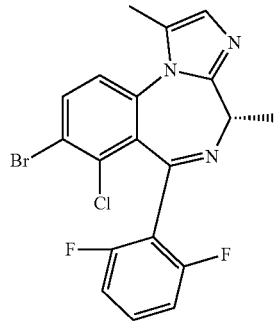 [SMILES: Cc1cnc2n1-c1ccc(Br)c(Cl)c1C(c1c(F)cccc1F)=N[C@H]2C]

a) 7-brom-6-chloro-5-(2,6-difluorophenyl)-3-methyl-1,3-dihydro-1,4-benzodiazepine-2-thione In analogy to experiment of example 3 a, (3S)-7-bromo-6-chloro-5-(2,6-difluorophenyl)-3-methyl-1,3-dihydro-1,4-benzodiazepin-2-one (building block L) was converted into the title compound (352 mg, 73%) which was obtained as a yellow solid. MS: 431.2 ([{$^{79}$Br, $^{35}$Cl} M+H]$^+$), 433.1 ([{$^{81}$Br, $^{35}$Cl or $^{79}$Br, $^{37}$Cl} M+H]$^+$), ESI pos.

b) 7-bromo-6-chloro-5-(2,6-difluorophenyl)-3-methyl-3H-1,4-benzodiazepin-2-amine In analogy to experiment of example 1 b, 7-bromo-6-chloro-5-(2,6-difluorophenyl)-3-methyl-1,3-dihydro-1,4-benzodiazepine-2-thione was converted into the title compound (269 mg, 78%) which was obtained as a yellow solid. MS: 398.1 ([{$^{79}$Br, $^{35}$Cl} M+H]$^+$), 400.1 ([{$^{81}$Br, $^{35}$Cl or $^{79}$Br, $^{37}$Cl} M+H]$^+$), ESI pos.

c) (4S)-8-bromo-7-chloro-6-(2,6-difluorophenyl)-1,4-dimethyl-4H-imidazo[1,2-a][1,4]benzodiazepine In analogy to experiment of example 111, 7-bromo-6-chloro-5-(2,6-difluorophenyl)-3-methyl-3H-1,4-benzodiazepin-2-amine was converted into the enantiopure (−)-title compound (26 mg, 9%) which was obtained as a light yellow waxy solid. MS: 436.1 ([{$^{79}$Br, $^{35}$Cl} M+H]$^+$), 438.1 ([{$^{81}$Br, $^{35}$Cl or $^{79}$Br, $^{37}$Cl} M+H]$^+$), ESI pos.

Example 117

(4S)-7-chloro-6-(2,6-difluorophenyl)-N',N',4-trimethyl-8-(trifluromethyl)-4H-[1,2,4]triazolo[1,5-a][1,4]benzodiazepine-2-carbohydrazide

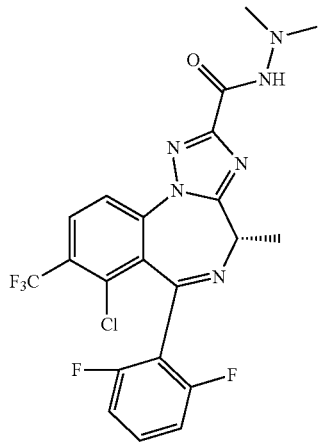 [SMILES: C[C@@H]1N=C(c2c(F)cccc2F)c2c(ccc(C(F)(F)F)c2Cl)-n2nc(C(=O)NN(C)C)nc21]

In analogy to experiment of example 17, 7-chloro-6-(2,6-difluorophenyl)-4-methyl-8-(trifluoromethyl)-4H-[1,2,4]triazolo[1,5-a][1,4]benzodiazepine-2-carboxylic acid using 1,1-dimethylhydrazine hydrochloride was converted into the enantiopure (−)-title compound (11 mg, 11%) which was obtained as a white solid. MS: 499.1 ([{$^{35}$Cl} M+H]$^+$), 501.1 ([{$^{37}$Cl} M+H]$^+$), ESI pos.

Example 118

(4S)-7-chloro-6-(2,6-difluorophenyl)-4-methyl-N-pyrrolidin-1-yl-8-(trifluoromethyl)-4H-[1,2,4]triazolo[1,5-a][1,4]benzodiazepine-2-carboxamide

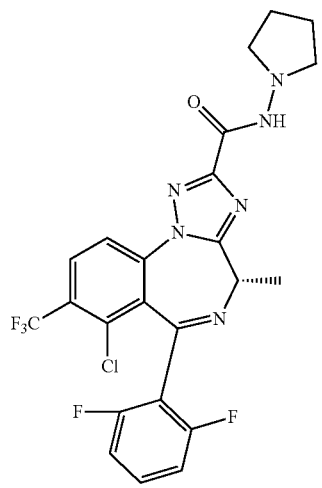 [SMILES: C[C@@H]1N=C(c2c(F)cccc2F)c2c(ccc(C(F)(F)F)c2Cl)-n2nc(C(=O)NN3CCCC3)nc21]

In analogy to experiment of example 17, 7-chloro-6-(2,6-difluorophenyl)-4-methyl-8-(trifluoromethyl)-4H-[1,2,4]triazolo[1,5-a][1,4]benzodiazepine-2-carboxylic acid using pyrrolidin-1-amine hydrochloride was converted into the enantiopure (−)-title compound (9.2 mg, 9%) which was obtained as a white solid. MS: 525.2 ([{$^{35}$Cl} M+H]$^+$), 527.2 ([{$^{37}$Cl} M+H]$^+$), ESI pos.

Example 119

1-oxa-6-azaspiro[3.3]heptan-6-yl-[(4S)-7-chloro-6-(3-fluoro-2-pyridyl)-4-methyl-8-(trifluoromethyl)-4H-[1,2,4]triazolo[1,5-a][1,4]benzodiazepin-2-yl]methanone

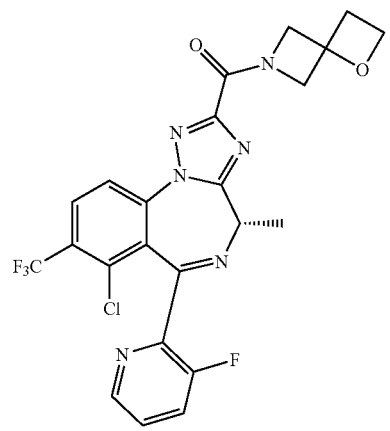 [SMILES: C[C@@H]1N=C(c2ncccc2F)c2c(ccc(C(F)(F)F)c2Cl)-n2nc(C(=O)N3CC4(CCO4)C3)nc21]

In analogy to experiment of example 17, 7-chloro-6-(3-fluoro-2-pyridyl)-4-methyl-8-(trifluoromethyl)-4H-[1,2,4]triazolo[1,5-a][1,4]benzodiazepine-2-carboxylic acid using 1-oxa-6-azaspiro[3.3]heptane oxalate was converted into the enantiopure (+)-title compound (2.6 mg, 2%) which was obtained as a white solid. MS: 521.0 ([{$^{35}$Cl} M+H]$^+$), 523.0 ([{$^{37}$Cl} M+H]$^+$), ESI pos.

Example 120

6-oxa-2-azaspiro[3.4]octan-2-yl-[(4S)-7-chloro-6-(3-fluoro-2-pyridyl)-4-methyl-8-(trifluoromethyl)-4H-[1,2,4]triazolo[1,5-a][1,4]benzodiazepin-2-yl]methanone

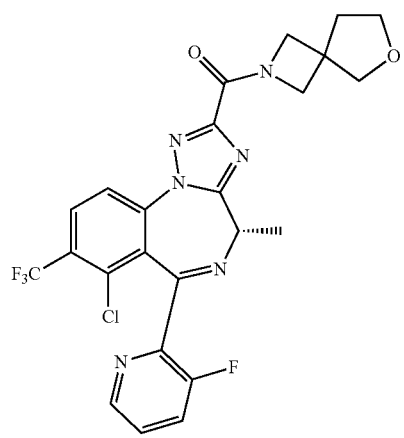 [SMILES: C[C@@H]1N=C(c2ncccc2F)c2c(ccc(C(F)(F)F)c2Cl)-n2nc(C(=O)N3CC4(CCOC4)C3)nc21]

In analogy to experiment of example 85 b, ethyl (4S)-7-chloro-6-(3-fluoro-2-pyridyl)-4-methyl-8-(trifluoromethyl)-4H-[1,2,4]triazolo[1,5-a][1,4]benzodiazepine-2-carboxylate using 6-oxa-2-azaspiro[3.4]octane oxalate was converted into the enantiopure (+)-title compound (13.2 mg, 9%) which was obtained as a white solid. MS: 535.0 ([$^{35}$Cl] M+H]$^+$), 537.0 ([$^{37}$Cl] M+H]$^+$), ESI pos.

Example 121

3-[(4S)-7-chloro-6-(2,6-difluorophenyl)-4-methyl-8-(trifluoromethyl)-4H-[1,2,4]triazolo[1,5-a][1,4]benzodiazepin-2-yl]oxazolidin-2-one

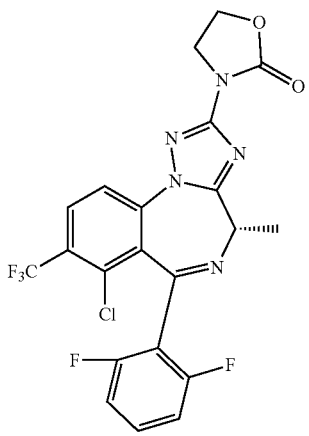 [SMILES: C[C@@H]1N=C(c2c(F)cccc2F)c2c(ccc(C(F)(F)F)c2Cl)-n2nc(N3CCOC3=O)nc21]

a) tert-butyl N-[7-chloro-6-(2,6-difluorophenyl)-4-methyl-8-(trifluoromethyl)-4H-[1,2,4]triazolo[1,5-a][1,4]benzodiazepin-2-yl]carbamate In analogy to experiment of example 49 a, 7-chloro-6-(2,6-difluorophenyl)-4-methyl-8-(trifluoromethyl)-4H-[1,2,4]triazolo[1,5-a][1,4]benzodiazepine-2-carboxylic acid was converted into the title compound (1.8 g, 72%) which was obtained as a yellow solid. MS: 472.2 ([$^{35}$Cl] M+H]$^+$), 474.2 ([$^{37}$Cl] M+H]$^+$), ESI pos.

b) 7-chloro-6-(2,6-difluorophenyl)-4-methyl-8-(trifluoromethyl)-4H-[1,2,4]triazolo[1,5-a][1,4]benzodiazepin-2-amine In analogy to experiment of example 49 b, tert-butyl N-[7-chloro-6-(2,6-difluorophenyl)-4-methyl-8-(trifluoromethyl)-4H-[1,2,4]triazolo[1,5-a][1,4]benzodiazepin-2-yl]carbamate was converted into the title compound (1.2 g, 80%) which was obtained as a white solid. MS: 428.0 ([$^{35}$Cl] M+H]$^+$), 430.0 ([$^{37}$Cl] M+H]$^+$), ESI pos.

c) 2-chloroethyl N-[7-chloro-6-(2,6-difluorophenyl)-4-methyl-8-(trifluoromethyl)-4H-[1,2,4]triazolo[1,5-a][1,4]benzodiazepin-2-yl]carbamate In analogy to experiment of example 50 a, 7-chloro-6-(2,6-difluorophenyl)-4-methyl-8-(trifluoromethyl)-4H-[1,2,4]triazolo[1,5-a][1,4]benzodiazepin-2-amine using 2-chloroethyl carbonochloridate was converted into the title compound (200 mg, 49%) which was obtained as a yellow solid. MS: 534.1 ([$^{35}$Cl] M+H]$^+$), 536.1 ([$^{35}$Cl] M+H]$^+$), ESI pos.

d) 3-[(4S)-7-chloro-6-(2,6-difluorophenyl)-4-methyl-8-(trifluoromethyl)-4H-[1,2,4]triazolo[1,5-a][1,4]benzodiazepin-2-yl]oxazolidin-2-one In analogy to experiment of example 50 b, 2-chloroethyl N-[7-chloro-6-(2,6-difluorophenyl)-4-methyl-8-(trifluoromethyl)-4H-[1,2,4]triazolo[1,5-a][1,4]benzodiazepin-2-yl]carbamate using triethylamine was converted into the enantiopure (−)-title compound (17 mg, 9%) which was obtained as a white solid. MS: 498.0 ([$^{35}$Cl] M+H]$^+$), 500.0 ([$^{35}$Cl] M+H]$^+$), ESI pos.

Example 122

[(4S)-7-chloro-6-(2,6-difluorophenyl)-4-methyl-8-(trifluoromethyl)-4H-[1,2,4]triazolo[1,5-a][1,4]benzodiazepin-2-yl]-[3-(difluoromethyl)azetidin-1-yl]methanone

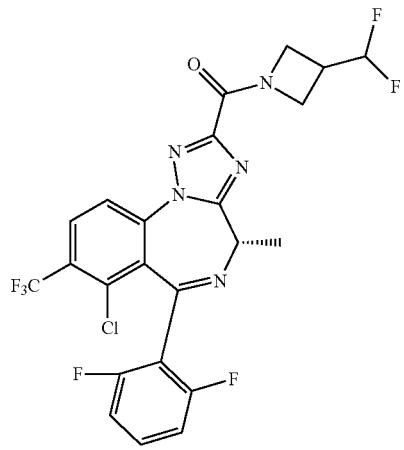 [SMILES: C[C@@H]1N=C(c2c(F)cccc2F)c2c(ccc(C(F)(F)F)c2Cl)-n2nc(C(=O)N3CC(C(F)F)C3)nc21]

In analogy to experiment of example 17, 7-chloro-6-(2,6-difluorophenyl)-4-methyl-8-(trifluoromethyl)-4H-[1,2,4]triazolo[1,5-a][1,4]benzodiazepine-2-carboxylic acid using 3-(difluoromethyl)azetidine hydrochloride was converted into the enantiopure (−)-title compound (28 mg, 18%) which was obtained as a white solid. MS: 546.1 ([$^{35}$Cl] M+H]$^+$), 548.1 ([$^{37}$Cl] M+H]$^+$), ESI pos.

Example 123

[(4S)-7-chloro-6-(3-fluoro-2-pyridyl)-4-methyl-8-(trifluoromethyl)-4H-[1,2,4]triazolo[1,5-a][1,4]benzodiazepin-2-yl]-[(3S)-3-fluoropyrrolidin-1-yl]methanone

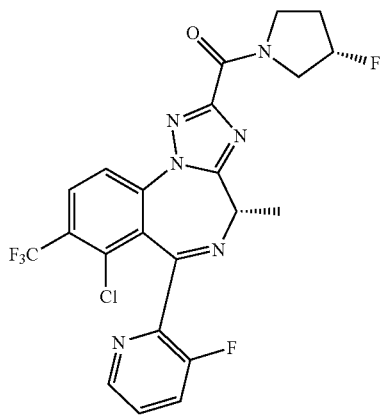 [SMILES: C[C@@H]1N=C(c2ncccc2F)c2c(ccc(C(F)(F)F)c2Cl)-n2nc(C(=O)N3CC[C@H](F)C3)nc21]

In analogy to experiment of example 85 b, ethyl (4S)-7-chloro-6-(3-fluoro-2-pyridyl)-4-methyl-8-(trifluoromethyl)-4H-[1,2,4]triazolo[1,5-a][1,4]benzodiazepine-2-carboxylate using (3S)-3-fluoropyrrolidine hydrochloride was converted into the enantiopure (+)-title compound (11.3 mg, 5%) which was obtained as a white solid. MS: 511.3 ([$^{35}$Cl] M+H]$^+$), 513.3 ([$^{37}$Cl] M+H]$^+$), ESI pos.

Example 124

[(4S)-7-chloro-6-(3-fluoro-2-pyridyl)-4-methyl-8-(trifluoromethyl)-4H-[1,2,4]triazolo[1,5-a][1,4]benzodiazepin-2-yl]-(1,1-dioxo-1,4-thiazinan-4-yl)methanone

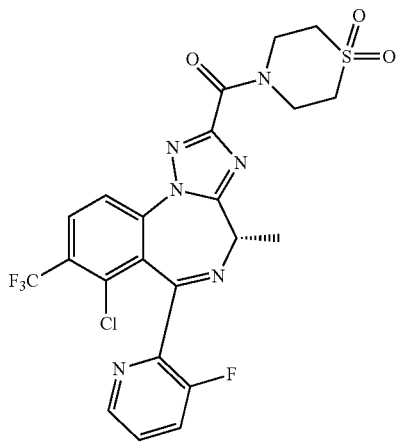 [SMILES: C[C@@H]1N=C(c2ncccc2F)c2c(ccc(C(F)(F)F)c2Cl)-n2nc(C(=O)N3CCS(=O)(=O)CC3)nc21]

In analogy to experiment of example 17, 7-chloro-6-(3-fluoro-2-pyridyl)-4-methyl-8-(trifluoromethyl)-4H-[1,2,4]triazolo[1,5-a][1,4]benzodiazepine-2-carboxylic acid using thiomorpholine 1,1-dioxide hydrochloride was converted into the enantiopure (+)-title compound (18 mg, 7%) which was obtained as a light yellow solid. MS: 557.3 ([$^{35}$Cl] M+H]$^+$), 559.3 ([$^{35}$Cl] M+H]$^+$), ESI pos.

Example 125

1-[(4S)-7-chloro-6-(2,6-difluorophenyl)-4-methyl-8-(trifluoromethyl)-4H-[1,2,4]triazolo[1,5-a][1,4]benzodiazepin-2-yl]-3-(oxetan-3-yl)urea

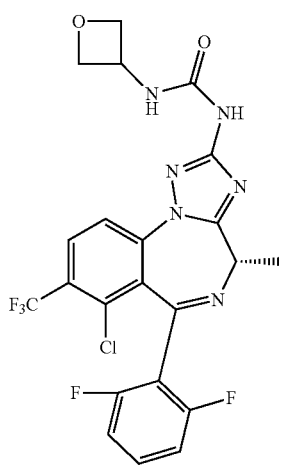 [SMILES: C[C@@H]1N=C(c2c(F)cccc2F)c2c(ccc(C(F)(F)F)c2Cl)-n2nc(NC(=O)NC3COC3)nc21]

In analogy to experiment of example 57, 7-chloro-6-(2,6-difluorophenyl)-4-methyl-8-(trifluoromethyl)-4H-[1,2,4]triazolo[1,5-a][1,4]benzodiazepin-2-amine using oxetan-3-amine was converted into the enantiopure (−)-title compound (18.3 mg, 15%) which was obtained as a white solid. MS: 527.1 ([$^{35}$Cl] M+H]$^+$), 529.1 ([$^{37}$Cl] M+H]$^+$), ESI pos.

Example 126

1-[(4S)-7-chloro-6-(2,6-difluorophenyl)-4-methyl-8-(trifluoromethyl)-4H-[1,2,4]triazolo[1,5-a][1,4]benzodiazepin-2-yl]-3-cyclopropyl-urea

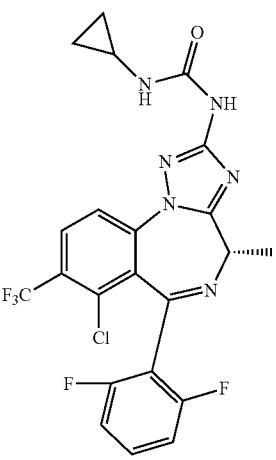 [SMILES: C[C@@H]1N=C(c2c(F)cccc2F)c2c(ccc(C(F)(F)F)c2Cl)-n2nc(NC(=O)NC3CC3)nc21]

In analogy to experiment of example 57, 7-chloro-6-(2,6-difluorophenyl)-4-methyl-8-(trifluoromethyl)-4H-[1,2,4]triazolo[1,5-a][1,4]benzodiazepin-2-amine using cyclopropanamine was converted into the enantiopure (−)-title compound (25 mg, 22%) which was obtained as a white solid. MS: 511.2 ([{$^{35}$Cl} M+H]$^+$), 513.2 ([{$^{35}$Cl} M+H]$^+$), ESI pos.

Example 127

N-[(4S)-7-chloro-6-(2,6-difluorophenyl)-4-methyl-8-(trifluoromethyl)-4H-[1,2,4]triazolo[1,5-a][1,4]benzodiazepin-2-yl]-3-methoxy-azetidine-1-carboxamide

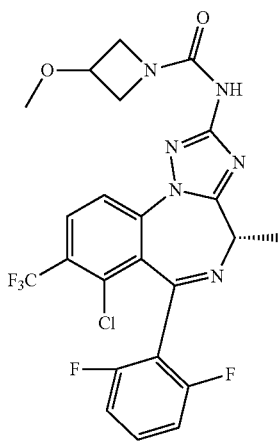

In analogy to experiment of example 57, 7-chloro-6-(2,6-difluorophenyl)-4-methyl-8-(trifluoromethyl)-4H-[1,2,4]triazolo[1,5-a][1,4]benzodiazepin-2-amine using 3-methoxyazetidine hydrochloride was converted into the enantiopure (−)-title compound (3.8 mg, 5%) which was obtained as a white solid. MS: 541.1 ([{$^{35}$Cl} M+H]$^+$), 543.1 ([{$^{35}$Cl} M+H]$^+$), ESI pos.

Example 128

N-[(4S)-7-chloro-6-(2,6-difluorophenyl)-4-methyl-8-(trifluoromethyl)-4H-[1,2,4]triazolo[1,5-a][1,4]benzodiazepin-2-yl]-3-fluoro-azetidine-1-carboxamide

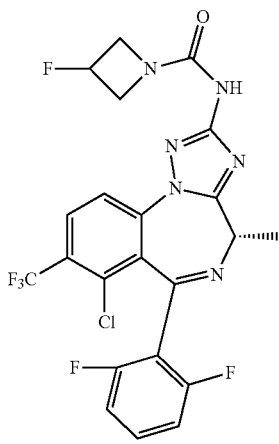 [SMILES: C[C@@H]1N=C(c2c(F)cccc2F)c2c(ccc(C(F)(F)F)c2Cl)-n2nc(NC(=O)N3CC(F)C3)nc21]

In analogy to experiment of example 57, 7-chloro-6-(2,6-difluorophenyl)-4-methyl-8-(trifluoromethyl)-4H-[1,2,4] triazolo[1,5-a][1,4]benzodiazepin-2-amine using 3-fluoro-azetidine hydrochloride was converted into the enantiopure (−)-title compound (8.1 mg, 6%) which was obtained as an off-white solid. MS: 529.1 ([{$^{35}$Cl} M+H]$^+$), 531.1 ([{$^{35}$Cl} M+H]$^+$), ESI pos.

Example 129

1-[(4S)-7-chloro-6-(2,6-difluorophenyl)-4-methyl-8-(trifluoromethyl)-4H-[1,2,4]triazolo[1,5-a][1,4]benzodiazepin-2-yl]-3-methyl-urea

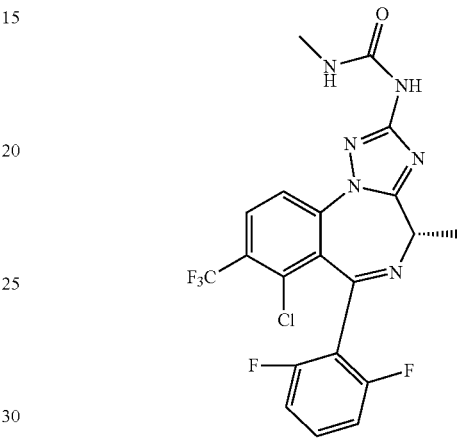

In analogy to experiment of example 57, 7-chloro-6-(2,6-difluorophenyl)-4-methyl-8-(trifluoromethyl)-4H-[1,2,4] triazolo[1,5-a][1,4]benzodiazepin-2-amine using methanamine hydrochloride was converted into the enantiopure (−)-title compound (9.9 mg, 8%) which was obtained as a white solid. MS: 485.1 ([{$^{35}$Cl} M+H]$^+$), 487.1 ([{$^{35}$Cl} M+H]$^+$), ESI pos.

Example 130

N-[(4S)-7-chloro-6-(2,6-difluorophenyl)-4-methyl-8-(trifluoromethyl)-4H-[1,2,4]triazolo[1,5-a][1,4]benzodiazepin-2-yl]-3-oxa-6-azabicyclo[3.1.1]heptane-6-carboxamide

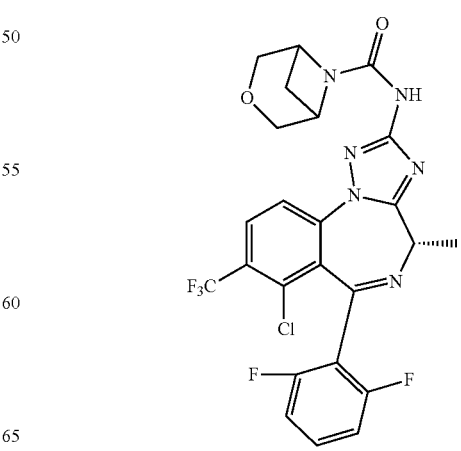

In analogy to experiment of example 57, 7-chloro-6-(2,6-difluorophenyl)-4-methyl-8-(trifluoromethyl)-4H-[1,2,4]triazolo[1,5-a][1,4]benzodiazepin-2-amine using 3-oxa-6-azabicyclo[3.1.1]heptane hydrochloride was converted into the enantiopure (−)-title compound (4.9 mg, 3%) which was obtained as a white solid. MS: 553.1 ([{$^{35}$Cl} M+H]$^+$), 555.1 ([{$^{35}$Cl} M+H]$^+$), ESI pos.

Example 131

N-[(4S)-7-chloro-6-(2,6-difluorophenyl)-4-methyl-8-(trifluoromethyl)-4H-[1,2,4]triazolo[1,5-a][1,4]benzodiazepin-2-yl]-1,1-dioxo-1,4-thiazinane-4-carboxamide

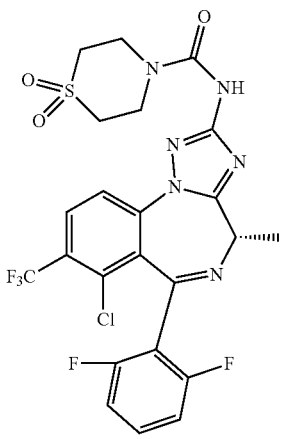 [SMILES: C[C@@H]1N=C(c2c(F)cccc2F)c2c(ccc(C(F)(F)F)c2Cl)-n2nc(NC(=O)N3CCS(=O)(=O)CC3)nc21]

In analogy to experiment of example 57, 7-chloro-6-(2,6-difluorophenyl)-4-methyl-8-(trifluoromethyl)-4H-[1,2,4]triazolo[1,5-a][1,4]benzodiazepin-2-amine using 1,4-thiazinane 1,1-dioxide hydrochloride was converted into the enantiopure (−)-title compound (16.1 mg, 12%) which was obtained as a white solid. MS: 589.0 ([{$^{35}$Cl} M+H]$^+$), 591.0 ([{$^{35}$Cl} M+H]$^+$), ESI pos.

Example 132

[(4S)-7-chloro-6-(2,6-difluorophenyl)-4-methyl-8-(trifluoromethyl)-4H-imidazo[1,2-a][1,4]benzodiazepin-1-yl]methanol

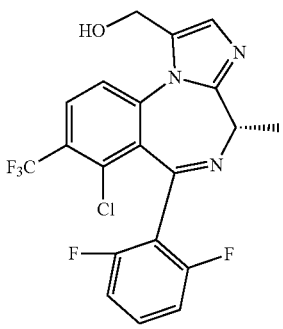 [SMILES: C[C@@H]1N=C(c2c(F)cccc2F)c2c(ccc(C(F)(F)F)c2Cl)-n2c(CO)cnc21]

To a solution of (4S)-7-chloro-6-(2,6-difluorophenyl)-1,4-dimethyl-8-(trifluoromethyl)-4H-imidazo[1,2-a][1,4]benzodiazepine (150 mg, 0.352 mmol) in 1,4-dioxane (3 mL) was added selenium dioxide (78.2 mg, 0.705 mmol). The reaction mixture was stirred at 110° C. for 4 h, cooled and filtered over dicalite. The filtrate was concentrated in vacuo. The residue was purified by flash column chromatography (silica, ethyl acetate/dichloromethane 1:1), followed by SFC (chiral IC, 10% methanol) to afford the enantiopure (−)-title compound (42.0 mg, 27%) as a white solid. MS: 442.2 ([{$^{35}$Cl} M+H]$^+$), 444.2 ([{$^{35}$Cl} M+H]$^+$), ESI pos.

Example 133

(10S)-6-chloro-8-(2,6-difluorophenyl)-10-methyl-5-(trifluoromethyl)-1,9,12-triazatetracyclo[9.6.0.02,7.013,17]heptadeca-2,4,6,8,11,13(17)-hexaene

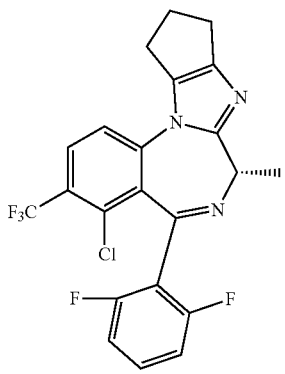 [SMILES: C[C@@H]1N=C(c2c(F)cccc2F)c2c(ccc(C(F)(F)F)c2Cl)-n2c1nc1c2CCC1]

a) trans-2-[(E/Z)-[6-chloro-5-(2,6-difluorophenyl)-3-methyl-7-(trifluoromethyl)-1,3-dihydro-1,4-benzodiazepin-2-ylidene]amino]cyclopentanol To a mixture of sodium carbonate (241 mg, 2.27 mmol) in ethanol (7.2 mL) and water (3.6 mL) was added (3S)-6-chloro-5-(2,6-difluorophenyl)-3-methyl-7-(trifluoromethyl)-1,3-dihydro-1,4-benzodiazepine-2-thione (400 mg, 0.99 mmol) followed by trans-2-aminocyclopentanol hydrochloride (270 mg, 1.96 mmol). The reaction mixture was stirred at 80° C. overnight, then concentrated in vacuo. The residue was extracted with water (5 mL) and ethyl acetate (2×50 mL). The combined organic layers were washed with brine (10 mL), dried (Na$_2$SO$_4$), filtered and concentrated in vacuo. The residue was purified by flash column chromatography (silica, 0-70% ethyl acetate in heptane) to afford the title compound (347 mg, 71%) as a light yellow oil. MS: 472.2 ([{$^{35}$Cl} M+H]$^+$), 474.2 ([{$^{37}$Cl} M+H]$^+$), ESI pos.

b) (10S)-6-chloro-8-(2,6-difluorophenyl)-10-methyl-5-(trifluoromethyl)-1,9,12-triazatetracyclo[9.6.0.02.7.013.17]heptadeca-2.4.6.8.11.13(17)-hexaene To a solution of trans-2-[(E/Z)-[6-chloro-5-(2,6-difluorophenyl)-3-methyl-7-(trifluoromethyl)-1,3-dihydro-1,4-benzodiazepin-2-ylidene]amino]cyclopentanol (340 mg, 0.685 mmol) in dichloromethane (3.8 mL) at 0° C. was added Dess-Martin periodinane (310 mg, 0.731 mmol). The reaction mixture was stirred at room temperature for 4.5 h. The reaction mixture was quenched by addition of saturated aqueous sodium bicarbonate (5 mL) and aqueous sodium thiosulfate (10%, 5 mL) and stirred vigorously for 15 min at room temperature. The biphasic mixture was then extracted with dichloromethane (2×50 mL). The combined organic layers were washed with saturated aqueous sodium bicarbonate (5 mL), dried (Na$_2$SO$_4$), filtered and concentrated in vacuo. The residue was purified by flash column chromatography (silica, 0-50% ethyl acetate in heptane) followed by SFC (chiral IC, 10% ethanol) to afford the enantiopure (−)-title compound (51 mg, 16%) as an off-white foam. MS: 452.2 ([{$^{35}$Cl} M+H]$^+$), 454.2 ([{$^{37}$Cl} M+H]$^+$), ESI pos.

Example 134

N-[(4S)-7-chloro-6-(2,6-difluorophenyl)-4-methyl-8-(trifluoromethyl)-4H-[1,2,4]triazolo[1,5-a][1,4]benzodiazepin-2-yl]-3,3-dioxo-3λ$^6$-thia-6-azabicyclo[3.1.1]heptane-6-carboxamide

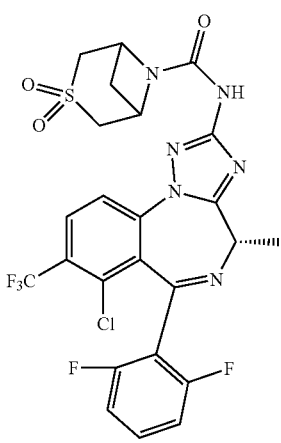 [SMILES: C[C@@H]1N=C(c2c(F)cccc2F)c2c(ccc(C(F)(F)F)c2Cl)-n2nc(NC(=O)N3C4CC3CS(=O)(=O)C4)nc21]

In analogy to experiment of example 57, 7-chloro-6-(2,6-difluorophenyl)-4-methyl-8-(trifluoromethyl)-4H-[1,2,4]triazolo[1,5-a][1,4]benzodiazepin-2-amine using 3λ$^6$-thia-6-azabicyclo[3.1.1]heptane 3,3-dioxide trifluoroacetate was converted into the enantiopure (−)-title compound (12.7 mg, 6%) which was obtained as a white solid. MS: 601.1 ([{$^{35}$Cl} M+H]$^+$), 603.1 ([{$^{35}$Cl} M+H]$^+$), ESI pos.

Example 135

[(4S)-7-chloro-6-(3-fluoro-2-pyridyl)-4-methyl-8-(trifluoromethyl)-4H-[1,2,4]triazolo[1,5-a][1,4]benzodiazepin-2-yl]-(3-methylazetidin-1-yl)methanone

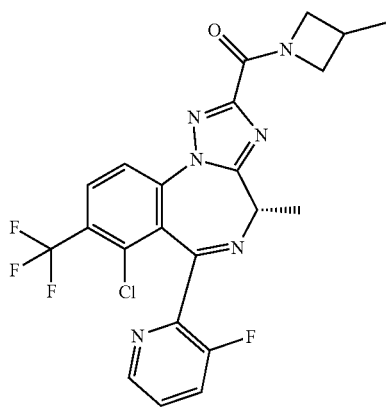 [SMILES: CC1CN(C(=O)c2nc3n(n2)-c2ccc(C(F)(F)F)c(Cl)c2C(c2ncccc2F)=N[C@H]3C)C1]

In analogy to experiment of example 85 b, ethyl (4S)-7-chloro-6-(3-fluoro-2-pyridyl)-4-methyl-8-(trifluoromethyl)-4H-[1,2,4]triazolo[1,5-a][1,4]benzodiazepine-2-carboxylate using 3-methylazetidine hydrochloride was converted into the enantiopure (+)-title compound (30.4 mg, 16%) which was obtained as a white solid. MS: 493.1 ([{$^{35}$Cl} M+H]$^+$), 495.1 ([{$^{35}$Cl} M+H]$^+$), ESI pos.

Example 136

(4S)-7-chloro-6-(3-fluoro-2-pyridyl)-1,4-dimethyl-8-(trifluoromethyl)-4H-imidazo[1,2-a][1,4]benzodiazepine

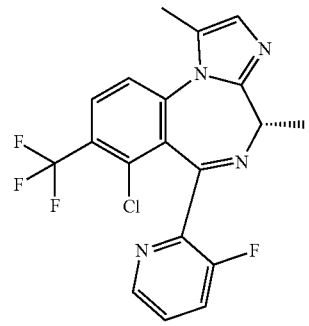 [SMILES: Cc1cnc2n1-c1ccc(C(F)(F)F)c(Cl)c1C(c1ncccc1F)=N[C@H]2C]

a) 1-[(E/Z)-[(3S)-6-chloro-5-(3-fluoro-2-pyridyl)-3-methyl-7-(trifluoromethyl)-1,3-dihydro-1,4-benzodiazepin-2-ylidene]amino]propan-2-ol To a previously cooled solution of (3S)-6-chloro-5-(3-fluoro-2-pyridyl)-3-methyl-7-(trifluoromethyl)-1,3-dihydro-1,4-benzodiazepin-2-one (building block X, 300 mg, 0.80 mmol) in tetrahydrofuran (6 mL) at −70° C. was added a solution of t-BuOK in tetrahydrofuran (1.0 m, 1.61 mL, 1.61 mmol) over 5 min. The orange solution was warmed up to −40° C. and stirred for 20 min, before addition over 2 min of diethyl chlorophosphate (0.35 mL, 2.42 mmol) in tetrahydrofuran (1 mL). The resulting red-orange solution was stirred for 5 min at −40° C. and then warmed over 10 min to 0-5° C. and stirred for further 1 h. This solution was added to a solution of anhydrous 1-amino-2-propanol (303 mg, 4.04 mmol) in tetrahydrofuran (1 mL). The reaction mixture was warmed up to 20° C. and stirred at 20° C. for 16 h, then poured into water (10 mL) and extracted with ethyl acetate (3×10 mL). The combined organic layers were washed with brine (10 mL), dried (Na$_2$SO$_4$), filtered and concentrated in vacuo. The residue was purified by flash column chromatography (silica, petroleum ether/ethyl acetate 3:7 to 0:1) to afford the title compound (200 mg, 58%) as a light brown oil, which was used in the following step without further characterization.

b) (4S)-7-chloro-6-(3-fluoro-2-pyridyl)-1,4-dimethyl-8-(trifluoromethyl-4H-imidazo[1,2-a][1,4]benzodiazepine To a solution of 1-[(E/Z)-[(3S)-6-chloro-5-(3-fluoro-2-pyridyl)-3-methyl-7-(trifluoromethyl)-1,3-dihydro-1,4-benzodiazepin-2-ylidene]amino]propan-2-ol (190 mg, 0.44 mmol) in dry dichloromethane (2.5 mL) was added Dess-Martin periodane (282 mg, 0.66 mmol) and sodium bicarbonate (149 mg, 1.77 mmol). The reaction mixture was stirred at 20° C. for 1 h, then quenched by addition of aqueous sodium sulfite (5 mL) and extracted with dichloromethane (3×5 mL). The combined organic layers were washed with aqueous sodium sulfite (2×5 mL) and brine (5 mL), dried (Na$_2$SO$_4$) and concentrated in vacuo. The residue was purified by preparative HPLC (Waters Xbridge, water containing 10 mM ammoniumbicarbonate/acetonitrile) followed by chiral SFC (Daicel Chiralpak AD-H, 15% ethanol containing 0.1% aqueous ammonia) to afford the enantiopure (+)-title compound (25.1 mg, 14%) which was obtained as a white solid. MS: 409.1 ([{$^{35}$Cl} M+H]$^+$), 411.1 ([{$^{37}$C} M+H]$^+$), ESI pos.

Example 137

[(4S)-7-chloro-6-(3-fluoro-2-pyridyl)-4-methyl-8-(trifluoromethyl)-4H-[1,2,4]triazolo[1,5-a][1,4]benzodiazepin-2-yl]-(3-ethoxyazetidin-1-yl)methanone

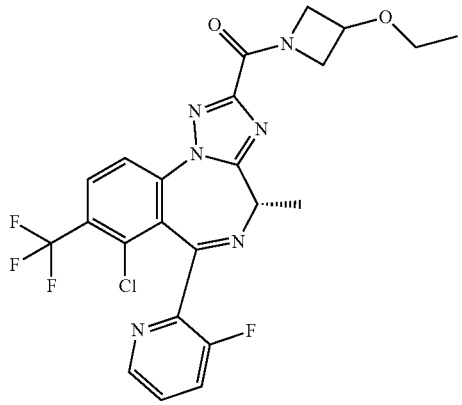 [SMILES: CCOC1CN(C(=O)c2nc3n(n2)-c2ccc(C(F)(F)F)c(Cl)c2C(c2ncccc2F)=N[C@H]3C)C1]

In analogy to experiment of example 85 b, ethyl (4S)-7-chloro-6-(3-fluoro-2-pyridyl)-4-methyl-8-(trifluoromethyl)-4H-[1,2,4]triazolo[1,5-a][1,4]benzodiazepine-2-carboxylate using 3-ethoxyazetidine hydrochloride was converted into the enantiopure (+)-title compound (25 mg, 14%) which was obtained as a white solid. MS: 523.4 ([{$^{35}$Cl} M+H]$^+$), 525.4 ([{$^{37}$Cl} M+H]$^+$), ESI pos.

Example 138

(4S)-7-chloro-6-(3-fluoro-2-pyridyl)-N-(2-hydroxyethyl)-4-methyl-8-(trifluoromethyl)-4H-[1,2,4]triazolo[1,5-a][1,4]benzodiazepine-2-carboxamide

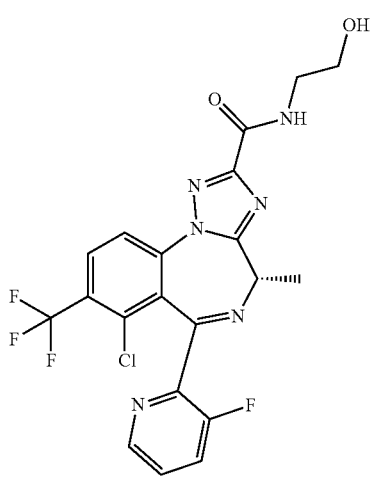 [SMILES: C[C@@H]1N=C(c2ncccc2F)c2c(ccc(C(F)(F)F)c2Cl)-n2nc(C(=O)NCCO)nc21]

A mixture of ethyl (4S)-7-chloro-6-(3-fluoro-2-pyridyl)-4-methyl-8-(trifluoromethyl)-4H-[1,2,4]triazolo[1,5-a][1,4]benzodiazepine-2-carboxylate (90 mg, 0.19 mmol) and 2-hydroxyethylamine (59 mg, 0.96 mmol) in ethanol (1 mL) was stirred at 30° C. for 12 h. The reaction mixture was purified by preparative HPLC (Waters Xbridge, water containing 0.05% ammonium hydroxide/acetonitrile) followed by chiral HPLC (Chiralpak AD-H, isopropanol) and, finally, by preparative HPLC (Waters Xbridge, water containing 10 mM ammonium bicarbonate/acetonitrile) to afford the enantiopure (+)-title compound (11.8 mg, 13%) which was obtained as a white solid. MS: 483.0 ([{$^{35}$Cl} M+H]$^+$), 485.0 ([{$^{7}$Cl} M+H]$^+$), ESI pos.

Example 139

(4S)-7-chloro-6-(3-fluoro-2-pyridyl)-2,4-dimethyl-8-(trifluoromethyl)-4H-imidazo[1,2-a][1,4]benzodiazepine

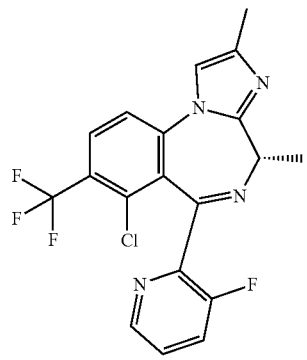 [SMILES: Cc1cn2c(n1)[C@H](C)N=C(c1ncccc1F)c1c-2ccc(C(F)(F)F)c1Cl]

a) 2-[(E/Z)-[6-chloro-5-(3-fluoro-2-pyridyl-3-methyl-7-(trifluoromethyl)-1,3-dihydro-1,4-benzodiazepin-2-ylidene]amino]propan-1-ol In analogy to experiment of example 136 a, (3S)-6-chloro-5-(3-fluoro-2-pyridyl)-3-methyl-7-(trifluoromethyl)-1,3-dihydro-1,4-benzodiazepin-2-one (building block X) using 2-aminopropan-1-ol was converted into the title compound (127 mg, 75%) which was obtained as a colorless oil. MS: 429.0 ([{$^{35}$Cl} M+H]$^+$), 431.0 ([{$^{35}$Cl} M+H]$^+$), ESI pos.

b) (4S)-7-chloro-6-(3-fluoro-2-pyridyl)-2,4-dimethyl-8-(trifluoromethyl)-4H-imidazo[1,2-a][1,4]benzodiazepine In analogy to experiment of example 136 b, 2-[(E/Z)-[6-chloro-5-(3-fluoro-2-pyridyl)-3-methyl-7-(trifluoromethyl)-1,3-dihydro-1,4-benzodiazepin-2-ylidene]amino]propan-1-ol was converted into the enantiopure (+)-title compound (23.9 mg, 19%) which was obtained as an off-white solid. MS: 409.1 ([{$^{35}$Cl} M+H]$^+$), 411.1 ([{$^{7}$Cl} M+H]$^+$), ESI pos.

Example 140

[(4S)-7-chloro-6-(3-fluor-2-pyridyl)-4-methyl-8-(trifluoromethyl)-4H-[1,2,4]triazolo[1,5-a][1,4]benzodiazepin-2-yl]-[3-(difluoromethoxy)azetidin-1-yl]methanone

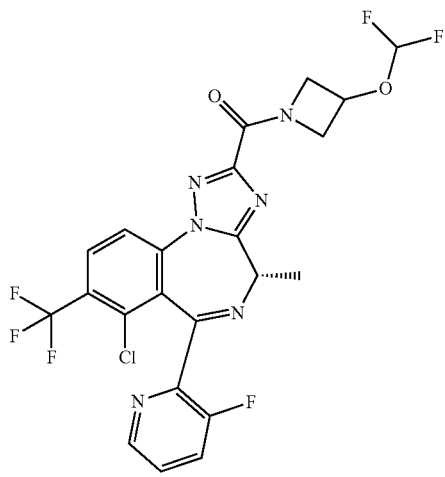 [SMILES: C[C@@H]1N=C(c2ncccc2F)c2c(ccc(C(F)(F)F)c2Cl)-n2nc(C(=O)N3CC(OC(F)F)C3)nc21]

a) 3-(difluoromethoxy)azetidine trifluoroacetate

To a solution of tert-butyl 3-(difluoromethoxy)azetidine-1-carboxylate (150 mg, 0.67 mmol) in dichloromethane (2.5 mL) at 0° C. was added trifluoroacetic acid (0.5 mL). The reaction mixture was stirred at 0° C. for 1 h, then concentrated in vacuo to afford the title compound (101 mg, crude) which was used in the following step without further purification. $^1$H NMR (CDCl$_3$, 400 MHz) δ: 6.52-6.10 (m, 1H), 5.23 (br t, J=6.4 Hz, 1H), 4.47 (br d, J=2.5 Hz, 2H), 4.39-4.24 (m, 2H).

b) [(4S)-7-chloro-6-(3-fluoro-2-pyridyl)-4-methyl-8-(trifluoromethyl)-4H-[1,2,4]triazolo[1,5-a][1,4]benzodiazepin-2-yl]-[3-(difluoromethoxy)azetidin-1-yl]methanone In analogy to experiment of example 85 b, ethyl (4S)-7-chloro-6-(3-fluoro-2-pyridyl)-4-methyl-8-(trifluoromethyl)-4H-[1,2,4]triazolo[1,5-a][1,4]benzodiazepine-2-carboxylate using 3-(difluoromethoxy)azetidine trifluoroacetate was converted into the enantiopure (+)-title compound (16.4 mg, 14%) which was obtained as an off-white solid. MS: 545.1 ([{$^{35}$Cl} M+H]$^+$), 547.1 ([{$^{37}$Cl} M+H]$^+$), ESI pos.

Example 141

(4S)-7-chloro-6-(3-fluoro-2-pyridyl)-N-(2-hydroxyethyl)-4-methyl-8-(trifluoromethyl)-4H-imidazo[1,2-a][1,4]benzodiazepine-2-carboxamide

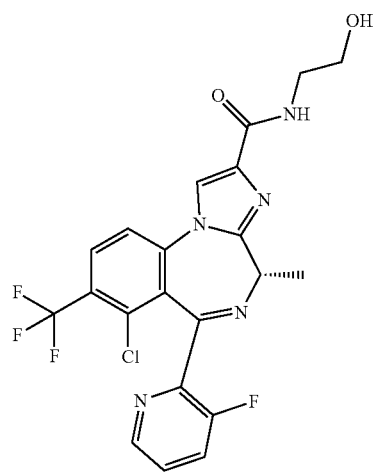 [SMILES: C[C@@H]1N=C(c2ncccc2F)c2c(ccc(C(F)(F)F)c2Cl)-n2cc(C(=O)NCCO)nc21]

a) 6-chloro-5-(3-fluoro-2-pyridyl)-3-methyl-7-(trifluoromethyl)-3H-1,4-benzodiazepin-2-amine Ammonia was bubbled into tetrahydrofuran (25 mL) at −20° C. for 10 min. To a solution of (3S)-6-chloro-5-(3-fluoro-2-pyridyl)-3-methyl-7-(trifluoromethyl)-1,3-dihydro-1,4-benzodiazepin-2-one (building block X, 5 g, 13.5 mmol) in tetrahydrofuran (100 mL) was added sodium hydride (1.08 g, 26.9 mmol) at 0° C. The mixture was stirred for 20 min at 0° C., then diethyl chlorophosphate (2.92 mL, 20.2 mmol) was added. The mixture was stirred at 0° C. for 1 h, then poured into the ammonia in tetrahydrofuran solution. The reaction mixture was stirred at 0° C. for 1 h, poured into saturated aqueous ammonium chloride (100 mL) and extracted with ethyl acetate (3×100 mL). The combined organic layers were washed with brine (100 mL), dried (Na$_2$SO$_4$) and concentrated in vacuo. The residue was purified by flash column chromatography (silica, petroleum ether/ethyl acetate 3:1, then dichloromethane/methanol 20:1) followed by preparative HPLC (Phenomenex luna C18, water containing 0.1% trifluoroacetic acid/acetonitrile) to afford the title compound (2.3 g, 62%) as a white solid. MS: 370.9 ([{$^{35}$Cl} M+H]$^+$), 372.9 ([{$^{35}$Cl} M+H]$^+$), ESI pos.

b) ethyl 7-chloro-6-(3-fluoro-2-pyridyl)-4-methyl-8-(trifluoromethyl)-4H-imidazo[1,2-a][1,4]benzodiazepine-2-carboxylate In analogy to experiment of example 1 c, 6-chloro-5-(3-fluoro-2-pyridyl)-3-methyl-7-(trifluoromethyl)-3H-1,4-benzodiazepin-2-amine using potassium carbonate was converted into the title compound (400 mg, 16%) which was obtained as a yellow solid. MS: 467.1 ([{$^{35}$Cl} M+H]$^+$), 469.0 ([{$^{37}$Cl} M+H]$^+$), ESI pos.

c) (4S)-7-chloro-6-(3-fluoro-2-pyridyl)-N-(2-hydroxyethyl)-4-methyl-8-(trifluoromethyl)-4H-imidazo[1,2-a][1,4]benzodiazepine-2-carboxamide In analogy to experiment of example 138, ethyl 7-chloro-6-(3-fluoro-2-pyridyl)-4-methyl-8-(trifluoromethyl)-4H- imidazo[1,2-a][1,4]benzodiazepine-2-carboxylate was converted into the enantiopure (−)-title compound (5.3 mg, 2%) which was obtained as a white solid. MS: 482.0 ([{$^{35}$Cl} M+H]$^+$), 484.0 ([{$^{37}$Cl} M+H]$^+$), ESI pos.

Example 142

[(4S)-7-chloro-6-(3-fluoro-2-pyridyl)-4-methyl-8-(trifluoromethyl)-4H-[1,2,4]triazolo[1,5-a][1,4]benzodiazepin-2-yl]-[3-(difluoromethyl)azetidin-1-yl]methanone

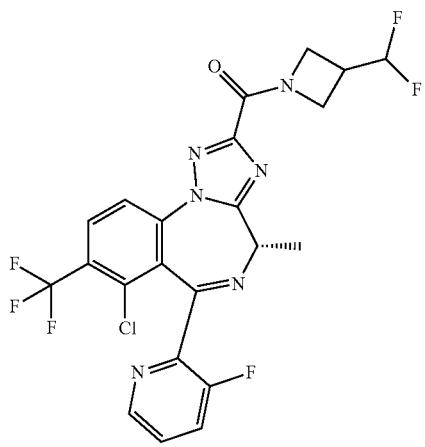 [SMILES: C[C@@H]1N=C(c2ncccc2F)c2c(ccc(C(F)(F)F)c2Cl)-n2nc(C(=O)N3CC(C(F)F)C3)nc21]

In analogy to experiment of example 6 d, 7-chloro-6-(3-fluoro-2-pyridyl)-4-methyl-8-(trifluoromethyl)-4H-[1,2,4]triazolo[1,5-a][1,4]benzodiazepine-2-carboxylic acid using 3-(difluoromethyl)azetidine hydrochloride was converted into the enantiopure (+)-title compound (4.5 mg, 2%) which was obtained as a white solid. MS: 529.1 ([{$^{35}$Cl} M+H]$^+$), 531.1 ([{$^{35}$Cl} M+H]$^+$), ESI pos.

Example 143

1-[(4S)-7-chloro-6-(3-fluoro-2-pyridyl)-4-methyl-8-(trifluoromethyl)-4H-[1,2,4]triazolo[1,5-a][1,4]benzodiazepin-2-yl]-3-cyclopropyl-urea a) tert-butyl N-[7-chloro-6-(3-fluoro-2-pyridyl)-4-methyl-8-(trifluoromethyl)-4H-[1,2,4]triazolo[1,5-a][1,4]benzodiazepin-2-yl]carbamate In analogy to experiment of example 49 a, 7-chloro-6-(3-fluoro-2-pyridyl)-4-methyl-8-(trifluoromethyl)-4H-[1,2,4]triazolo[1,5-a][1,4]benzodiazepine-2-carboxylic acid was converted into the title compound (710 mg, 61%) which was obtained as a yellow solid in low purity (50%) and used in the following step without further purification. MS: 455.1 ([{$^{35}$Cl} M−C$_4$H$_8$+H]$^+$), 511.2 ([{$^{35}$Cl} M+H]$^+$), ESI pos.

b) 7-chloro-6-(3-fluoro-2-pyridyl-4-methyl-8-(trifluoromethyl)-4H-[1,2,4]triazolo[1,5-a][1,4]benzodiazepin-2-amine In analogy to experiment of example 49 b, tert-butyl N-[7-chloro-6-(3-fluoro-2-pyridyl)-4-methyl-8-(trifluoromethyl)-4H-[1,2,4]triazolo[1,5-a][1,4]benzodiazepin-2-yl]carbamate was converted into the title compound (300 mg, 53%) which was obtained as a light yellow solid in low purity (50%) and used in the following step without further purification. MS: 411.0 ([{$^{35}$Cl} M+H]$^+$), 413.0 ([{$^{35}$Cl} M+H]$^+$), ESI pos.

c) 1-[(4S)-7-chloro-6-(3-fluoro-2-pyridyl)-4-methyl-8-(trifluoromethyl)-4H-[1,2,4]triazolo[1,5-a][1,4]benzodiazepin-2-yl]-3-cyclopropyl-urea In analogy to experiment of example 57, 7-chloro-6-(3-fluoro-2-pyridyl)-4-methyl-8-(trifluoromethyl)-4H-[1,2,4]triazolo[1,5-a][1,4]benzodiazepin-2-amine using cyclopropanamine was converted into the enantiopure (+)-title compound (11.7 mg, 10%) which was obtained as a white solid. MS: 494.1 ([{$^{35}$Cl} M+H]$^+$), 496.1 ([{$^7$Cl} M+H]$^+$), ESI pos.

Example 144

2-[(4S)-7-chloro-6-(3-fluoro-2-pyridyl)-4-methyl-8-(trifluoromethyl)-4H-[1,2,4]triazolo[1,5-a][1,4]benzodiazepin-2-yl]-5-methyl-1,3,4-oxadiazole

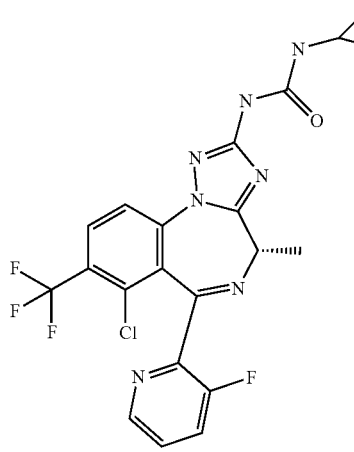

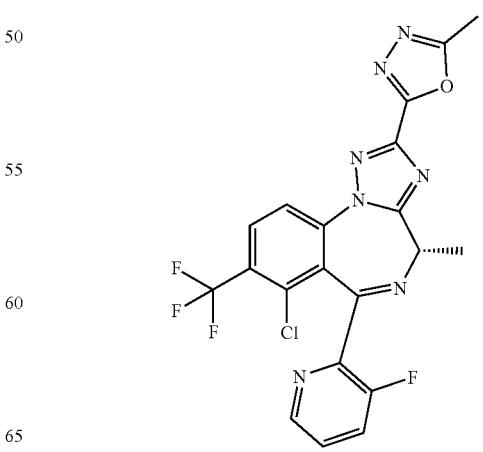

a) N'-acetyl-7-chloro-6-(3-fluoro-2-pyridyl)-4-methyl-8-(trifluoromethyl)-4H-[1,2,4]triazolo[1,5-a][1,4]benzodiazepine-2-carbohydrazide In analogy to experiment of example 6 d, 7-chloro-6-(3-fluoro-2-pyridyl)-4-methyl-8-(trifluoromethyl)-4H-[1,2,4]triazolo[1,5-a][1,4]benzodiazepine-2-carboxylic acid was converted into the title compound (230 mg, 58%) which was obtained as a yellow solid. MS: 496.0 ([{$^{35}$Cl} M+H]$^+$), 498.0 ([{$^{37}$Cl} M+H]$^+$), ESI pos.

b) 2-[(4S)-7-chloro-6-(3-fluoro-2-pyridyl)-4-methyl-8-(trifluoromethyl)-4H-[1,2,4]triazolo[1,5-a][1,4]benzodiazepin-2-yl]-5-methyl-1,3,4-oxadiazole A mixture of N'-acetyl-7-chloro-6-(3-fluoro-2-pyridyl)-4-methyl-8-(trifluoromethyl)-4H-[1,2,4]triazolo[1,5-a][1,4]benzodiazepine-2-carbohydrazide (220 mg, 0.44 mmol) and Burgess reagent (317 mg, 1.33 mmol) in tetrahydrofuran (2 mL) was stirred at 25° C. for 1 h. The reaction mixture was concentrated in vacuo. The residue was purified by preparative HPLC (Waters Xbridge, water containing 0.05% aqueous ammonia/acetonitrile) followed by chiral HPLC (Daicel Chiralpak AD, methanol containing 0.1% aqueous ammonia) to afford the enantiopure (+)-title compound (24.8 mg, 12%) which was obtained as an off-white solid. MS: 478.0 ([{$^{35}$Cl} M+H]$^+$), 480.0 ([{$^{37}$Cl} M+H]$^+$), ESI pos.

Example 145

[(4S)-7-chloro-6-(3-fluoro-2-pyridyl)-4-methyl-8-(trifluoromethyl)-4H-imidazo[1,2-a][1,4]benzodiazepin-2-yl]-(3-methoxyazetidin-1-yl)methanone

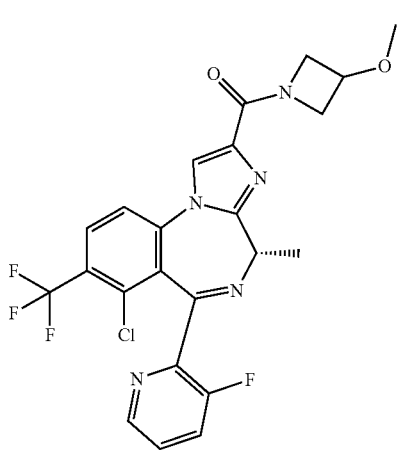 [SMILES: COC1CN(C(=O)c2cn3c(n2)[C@H](C)N=C(c2ncccc2F)c2c-3ccc(C(F)(F)F)c2Cl)C1]

a) 7-chloro-6-(3-fluoro-2-pyridyl)-4-methyl-8-(trifluoromethyl)-4H-imidazo[1,2-a][1,4]benzodiazepine-2-carboxylic acid To a solution of ethyl 7-chloro-6-(3-fluoro-2-pyridyl)-4-methyl-8-(trifluoromethyl)-4H-imidazo[1,2-a][1,4]benzodiazepine-2-carboxylate (130 mg, 0.28 mmol) in dichloromethane (1 mL) was added boron tribromide (112 mg, 0.83 mmol). The reaction mixture was stirred at 25° C. for 12 h, before being quenched by addition of ethanol and concentrated in vacuo. The residue was purified by reverse phase flash column chromatography (C18, water containing 0.1% trifluoroacetic acid/acetonitrile) to afford the title compound (45 mg, 37%) as a yellow solid. MS: 439.0 ([{$^{35}$Cl} M+H]$^+$), 441.0 ([{$^{35}$Cl} M+H]$^+$), ESI pos.

b) [(4S)-7-chloro-6-(3-fluoro-2-pyridyl)-4-methyl-8-(trifluoromethyl)-4H-imidazo[1,2-a][1,4]benzodiazepin-2-yl]-(3-methoxyazetidin-1-yl)methanone In analogy to experiment of example 6 d, 7-chloro-6-(3-fluoro-2-pyridyl)-4-methyl-8-(trifluoromethyl)-4H-imidazo[1,2-a][1,4]benzodiazepine-2-carboxylic acid using 3-methoxyazetidine hydrochloride was converted into the enantiopure (–)-title compound (4.2 mg, 8%) which was obtained as a white solid. MS: 508.1 ([{$^{35}$Cl} M+H]$^+$), 510.1 ([{$^{37}$Cl} M+H]$^+$), ESI pos.

Example 146

1-[(4S)-7-chloro-6-(3-fluoro-2-pyridyl)-4-methyl-8-(trifluoromethyl)-4H-[1,2,4]triazolo[1,5-a][1,4]benzodiazepin-2-yl]-3-(oxetan-3-yl)urea

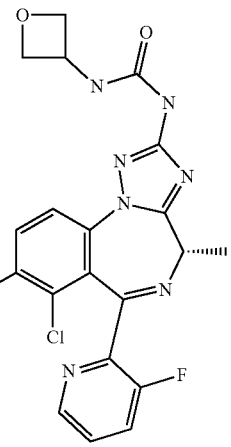

In analogy to experiment of example 57, 7-chloro-6-(3-fluoro-2-pyridyl)-4-methyl-8-(trifluoromethyl)-4H-[1,2,4]triazolo[1,5-a][1,4]benzodiazepin-2-amine using oxetan-3-amine was converted into the enantiopure (+)-title compound (14.5 mg, 12%) which was obtained as an off-white solid. MS: 510.0 ([{$^{35}$Cl} M+H]$^+$), 512.0 ([{$^{37}$Cl} M+H]$^+$), ESI pos.

Example 147

3-[(4S)-7-chloro-6-(3-fluoro-2-pyridyl)-4-methyl-8-(trifluoromethyl)-4H-[1,2,4]triazolo[1,5-a][1,4]benzodiazepin-2-yl]oxazolidin-2-one

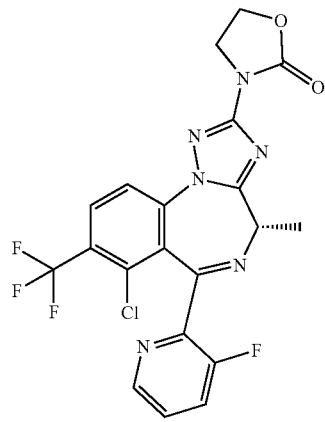 [SMILES: C[C@@H]1N=C(c2ncccc2F)c2c(ccc(C(F)(F)F)c2Cl)-n2nc(N3CCOC3=O)nc21]

a) 2-chloroethyl N-(2-chloroethoxycarbonyl)-N-[7-chloro-6-(3-fluoro-2-pyridyl-4-methyl-8-(trifluoromethyl)-4H-[1,2,4]triazolo[1,5-a][1,4]benzodiazepin-2-yl]carbamate To a solution of 7-chloro-6-(3-fluoro-2-pyridyl)-4-methyl-8-(trifluoromethyl)-4H-[1,2,4]triazolo[1,5-a][1,4]benzodiazepin-2-amine (220 mg, 0.54 mmol) and pyridine (170 mg, 2.14 mmol) in acetonitrile (3 mL) was slowly added 2-chloroethyl chloroformate (153 mg, 1.07 mmol) at 0° C. The mixture was stirred at 0° C. for 0.5 h, then a further amount of pyridine (90 mg, 1.14 mmol) and 2-chloroethyl chloroformate (80 mg, 0.56 mmol) were added. The mixture was stirred at 15° C. for 0.5 h, before being diluted with water (5 mL) and extracted with ethyl acetate (3×5 mL). The combined organic layers were washed with brine (5 mL), dried ($Na_2SO_4$) and concentrated in vacuo to afford the title compound (340 mg, quantitative) as a brown oil. MS: 622.9 ($[\{^{35}Cl, ^{35}Cl\} M+H]^+$), 624.9 ($[\{^{35}Cl, ^{37}Cl\} M+H]^+$), ESI pos.

b) 3-[4(4S)-7-chloro-6-(3-fluoro-2-pyridyl)-4-methyl-8-(trifluoromethyl)-4H-[1,2,4]triazolo[1,5-a][1,4]benzodiazepin-2-yl]oxazolidin-2-one To a solution of 2-chloroethyl N-(2-chloroethoxycarbonyl)-N-[7-chloro-6-(3-fluoro-2-pyridyl)-4-methyl-8-(trifluoromethyl)-4H-[1,2,4]triazolo[1,5-a][1,4]benzodiazepin-2-yl]carbamate (340 mg, 0.55 mmol) in N,N-dimethylformamide (4 mL) was added triethylamine (276 mg, 2.73 mmol). The mixture was stirred at 120° C. for 1.5 h, then concentrated in vacuo. The residue was purified by flash column chromatography (silica, petroleum ether/ethyl acetate 1:1) followed by preparative HPLC (Waters Xbridge, water containing 10 mM ammonium hydrogenocarbonate/acetonitrile) and, finally, by chiral SFC (Daicel Chiralpak AD, 30% isopropanol) to afford the enantiopure (+)-title compound (3.5 mg, 1%) which was obtained as a pink solid. MS: 481.0 ($[\{^{35}Cl\} M+H]^+$), ESI pos.

Example 148

(4S)-7-chloro-6-(2,6-difluorophenyl)-2,4-dimethyl-8-(trifluoromethyl)-4H-imidazo[1,2-a][1,4]benzodiazepine

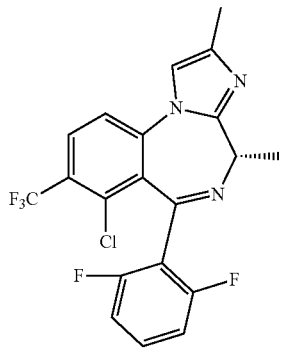 [SMILES: Cc1cn2c(n1)[C@H](C)N=C(c1c(F)cccc1F)c1c-2ccc(C(F)(F)F)c1Cl]

a) 6-chloro-5-(2,6-difluorophenyl)-3-methyl-2-(methylthio)-7-(trifluoromethyl)-3H-1,4-benzodiazepine To a solution of 6-chloro-5-(2,6-difluorophenyl)-3-methyl-7-(trifluoromethyl)-1,3-dihydro-1,4-benzodiazepine-2-thione (420 mg, 1.04 mmol) in N,N-dimethylformamide (4 mL) was added potassium carbonate (430 mg, 3.11 mmol) and iodomethane (221 mg, 0.097 mL, 1.56 mmol). The reaction mixture was stirred at room temperature for 1 h, before addition of water. The aqueous layer was extracted with ethyl acetate. The organic layer was washed with brine, dried ($Na_2SO_4$) and concentrated in vacuo. The residue was purified by flash column chromatography (silica, 0-20% ethyl acetate in heptane) to afford the title compound (330 mg, 76%) as a white solid. MS: 419.0 ($[\{^{35}Cl\} M+H]^+$), 421.0 ($[\{^{37}Cl\} M+H]^+$), ESI pos.

b) 2-[(E/Z)-[6-chloro-5-(2,6-difluorophenyl)-3-methyl-7-(trifluoromethyl)-1,3-dihydro-1,4-benzodiazepin-2-ylidene]amino]propan-1-ol To a solution of 6-chloro-5-(2,6-difluorophenyl)-3-methyl-2-(methylthio)-7-(trifluoromethyl)-3H-1,4-benzodiazepine (182 mg, 0.435 mmol) in 1-butanol (1 mL) was added 2-aminopropan-1-ol (163 mg, 0.169 mL, 2.17 mmol). The reaction was stirred at 130° C. over night then cooled to room temperature. The reaction mixture was extracted with ethyl acetate, washed with brine, dried ($Na_2SO_4$) and concentrated in vacuo. The residue was purified by flash column chromatography (silica, heptane/ethyl acetate 1:1 to 0:1) to afford the title compound (81.1 mg, 42%) as a light yellow foam. MS: 444.2 ($[\{^{35}Cl\} M+H]^+$), 446.1 ($[\{^{37}Cl\} M+H]^+$), ESI pos.

c) (4S)-7-chloro-6-(2,6-difluorophenyl)-2,4-dimethyl-8-(trifluoromethyl)-4H-imidazo[1,2-a][1,4]benzodiazepine In analogy to experiment of example 136 b, 2-[(E/Z)-[6-chloro-5-(2,6-difluorophenyl)-3-methyl-7-(trifluoromethyl)-1,3-dihydro-1,4-benzodiazepin-2-ylidene]amino]propan-1-ol was converted into the enantiopure (−)-title compound (20 mg, 28%) %) which was obtained as a white foam. MS: 426.1 ([{$^{35}$Cl} M+H]$^+$), 428.1 ([{$^{37}$Cl} M+H]$^+$), ESI pos.

Example 149

[(4S)-7-chloro-6-(2,6-difluorophenyl)-4-methyl-8-(trifluoromethyl)-4H-imidazo[1,2-a][1,4]benzodiazepin-2-yl]methanol

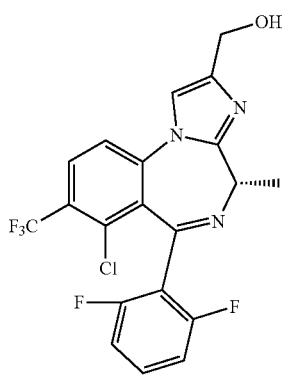 [SMILES: C[C@@H]1N=C(c2c(F)cccc2F)c2c(ccc(C(F)(F)F)c2Cl)-n2cc(CO)nc21]

To a solution of ethyl 7-chloro-6-(2,6-difluorophenyl)-4-methyl-8-(trifluoromethyl)-4H-imidazo[1,2-a][1,4]benzodiazepine-2-carboxylate (100 mg, 0.210 mmol) in tetrahydrofuran (1 mL), lithium borohydride (0.41 mL, 0.830 mmol) was added at 0° C. and the mixture was stirred at 0° C. for 1 h. The reaction mixture was diluted with water (20 mL) and extracted with ethyl acetate (3×20 mL). The combined organic layers were washed with brine (2×20 mL), dried (Na$_2$SO$_4$) and concentrated in vacuo. The residue was purified by preparative HPLC (Waters Xbridge, water containing 0.05% ammonium hydroxyde/acetonitrile) followed by chiral SFC (Daicel Chiralcel OJ-H, methanol containing 0.1% ammonium hydroxide) to afford the enantiopure (−)-title compound (3.6 mg, 3%) as a white solid. MS: 442.1 ([{$^{35}$Cl} M+H]$^+$), ESI pos.

Example 150

(4S)-7-chloro-6-(2,6-difluorophenyl)-4-methyl-8-(trifluoromethyl)-4H-imidazo[1,2-a][1,4]benzodiazepine

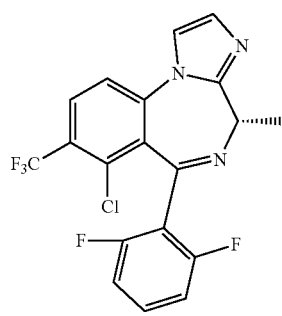 [SMILES: C[C@@H]1N=C(c2c(F)cccc2F)c2c(ccc(C(F)(F)F)c2Cl)-n2ccnc21]

To a mixture of (3S)-6-chloro-5-(2,6-difluorophenyl)-3-methyl-7-(trifluoromethyl)-1,3-dihydro-1,4-benzodiazepine-2-thione (400 mg, 0.989 mmol) in 1-butanol (16.5 mL), was added 2,2-diethoxyethylamine (132 mg, 0.144 mL, 0.988 mmol) and p-toluenesulfonic acid monohydrate (9.4 mg, 0.049 mmol). The reaction mixture was stirred at 125° C. for 3 h, then a further amount of p-toluenesulfonic acid monohydrate (188 mg, 0.988 mmol) was added. The reaction mixture was stirred at 125° C. overnight, then a final amount of 2,2-diethoxyethylamine (26 mg, 0.029 mL, 0.198 mmol) and p-toluenesulfonic acid monohydrate (56 mg, 0.296 mmol) were added. The mixture was stirred at 125° C. for 3 h, before being cooled to room temperature and concentrated in vacuo. Following addition of water (100 mL) and ethyl acetate (15 mL), the solution was basified to pH 9 by addition of aqueous NaOH (1.0 m). The resulting mixture was extracted with EtOAc (2×100 mL) and the combined organic layers were washed with brine, dried (Na$_2$SO$_4$) and concentrated in vacuo. The residue was purified by flash column chromatography (silica, 30-100% ethyl acetate in heptane) to provide 222 mg of crude product. 38 mg were submitted to chiral SFC (Daicel Chiralpak IG, 10% methanol) to afford the enantiopure (−)-title compound (18 mg, 4%) as a light brown solid. MS: 413.0 ([{$^{35}$Cl} M+H]$^+$), ESI pos.

Example 151

[(4S)-7-chloro-6-(3-fluoro-2-pyridyl)-4-methyl-8-(trifluoromethyl)-4H-imidazo[1,2-a][1,4]benzodiazepin-1-yl]methanol

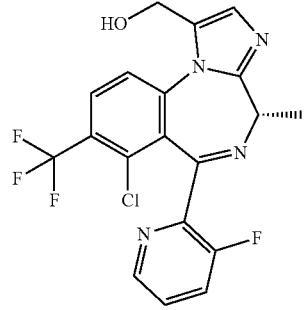 [SMILES: C[C@@H]1N=C(c2ncccc2F)c2c(ccc(C(F)(F)F)c2Cl)-n2c(CO)cnc21]

a) 1-amino-3-[tert-butyl(diphenyl)silyl]oxy-propan-2-ol

A solution of tert-butylchlorodiphenylsilane (7.24 g, 26.3 mmol) and imidazole (2.99 g, 43.9 mmol) in N,N-dimethylformamide (200 mL) was purged with nitrogen 3 times, then 3-amino-1,2-propanediol (2.00 g, 22.0 mmol) was added. The reaction mixture was stirred at 25° C. for 2 h, then poured into water, extracted with ethyl acetate, dried (Na$_2$SO$_4$) and concentrated in vacuo. The residue was purified by flash column chromatography (silica, ethyl acetate, then dichloromethane/methanol 10:1) followed by reversed phase column chromatography (C18, water containing 0.1% formic acid/acetonitrile 1:0 to 3:7) to afford the title compound (1.00 g, 14%) as a colorless oil, which was used as such in the following step without further characterization.

b) diphenyl [6-chloro-5-(3-fluoro-2-pyridyl)-3-methyl-7-(trifluoromethyl)-3H-1,4-benzodiazepin-2-yl] phosphate To a solution of 6-chloro-5-(3-fluoro-2-pyridyl)-3-methyl-7-(trifluoromethyl)-1,3-dihydro-1,4-benzodiazepin- 2-one (building block X, 3.0 g, 8.07 mmol) in tetrahydrofuran (40 mL) was added sodium hydride (646 mg, 16.14 mmol) at 0° C. The mixture was stirred for 15 min, then diphenyl chlorophosphate (3.25 g, 12.1 mmol) was added, and the mixture was stirred at 0° C. for another 1 h. The reaction mixture was used in the following step without further purification. MS: 604.2 ([{$^{35}$Cl} M+H]$^+$), 606.1 ([{$^{37}$Cl} M+H]$^+$), ESI pos.

c) 1-[tert-butyl(diphenyl)silyl]oxy-3-[[6-chloro-5-(3-fluoro-2-pyridyl)-3-methyl-7-(trifluoromethyl)-3H-1,4-benzodiazepin-2-yl]amino]propan-2-ol To a solution of 1-amino-3-[tert-butyl(diphenyl)silyl]oxy-propan-2-ol (665 mg, 2.02 mmol) and triethylamine (204 mg, 2.02 mmol) in tetrahydrofuran (5 mL) was added slowly diphenyl [6-chloro-5-(3-fluoro-2-pyridyl)-3-methyl-7-(trifluoromethyl)-3H-1,4-benzodiazepin-2-yl] phosphate (406 mg, 0.67 mmol). The reaction mixture was stirred at 15° C. for 2 h, then poured into water, extracted with ethyl acetate, dried (Na$_2$SO$_4$) and concentrated in vacuo. The residue was purified by reversed phase column chromatography (C18, water containing 0.1% formic acid/acetonitrile 1:0 to 1:4) to afford the title compound (200 mg, 44%) as a white solid. MS: 683.2 ([{$^{35}$Cl} M+H]$^+$), ESI pos.

d) tert-butyl-diphenyl-[[7-chloro-6-(3-fluoro-2-pyridyl)-4-methyl-8-(trifluoromethyl)-4H-imidazo[1,2-a][1,4]benzodiazepin-1-yl]methoxy]silane To a mixture of 1-[tert-butyl(diphenyl)silyl]oxy-3-[[6-chloro-5-(3-fluoro-2-pyridyl)-3-methyl-7-(trifluoromethyl)-3H-1,4-benzodiazepin-2-yl]amino]propan-2-ol (190 mg, 0.280 mmol) and sodium bicarbonate (117 mg, 1.39 mmol) in dichloroethane (10 mL) was added Dess-Martin periodane (354 mg, 0.830 mmol) portionwise at 15° C. The mixture was stirred at 15° C. for 4 h, then slowly poured into water (10 mL) and extracted with dichloromethane (3×10 mL). The combined organic layers were washed with brine (20 mL), dried (Na$_2$SO$_4$) and concentrated in vacuo. The residue was purified by reversed phase column chromatography (C18, water containing 0.1% formic acid/acetonitrile 1:0 to 1:2) to afford the title compound (150 mg, 81%) as a white solid. MS: 663.3 ([{$^{35}$Cl} M+H]$^+$), ESI pos.

e) [(4S)-7-chloro-6-(3-fluoro-2-pyridyl)-4-methyl-8-(trifluoromethyl)-4H-imidazo[1,2-a][1,4]benzodiazepin-1-yl]methanol A solution of tert-butyl-diphenyl-[[7-chloro-6-(3-fluoro-2-pyridyl)-4-methyl-8-(trifluoromethyl)-4H-imidazo[1,2-a][1,4]benzodiazepin-1-yl]methoxy]silane (140.0 mg, 0.210 mmol) and ammonium fluoride (78.2 mg, 2.11 mmol) in methanol (4 mL) was stirred at 50° C. for 2 h. The solution was cooled to room temperature and purified by preparative HPLC (Waters Xbridge, water containing 10 mM ammonium hydrogenocarbonate/acetonitrile) followed by chiral SFC (Chiralpak AD-3, 25% ethanol) to afford the enantiopure (+)-title compound (17 mg, 19%) as a white solid. MS: 425.0 ([{$^{35}$Cl} M+H]$^+$), ESI pos.

Example 152

(4S)-7-chloro-N-(2-fluoroethyl)-6-(3-fluoro-2-pyridyl)-4-methyl-8-(trifluoromethyl)-4H-[1,2,4]triazolo[1,5-a][1,4]benzodiazepine-2-carboxamide

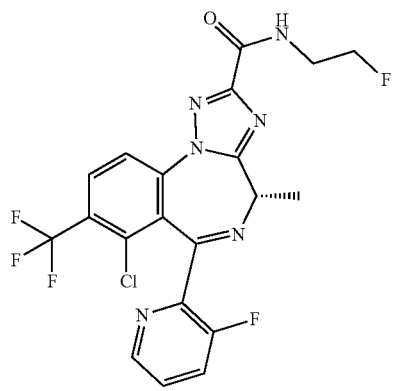 [SMILES: C[C@@H]1N=C(c2ncccc2F)c2c(ccc(C(F)(F)F)c2Cl)-n2nc(C(=O)NCCF)nc21]

In analogy to experiment of example 85 b, ethyl (4S)-7-chloro-6-(3-fluoro-2-pyridyl)-4-methyl-8-(trifluoromethyl)-4H-[1,2,4]triazolo[1,5-a][1,4]benzodiazepine-2-carboxylate using 2-fluoroethylamine hydrochloride was converted into the enantiopure (−)-title compound (31 mg, 20%) which was obtained as an off-white solid. MS: 485.0 ([{$^{35}$Cl} M+H]$^+$), ESI pos.

Example 153

[(4S)-7-chloro-6-(3-fluoro-2-pyridyl)-4-methyl-8-(trifluoromethyl)-4H-imidazo[1,2-a][1,4]benzodiazepin-2-yl]methanol

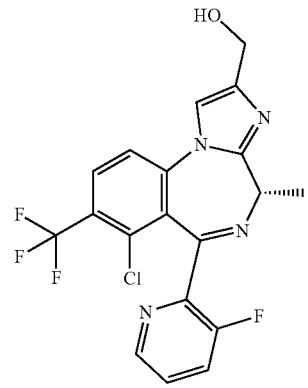 [SMILES: C[C@@H]1N=C(c2ncccc2F)c2c(ccc(C(F)(F)F)c2Cl)-n2cc(CO)nc21]

To a solution of ethyl 7-chloro-6-(3-fluoro-2-pyridyl)-4-methyl-8-(trifluoromethyl)-4H-imidazo[1,2-a][1,4]benzodiazepine-2-carboxylate (150 mg, 0.320 mmol) in tetrahydrofuran (3 mL) was slowly added lithium aluminium hydride (37 mg, 0.960 mmol) at −20° C. The reaction mixture was stirred at −20° C. for 1 h, then poured onto saturated aqueous ammonim chloride (10 mL), diluted with water (20 mL) and extracted with ethyl acetate (3×20 mL). The combined organic layers were washed with brine (30 mL), dried (Na$_2$SO$_4$) and concentrated in vacuo. The residue was purified by preparative HPLC (Waters Xbridge, water containing 10 mM ammonium hydrogenocarbonate/acetonitrile) followed by chiral SFC (Daicel Chiralpak IC, methanol) to afford the enantiopure (−)-title compound (20.7 mg, 10%) which was obtained as a light yellow solid. MS: 425.2 ([{$^{35}$Cl} M+H]$^+$), ESI pos.

Example 154

(4S)-7-chloro-6-(3-fluoro-2-pyridyl)-N-(2-hydroxyethyl)-1,4-dimethyl-8-(trifluoromethyl)-4H-imidazo[1,2-a][1,4]benzodiazepine-2-carboxamide

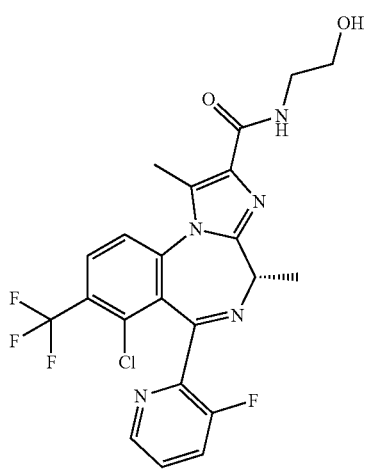

a) methyl 2-[[6-chloro-5-(3-fluoro-2-pyridyl)-3-methyl-7-(trifluoromethyl)-3H-1,4-benzodiazepin-2-yl]amino]-3-hydroxy-butanoate To a solution of 6-chloro-5-(3-fluoro-2-pyridyl)-3-methyl-7-(trifluoromethyl)-1,3-dihydro-1,4-benzodiazepin-2-one (building block X, 3.0 g, 8.07 mmol) in tetrahydrofuran (30 mL) was added sodium hydride (646 mg, 16.14 mmol) portionwise at 0° C. The mixture was stirred for 30 min, then diphenyl chlorophosphate (3.25 g, 12.1 mmol) was added. The reaction mixture was stirred at 0° C. for another 1 h (phosphate intermediate). A mixture of L-threonine methyl ester hydrochloride (4.11 g, 24.2 mmol) and triethylamine (2.45 g, 24.2 mmol) in tetrahydrofuran (40 mL) was stirred at 15° C. for 10 min. The phosphate intermediate mixture was slowly added at −20° C. The reaction mixture was warmed up to 15° C., stirred for 4 h, then poured slowly into saturated aqueous ammonium chloride (50 mL), diluted with water (50 mL) and extracted with ethyl acetate (3×30 mL). The combined organic layers were washed with brine (50 mL), dried (Na$_2$SO$_4$) and concentrated in vacuo. The residue was purified by flash column chromatography (silica, petroleumether/ethyl acetate 10:1 to 1:1) to afford the title compound (2.1 g, 51%) as an orange solid. MS: 486.9 ([{$^{35}$Cl} M+H]$^+$), ESI pos.

b) methyl 7-chloro-6-(3-fluoro-2-pyridyl-1,4-dimethyl-8-(trifluoromethyl)-4H-imidazo[1,2-a][1,4]benzodiazepine-2-carboxylate In analogy to experiment of example 151 d, methyl 2-[[6-chloro-5-(3-fluoro-2-pyridyl)-3-methyl-7-(trifluoromethyl)-3H-1,4-benzodiazepin-2-yl]amino]-3-hydroxy-butanoate was converted into the title compound (450 mg, 22%) which was obtained as a yellow solid. MS: 467.0 ([{$^{35}$Cl} M+H]$^+$), 469.0 ([{$^{35}$Cl} M+H]$^+$), ESI pos.

c) 7-chloro-6-(3-fluoro-2-pyridyl)-1,4-dimethyl-8-(trifluoromethyl)-4H-imidazo[1,2-a][1,4]benzodiazepine-2-carboxylic acid To a solution of methyl 7-chloro-6-(3-fluoro-2-pyridyl)-1,4-dimethyl-8-(trifluoromethyl)-4H-imidazo[1,2-a][1,4]benzodiazepine-2-carboxylate (200 mg, 0.43 mmol) in tetrahydrofuran (1 mL) was slowly added triethylamine (1.0 mL, 7.19 mmol) and saturated aqueous lithium bromide (1.0 mL, 0.43 mmol) at 0° C. The reaction mixture was stirred at 15° C. for 4 h. Aqueous hydrochloric acid (1.0 m) was added until pH=4-5. The aqueous layer was extracted with ethyl acetate (3×20 mL). The combined organic layers were washed with brine (20 mL), dried (Na$_2$SO$_4$) and concentrated in vacuo to afford the title compound (120 mg, 46%) as a yellow solid (purity: 74%). MS: 453.1 ([{$^{35}$Cl} M+H]$^+$), ESI pos.

d) (4S)-7-chloro-6-(3-fluoro-2-pyridyl)-N-(2-hydroxyethyl)-1,4-dimethyl-8-(trifluoromethyl)-4H-imidazo[1,2-a][1,4]benzodiazepine-2-carboxamide In analogy to experiment of example 6 d, 7-chloro-6-(3-fluoro-2-pyridyl)-1,4-dimethyl-8-(trifluoromethyl)-4H-imidazo[1,2-a][1,4]benzodiazepine-2-carboxylic acid using 2-aminoethanol was converted into the enantiopure (−)-title compound (17.3 mg, 14%) which was obtained as a white solid. MS: 496.1 ([{$^{35}$Cl} M+H]$^+$), ESI pos.

Example 155

(4S)-7-chloro-6-(3-fluoro-2-pyridyl)-4-methyl-N-[(2S)-2-hydroxypropyl]-8-(trifluoromethyl)-4H-imidazo[1,2-a][1,4]benzodiazepine-2-carboxamide

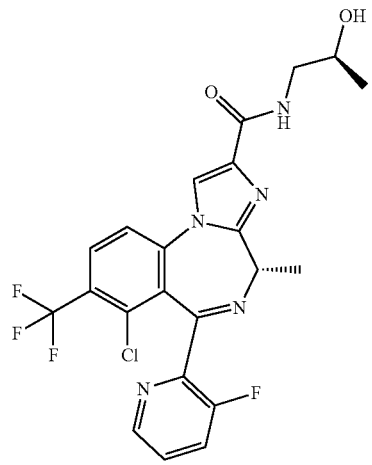 [SMILES: C[C@H](O)CNC(=O)c1cn2c(n1)[C@H](C)N=C(c1ncccc1F)c1c-2ccc(C(F)(F)F)c1Cl]

In analogy to experiment of example 138, ethyl 7-chloro-6-(3-fluoro-2-pyridyl)-4-methyl-8-(trifluoromethyl)-4H-imidazo[1,2-a][1,4]benzodiazepine-2-carboxylate was converted into the enantiopure (−)-title compound (23 mg, 14%) which was obtained as a white solid. MS: 496.1 ([{$^{35}$Cl} M+H]$^+$), ESI pos.

Example 156

[3-(difluoromethyl)azetidin-1-yl]-[(4S)-7-chloro-6-(3-fluoro-2-pyridyl)-4-methyl-8-(trifluoromethyl)-4H-imidazo[1,2-a][1,4]benzodiazepin-2-yl]methanone

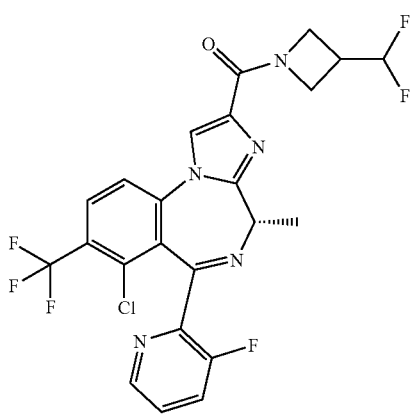 [SMILES: C[C@@H]1N=C(c2ncccc2F)c2c(ccc(C(F)(F)F)c2Cl)-n2cc(C(=O)N3CC(C(F)F)C3)nc21]

In analogy to experiment of example 6 d, 7-chloro-6-(3-fluoro-2-pyridyl)-4-methyl-8-(trifluoromethyl)-4H-imidazo[1,2-a][1,4]benzodiazepine-2-carboxylic acid using 3-(difluoromethyl)azetidine hydrochloride was converted into the enantiopure (−)-title compound (37 mg, 28%) which was obtained as a white solid. MS: 528.0 ([{$^{35}$Cl} M+H]$^+$), ESI pos.

Example 157

(4S)-7-chloro-6-(3-fluoro-2-pyridyl)-4-methyl-N-[(2R)-2-hydroxypropyl]-8-(trifluoromethyl)-4H-imidazo[1,2-a][1,4]benzodiazepine-2-carboxamide

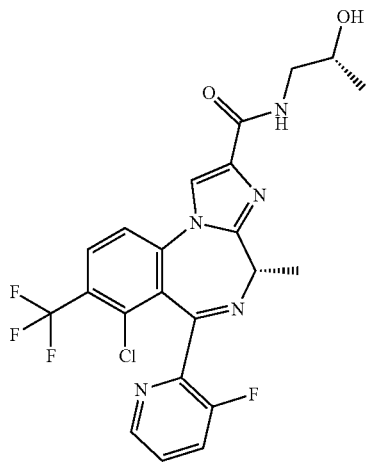 [SMILES: C[C@@H]1N=C(c2ncccc2F)c2c(ccc(C(F)(F)F)c2Cl)-n2cc(C(=O)NC[C@@H](C)O)nc21]

In analogy to experiment of example 6 d, 7-chloro-6-(3-fluoro-2-pyridyl)-4-methyl-8-(trifluoromethyl)-4H-imidazo[1,2-a][1,4]benzodiazepine-2-carboxylic acid using (2R)-1-aminopropan-2-ol was converted into the enantiopure (−)-title compound (40 mg, 35%) which was obtained as a white solid. MS: 496.2 ([{$^{35}$Cl} M+H]$^+$), ESI pos.

Example 158

(3-ethoxyazetidin-1-yl)-[(4S)-7-chloro-6-(3-fluoro-2-pyridyl)-4-methyl-8-(trifluoromethyl)-4H-imidazo[1,2-a][1,4]benzodiazepin-2-yl]methanone

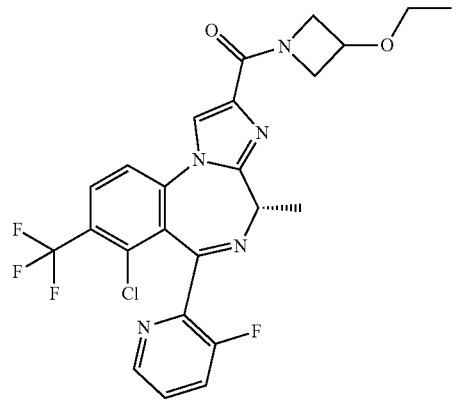 [SMILES: CCOC1CN(C(=O)c2cn3c(n2)[C@H](C)N=C(c2ncccc2F)c2c-3ccc(C(F)(F)F)c2Cl)C1]

In analogy to experiment of example 6 d, 7-chloro-6-(3-fluoro-2-pyridyl)-4-methyl-8-(trifluoromethyl)-4H-imidazo[1,2-a][1,4]benzodiazepine-2-carboxylic acid using 3-ethoxyazetidine hydrochloride was converted into the enantiopure (−)-title compound (13 mg, 22%) which was obtained as a white solid. MS: 522.2 ([{$^{35}$Cl} M+H]$^+$), ESI pos.

Example 159

(4S)-7-chloro-6-(3-fluoro-2-pyridyl)-N-(2-hydroxy-2-methyl-propyl)-4-methyl-8-(trifluoromethyl)-4H-imidazo[1,2-a][1,4]benzodiazepine-2-carboxamide

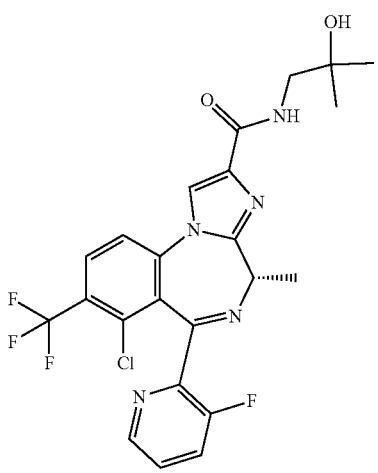 [SMILES: C[C@@H]1N=C(c2ncccc2F)c2c(ccc(C(F)(F)F)c2Cl)-n2cc(C(=O)NCC(C)(C)O)nc21]

In analogy to experiment of example 6 d, 7-chloro-6-(3-fluoro-2-pyridyl)-4-methyl-8-(trifluoromethyl)-4H-imidazo[1,2-a][1,4]benzodiazepine-2-carboxylic acid using 1-amino-2-methyl-propan-2-ol was converted into the enantiopure (−)-title compound (10.5 mg, 12%) which was obtained as an off-white solid. MS: 510.2 ([{$^{35}$Cl} M+H]$^+$), ESI pos.

Example 160

(3-hydroxy-3-methyl-azetidin-1-yl)-[(4S)-7-chloro-6-(3-fluoro-2-pyridyl)-4-methyl-8-(trifluoromethyl)-4H-imidazo[1,2-a][1,4]benzodiazepin-2-yl]methanone

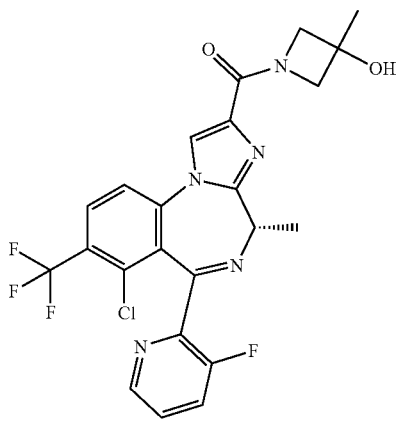 [SMILES: C[C@@H]1N=C(c2ncccc2F)c2c(ccc(C(F)(F)F)c2Cl)-n2cc(C(=O)N3CC(C)(O)C3)nc21]

In analogy to experiment of example 6 d, 7-chloro-6-(3-fluoro-2-pyridyl)-4-methyl-8-(trifluoromethyl)-4H-imidazo[1,2-a][1,4]benzodiazepine-2-carboxylic acid using 3-methylazetidin-3-ol hydrochloride was converted into the enantiopure (−)-title compound (22 mg, 25%) which was obtained as an off-white solid. MS: 507.9 ([{$^{35}$Cl} M+H]$^+$), ESI pos.

Example 161

(3-fluoroazetidin-1-yl)-[(4S)-7-chloro-6-(3-fluoro-2-pyridyl)-4-methyl-8-(trifluoromethyl)-4H-imidazo[1,2-a][1,4]benzodiazepin-2-yl]methanone

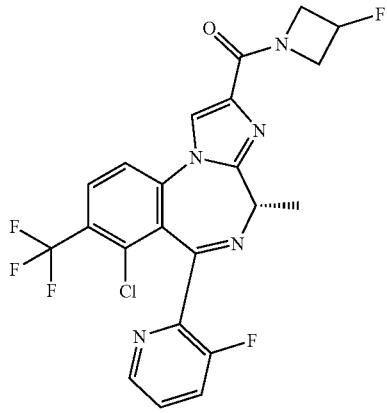 [SMILES: C[C@@H]1N=C(c2ncccc2F)c2c(ccc(C(F)(F)F)c2Cl)-n2cc(C(=O)N3CC(F)C3)nc21]

In analogy to experiment of example 6 d, 7-chloro-6-(3-fluoro-2-pyridyl)-4-methyl-8-(trifluoromethyl)-4H-imidazo[1,2-a][1,4]benzodiazepine-2-carboxylic acid using 3-fluoroazetidine was converted into the enantiopure (−)-title compound (60 mg, 30%) which was obtained as a white solid. MS: 496.0 ([{$^{35}$Cl} M+H]$^+$), ESI pos.

Example 162

(4S)-7-chloro-6-(3-fluoro-2-pyridyl)-1,4-dimethyl-N-[(2R)-2-hydroxypropyl]-8-(trifluoromethyl)-4H-imidazo[1,2-a][1,4]benzodiazepine-2-carboxamide

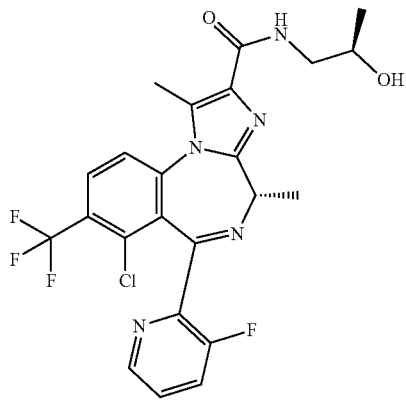 [SMILES: Cc1c(C(=O)NC[C@@H](C)O)nc2n1-c1ccc(C(F)(F)F)c(Cl)c1C(c1ncccc1F)=N[C@H]2C]

In analogy to experiment of example 6 d, 7-chloro-6-(3-fluoro-2-pyridyl)-1,4-dimethyl-8-(trifluoromethyl)-4H-imidazo[1,2-a][1,4]benzodiazepine-2-carboxylic acid using (2R)-1-aminopropan-2-ol was converted into the enantiopure (−)-title compound (11.5 mg, 17%) which was obtained as a white solid. MS: 510.0 ([{$^{35}$Cl} M+H]$^+$), ESI pos.

Example 163

(3-methylazetidin-1-yl)-[(4S)-7-chloro-6-(3-fluoro-2-pyridyl)-4-methyl-8-(trifluoromethyl)-4H-imidazo[1,2-a][1,4]benzodiazepin-2-yl]methanone

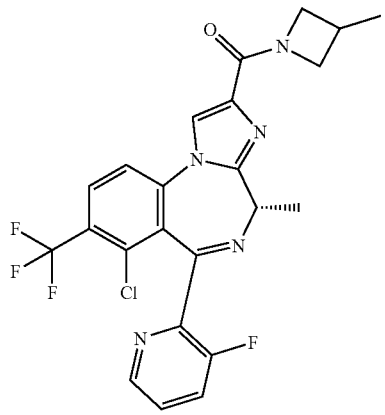 [SMILES: CC1CN(C(=O)c2cn3c(n2)[C@H](C)N=C(c2ncccc2F)c2c-3ccc(C(F)(F)F)c2Cl)C1]

In analogy to experiment of example 6 d, 7-chloro-6-(3-fluoro-2-pyridyl)-4-methyl-8-(trifluoromethyl)-4H-imidazo[1,2-a][1,4]benzodiazepine-2-carboxylic acid using 3-methylazetidine hydrochloride was converted into the enantiopure (−)-title compound (20 mg, 29%) which was obtained as a white solid. MS: 492.0 ([{$^{35}$Cl} M+H]$^+$), ESI pos.

Example 164

(4S)-7-chloro-6-(3-fluoro-2-pyridyl)-N-[(1-hydroxy-cyclopropyl)methyl]-4-methy-8-(trifluoromethyl)-4H-imidazo[1,2-a][1,4]benzodiazepine-2-carboxamide

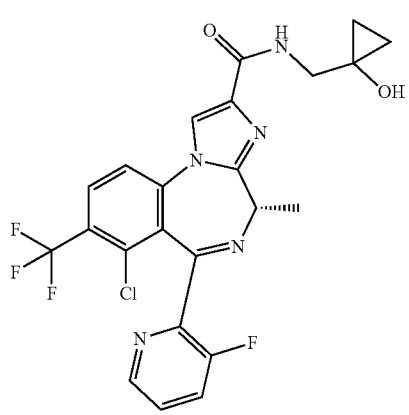 [SMILES: C[C@@H]1N=C(c2ncccc2F)c2c(ccc(C(F)(F)F)c2Cl)-n2cc(C(=O)NCC3(O)CC3)nc21]

In analogy to experiment of example 6 d, 7-chloro-6-(3-fluoro-2-pyridyl)-4-methyl-8-(trifluoromethyl)-4H-imidazo[1,2-a][1,4]benzodiazepine-2-carboxylic acid using 1-(aminomethyl)cyclopropanol was converted into the enantiopure (−)-title compound (61 mg, 29%) which was obtained as a white solid. MS: 508.1 ([$\{^{35}Cl\}$ M+H]$^+$), ESI pos.

Example 165

(4S)-7-chloro-6-(3-fluoro-2-pyridyl)-N-(trans-3-hydroxycyclobutyl)-4-methyl-8-(trifluoromethyl)-4H-imidazo[1,2-a][1,4]benzodiazepine-2-carboxamide

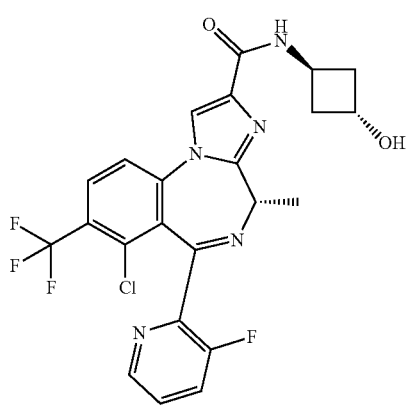 [SMILES: C[C@@H]1N=C(c2ncccc2F)c2c(ccc(C(F)(F)F)c2Cl)-n2cc(C(=O)N[C@H]3C[C@H](O)C3)nc21]

In analogy to experiment of example 6 d, 7-chloro-6-(3-fluoro-2-pyridyl)-4-methyl-8-(trifluoromethyl)-4H-imidazo[1,2-a][1,4]benzodiazepine-2-carboxylic acid using trans-3-aminocyclobutanol hydrochloride was converted into the enantiopure (−)-title compound (34 mg, 33%) which was obtained as an off-white solid. MS: 508.1 ([$\{^{35}Cl\}$ M+H]$^+$), ESI pos.

Example 166

(4S)-7-chloro-6-(3-fluoro-2-pyridyl)-N-(cis-3-hydroxycyclobutyl)-4-methyl-8-(trifluoromethyl)-4H-imidazo[1,2-a][1,4]benzodiazepine-2-carboxamide

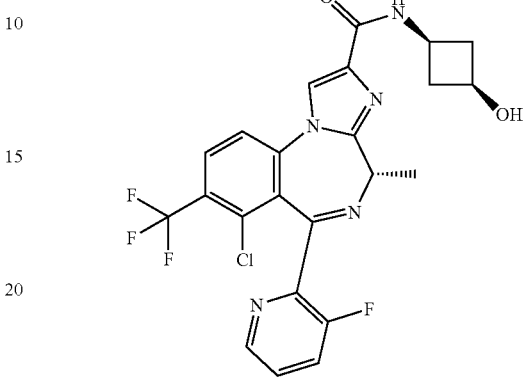

In analogy to experiment of example 6 d, 7-chloro-6-(3-fluoro-2-pyridyl)-4-methyl-8-(trifluoromethyl)-4H-imidazo[1,2-a][1,4]benzodiazepine-2-carboxylic acid using cis-3-aminocyclobutanol hydrochloride was converted into the enantiopure (−)-title compound (50 mg, 43%) which was obtained as a white solid. MS: 508.0 ([$\{^{35}Cl\}$ M+H]$^+$), ESI pos.

Assay Procedures

Membrane Preparation and Binding Assay for γ1-Containing $GABA_A$ Subtypes

The affinity of compounds at $GABA_A$ γ1 subunit-containing receptors was measured by competition for [$^3$H] RO7239181 (67.3 Ci/mmol; Roche) binding to membranes from HEK293F cells (ThermoFisher R79007) expressing human (transiently transfected) receptors of composition α5β2γ1, α2β2γ1, α1β2γ1. For better protein expression of the α2 subunit-containing receptors, the 28 amino acid long signal peptide (Met1 to Ala28) of the human $GABA_A$ α2 subunit was substituted by the 31 amino acid long signal peptide (Met1 to Ser31) of human $GABA_A$ α5 subunit.

Harvested pellets from HEK293F cells expressing the different $GABA_A$ receptor subtypes were resuspended in Mannitol Buffer pH 7.2-7.4 (Mannitol 0.29 M, Triethylamine 10 mM, Acetic acid 10 mM, EDTA 1 mM plus protease inhibitors (20 tablets Complete, Roche Diagnostics Cat. No. 05 056 489 001 per liter)), washed two times and then resuspended at 1:10 to 1:15 dilution in the same buffer. Cell disruption was performed by stirring the suspension in a Parr vessel #4637 at 435 psi for 15 minutes, and then the suspensions were centrifuged at 1000×g for 15 minutes at 4° C. (Beckman Avanti J-HC; rotor JS-4.2). The supernatant (S1) was transferred in a 2 l Schott flask and the pellet (P1) was resuspended with Mannitol Buffer up to 175 ml. The resuspended pellet was transferred into a 250 ml Corning centrifugal beaker and centrifuged at 1500×g for 10 minutes at 4° C. (Beckman Avanti J-HC; rotor JS-4.2). The supernatant (S1) was then transferred in the 2 l Schott flask and the pellet was discarded. The supernatants (S1) were centrifuged in 500 ml Beckman polypropylene centrifugal beaker at 15'000×g for 30 minutes at 4° C. (Beckman Avanti J-20 XP; rotor JLA-10.500). The pellet (P2) was resuspended with Mannitol Buffer 1:1 and frozen at −80° C. The supernatant (S2) was centrifuged in 100 ml Beckman polypropylene centrifugal tubes at 48000×g for 50 minutes at 4° C. (Beckman Avanti J-20 XP; rotor JA-18). The supernatant (S3) was discarded and the pellet (P3) was resuspended with 1:1 Mannitol Buffer. The P2 and P3 protein concentration was determined with the BIORAD Standard assay method with bovine serum albumin as standard and measured on the NANO-Drop 1000. The membrane suspension was aliquots (500 µl per tube) and stored at −80° C. until required.

Membrane homogenates were resuspended and polytronised (Polytron PT1200E Kinematica AG) in Potassium Phosphate 10 mM, KCl 100 mM binding buffer at pH 7.4 to a final assay concentration determined with a previous experiment.

Radioligand binding assays were carried out in a volume of 200 µL (96-well plates) which contained 100 µL of cell membranes, [$^3$H]RO7239181 at a concentration of 1.5 nM (α5β2γ1) or 20-30 nM (α1β2γ1, α2β2γ1) and the test compound in the range of [0.3-10000]×10$^{-9}$ M. Nonspecific binding was defined by 10×10$^{-6}$ (α5β2γ1) and 30×10$^{-6}$ M RO7239181 and typically represented less than 5% (α5β2γ1) and less than 20% (α1β2γ1, α2β2γ1) of the total binding. Assays were incubated to equilibrium for 1 hour at 4° C. and then, membranes were filtered onto unifilter (96-well white microplate with bonded GF/C filters preincubated 20-50 minutes in 0.3% Polyethylenimine) with a Filtermate 196 harvester (Packard BioScience) and washed 4 times with cold Potassium Phosphate 10 mM pH 7.4, KCl 100 mM binding buffer. After anhydrousing, filter-retained radioactivity was detected by liquid scintillation counting. $K_i$ values were calculated using Excel-Fit (Microsoft) and are the means of two determinations.

The compounds of the accompanying examples were tested in the above described assays, and the preferred compounds were found to possess a $K_i$ value for the displacement of [$^3$H]RO7239181 from GABA$_A$ γ1 subunit-containing receptors (e.g. α5β2γ1, α2β2γ1, α1β2γ1) of 100 nM or less. Most preferred are compounds with a Ki (nM)<50. Representative test results, obtained by the above described assay measuring binding affinity to HEK293 cells expressing human (h) receptors, are shown in the Table 1.

Preparation of [$^3$H]RO7239181, 6-chloro-5-(2,6-difluorophenyl)-7-methyl-1-(tritritiomethyl)-3H-1,4-benzodiazepin-2-one

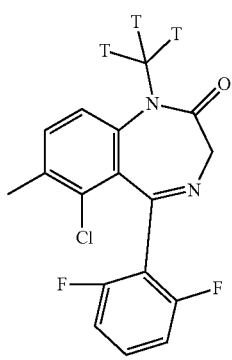

a) 5-chloro-2-methyl-3,1-benzoxazin-4-one

A solution of 2-amino-6-chlorobenzoic acid (250 g, 1.46 mol) in acetic anhydride (1250 mL) was stirred at 140° C. for 2 h. The reaction mixture was concentrated in vacuo. The resulting crude residue was suspended in ethyl acetate (1000 mL), stirred for 30 min, filtered and dried in vacuo to afford the title compound (238 g, 84%) as a grey solid. $^1$H NMR (DMSO-d6, 400 MHz): δ: 7.80 (app t, J=8.0 Hz, 1H), 7.62 (d, J=8.0 Hz, 1H), 7.49 (d, J=7.6 Hz, 1H), 2.36 (s, 3H).

b) N-[3-chloro-2-(2,6-difluorobenzoyl)phenyl]acetamide

To a solution of 5-chloro-2-methyl-3,1-benzoxazin-4-one (100 g, 511.2 mmol) and 2-bromo-1,3-difluorobenzene (118.4 g, 613.5 mmol) in tetrahydrofuran (1000 mL) was added dropwise i-PrMgCl·LiCl (1.3 M, 500 mL, 650 mmol) at −70° C. under nitrogen. The mixture was allowed to warm up to room temperature within 1 h, quenched with saturated aqueous ammonium chloride (1500 mL) and extracted with ethyl acetate (2×1500 mL). The organic phase was washed with brine (2000 mL), dried (Na$_2$SO$_4$) and concentrated in vacuo. The residue was suspended in ethyl acetate (150 mL). The resulting suspension was stirred at room temperature for 20 min, filtered and dried in vacuo to afford the title compound (113 g, 71%) as an off-white solid. $^1$H NMR (DMSO-d6, 400 MHz): δ: 9.85 (s, 1H), 7.65-7.45 (m, 1H), 7.40 (t, J=7.2 Hz, 1H), 7.38-7.34 (m, 2H), 7.16 (t, J=8.8 Hz, 2H), 1.85 (s, 3H).

c) (2-amino-6-chloro-phenyl-(2,6-difluorophenyl)methanone

To a solution of N-[3-chloro-2-(2,6-difluorobenzoyl)phenyl]acetamide (113 g, 364.9 mmol) in ethanol (250 mL) was added aqueous hydrochloric acid (12 M, 200 mL). The reaction mixture was stirred at 100° C. for 1 h, then diluted with ethyl acetate (1100 mL). The organic phase was washed with water (1100 mL), saturated aqueous sodium bicarbonate (1100 mL) and brine (1100 mL), dried over sodium sulfate and concentrated in vacuo. Petroleum ether (120 mL) was added to the crude and the suspension was stirred at room temperature for 20 min. The solid was filtered and dried to afford the title compound (88 g, 90%) as a yellow solid. $^1$H NMR (DMSO-d6, 400 MHz): δ: 7.62-7.56 (m, 1H), 7.21-7.15 (m, 3H), 6.83 (d, J=7.6 Hz, 1H), 6.74 (s, 2H), 6.58 (d, J=7.6 Hz, 1H).

d) (6-amino-3-bromo-2-chloro-phenyl)-(2,6-difluorophenyl)methanone

To a solution of (2-amino-6-chloro-phenyl)-(2,6-difluorophenyl)methanone (88.0 g, 328.8 mmol) in dichloromethane (225 mL) and N,N-dimethylformamide (225 mL) was added 1-bromopyrrolidine-2,5-dione (64.4 g, 362 mmol) at 0° C. The reaction mixture was stirred at 30° C. for 1 h. The mixture was diluted with dichloromethane (600 mL) and washed with water (500 mL) and brine (4×500 mL), dried (Na$_2$SO$_4$) and concentrated in vacuo. The residue was purified by chromatography (silica, petroleum ether/ethyl acetate, 1:0 to 2:1). The solid was suspended in petroleum ether (200 mL) and stirred at room temperature for 20 min. The suspension was filtered and the solid was dried in vacuo to afford the title compound (96.0 g, 84%) as a yellow solid. MS: 345.9 ([{$^{79}$Br, $^{35}$Cl} M+H]$^+$), 347.8 ([{$^{81}$Br, $^{35}$Cl or $^{79}$Br, $^{37}$Cl} M+H]$^+$), ESI pos.

e) 7-bromo-6-chloro-5-(2,6-difluorophenyl)-1,3-dihydro-1,4-benzodiazepin-2-one

To a solution of (6-amino-3-bromo-2-chloro-phenyl)-(2,6-difluorophenyl)methanone (25.0 g, 72.1 mmol) in pyridine (625 mL) was added ethyl 2-aminoacetate hydrochloride (70.5 g, 505 mmol). The reaction mixture was stirred at 135° C. for 36 h. The reaction mixture was concentrated in vacuo to remove pyridine. The residue was diluted with ethyl acetate (2000 mL) and washed with aqueous HCl (1.0 M, 3×1500 mL), water (2000 mL) and brine (2×1000 mL), dried ($Na_2SO_4$), filtered and concentrated in vacuo. The crude product was purified by flash column chromatography (silica, petroleum ether/ethyl acetate 10:1 to 2:1) to afford the title compound (10.1 g, 12%) as an off-white solid. MS: 385.0 ([{$^{79}$Br, $^{35}$Cl} M+H]$^+$), ESI pos.

f) 6-chloro-5-(2,6-difluorophenyl)-7-methyl-1,3-dihydro-1,4-benzodiazepin-2-one A microwave tube was charged with 7-bromo-6-chloro-5-(2,6-difluorophenyl)-1,3-dihydro-1,4-benzodiazepin-2-one (450 mg, 1.17 mmol), trimethylboroxine (205 mg, 228 μL, 1.63 mmol), potassium carbonate (242 mg, 1.75 mmol) and tetrakis(triphenylphosphine)palladium (0) (67.4 mg, 58.4 μmol). Degassed 1,4-dioxane (8.1 mL) and $H_2O$ (2.7 ml) were added then the vial was capped. The suspension was reacted in microwave at 130° C. for 30 min to give complete conversion. The mixture was evaporated, treated with sat. aq. $NaHCO_3$ (20 mL) and extracted with EtOAc (2×20 mL). The organic layers were dried ($Na_2SO_4$, filtered and solvents were evaporated. The residue was purified by flash column chromatography (silica, 40 g, $CH_2Cl_2$/EtOAc in heptane 10% to 40% to 70%) to give the title compound (344 mg, 92%) as light yellow solid. MS (ESI): 321.1 ([M+H]$^+$).

g) 6-chloro-5-(2,6-difluorophenyl)-7-methyl-1-(tri-tritiomethyl)-3H-1,4-benzodiazepin-2-one To a solution of [$^3$H]methyl nosylate (1.85 GBq, 50 mCi, 0.61 μmol) in THF (200 μL) were added the N-desmethyl precursor 6-chloro-5-(2,6-difluorophenyl)-7-methyl-1,3-dihydro-1,4-benzodiazepin-2-one (0.43 mg, 1.34 μmol) dissolved in THF (200 μL) and 10 equivalents of sodium tert-butylate (0.5 M in THF, 13.4 μmol). After stirring for 4 h at room temperature the reaction mixture was treated with $H_2O$, evaporated, and the crude product was purified by HPLC (X-Terra Prep RP-18, 10×150 mm, MeCN/$H_2O$ (containing 5% of MeCN) 40:60.4 ml/min, 230 nm). The pure tritium-labeled compound was isolated by solid phase extraction (Sep-Pak Plus C18) and eluted from the cartridge as ethanolic solution to yield 1.6 GBq (43.2 mCi) of the target compound in >99% radio-chemical purity and a specific activity of 2.49 TBq/mmol (67.3 Ci/mmol) as determined by mass spectrometry (MS). The identity of the labeled compound was confirmed by HPLC (by co-injecting the unlabeled reference standard) and by MS.

MS: m/z=335 [M(H)+H]$^+$ (16%), 337 [M($^3$H)+H]$^+$ (0%), 339 [M($^3$H$_2$)+H]$^+$. (16%), 341 [M($^3$H$_3$)+H]$^+$ (68%).

Membrane Preparation and Binding Assay for γ2-Containing $GABA_A$ Subtypes

The affinity of compounds at $GABA_A$ γ2 subunit-containing receptors was measured by competition for [$^3$H]Flumazenil (81.1 Ci/mmol; Roche) binding to HEK293F cells expressing human (transiently transfected) receptors of composition α1β3γ2.

Harvested pellets from HEK293F cells expressing the different $GABA_A$ γ2 receptor subtypes were resuspended in Mannitol Buffer pH 7.2-7.4 and processed as described above for the cells expressing the $GABA_A$ γ1 subunit-containing receptors.

Radioligand binding assays were carried out in a volume of 200 μL (96-well plates) which contained 100 μL of cell membranes, [$^3$H]Flumazenil at a concentration of 1 nM and the test compound in the range of [0.1·10$^{-3}$-10]×10$^{-6}$ M. Nonspecific binding was defined by 10$^{-5}$ M Diazepam and typically represented less than 5% of the total binding. Assays were incubated to equilibrium for 1 hour at 4° C. and harvested onto GF/C uni-filters (Packard) by filtration using a Packard harvester and washing with ice-cold wash buffer (50 mM Tris; pH 7.5). After anhydrousing, filter-retained radioactivity was detected by liquid scintillation counting. $K_i$ values were calculated using Excel-Fit (Microsoft) and are the means of two determinations.

The compounds of the accompanying examples were tested in the above described assay, and the preferred compounds were found to possess large $K_i$ value for displacement of [$^3$H]Flumazenil from the α1β3γ2 subtype of the human $GABA_A$ receptor of 100 nM or above. Most preferred are compounds with a $K_i$ α1β3γ2 (nM)>300. In a preferred embodiment the compounds of the invention are binding selectively for the γ1 subunit-containing $GABA_A$ receptors relative to γ2 subunit-containing $GABA_A$ receptors. In particular, compounds of the present invention have γ2 selectivity ratio defined as "$K_i$ α1β3γ2 (nM)/$K_i$ α2β2γ1 (nM)" above 10-fold, or LogSel defined as "Log[$K_i$ α1β3γ2 (nM)/$K_i$ α2β2γ1 (nM)]" above 1. Representative test results, obtained by the above described assay measuring binding affinity to HEK293 cells expressing human (h) receptors, are shown in the Table 1 below.

TABLE 1

| Example | $K_i$ h-$GABA_A$ α5β2γ1 (nM) | $K_i$ h-$GABA_A$ α2β2γ1 (nM) | $K_i$ h-$GABA_A$ α1β2γ1 (nM) | $K_i$ h-$GABA_A$ α1β3γ2 (nM) | γ2/γ1 Selectivity Ratio | LogSel |
|---|---|---|---|---|---|---|
| 1 | 3.19 | 25.0 | 35.1 | 637.6 | 25.5 | 1.41 |
| 2 | 1.26 | 6.5 | ND | 254.9 | 39.3 | 1.59 |
| 3 | 1.28 | 30.2 | ND | 454.7 | 15.0 | 1.18 |
| 4 | 1.14 | 8.8 | ND | 216 | 24.4 | 1.39 |
| 5 | 1.20 | 9.6 | ND | 307.4 | 31.9 | 1.50 |
| 6 | 0.75 | 5.5 | ND | 1437.6 | 260.9 | 2.42 |
| 7 | 0.75 | 6.0 | ND | 455.2 | 75.6 | 1.88 |
| 8 | 1.08 | 8.2 | ND | 367.9 | 44.7 | 1.65 |
| 9 | 1.15 | 5.5 | ND | 988.9 | 179.8 | 2.25 |
| 10 | 0.79 | 3.06 | ND | 445.2 | 145.5 | 2.16 |
| 11 | 0.84 | 2.71 | ND | 450.9 | 166.3 | 2.22 |
| 12 | 9.30 | 36.7 | ND | 505.5 | 13.8 | 1.14 |
| 13 | 0.60 | 2.58 | ND | 368.4 | 142.7 | 2.15 |
| 14 | 1.11 | 7.1 | 8.5 | 772.9 | 108.2 | 2.03 |
| 15 | 0.40 | 6.0 | ND | 278.3 | 46.3 | 1.67 |
| 16 | 1.20 | 5.2 | 9.2 | 571.4 | 109.6 | 2.04 |
| 17 | 1.30 | 2.59 | ND | 579.1 | 223.3 | 2.35 |
| 18 | 0.69 | 11.9 | ND | 437.1 | 36.8 | 1.57 |
| 19 | 1.98 | 32.5 | ND | 2650.2 | 81.5 | 1.91 |
| 20 | 0.89 | 5.24 | ND | 593.4 | 113.1 | 2.05 |
| 21 | 0.69 | 4.43 | 8.3 | 243.5 | 55.0 | 1.74 |
| 22 | 1.02 | 11.4 | ND | 1556.7 | 136.7 | 2.14 |
| 23 | 1.63 | 11.8 | 29.0 | 1139.6 | 96.8 | 1.99 |
| 24 | 0.45 | 3.14 | ND | 272.6 | 86.7 | 1.94 |
| 25 | 1.44 | 3.98 | ND | 688.5 | 172.8 | 2.24 |
| 26 | 2.48 | 8.6 | 38.1 | 1840.7 | 213.1 | 2.33 |
| 27 | 1.08 | 11.4 | ND | 706.6 | 61.8 | 1.79 |
| 28 | 1.08 | 3.92 | ND | 577.9 | 147.4 | 2.17 |
| 29 | 0.69 | 10.0 | ND | 1091.4 | 109.1 | 2.04 |
| 30 | 1.39 | 7.21 | ND | 659.6 | 91.5 | 1.96 |
| 31 | 1.33 | 17.0 | ND | 565.3 | 33.2 | 1.52 |
| 32 | 0.60 | 2.44 | ND | 163.5 | 67.1 | 1.83 |
| 33 | 0.69 | 10.77 | ND | 659.2 | 61.2 | 1.79 |
| 34 | 2.11 | 14.32 | ND | 2181.9 | 152.4 | 2.18 |
| 35 | 0.73 | 6.53 | ND | 777.9 | 119.1 | 2.08 |
| 36 | 0.95 | 3.46 | 8.25 | 778.4 | 224.7 | 2.35 |
| 37 | 1.80 | 4.49 | ND | 771.5 | 171.8 | 2.24 |

TABLE 1-continued

| Example | Ki h-GABA$_A$ α5β2γ1 (nM) | Ki h-GABA$_A$ α2β2γ1 (nM) | Ki h-GABA$_A$ α1β2γ1 (nM) | Ki h-GABA$_A$ α1β3γ2 (nM) | γ2/γ1 Selectivity Ratio | LogSel |
|---|---|---|---|---|---|---|
| 38 | 4.46 | 28.24 | ND | 2198.5 | 77.8 | 1.89 |
| 39 | 6.85 | 17.66 | ND | 4199.8 | 237.9 | 2.38 |
| 40 | 0.90 | 7.35 | ND | 671.6 | 91.4 | 1.96 |
| 41 | 0.74 | 3.28 | ND | 388.7 | 118.6 | 2.07 |
| 42 | 4.24 | 50.10 | ND | 2631 | 52.5 | 1.72 |
| 43 | 1.26 | 4.75 | ND | 836.9 | 176.3 | 2.25 |
| 44 | 9.52 | 25.93 | ND | 6615.1 | 255.1 | 2.41 |
| 45 | 2.20 | 5.39 | ND | 1348.8 | 250.3 | 2.40 |
| 46 | 2.14 | 5.91 | ND | 867.2 | 146.6 | 2.17 |
| 47 | 1.44 | 3.43 | ND | 1011.5 | 294.7 | 2.47 |
| 48 | 3.22 | 18.64 | ND | 1308.4 | 70.2 | 1.85 |
| 49 | 1.41 | 15.67 | ND | 619.4 | 39.5 | 1.60 |
| 50 | 0.89 | 4.50 | ND | 375.5 | 83.5 | 1.92 |
| 51 | 2.50 | 29.26 | ND | 1560 | 53.3 | 1.73 |
| 52 | 1.26 | 12.38 | ND | 577.5 | 46.6 | 1.67 |
| 53 | 1.65 | 61.38 | ND | 2546.5 | 41.5 | 1.62 |
| 54 | 0.97 | 4.38 | 15.2 | 581.3 | 132.7 | 2.12 |
| 55 | 1.15 | 5.40 | ND | 555.4 | 102.8 | 2.01 |
| 56 | 0.85 | 4.63 | ND | 432.4 | 93.4 | 1.97 |
| 57 | 1.84 | 17.8 | ND | 822.2 | 46.2 | 1.67 |
| 58 | 2.30 | 7.0 | 23.9 | 1093.2 | 156.8 | 2.20 |
| 59 | 1.26 | 7.0 | ND | 639.9 | 90.9 | 1.96 |
| 60 | 1.49 | 12.3 | ND | 602.3 | 49.1 | 1.69 |
| 61 | 1.45 | 4.18 | ND | 585.3 | 140.0 | 2.15 |
| 62 | 3.70 | 9.0 | ND | 772.8 | 85.7 | 1.93 |
| 63 | 1.33 | 4.25 | ND | 605.7 | 142.6 | 2.15 |
| 64 | 1.16 | 5.4 | ND | 888.9 | 165.6 | 2.22 |
| 65 | 0.50 | 5.8 | ND | 491.7 | 84.8 | 1.93 |
| 66 | 1.24 | 6.1 | ND | 240.6 | 39.7 | 1.60 |
| 67 | 0.79 | 5.2 | ND | 502.7 | 96.5 | 1.98 |
| 68 | 1.48 | 7.2 | ND | 318.5 | 44.0 | 1.64 |
| 69 | 0.77 | 19.2 | ND | 1154 | 60.1 | 1.78 |
| 70 | 1.08 | 18.7 | ND | 500.4 | 26.7 | 1.43 |
| 71 | 1.84 | 11.9 | ND | 388.7 | 32.8 | 1.52 |
| 72 | 1.10 | 7.2 | ND | 727.2 | 100.6 | 2.00 |
| 73 | 2.97 | 49.1 | ND | 2165.6 | 44.1 | 1.64 |
| 74 | 0.70 | 9.6 | ND | 593.2 | 61.8 | 1.79 |
| 75 | 1.14 | 13.8 | ND | 736.7 | 53.4 | 1.73 |
| 76 | 1.64 | 6.1 | ND | 967.6 | 157.7 | 2.20 |
| 77 | 1.00 | 10.2 | ND | 278.8 | 27.2 | 1.44 |
| 78 | 18.61 | 96.3 | ND | 6901.8 | 71.6 | 1.86 |
| 79 | 7.80 | 48.42 | ND | 3719.2 | 76.8 | 1.89 |
| 80 | 1.90 | 14.30 | ND | 978.6 | 68.5 | 1.84 |
| 81 | 1.63 | 6.45 | ND | 563.1 | 87.4 | 1.94 |
| 82 | 3.55 | 19.84 | ND | 2129.6 | 107.3 | 2.03 |
| 83 | 5.54 | 70.78 | ND | 5489.3 | 77.6 | 1.89 |
| 84 | 2.80 | 28.40 | ND | 976.6 | 34.4 | 1.54 |
| 85 | 8.51 | 60.89 | 223.8 | 8856.8 | 145.5 | 2.16 |
| 86 | 6.13 | 37.02 | ND | 2050.9 | 55.4 | 1.74 |
| 87 | 5.50 | 55.17 | ND | 3294.2 | 59.7 | 1.78 |
| 88 | 10.07 | 90.64 | ND | 2824.8 | 31.2 | 1.49 |
| 89 | 6.15 | 69.68 | ND | 6351.4 | 91.2 | 1.96 |
| 90 | 6.09 | 21.82 | ND | 4738.4 | 217.2 | 2.34 |
| 91 | 1.50 | 23.73 | ND | 752.2 | 31.7 | 1.50 |
| 92 | 4.45 | 44.89 | ND | 3277.8 | 73.0 | 1.86 |
| 93 | 2.25 | 3.30 | ND | 1290.7 | 390.6 | 2.59 |
| 94 | 1.43 | 3.89 | ND | 586.2 | 150.7 | 2.18 |
| 95 | 20.20 | 47.60 | ND | 9442.7 | 198.4 | 2.30 |
| 96 | 2.65 | 6.42 | ND | 933 | 145.4 | 2.16 |
| 97 | 8.64 | 14.85 | ND | 3593.1 | 242.0 | 2.38 |
| 98 | 29.75 | 81.75 | ND | 8109.6 | 99.2 | 2.00 |
| 99 | 3.29 | 4.45 | ND | 1553.9 | 348.9 | 2.54 |
| 100 | 7.53 | 41.50 | ND | 9107 | 219.5 | 2.34 |
| 101 | 14.45 | 38.01 | ND | 8679.6 | 228.3 | 2.36 |
| 102 | 6.83 | 51.5 | ND | 7252.6 | 140.7 | 2.15 |
| 103 | 9.87 | 25.3 | 177.9 | >30000.0 | 1183.4 | 3.07 |
| 104 | 6.36 | 37.3 | ND | 6297.9 | 168.8 | 2.23 |
| 105 | 5.05 | 13.9 | ND | 5132.6 | 368.4 | 2.57 |
| 106 | 2.94 | 22.6 | 104.4 | 4189.9 | 185.1 | 2.27 |
| 107 | 2.50 | 11.6 | 65.1 | 3704.7 | 319.1 | 2.50 |
| 108 | 2.59 | 3.92 | ND | 688.3 | 175.8 | 2.24 |
| 109 | 3.07 | 12.1 | 40.8 | 3120.5 | 258.7 | 2.41 |
| 110 | 2.64 | 12.1 | ND | 2479.9 | 205.1 | 2.31 |
| 111 | 1.24 | 5.16 | ND | 235.5 | 45.6 | 1.66 |
| 112 | 9.85 | 62.0 | ND | >30000.0 | 484.1 | 2.68 |
| 113 | 7.04 | 18.9 | ND | 11423.5 | 604.3 | 2.78 |
| 114 | 3.73 | 9.5 | 23.2 | 3092.7 | 325.5 | 2.51 |
| 115 | 2.63 | 12.3 | ND | 826.8 | 67.4 | 1.83 |
| 116 | 2.47 | 5.7 | ND | 94.5 | 16.4 | 1.22 |
| 117 | 3.14 | 20.0 | 99.2 | 5513.4 | 276.4 | 2.44 |
| 118 | 4.18 | 24.4 | ND | 4451.5 | 182.7 | 2.26 |
| 119 | 10.34 | 80.9 | ND | 12632.3 | 156.1 | 2.19 |
| 120 | 8.55 | 80.4 | ND | 5330.8 | 66.3 | 1.82 |
| 121 | 1.43 | 5.5 | 39.1 | 1210.3 | 218.2 | 2.34 |
| 122 | 3.82 | 10.6 | ND | 3053.4 | 287.8 | 2.46 |
| 123 | 9.75 | 91.9 | ND | >30000.0 | 326.6 | 2.51 |
| 124 | 6.32 | 26.2 | ND | 14363.8 | 547.2 | 2.74 |
| 125 | 1.70 | 6.19 | ND | 1604 | 259.0 | 2.41 |
| 126 | 3.23 | 10.20 | ND | 4604.3 | 451.4 | 2.65 |
| 127 | 5.46 | 49.36 | ND | 4763.3 | 96.5 | 1.98 |
| 128 | 4.20 | 34.85 | ND | 3880.9 | 111.4 | 2.05 |
| 129 | 1.58 | 6.00 | 49.9 | 3350.8 | 558.0 | 2.75 |
| 130 | 6.90 | 36.63 | ND | 4192.6 | 114.5 | 2.06 |
| 131 | 3.38 | 13.79 | ND | 2434.2 | 176.5 | 2.25 |
| 132 | 2.63 | 33.77 | ND | 2560.6 | 75.8 | 1.88 |
| 133 | 5.23 | 23.30 | ND | 827.3 | 35.5 | 1.55 |
| 134 | 2.36 | 19.33 | ND | 1482.9 | 76.7 | 1.88 |
| 135 | 9.35 | 50.62 | ND | >30000.0 | 592.7 | 2.77 |
| 136 | 6.22 | 37.47 | ND | 6128.4 | 163.5 | 2.21 |
| 137 | 6.58 | 42.59 | 130.2 | 10477.1 | 246.0 | 2.39 |
| 138 | 17.15 | 89.61 | ND | >30000.0 | 334.8 | 2.52 |
| 139 | 5.54 | 30.76 | ND | 3063.5 | 99.6 | 2.00 |
| 140 | 6.63 | 28.82 | ND | >30000.0 | 1041.0 | 3.02 |
| 141 | 12.43 | 55.92 | ND | 12210.7 | 218.4 | 2.34 |
| 142 | 8.06 | 39.68 | ND | >30000.0 | 756.0 | 2.88 |
| 143 | 7.35 | 45.42 | ND | 13470.2 | 296.6 | 2.47 |
| 144 | 8.30 | 73.48 | 179.2 | 13487.8 | 183.6 | 2.26 |
| 145 | 18.37 | 93.07 | ND | 13183.6 | 141.7 | 2.15 |
| 146 | 7.20 | 36.09 | ND | 13147.8 | 364.3 | 2.56 |
| 147 | 7.44 | 49.35 | ND | 12602.9 | 255.4 | 2.41 |
| 148 | 2.10 | 10.2 | ND | 865.9 | 84.7 | 1.93 |
| 149 | 1.59 | 8.3 | ND | 1111.1 | 134.1 | 2.13 |
| 150 | 1.33 | 7.3 | ND | 757.6 | 103.2 | 2.01 |
| 151 | 23.96 | 92.8 | ND | 13181.5 | 142.0 | 2.15 |
| 152 | 20.39 | 89.9 | ND | >30000.0 | 333.7 | 2.52 |
| 153 | 6.76 | 61.7 | ND | 6022.6 | 97.7 | 1.99 |
| 154 | 22.98 | 68.7 | ND | 11443.5 | 166.6 | 2.22 |
| 155 | 10.75 | 49.3 | ND | 8992.1 | 182.4 | 2.26 |
| 156 | 15.49 | 93.1 | ND | 10803.2 | 116.1 | 2.06 |
| 157 | 13.38 | 60.0 | ND | 11143.9 | 185.8 | 2.27 |
| 158 | 21.69 | 94.1 | ND | >30000.0 | 318.9 | 2.50 |
| 159 | 11.41 | 42.6 | 70.4 | 8324.8 | 195.6 | 2.29 |
| 160 | 19.24 | 66.3 | ND | 13337.2 | 201.1 | 2.30 |
| 161 | 21.27 | 72.7 | ND | >30000.0 | 412.4 | 2.62 |
| 162 | 13.60 | 55.7 | ND | 11710.4 | 210.1 | 2.32 |
| 163 | 20.55 | 100.8 | ND | 13508.2 | 134.0 | 2.13 |
| 164 | 10.63 | 33.7 | ND | 8523.1 | 253.2 | 2.40 |
| 165 | 9.55 | 43.3 | ND | 7771.8 | 179.6 | 2.25 |
| 166 | 9.14 | 43.4 | ND | 10190.6 | 234.5 | 2.37 |

Functional Expression of GABA$_A$ Receptors:

*Xenopus* oocytes Preparation

*Xenopus laevis* oocytes at maturation stages V-VI were used for the expression of cloned mRNA encoding GABA$_A$ receptor subunits. Oocytes ready for RNA micro-injection were bought from Ecocyte, Castrop-Rauxel, Germany and stored in modified Barth's medium (composition in mM: NaCl 88, KCl 1, NaHCO$_3$ 2.4, HEPES 10, MgSO$_4$ 0.82, CaNO$_3$ 0.33, CaCl$_2$ 0.33, pH=7.5) at 20° C. until the experiment.

*Xenopus* oocytes Microinjection

Oocytes were plated in 96-well plates for microinjection using the Roboinject automated instrument (MultiChannel-Systems, Reutlingen, Germany). Approximately 50 nL of an aqueous solution containing the RNA transcripts for the subunits of the desired GABA$_A$ receptor subtype was injected into each oocyte. RNA concentrations ranged between 20 and 200 pg/μL/subunit and were adjusted in pilot experiments to obtain GABA responses of a suitable size and a maximal effect of Flunitrazepam, Triazolam and Midazolam, reference benzodiazepine positive allosteric modulators (PAM) at the $GABA_A$ receptor benzodiazepine (BZD) binding site. Oocytes were kept in modified Barth's medium (composition in mM: NaCl 88, KCl 1, $NaHCO_3$ 4, HEPES 10, $MgSO_4$ 0.82, $CaNO_3$ 0.33, $CaCl_2$ 0.33, pH=7.5) at 20° C. until the experiment.

Electrophysiology

Electrophysiological experiments were performed using the Roboocyte instrument (MultiChannelSystems, Reutlingen, Germany) on days 3 to 5 after the micro-injection of mRNA. During the experiment the oocytes were constantly superfused by a solution containing (in mM) NaCl 90, KCl 1, HEPES 5, $MgCl_2$ 1, $CaCl_2$ 1 (pH 7.4). Oocytes were impaled by two glass microelectrodes (resistance: 0.5-0.8 MΩ) which were filled with a solution containing KCl 1M+K-acetate 1.5 M and voltage-clamped to −80 mV. The recordings were performed at room temperature using the Roboocyte two-electrode voltage clamp system (Multichannelsystem). After an initial equilibration period of 1.5 min GABA was added for 1.5 min at a concentration evoking approximately 20% of a maximal current response ($EC_{20}$). After another rest interval of 2.5 min GABA was again added evoking a response of similar amplitude and shape. 0.5 min after the onset of this second GABA application the test compound, at a concentration corresponding to approximatively 30-fold its $K_i$ α2β2γ1, was added while GABA was still present. Current traces were recorded at a digitization rate of 10 Hz during and shortly before and after the GABA application.

Each compound and concentration was tested on at least 3 oocytes. Different oocytes were used for different compound concentrations. The reference PAMs, Flunitrazepam, Triazolam and Midazolam, potentiated the GABA-induced current in α2β2γ1 $GABA_A$ receptor subtype expressing oocytes by approximatively 60%.

Data Analysis

For the analysis, the digitized current traces of the first and second GABA response were superimposed and, if necessary, rescaled to equal maximal amplitudes. The ratio between the two responses during the time interval of test compound application was calculated point by point. The extremum of the resulting "ratio trace" was taken as the efficacy ("Fold increase") of the compound expressed as "% modulation of GABA $EC_{20}$" (100*(Fold increase-1)).

The results are shown in Table 2.

TABLE 2

| Example | Ki h-$GABA_A$ α2β2γ1 (nM) | Fold increase h-GABA-A α2β2γ1 oocyte @ 30-fold Ki | Efficacy (GABA)% |
|---|---|---|---|
| 1 | 25.0 | 1.77 | 77 |
| 2 | 6.5 | 1.42 | 42 |
| 3 | 30.2 | ND | — |
| 4 | 8.8 | 2.05 | 105 |
| 5 | 9.6 | 1.78 | 78 |
| 6 | 5.5 | 2.01 | 101 |
| 7 | 6.0 | 1.68 | 68 |
| 8 | 8.2 | 1.98 | 98 |
| 9 | 5.5 | 2.23 | 123 |
| 10 | 3.1 | 1.70 | 70 |
| 11 | 2.7 | 1.62 | 62 |
| 12 | 36.7 | 2.25 | 125 |
| 13 | 2.6 | 1.59 | 59 |
| 14 | 7.1 | 1.57 | 57 |
| 15 | 6.0 | 1.62 | 62 |
| 16 | 5.2 | 1.52 | 52 |
| 17 | 2.6 | 1.44 | 44 |
| 18 | 11.9 | 1.70 | 70 |
| 19 | 32.5 | 1.97 | 97 |
| 20 | 5.2 | 1.78 | 78 |
| 21 | 4.4 | 1.67 | 67 |
| 22 | 11.4 | 1.78 | 78 |
| 23 | 11.8 | 1.63 | 63 |
| 24 | 3.1 | 1.88 | 88 |
| 25 | 4.0 | 1.63 | 63 |
| 26 | 8.6 | 1.75 | 75 |
| 27 | 11.4 | 1.69 | 69 |
| 28 | 3.9 | 1.56 | 56 |
| 29 | 10.0 | 1.80 | 80 |
| 30 | 7.2 | 1.78 | 78 |
| 31 | 17.0 | 1.66 | 66 |
| 32 | 2.4 | 1.26 | 26 |
| 33 | 10.8 | 1.56 | 56 |
| 34 | 14.3 | 1.71 | 71 |
| 35 | 6.5 | 1.67 | 67 |
| 36 | 3.5 | 1.71 | 71 |
| 37 | 4.5 | 1.47 | 47 |
| 38 | 28.2 | 2.16 | 116 |
| 39 | 17.7 | 1.89 | 89 |
| 40 | 7.4 | 1.89 | 89 |
| 41 | 3.3 | 1.67 | 67 |
| 42 | 50.1 | 2.14 | 114 |
| 43 | 4.7 | 1.71 | 71 |
| 44 | 25.9 | 2.33 | 133 |
| 45 | 5.4 | 1.41 | 41 |
| 46 | 5.9 | 1.73 | 73 |
| 47 | 3.4 | 1.74 | 74 |
| 48 | 18.6 | 1.94 | 94 |
| 49 | 15.7 | 1.75 | 75 |
| 50 | 4.5 | 1.60 | 60 |
| 51 | 29.3 | 1.49 | 49 |
| 52 | 12.4 | 1.41 | 41 |
| 53 | 61.4 | 1.73 | 73 |
| 54 | 4.4 | 1.80 | 80 |
| 55 | 5.4 | 1.58 | 58 |
| 56 | 4.6 | 1.72 | 72 |
| 57 | 17.8 | 1.76 | 76 |
| 58 | 7.0 | 2.12 | 112 |
| 59 | 7.0 | 1.74 | 74 |
| 60 | 12.3 | 2.07 | 107 |
| 61 | 4.2 | 1.99 | 99 |
| 62 | 9.0 | 1.93 | 93 |
| 63 | 4.2 | 1.79 | 79 |
| 64 | 5.4 | 1.75 | 75 |
| 65 | 5.8 | 1.80 | 80 |
| 66 | 6.1 | 1.58 | 58 |
| 67 | 5.2 | 1.47 | 47 |
| 68 | 7.2 | 2.07 | 107 |
| 69 | 19.2 | 1.97 | 97 |
| 70 | 18.7 | 1.73 | 73 |
| 71 | 11.9 | 1.51 | 51 |
| 72 | 7.2 | 1.44 | 44 |
| 73 | 49.1 | 1.58 | 58 |
| 74 | 9.6 | 1.75 | 75 |
| 75 | 13.8 | 1.41 | 41 |
| 76 | 6.1 | 1.52 | 52 |
| 77 | 10.2 | 1.69 | 69 |
| 78 | 96.3 | 1.98 | 98 |
| 79 | 48.4 | 2.29 | 129 |
| 80 | 14.3 | 1.89 | 89 |
| 81 | 6.4 | 1.53 | 53 |
| 82 | 19.8 | 1.75 | 75 |
| 83 | 70.8 | 2.54 | 154 |
| 84 | 28.4 | 2.75 | 175 |
| 85 | 60.9 | 2.40 | 140 |

TABLE 2-continued

| Example | Ki h-GABA$_A$ α2β2γ1 (nM) | Fold increase h-GABA-A α2β2γ1 oocyte @ 30-fold Ki | Efficacy (GABA)% |
|---|---|---|---|
| 86 | 37.0 | 1.97 | 97 |
| 87 | 55.2 | 1.84 | 84 |
| 88 | 90.6 | 2.62 | 162 |
| 89 | 69.7 | 2.13 | 113 |
| 90 | 21.8 | 2.04 | 104 |
| 91 | 23.7 | 1.75 | 75 |
| 92 | 44.9 | 1.44 | 44 |
| 93 | 3.3 | 1.75 | 75 |
| 94 | 3.9 | 1.76 | 76 |
| 95 | 47.6 | 2.26 | 126 |
| 96 | 6.4 | 1.52 | 52 |
| 97 | 14.8 | 1.95 | 95 |
| 98 | 81.7 | 2.58 | 158 |
| 99 | 4.5 | 1.52 | 52 |
| 100 | 41.5 | 2.28 | 128 |
| 101 | 38.0 | 1.97 | 97 |
| 102 | 51.5 | 2.43 | 143 |
| 103 | 25.4 | 2.13 | 113 |
| 104 | 37.3 | 2.17 | 117 |
| 105 | 13.9 | 1.98 | 98 |
| 106 | 22.6 | 1.90 | 90 |
| 107 | 14.0 | 2.03 | 103 |
| 108 | 3.9 | 1.46 | 46 |
| 109 | 12.1 | 2.26 | 126 |
| 110 | 12.1 | 2.19 | 119 |
| 111 | 5.2 | 1.35 | 35 |
| 112 | 62.0 | 2.36 | 136 |
| 113 | 18.9 | 1.76 | 76 |
| 114 | 9.5 | 1.88 | 88 |
| 115 | 12.3 | 1.49 | 49 |
| 116 | 5.7 | 1.35 | 35 |
| 117 | 20.0 | 1.92 | 92 |
| 118 | 24.4 | 2.20 | 120 |
| 119 | 80.9 | 2.24 | 124 |
| 120 | 80.4 | 2.78 | 178 |
| 121 | 5.5 | 1.52 | 52 |
| 122 | 10.6 | 1.91 | 91 |
| 123 | 91.8 | 2.62 | 162 |
| 124 | 26.2 | 2.45 | 145 |
| 125 | 6.2 | 1.73 | 73 |
| 126 | 10.2 | 1.38 | 38 |
| 127 | 49.4 | 2.12 | 112 |
| 128 | 34.8 | 1.98 | 98 |
| 129 | 6.0 | 1.36 | 36 |
| 130 | 36.6 | 2.16 | 116 |
| 131 | 13.8 | 2.04 | 104 |
| 132 | 33.8 | 2.05 | 105 |
| 133 | 23.3 | 1.41 | 41 |
| 134 | 19.3 | 2.01 | 101 |
| 135 | 50.6 | 2.18 | 118 |
| 136 | 37.5 | 2.16 | 116 |
| 137 | 42.6 | 2.29 | 129 |
| 138 | 89.6 | 3.04 | 204 |
| 139 | 30.8 | 2.49 | 149 |
| 140 | 28.8 | 2.21 | 121 |
| 141 | 55.9 | 2.12 | 112 |
| 142 | 39.7 | 2.23 | 123 |
| 143 | 45.4 | 2.10 | 110 |
| 144 | 73.5 | 2.69 | 169 |
| 145 | 93.1 | 2.68 | 168 |
| 146 | 36.1 | 2.11 | 111 |
| 147 | 49.3 | 2.13 | 113 |
| 148 | 10.2 | 1.73 | 73 |
| 149 | 8.3 | 1.71 | 71 |
| 150 | 7.3 | 1.70 | 70 |
| 151 | 92.8 | 3.53 | 253 |
| 152 | 89.9 | ND | — |
| 153 | 62.4 | 3.47 | 247 |
| 154 | 68.7 | 2.91 | 191 |
| 155 | 49.7 | 2.93 | 193 |
| 156 | 95.1 | 2.68 | 168 |
| 157 | 60.1 | 2.91 | 191 |
| 158 | 94.6 | 2.44 | 144 |
| 159 | 43.0 | 3.17 | 217 |
| 160 | 66.4 | 2.77 | 177 |
| 161 | 72.8 | 2.65 | 165 |
| 162 | 54.4 | 2.48 | 148 |
| 163 | 87.1 | 2.36 | 136 |
| 164 | 35.2 | 2.77 | 177 |
| 165 | 36.2 | 2.83 | 183 |
| 166 | 46.5 | 2.84 | 184 |

Reference Compounds

Benzodiazepines reference compounds (classical marketed benzodiazepines) and reference triazolo[1,5-a][1,4]benzodiazepines listed below were tested for their affinity towards the GABA$_A$ receptor α1β1γ1 and α2β2γ1 subtypes as well as in the GABA$_A$ receptor α1β3γ2 subtype. The results are shown in Table 3.

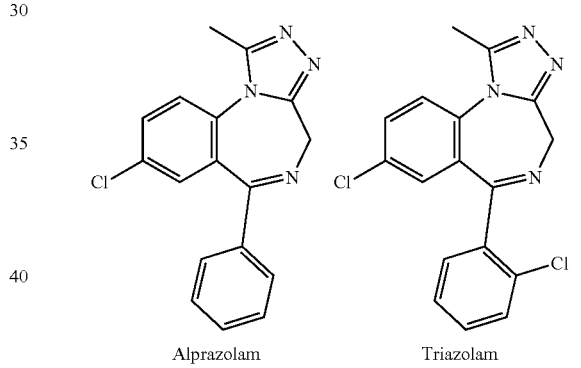

Alprazolam    Triazolam

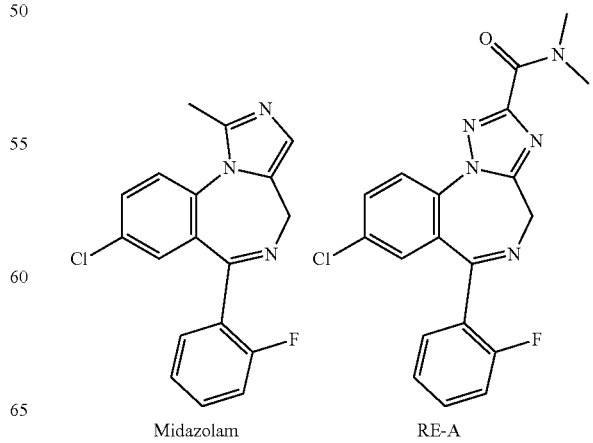

Midazolam    RE-A

-continued

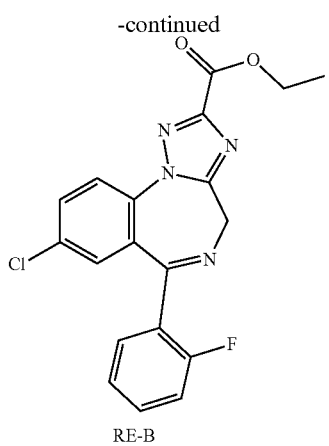

RE-B

TABLE 3

| Example | Ki h-GABA$_A$ α1β2γ1 (nM) | Ki h-GABA$_A$ α2β2γ1 (nM) | Ki h-GABA$_A$ α1β3γ2 (nM) | γ2/γ1 Selectivity Ratio | LogSel |
|---|---|---|---|---|---|
| Alprazolam | 5923 | 3945 | 19.6 | 0.0050 | −2.3 |
| Triazolam | 44.2 | 46.2 | 1.5 | 0.032 | −1.5 |
| Midazolam | 1153.2 | 737.7 | 5.0 | 0.0068 | −2.2 |
| RE-A | ND | 275.6 | 35.6 | 0.13 | −0.89 |
| RE-B | ND | 18.4 | 3.4 | 0.18 | −0.74 |
| Example 9 | ND | 5.5 | 988.9 | 179.8 | 2.25 |
| Example 19 | ND | 32.5 | 2650.2 | 81.5 | 1.91 |

RE-A is disclosed in the following patent applications: CH569739, CH567025, CH572057, CH569018, AT328458, DE2525691, DE2304307; and in the peer-reviewed publication: Helvetica Chimica Acta (1978), 61(2), 848-63.

RE-B is disclosed in the following patent applications: CH574426, DE2215943, AT328458, CH572057, CH551993, DE2304307, DE2234652.

Preparation of Pharmaceutical Compositions Comprising Compounds of the Invention Tablets comprising compounds of formula (I) are manufactured as follows:

| Ingredient | mg/tablet | | | |
|---|---|---|---|---|
|  | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Capsules comprising compounds of formula (I) are manufactured as follows:

| Ingredient | mg/capsule | | | |
|---|---|---|---|---|
|  | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

A compound of formula I lactose and corn starch are firstly mixed in a mixer and then in a comminuting machine. The mixture is returned to the mixer; the talc is added thereto and mixed thoapproximatively. The mixture is filled by machine into suitable capsules, e.g. hard gelatin capsules.

Injection solutions comprising compounds of formula (I) are manufactured as follows:

| Ingredient | mg/injection solution. |
|---|---|
| Compound of formula I | 3 |
| Polyethylene Glycol 400 | 150 |
| acetic acid | q.s. ad pH 5.0 |
| water for injection solutions | ad 1.0 ml |

What is claimed is:
1. A method for treating an acute neurological disorder in a subject, said method comprising administering an effective amount of a compound of the formula

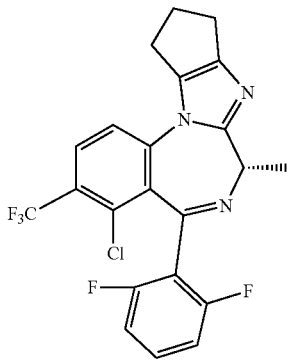 [SMILES: C[C@@H]1N=C(c2c(F)cccc2F)c2c(ccc(C(F)(F)F)c2Cl)-n2c1nc1c2CCC1]

or a pharmaceutically acceptable salt thereof.
2. The method according to claim 1, wherein said acute neurological disorder is anxiety.

* * * * *